US011912710B2

(12) United States Patent
Ryu et al.

(10) Patent No.: US 11,912,710 B2
(45) Date of Patent: Feb. 27, 2024

(54) SUBSTITUTED PYRIMIDO[4,5-B][1,4]DIAZEPINES AS PLK1 DEGRADATION INDUCERS

(71) Applicant: UPPTHERA, INC., Incheon (KR)

(72) Inventors: Soo Hee Ryu, Incheon (KR); Im Suk Min, Gyeonggi-do (KR); Han Kyu Lee, Gyeonggi-do (KR); Seong Hoon Kim, Incheon (KR); Hye Guk Ryu, Incheon (KR); Keum Young Kang, Incheon (KR); Sang Youn Kim, Incheon (KR); So Hyun Chung, Incheon (KR); Jun Kyu Lee, Gyeonggi-do (KR); Gibbeum Lee, Gyeonggi-do (KR)

(73) Assignee: UPPTHERA, INC., Incheon (KR)

( * ) Notice: Subject to any disclaimer, the term of this patent is extended or adjusted under 35 U.S.C. 154(b) by 0 days.

(21) Appl. No.: 18/019,047

(22) PCT Filed: Aug. 10, 2022

(86) PCT No.: PCT/KR2022/011963
§ 371 (c)(1),
(2) Date: Jan. 31, 2023

(87) PCT Pub. No.: WO2023/018238
PCT Pub. Date: Feb. 16, 2023

(65) Prior Publication Data
US 2023/0219966 A1 Jul. 13, 2023

(30) Foreign Application Priority Data

Aug. 10, 2021 (KR) .................. 10-2021-0105358
Aug. 12, 2021 (KR) .................. 10-2021-0106488
Sep. 3, 2021 (KR) .................. 10-2021-0117389
Sep. 24, 2021 (KR) .................. 10-2021-0126757
Jan. 20, 2022 (KR) .................. 10-2022-0008456
Feb. 17, 2022 (KR) .................. 10-2022-0020996
May 3, 2022 (KR) .................. 10-2022-0054880
Jun. 21, 2022 (KR) .................. 10-2022-0075838

(51) Int. Cl.
A61K 31/519 (2006.01)
C07D 487/04 (2006.01)
A61K 47/55 (2017.01)
C07D 519/00 (2006.01)

(52) U.S. Cl.
CPC .......... C07D 487/04 (2013.01); A61K 47/55 (2017.08); C07D 519/00 (2013.01)

(58) Field of Classification Search
CPC ...................... A61K 31/519; C07D 487/04
USPC ......................... 514/262.1; 544/256
See application file for complete search history.

(56) References Cited

U.S. PATENT DOCUMENTS

2016/0176916 A1 6/2016 Bradner et al.
2020/0325130 A1 10/2020 Crews et al.

FOREIGN PATENT DOCUMENTS

| CN | 106543185 | 3/2017 |
| CN | 109879877 | 6/2019 |
| WO | WO 2009/153197 | 12/2009 |
| WO | WO 2021/061894 | 4/2021 |

OTHER PUBLICATIONS

Bolden et al., "Inducible In Vivo Silencing of Brd4 Identifies Potential Toxicities of Sustained BET Protein Inhibition," *Cell Reports*, 8(6): 1919-1929, Sep. 18, 2014.
Burslem et al., "Small-Molecule Modulation of Protein Homeostasis," *Chemical Reviews*, 117(17): 11269-11301, Aug. 4, 2017.
Gheghiani et al., "PLK1 Activation in Late G2 Sets Up Commitment to Mitosis," *Cell Reports*, 19(10): 2060-2073, Jun. 6, 2017.
International Search Report and Written Opinion issued for International Application No. PCT/KR2022/011963 dated Dec. 12, 2022.
Mu et al., "Protein targeting chimeric molecules specific for dual bromodomain 4 (BRD4) and Polo-like kinase 1 (PLK1) proteins in acute myeloid leukemia cells," *Biochemical and Biophysical Research Communications*, 521(4): 833-839, Nov. 7, 2019.

*Primary Examiner* — Douglas M Willis
(74) *Attorney, Agent, or Firm* — Klarquist Sparkman, LLP

(57) ABSTRACT

The present disclosure relates to a novel PLK1 degradation inducing compound having a structure according to Formula I, a method for preparing the same, and the use thereof. The compounds of the present disclosure exhibit an effect of inducing PLK1 degradation. Therefore, the compounds of the present disclosure may be effectively utilized for preventing or treating PLK1-related diseases.

12 Claims, 1 Drawing Sheet

[Fig. 1]
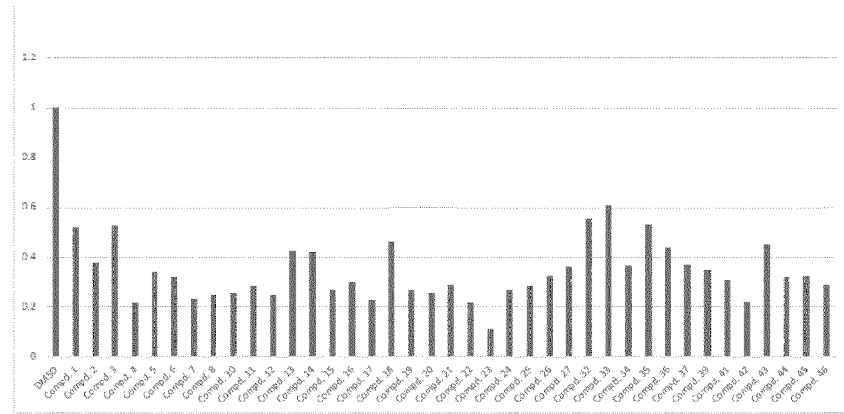

SUBSTITUTED PYRIMIDO[4,5-B][1,4]DIAZEPINES AS PLK1 DEGRADATION INDUCERS

CROSS REFERENCE TO RELATED APPLICATIONS

This is the U.S. National Stage of International Application No. PCT/KR2022/011963, filed Aug. 10, 2022, which will publish in English under PCT Article 21(2), which in turn claims the benefit of KR Application No. 10-2021-0105358 filed on Aug. 10, 2021; KR Patent Application No. 10-2021-0106488 filed on Aug. 12, 2021; KR Patent Application No. 10-2021-0117389, filed on Sep. 3, 2021; KR Patent Application No. 10-2021-0126757, filed on Sep. 24, 2021; KR Patent Application No. 10-2022-0008456, filed on Jan. 20, 2022; KR Patent Application No. 10-2022-0020996, filed on Feb. 17, 2022; KR Patent Application No. 10-2022-0054880, filed on May 3, 2022; and KR Patent Application No. 10-2022-0075838, filed on Jun. 21, 2022; each of these prior applications is incorporated herein by reference in its entirety.

FIELD

The present disclosure relates to a novel PLK1 degradation inducing compound, a method for preparing the same, and the use thereof. It can specifically act on abnormal cells, etc. and can be usefully used in the treatment of various diseases through efficient degradation of PLK1.

BACKGROUND

Polo-like kinase 1 (PLK1) is a serine/threonine kinase involved in the conversion of G2/M phase during cell growth and division. PLK1 is expressed and activated in a pulse form from the S phase to the G2/M phase, and rapidly degrades as mitosis ends.

PLK1 is overexpressed in various carcinomas such as colon cancer, lung cancer, bladder cancer, and melanoma, etc., and cancer cells overexpressing PLK1 tend to show resistance to various types of anticancer drugs. As the PLK1 dependence in various carcinomas was revealed as described above, there have been attempts to develop PLK1 inhibitor compounds such as volasertib (also known as BI6727), etc.

However, the conventional PLK1 inhibitors do not sufficiently inhibit PLK1 activity at concentrations that are clinically safe. Thus, there is a problem that even if the cell cycle of cancer cells is temporarily delayed, some cancer cells eventually restart the cell cycle, which may not obtain sufficient clinical effects (see Gheghiani et al., Cell Reports, 2017, etc.). In fact, many pharmaceutical companies such as Boehringer Ingelheim, GlaxoSmithKline, etc., have attempted to develop small-molecular compound-based PLK1 inhibitors, but most of them have failed or stopped in the clinical trial stage, and thus there are no commercially available PLK1 inhibitors to date. It shows that pharmacological mechanism that follows the method of inhibiting enzyme activity by binding to the active site of PLK1 like the small molecule compound inhibitors is not sufficiently effective in the development of new drugs intended to derive anticancer effects by inhibiting PLK1 activity of cancer cells.

Recently, a proteolysis targeting chimera (PROTAC) has been proposed as a small molecule-based platform technology capable of inducing proteolysis of a target protein in the body. The PROTAC is a bifunctional compound in which a ligand molecule that binds to disease-related target protein and an E3 ubiquitin ligase binding moiety are linked by a chemical linker. Theoretically, the PROTAC compound is capable of inducing degradation of the target protein by placing the disease-related target protein near the E3 ubiquitin ligase. Based on this new mechanism different from the existing inhibitors, a lot of PROTAC compounds have been developed as therapeutic agents for cancer and inflammatory diseases, etc., and being studied with various extensibility (e.g. as payloads of ADC (Antibody-Drug Conjugates)). However, it does not show activity in all ranges of binding moieties or linkers, and in order for PROTAC to exhibit the desired level of efficacy, it is known through several studies that each binding moiety and linker must have an appropriately linked structure (see US2020-0325130A). In particular, in the case of the CRBN(Cereblon) E3 ligase targeting moiety, depending on the type of the binding moiety or the structure of the compound linked thereto, there is a risk of degrading CRBN neo-substrate (GSPT1, IKZF1/3, etc.) or showing off-target toxicity accordingly. Therefore, it is important to select appropriate binding moieties and optimize the structure of the entire compound so as not to exhibit unexpected toxicity during PROTAC drug development.

In the case of the PROTAC compound using PLK1 as a target protein, Chinese Patent Laid-Open No. 106543185 A discloses some bifunctional compounds in which a volasertib derivative compound and a binding moiety for the E3 ubiquitin ligase CRBN are linked by a chemical linker. However, the related art document merely describes some limited forms of synthesis examples of PROTAC compounds, wherein in general, the target degradation activity and selectivity of PROTAC may vary significantly depending on selection of the target protein moiety, the E3 ubiquitin ligase binding moiety, and the like (see Burslem and Crews, 2017, etc.).

Further, the PROTAC compound described in the above-described document is characterized by a compound that simultaneously degrades PLK1 and BRD4, and degrade various proteins such as other PLK family proteins and BRD4, etc.), which may cause side effects due to off-target toxicities at the time of drug development. In particular, it is known that strong inhibition of BRD4 activity inevitably accompanies on-target toxicity such as blood toxicity and gastrointestinal toxicity along with pharmacological effects. Therefore, the PROTAC compound described in the above document would expect to face greater clinical side effects as more BRD4 protein gets degraded (see Bolden et al. Cell Reports, 2014).

Moreover, according to the document published by the inventors of the above document (see Mu et al. BBRC, 2019), it can be confirmed that the PROTAC compound, which simultaneously degrades PLK1 and BRD4, has much stronger BRD4 degradation ability than PLK1 degradation ability at the cellular level, and the cell cycle thereof almost stops in the G1 phase, etc., that is, the PROTAC compound actually acts only as a BRD4 inhibitor regardless of the way that the conventional PLK1 inhibitors exert pharmacological effects.

Therefore, there is an unsatisfied demand for effective PLK1 degradation inducing compound with no or minimal side effects. (e.g. off-target toxicity)

SUMMARY

The compounds of the present disclosure exhibit an effect of inducing PLK1 degradation. Therefore, the compounds of the present disclosure may be effectively utilized for preventing or treating PLK1-related diseases.

BRIEF DESCRIPTION OF THE DRAWINGS

FIG. 1 shows the luciferase assay results by treating Compound 1 to Compound 46 of the present invention.

DETAILED DESCRIPTION

Unless otherwise defined, all technical and scientific terms used herein have the same meaning as commonly understood by one of ordinary skill in the art to which this disclosure belongs. The terminology used in the description is for describing particular embodiments only and is not intended to be limiting of the disclosure.

An object of the present disclosure is to provide novel PLK1 degradation inducing compounds.

Another object of the present disclosure is to provide a method for preparing the compounds.

Still another object of the present disclosure is to provide a use of the compounds.

In order to achieve the above-described objects, the present inventors made efforts to study, and as a result, found that novel PROTAC compounds of the present invention specifically act on abnormal cells overexpressing PLK1 through appropriate structural combination and optimization of E3 Ligase binder, Target binding moiety, and Linker to induce effective PLK1 degradation and minimize side effects, and completed the present invention.

Selective PLK1 Degradation Inducing Compounds

The present disclosure provides novel compounds that induce effective polo-like kinase 1 (PLK1) degradation. Specifically, the present disclosure provides a bifunctional compound in which a PLK1 binding moiety and an E3 ubiquitin ligase-binding moiety are linked by a chemical linker.

In one general aspect, there is provided a compound represented by the following Formula I, a stereoisomer thereof or a pharmaceutically acceptable salt thereof:

ULM-Linker-PTM    [Formula I]

in the Formula I above,

ULM is a moiety represented by the following Formula 1;

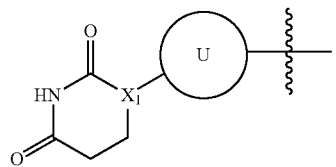

[Formula 1]

PTM is a moiety represented by the following Formula 2;

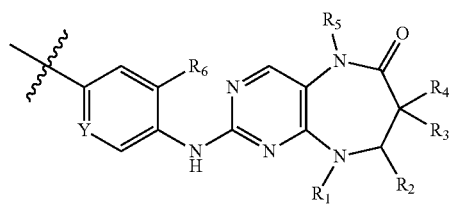

[Formula 2]

Linker is a group that chemically links ULM and PTM;

$X_1$ is CH or N;

ring U is phenyl or 5- to 6-membered heteroaryl {wherein at least one H of the phenyl or 5-to 6-membered heteroaryl ring may be substituted with $R_U$};

$R_U$ is —$C_{1-4}$alkyl, —$C_{1-4}$hydroxyalkyl, —$C_{1-4}$aminoalkyl, —$C_{1-4}$haloalkyl, —$C_{1-4}$alkoxy or -halo;

Y is $CR_7$;

$R_1$ is 3- to 7-membered cycloalkyl;

$R_2$ is —H or —$C_{1-4}$alkyl, $R_3$ and $R_4$ are each independently —H, —$C_{1-4}$alkyl or -halo;

$R_5$ is —$C_{1-4}$alkyl;

$R_6$ is —$C_{1-4}$alkyl or —$C_{1-4}$alkoxy; and $R_7$ is —H or -halo.

In one embodiment of the present disclosure,

ULM is a moiety represented by following Formula 1-1 or Formula 1-2;

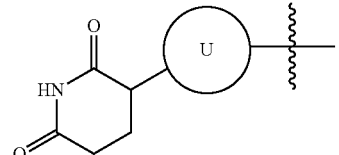

[Formula 1-1]

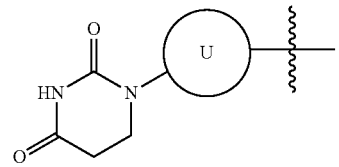

[Formula 1-2]

ring U is phenyl, pyridinyl, pyrimidinyl or pyrazolyl {wherein at least one H of the phenyl, pyridinyl, pyrimidinyl or pyrazolyl ring may be substituted with $R_U$}; and $R_U$ is —$C_{1-4}$alkyl, —$C_{1-4}$haloalkyl, —$C_{1-4}$alkoxy or -halo.

In one embodiment of the resent disclosure,

ULM is

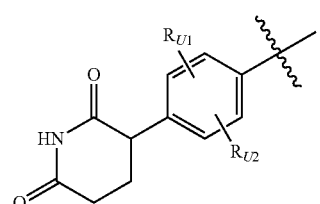

,

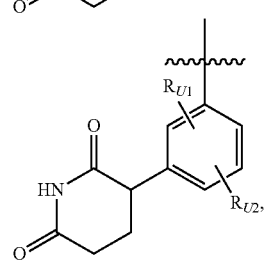

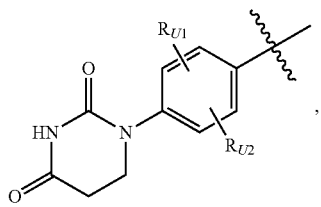,
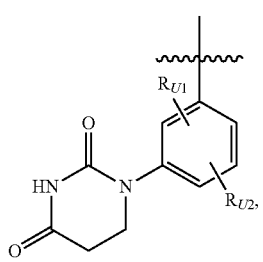,
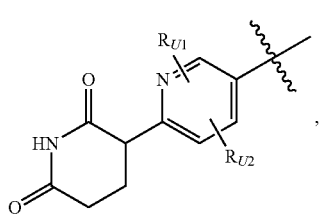,
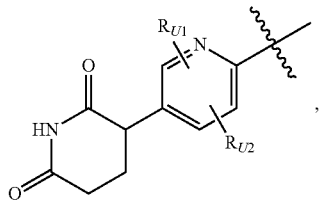,
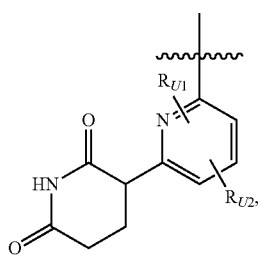,
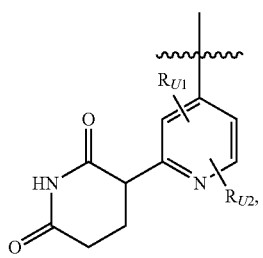,
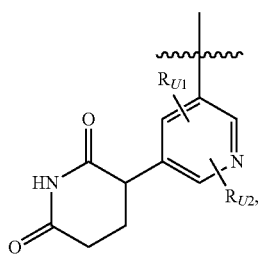,
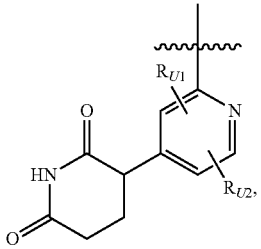,
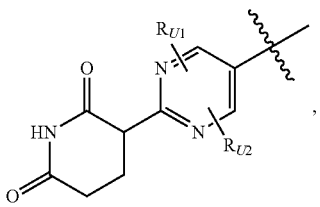,
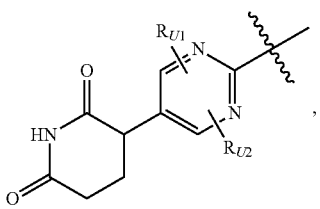,
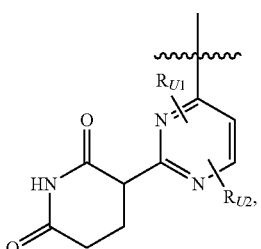,
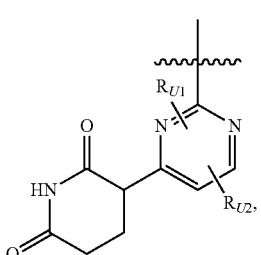,
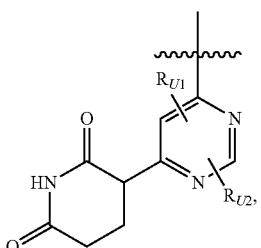,
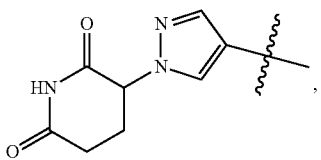,

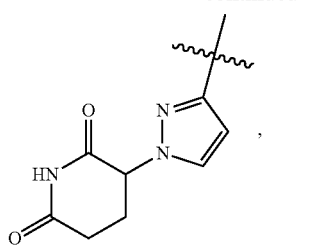
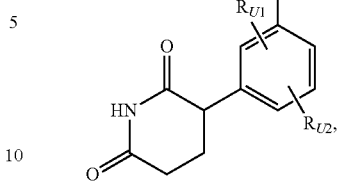
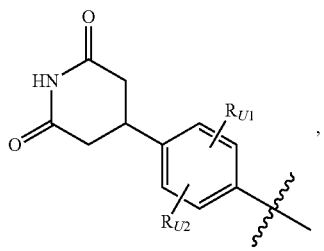
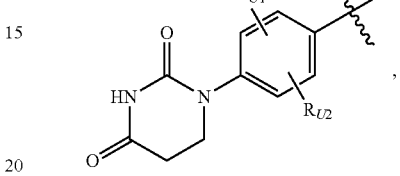
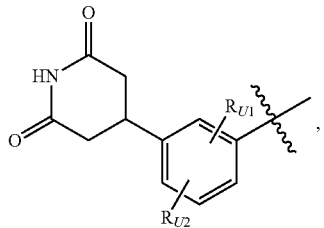
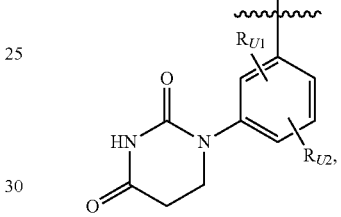
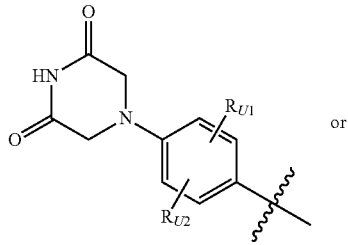 or
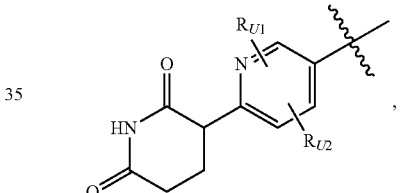
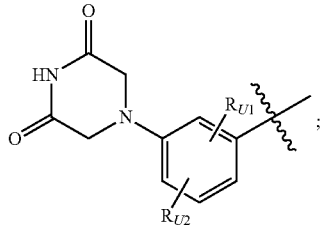;
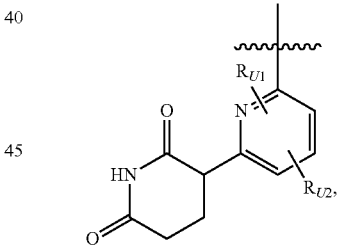
and
$R_{U1}$ and $R_{U2}$ are each independently —$C_{1-4}$alkyl, —$C_{1-4}$haloalkyl, —$C_{1-4}$alkoxy or -halo.
In one embodiment of the present disclosure, ULM is
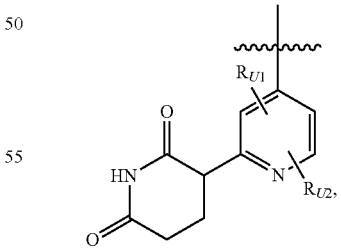
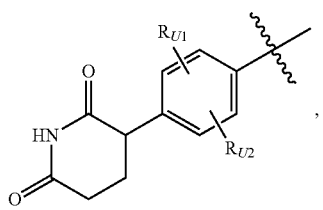
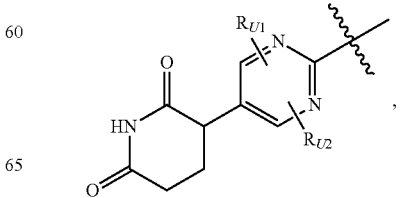

-continued

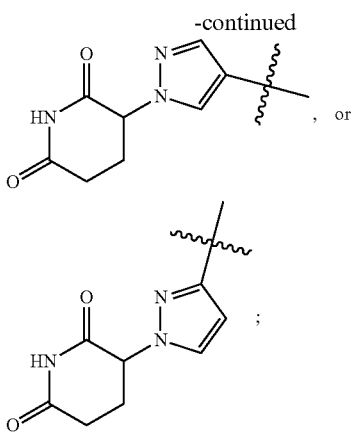

, or

;

and $R_{U1}$ and $R_{U2}$ are each independently —$C_{1-4}$alkyl, —$C_{1-4}$haloalkyl, —$C_{1-4}$alkoxy or -halo.

In one embodiment of the present disclosure,

PTM is

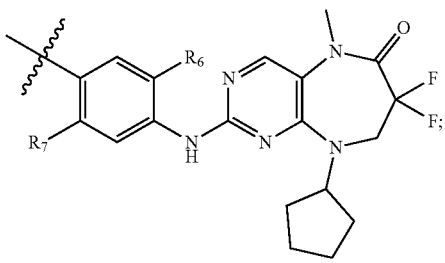

$R_6$ is —$C_{1-4}$alkyl, —$C_{1-4}$alkoxy or -halo; and
$R_7$ is —H or -halo.

In one embodiment of the present disclosure,

Linker is -$L_U$-$L_1$-$L_2$-$L_3$-$L_P$-;

$L_U$ is —$(CH_2)x$-, —$(CH_2)x$-NH—, —$(CH_2)x$-O—, —$C(=O)$—, phenyl or nothing (null) {wherein $L_U$ is linked with ULM [when the $L_U$ is nothing (null), $L_1$ is directly linked with ULM], and the x is 0, 1, 2, 3 or 4};

$L_1$ is heterocycloalkyl or nothing (null) {wherein, when the $L_1$ is nothing (null), $L_U$ and $L_2$ are directly linked, the heterocycloalkyl contains at least one N atom in the ring, and the at least one H of the heterocycloalkyl may be substituted with —$C_{1-4}$alkyl, —$C_{1-4}$haloalkyl, —$C_{1-4}$ alkoxy, —OH, -halo or =O};

$L_2$ is —$(CH_2)y_1$-, —$(CD_2)y_1$-, —$(CH_2)y_2$-C(=O)—$(CH_2)y_3$-, —$(CH_2)y_2$-NH—$(CH_2)y_3$-, —$(CH_2)y_2$-N($C_{1-4}$alkyl)-$(CH_2)y_3$-, —$(CH_2)y_1$-(O—$C_{1-4}$alkyl)z-O—$C_{1-4}$alkyl or nothing (null) {wherein the $y_1$ to $y_3$ are each independently 0, 1, 2, 3, 4, 5 or 6, and z is 0, 1, 2, 3, 4, 5 or 6};

$L_3$ is cycloalkyl, heterocycloalkyl or nothing (null) {wherein, when the $L_3$ is nothing (null), $L_2$ and $L_p$ are directly linked, the heterocycloalkyl contains at least one N atom in the ring, and at least one H of the cycloalkyl or heterocycloalkyl ring may be substituted with —$C_{1-4}$alkyl, —$C_{1-4}$haloalkyl or -halo}; and $L_P$ is —$(CH_2)p$-NH—C(=O)— or —$(CH_2)p$-O— {wherein —C(=O)— or —O— of the $L_p$ is linked with PTM, and p is 0, 1 or 2}.

In one embodiment of the present disclosure, $L_U$ is —$(CH_2)x$-, —$(CH_2)x$-NH—, —$(CH_2)x$-O— or phenyl {wherein the $L_U$ is linked with ULM, and the x is 0 or 1};

$L_1$ is 4- to 12-membered heterocycloalkyl or nothing (null) {wherein, when the $L_1$ is nothing (null), $L_U$ and $L_2$ are directly linked, the 4- to 12-membered heterocycloalkyl is single ring, bridged bicyclic ring or spiro ring, the 4- to 12-membered heterocycloalkyl contains at least one N atom in the ring, the N atom is directly linked with $L_U$ or ULM, and at least one H of the heterocycloalkyl ring may be substituted with —$C_{1-4}$alkyl, —OH or -halo};

$L_2$ is —$(CH_2)y_1$-, —$(CH_2)y_2$-C(=O)—$(CH_2)y_3$-, —$(CH_2)y_2$-NH—$(CH_2)y_3$-, —$(CH_2)y_2$-N($C_{1-4}$alkyl)-$(CH_2)y_3$-, —$(CH_2)y_1$-(O—$C_{1-4}$alkyl)z-O—$C_{1-4}$alkyl or nothing (null) {wherein the $y_1$ to $y_3$ are each independently 0, 1, 2 or 3, and z is 0, 1, 2 or 3};

$L_3$ is 4- to 6-membered cycloalkyl or 4- to 12-membered heterocycloalkyl {wherein the 4-to 12-membered heterocycloalkyl is single ring, bridged bicyclic ring or spiro ring, the 4- to 12-membered heterocycloalkyl contains at least one N atom in the ring, and at least one H of the 4- to 6-membered cycloalkyl or 4- to 12-membered heterocycloalkyl ring may be substituted with -halo}; and $L_P$ is —$(CH_2)p$-NH—C(=O)— or —$(CH_2)p$-O— {wherein —C(=O)— or —O— of the $L_p$ is linked with PTM, and p is 0 or 1}.

In a certain embodiment of the present disclosure, the compound represented by Formula I is a compound that is selected from the group consisting of Compound 1 to 46.

In the present disclosure, a pharmaceutically acceptable salt refers to any organic or inorganic acid addition salt with a concentration that is relatively non-toxic, is harmless, and has effective action to patients, wherein side effects caused by this salt does not deteriorate beneficial efficacy of the compound represented by Formula I. For example, the pharmaceutically acceptable salt may be an inorganic acid such as hydrochloric acid, phosphoric acid, sulfuric acid, nitric acid, or the like, or an organic acid such as methanesulfonic acid, p-toluenesulfonic acid, acetic acid, trifluoroacetic acid, maleic acid, succinic acid, oxalic acid, benzoic acid, tartaric acid, fumaric acid, manderic acid, propionic acid, citric acid, lactic acid, glycolic acid, gluconic acid, galacturonic acid, glutamic acid, glutaric acid, glucuronic acid, aspartic acid, ascorbic acid, carbonic acid, vanillic acid or hydroiodic acid, but is not limited thereto.

Use of the Selective PLK1 Degradation Inducing Compounds

An embodiment of the present disclosure is a composition for inducing PLK1 degradation including a compound represented by Formula I or a pharmaceutically acceptable salt thereof. The Formula I is the same as defined above.

In the experimental examples of the present disclosure, it was confirmed that the compounds of the present disclosure effectively induce the protein degradation of PLK1.

The PLK1 degradation-inducing PROTAC compound of the present disclosure is capable of fundamentally degrading the target protein, PLK1 in view of the mechanism of action, thereby achieving an excellent PLK1 inhibitory effect as compared to the conventional PLK1 μmall molecule inhibitor that inhibits the simple activity of PLK1.

Accordingly, the composition including the compound represented by Formula I of the present disclosure or a pharmaceutically acceptable salt thereof may be effectively employed for selective degradation of PLK1.

An embodiment of the present disclosure is a composition for preventing or treating PLK1-related diseases including the compound represented by Formula I or the pharmaceutically acceptable salt thereof. An another embodiment of the present disclosure is a method for the prevention or treatment of PLK-related diseases comprising administering the composition to a subject in need thereof. The Formula I is the same as defined above.

In the present disclosure, the PLK1-related disease refers to any disease or condition capable of being treated, alleviated, delayed, inhibited or prevented from induction of degradation or inhibition of activity of PLK1. In an embodiment, the PLK1-related disease may be a cancer (malignant tumor), a benign tumor, a neurological disease, or other genetic or non-genetic diseases caused by excessive cell division.

The cancer includes all cancers capable of exhibiting prophylactic or therapeutic efficacy due to inhibition of PLK1 activity, and may be solid cancer or blood cancer. For example, the cancer may be one or more selected from the group consisting of squamous cell carcinoma, small cell lung cancer, non-small cell lung cancer, lung adenocarcinoma, lung squamous cell carcinoma, peritoneal cancer, skin cancer, skin or intraocular melanoma, rectal cancer, anal muscle cancer, esophageal cancer, small intestine cancer, endocrine cancer, parathyroid cancer, adrenal cancer, soft tissue sarcoma, urethral cancer, chronic or acute leukemia, lymphocytic lymphoma, hepatocellular carcinoma, gastrointestinal cancer, gastric cancer, pancreatic cancer, glioblastoma, cervical cancer, ovarian cancer, liver cancer, bladder cancer, liver tumor, breast cancer, colon cancer, colorectal cancer, endometrial or uterine cancer, salivary gland cancer, kidney cancer, prostate cancer, vulvar cancer, thyroid cancer, head and neck cancer, brain cancer, osteosarcoma, solid tumor, blood cancer, bone cancer, large cell lymphoma, adrenocorticoid tumor, t cell lymphoma/leukemia, neuroendocrine cancer, neuroendocrine tumor, cholangiocarcinoma, neuroblastoma, glioblastoma, glioma, and the like, but is not limited thereto. The cancer includes not only primary cancer but also metastatic cancer.

The benign tumors include all benign tumors capable of exhibiting prophylactic or therapeutic efficacy due to the inhibition of PLK1 activity, such as benign tumors in pre-cancer stages, and may be solid tumors or blood tumors. For example, the tumor may be one or more selected from the group consisting of Barrett's esophagus, colon adenoma and polyp, breast fibroadenoma and cyst, monoclonal gammopathy of undetermined significance (MGUS), monoclonal lymphocytosis, and the like, but is not limited thereto.

The neurological diseases include all neurological diseases capable of exhibiting prophylactic or therapeutic efficacy due to the inhibition of PLK1 activity, and specifically, may be one or more selected from the group consisting of central nervous system disease, neurodegenerative disease, Alzheimer's disease, Parkinson's disease, multiple sclerosis, Huntington's disease, senile dementia, epilepsy, Lou Gehrig, stroke, and nerve damage and axonal degeneration-related disorders following brain or spinal cord injury, but is not limited thereto.

The pharmaceutical composition of the present disclosure may further include one or more active ingredients exhibiting the same or similar medicinal effects in addition to the compound represented by Formula I above, or the pharmaceutically acceptable salt thereof.

An embodiment of the present disclosure is a method of degrading PLK1 by administering a compound represented by Formula I or a pharmaceutically acceptable salt thereof to mammals including humans.

Another embodiment of the present disclosure is a method of degrading PLK1 by administering the compound represented by Formula I or the pharmaceutically acceptable salt thereof to a sample in vitro. The sample may be a cell, a cell culture, a body fluid or tissue of a mammal including a human, but is not limited thereto.

The present disclosure provides synthetic methods for Compound 1 to 46 shown in the table below.

TABLE 1

| Compound | Structure |
|---|---|
| 1 | 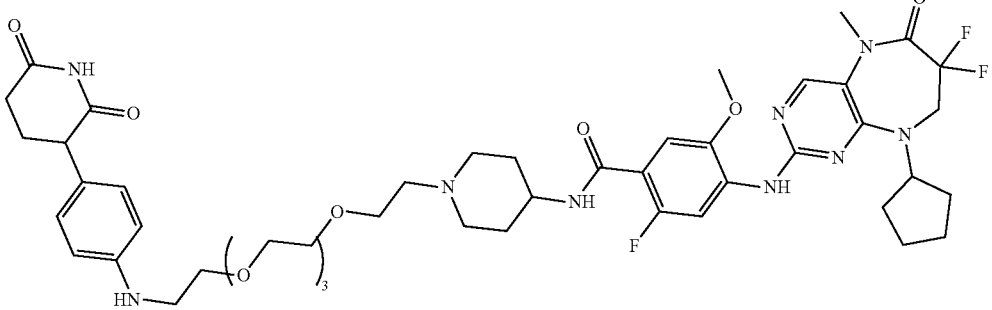 |

TABLE 1-continued

| Compound | Structure |
|---|---|
| 2 | 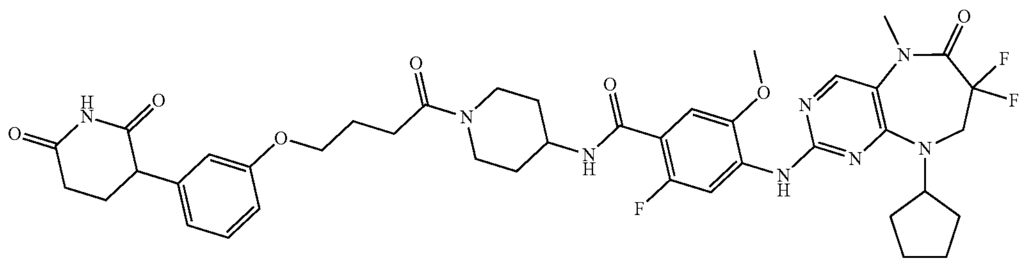 [SMILES: COc1cc(C(=O)NC2CCN(C(=O)CCCOc3cccc(C4CCC(=O)NC4=O)c3)CC2)c(F)cc1Nc1ncc2c(n1)N(C1CCCC1)CC(F)(F)C(=O)N2C] |
| 3 | 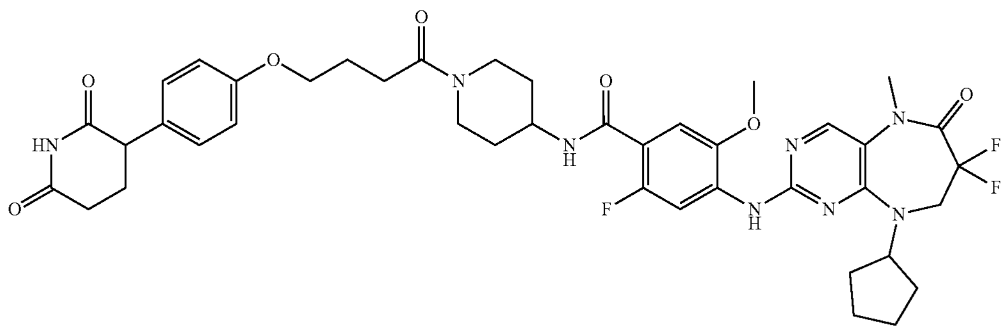 [SMILES: COc1cc(C(=O)NC2CCN(C(=O)CCCOc3ccc(C4CCC(=O)NC4=O)cc3)CC2)c(F)cc1Nc1ncc2c(n1)N(C1CCCC1)CC(F)(F)C(=O)N2C] |
| 4 | 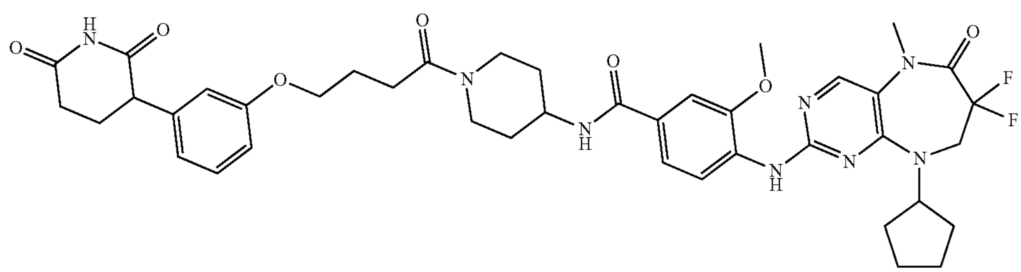 [SMILES: COc1cc(C(=O)NC2CCN(C(=O)CCCOc3cccc(C4CCC(=O)NC4=O)c3)CC2)ccc1Nc1ncc2c(n1)N(C1CCCC1)CC(F)(F)C(=O)N2C] |
| 5 | 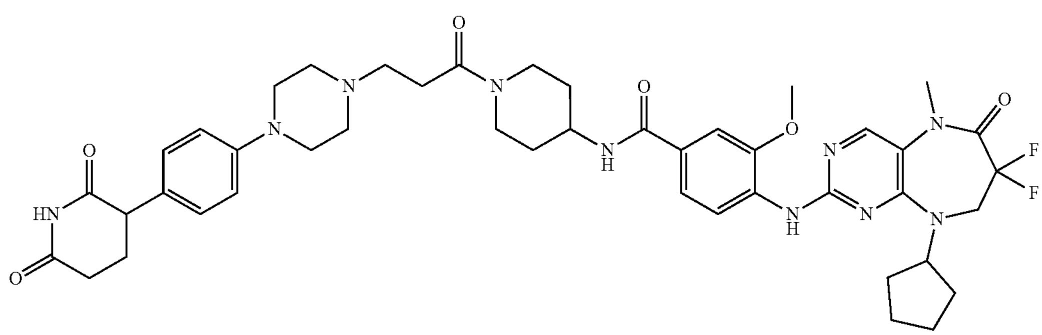 [SMILES: COc1cc(C(=O)NC2CCN(C(=O)CCN3CCN(c4ccc(C5CCC(=O)NC5=O)cc4)CC3)CC2)ccc1Nc1ncc2c(n1)N(C1CCCC1)CC(F)(F)C(=O)N2C] |
| 6 | 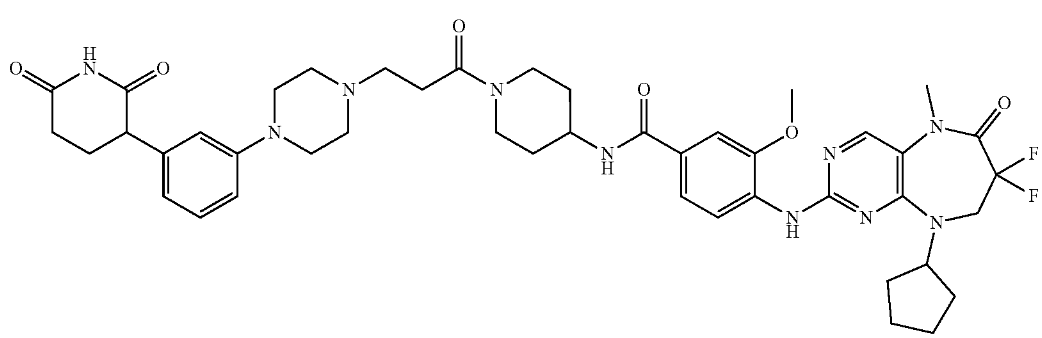 |

(trans)

TABLE 1-continued
| Compound | Structure |
|---|---|
| 7 | 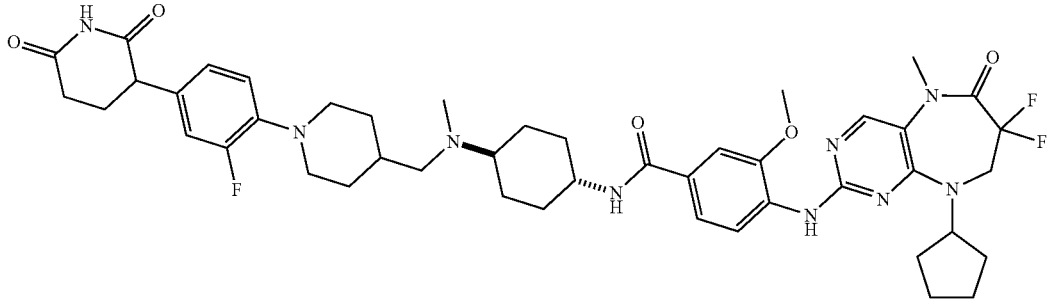 |
| 8 | 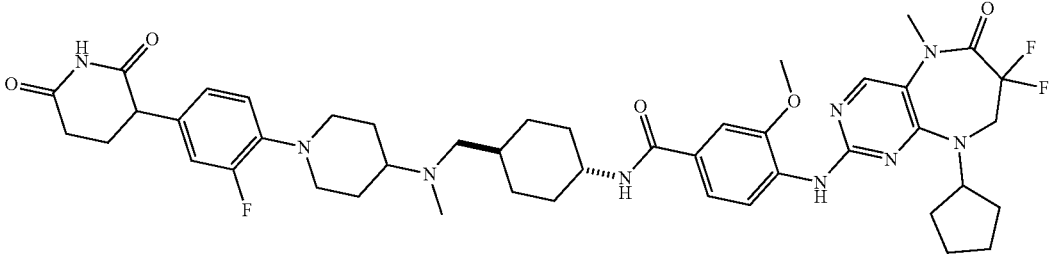 (trans) |
| 9 | 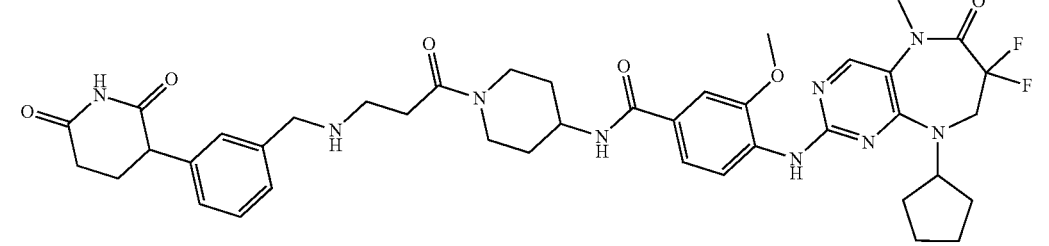 |
| 10 | 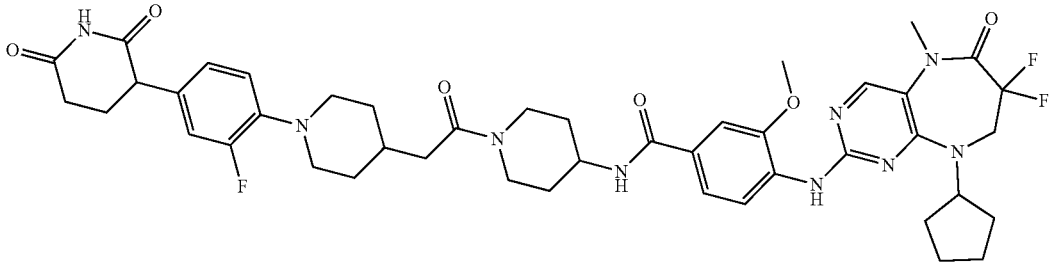 [SMILES: COc1cc(C(=O)NC2CCN(C(=O)CC3CCN(c4ccc(C5CCC(=O)NC5=O)cc4F)CC3)CC2)ccc1Nc1ncc2c(n1)N(C1CCCC1)CC(F)(F)C(=O)N2C] |
| 11 | 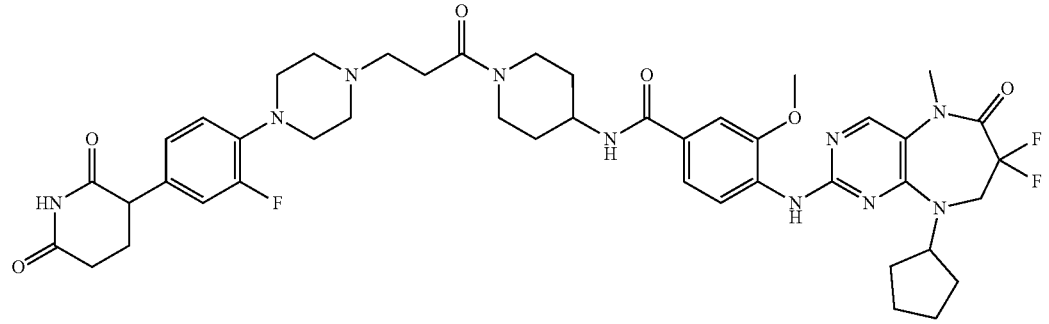 [SMILES: COc1cc(C(=O)NC2CCN(C(=O)CCN3CCN(c4ccc(C5CCC(=O)NC5=O)cc4F)CC3)CC2)ccc1Nc1ncc2c(n1)N(C1CCCC1)CC(F)(F)C(=O)N2C] |

TABLE 1-continued

| Compound | Structure |
| --- | --- |
| 12 | 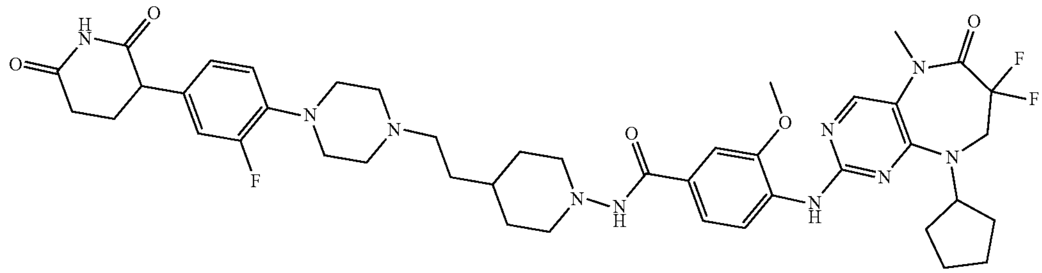 [SMILES: COc1cc(C(=O)NN2CCC(CCN3CCN(c4ccc(C5CCC(=O)NC5=O)cc4F)CC3)CC2)ccc1Nc1ncc2c(n1)N(C1CCCC1)CC(F)(F)C(=O)N2C] |
| 13 | 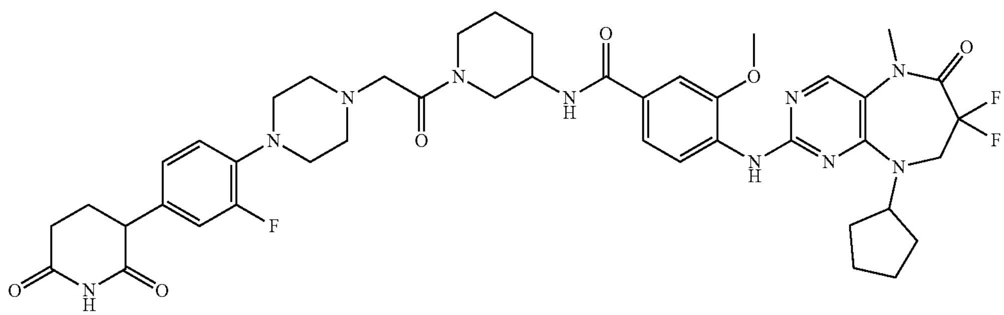 [SMILES: COc1cc(C(=O)NC2CCCN(C(=O)CN3CCN(c4ccc(C5CCC(=O)NC5=O)cc4F)CC3)C2)ccc1Nc1ncc2c(n1)N(C1CCCC1)CC(F)(F)C(=O)N2C] |
| 14 | 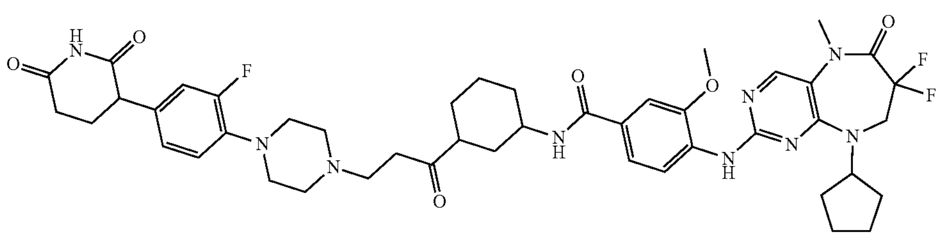 |
| 15 | |
| 16 | |

TABLE 1-continued

| Compound | Structure |
|---|---|
| 17 | 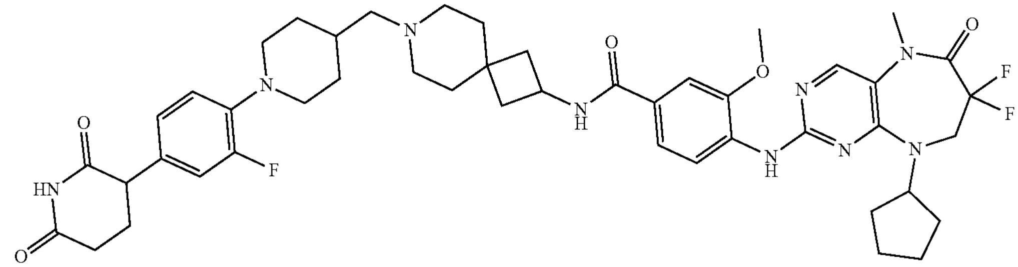 [SMILES: COc1cc(C(=O)NC2CC3(CCN(CC4CCN(c5ccc(C6CCC(=O)NC6=O)cc5F)CC4)CC3)C2)ccc1Nc1ncc2c(n1)N(C1CCCC1)CC(F)(F)C(=O)N2C] |
| 18 | 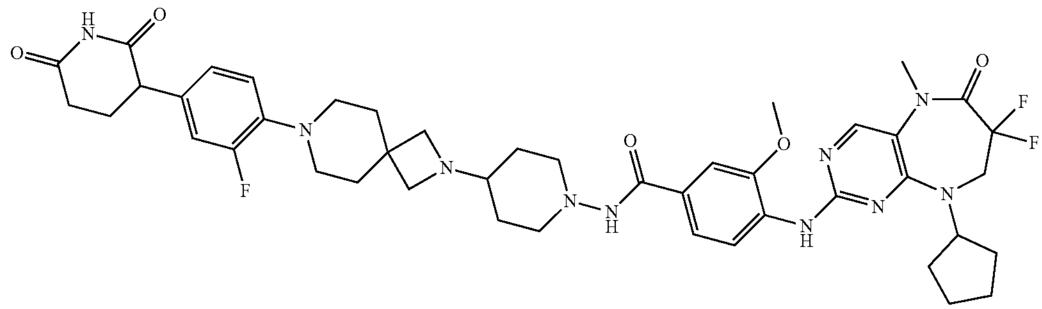 [SMILES: COc1cc(C(=O)NN2CCC(N3CC4(CCN(c5ccc(C6CCC(=O)NC6=O)cc5F)CC4)C3)CC2)ccc1Nc1ncc2c(n1)N(C1CCCC1)CC(F)(F)C(=O)N2C] |
| 19 | 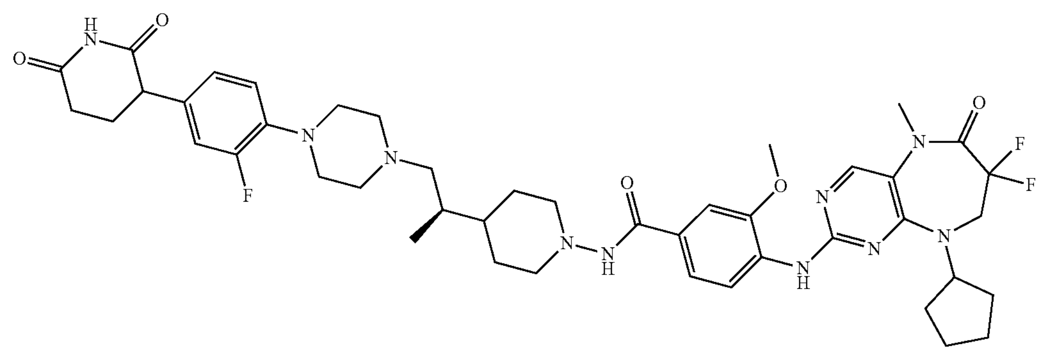 [SMILES: COc1cc(C(=O)NN2CCC([C@@H](C)CN3CCN(c4ccc(C5CCC(=O)NC5=O)cc4F)CC3)CC2)ccc1Nc1ncc2c(n1)N(C1CCCC1)CC(F)(F)C(=O)N2C] |
| 20 | 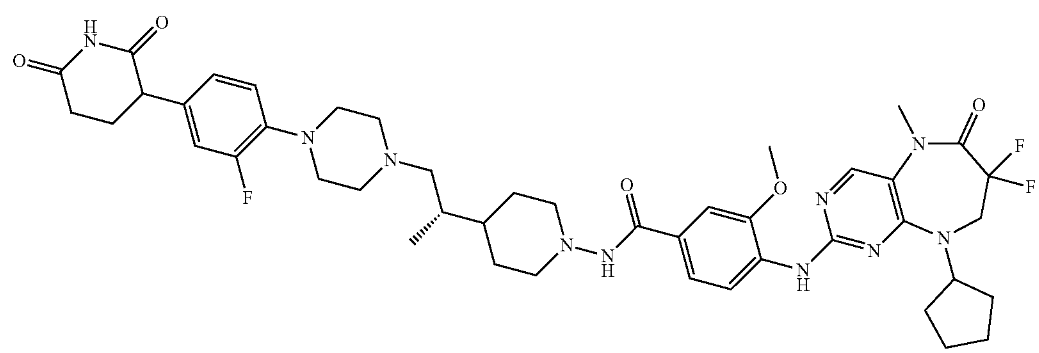 [SMILES: COc1cc(C(=O)NN2CCC([C@H](C)CN3CCN(c4ccc(C5CCC(=O)NC5=O)cc4F)CC3)CC2)ccc1Nc1ncc2c(n1)N(C1CCCC1)CC(F)(F)C(=O)N2C] |
| 21 | 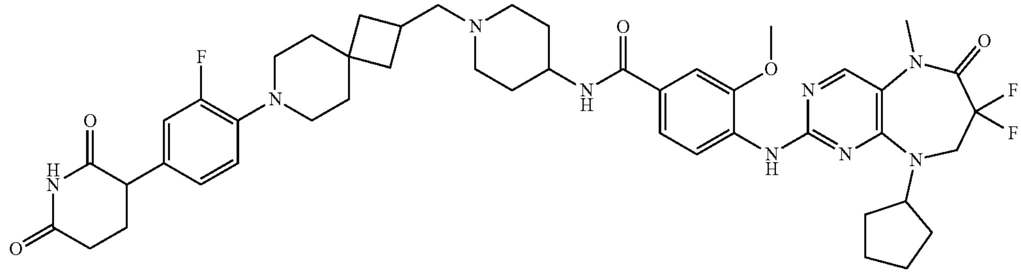 [SMILES: COc1cc(C(=O)NC2CCN(CC3CC4(CCN(c5ccc(C6CCC(=O)NC6=O)cc5F)CC4)C3)CC2)ccc1Nc1ncc2c(n1)N(C1CCCC1)CC(F)(F)C(=O)N2C] |

TABLE 1-continued
| Compound | Structure |
|---|---|
| 22 | 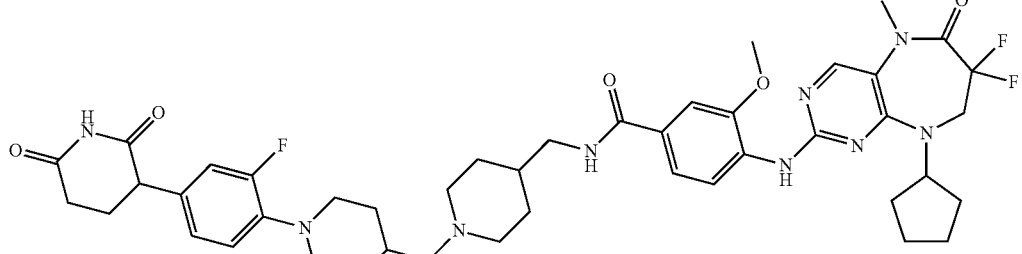 |
| 23 | 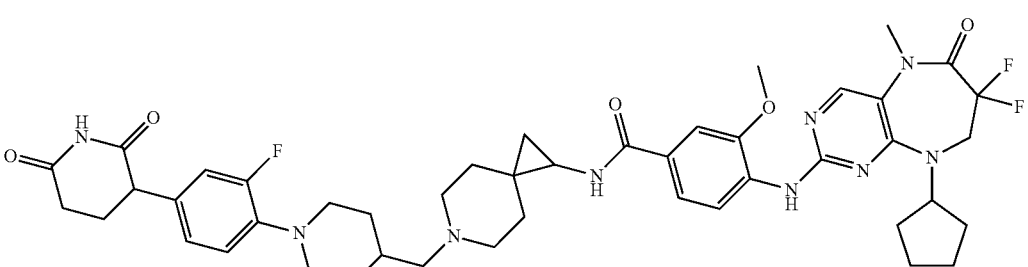 |
| 24 | 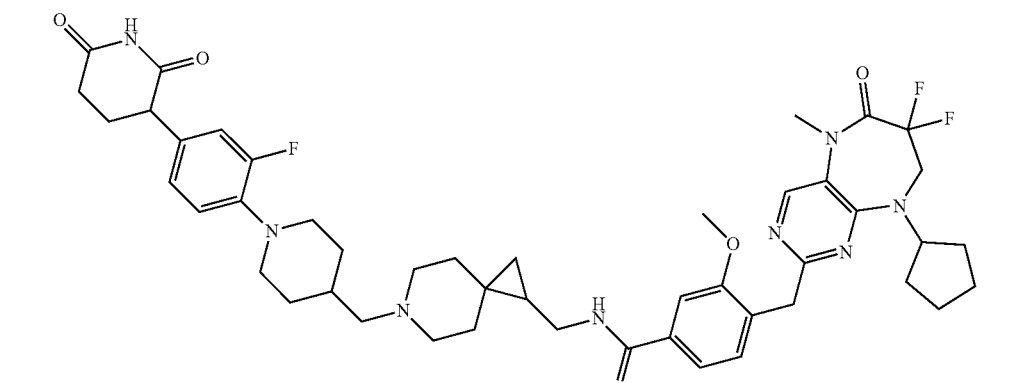 |
| 25 | 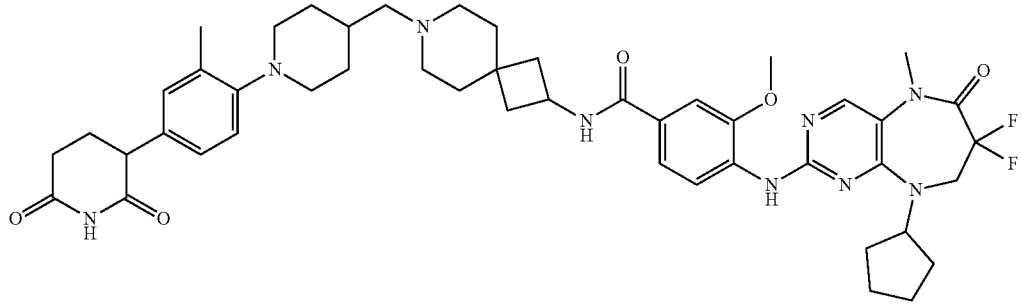 [SMILES: COc1cc(C(=O)NC2CC3(CCN(CC4CCN(c5ccc(C6CCC(=O)NC6=O)cc5C)CC4)CC3)C2)ccc1Nc1ncc2c(n1)N(C1CCCC1)CC(F)(F)C(=O)N2C] |

TABLE 1-continued
| Compound | Structure |
|---|---|
| 26 | 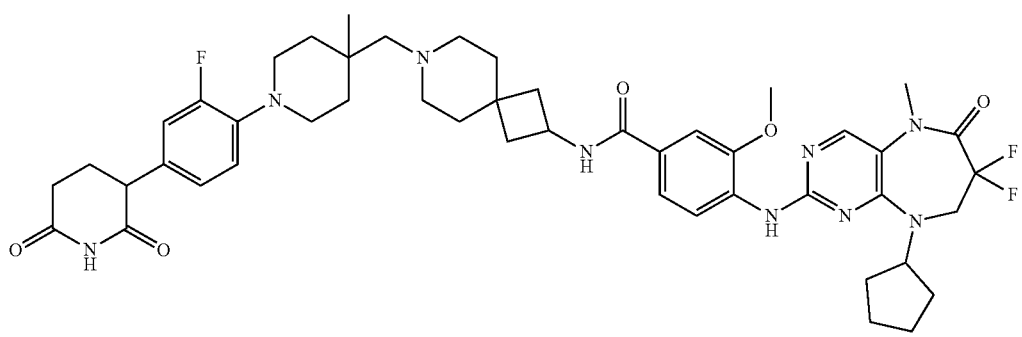 [SMILES: COc1cc(C(=O)NC2CC3(CCN(CC4(C)CCN(c5ccc(C6CCC(=O)NC6=O)cc5F)CC4)CC3)C2)ccc1Nc1ncc2c(n1)N(C1CCCC1)CC(F)(F)C(=O)N2C] |
| 27 | 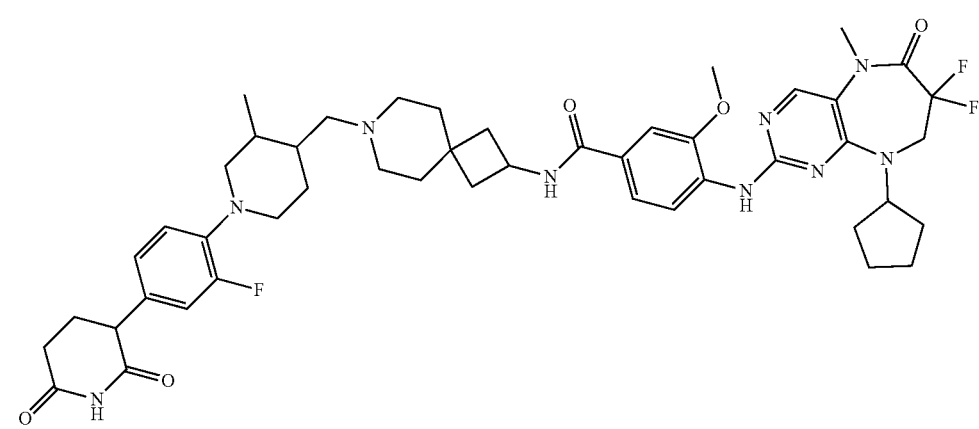 [SMILES: COc1cc(C(=O)NC2CC3(CCN(CC4CCN(c5ccc(C6CCC(=O)NC6=O)cc5F)CC4C)CC3)C2)ccc1Nc1ncc2c(n1)N(C1CCCC1)CC(F)(F)C(=O)N2C] |
| 28 | 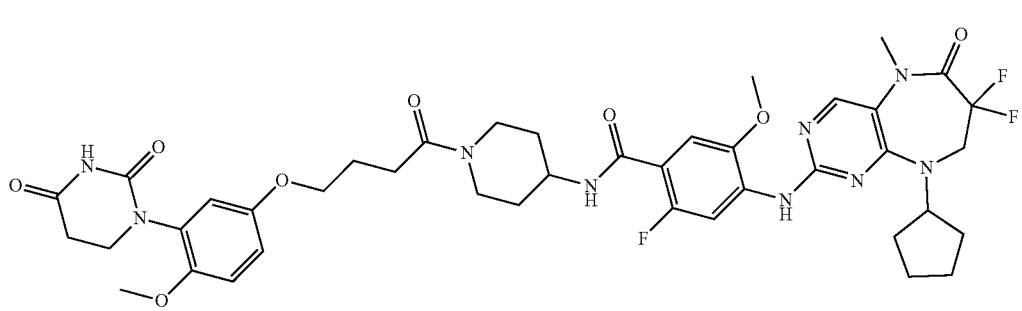 [SMILES: COc1cc(C(=O)NC2CCN(C(=O)CCCOc3ccc(OC)c(N4CCC(=O)NC4=O)c3)CC2)c(F)cc1Nc1ncc2c(n1)N(C1CCCC1)CC(F)(F)C(=O)N2C] |
| 29 | 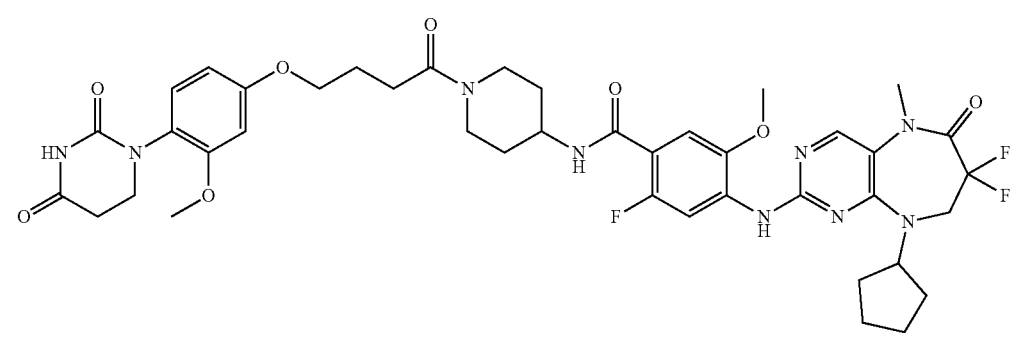 [SMILES: COc1cc(C(=O)NC2CCN(C(=O)CCCOc3ccc(N4CCC(=O)NC4=O)c(OC)c3)CC2)c(F)cc1Nc1ncc2c(n1)N(C1CCCC1)CC(F)(F)C(=O)N2C] |

TABLE 1-continued

| Compound | Structure |
|---|---|
| 30 | 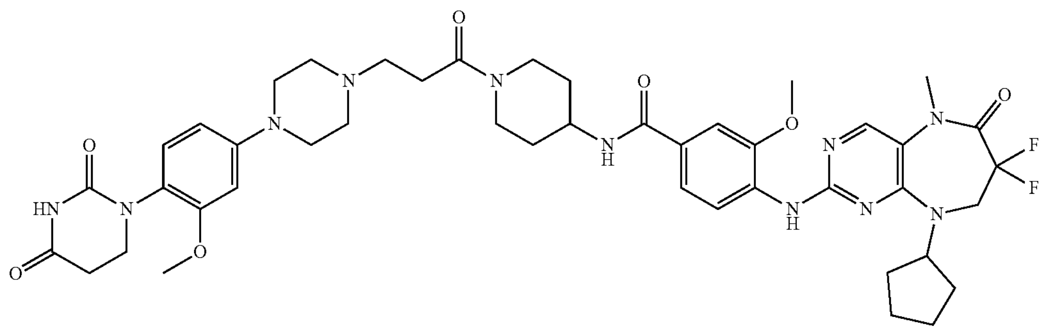 [SMILES: COc1cc(C(=O)NC2CCN(C(=O)CCN3CCN(c4ccc(N5CCC(=O)NC5=O)c(OC)c4)CC3)CC2)ccc1Nc1ncc2c(n1)N(C1CCCC1)CC(F)(F)C(=O)N2C] |
| 31 | 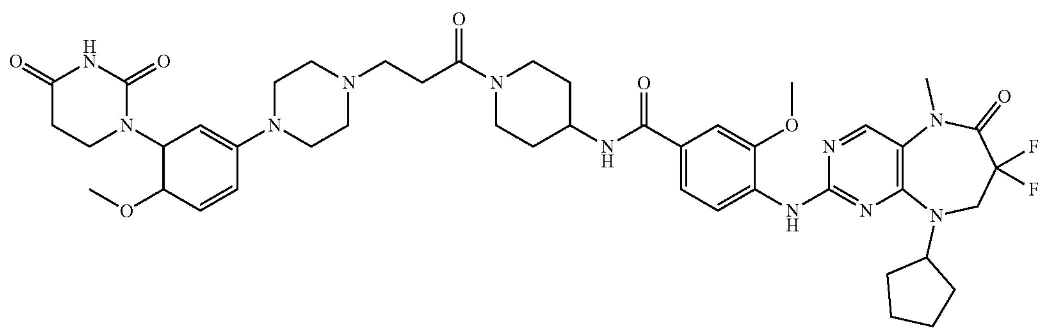 [SMILES: COc1cc(C(=O)NC2CCN(C(=O)CCN3CCN(C4=CC(N5CCC(=O)NC5=O)C(OC)C=C4)CC3)CC2)ccc1Nc1ncc2c(n1)N(C1CCCC1)CC(F)(F)C(=O)N2C] |
| 32 | 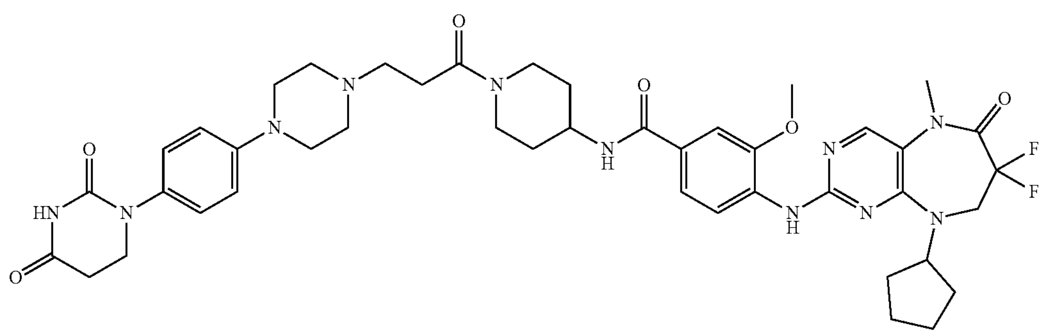 [SMILES: COc1cc(C(=O)NC2CCN(C(=O)CCN3CCN(c4ccc(N5CCC(=O)NC5=O)cc4)CC3)CC2)ccc1Nc1ncc2c(n1)N(C1CCCC1)CC(F)(F)C(=O)N2C] |
| 33 | 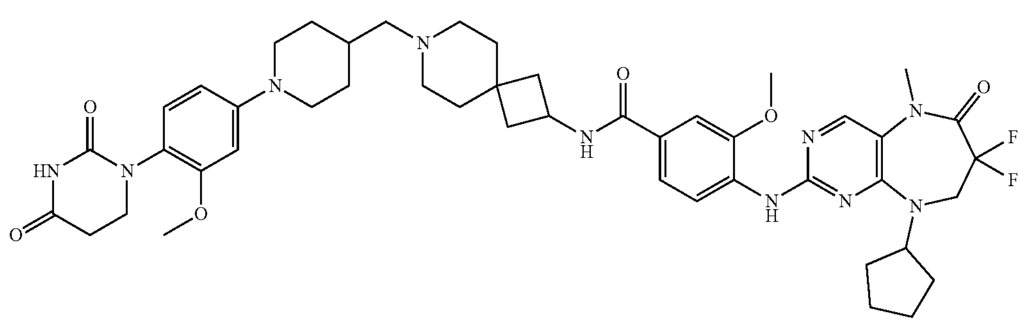 [SMILES: COc1cc(C(=O)NC2CC3(CCN(CC4CCN(c5ccc(N6CCC(=O)NC6=O)c(OC)c5)CC4)CC3)C2)ccc1Nc1ncc2c(n1)N(C1CCCC1)CC(F)(F)C(=O)N2C] |

TABLE 1-continued
| Compound | Structure |
| --- | --- |
| 34 | 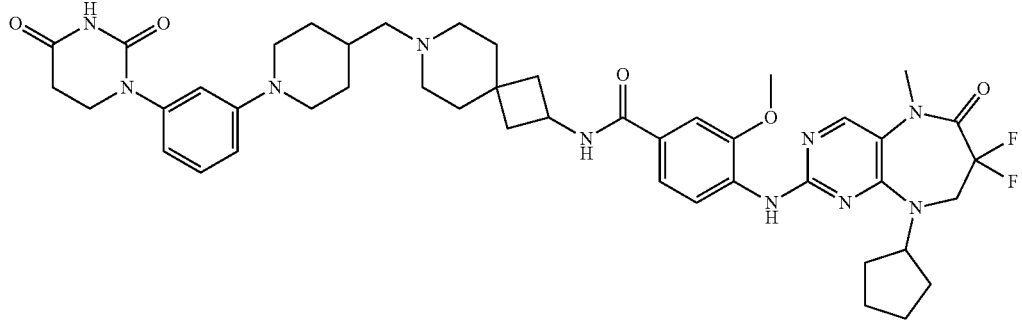 [SMILES: COc1cc(C(=O)NC2CC3(CCN(CC4CCN(c5cccc(N6CCC(=O)NC6=O)c5)CC4)CC3)C2)ccc1Nc1ncc2c(n1)N(C1CCCC1)CC(F)(F)C(=O)N2C] |
| 35 | 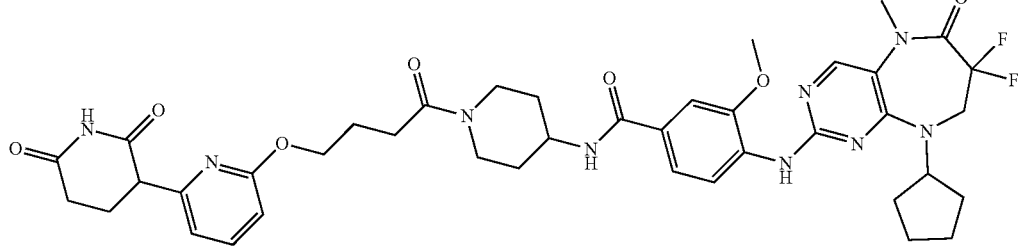 |
| 36 | 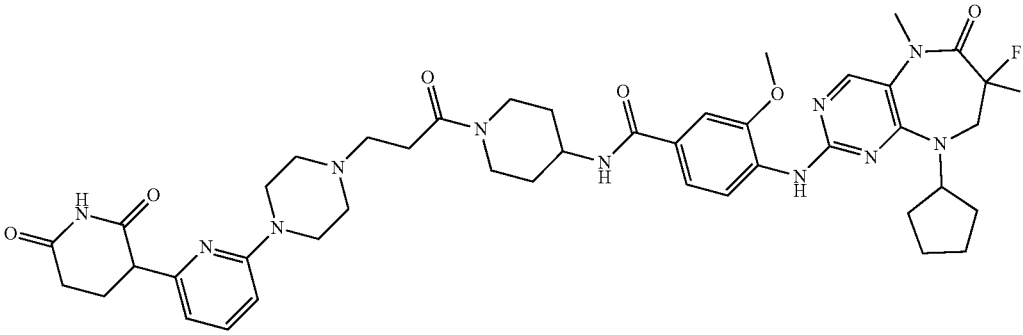 |
| 37 | 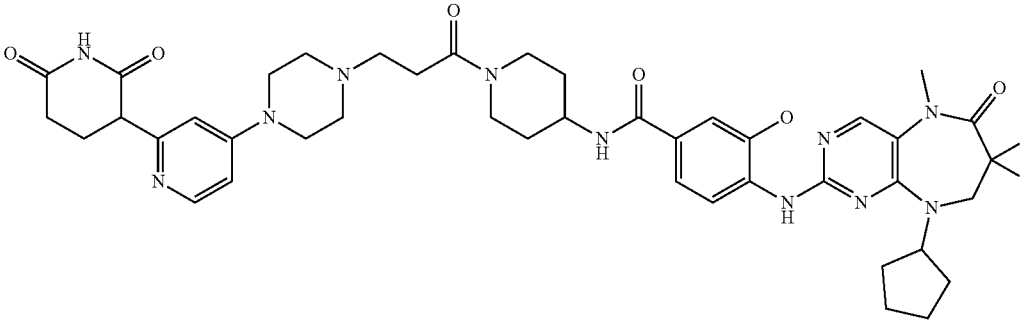 |
| 38 | 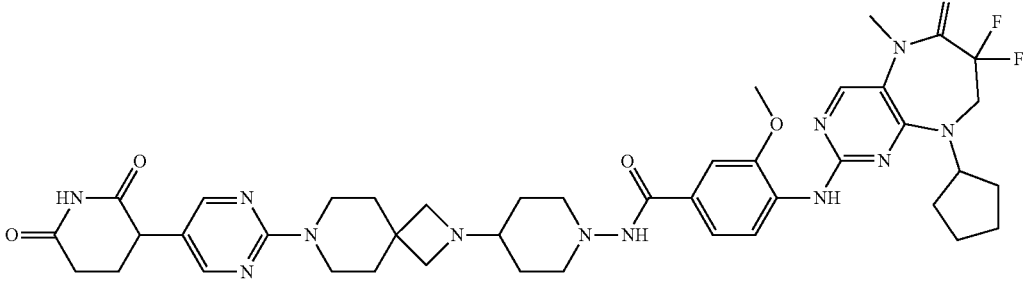 |

TABLE 1-continued
| Compound | Structure |
|---|---|
| 39 | 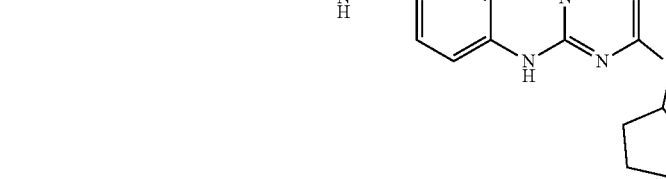 |
| 40 | 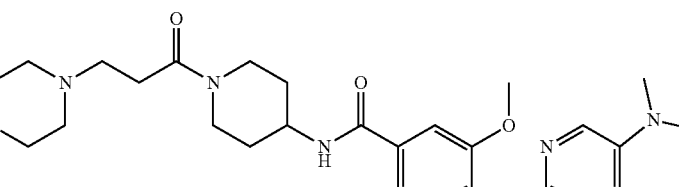 |
| 41 | 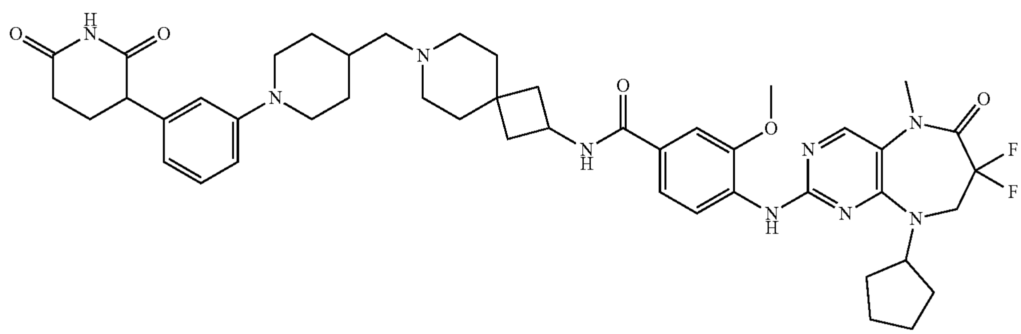 [SMILES: COc1cc(C(=O)NC2CC3(CCN(CC4CCN(c5cccc(C6CCC(=O)NC6=O)c5)CC4)CC3)C2)ccc1Nc1ncc2c(n1)N(C1CCCC1)CC(F)(F)C(=O)N2C] |
| 42 | 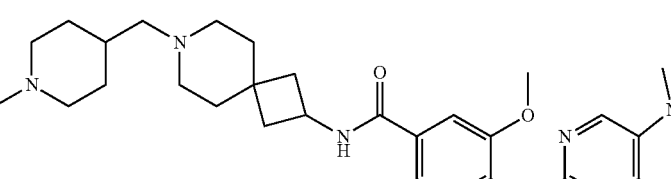 |
| 43 | 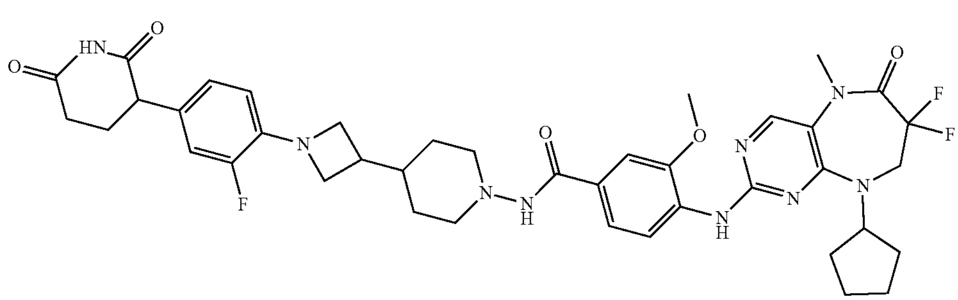 [SMILES: COc1cc(C(=O)NN2CCC(C3CN(c4ccc(C5CCC(=O)NC5=O)cc4F)C3)CC2)ccc1Nc1ncc2c(n1)N(C1CCCC1)CC(F)(F)C(=O)N2C] |

TABLE 1-continued

| Compound | Structure |
|---|---|
| 44 | 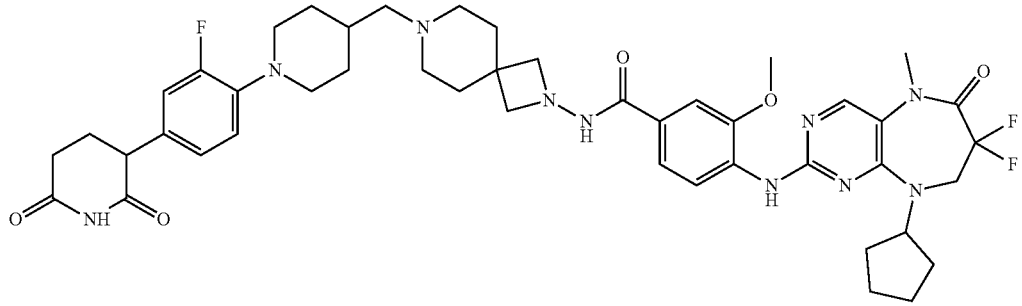 [SMILES: COc1cc(C(=O)NN2CC3(CCN(CC4CCN(c5ccc(C6CCC(=O)NC6=O)cc5F)CC4)CC3)C2)ccc1Nc1ncc2c(n1)N(C1CCCC1)CC(F)(F)C(=O)N2C] |
| 45 | 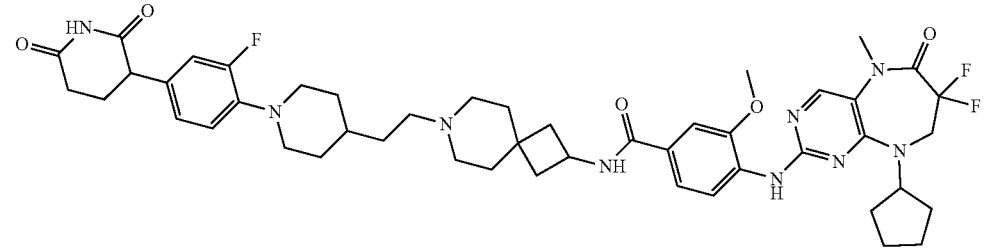 [SMILES: COc1cc(C(=O)NC2CC3(CCN(CCC4CCN(c5ccc(C6CCC(=O)NC6=O)cc5F)CC4)CC3)C2)ccc1Nc1ncc2c(n1)N(C1CCCC1)CC(F)(F)C(=O)N2C] |
| 46 | 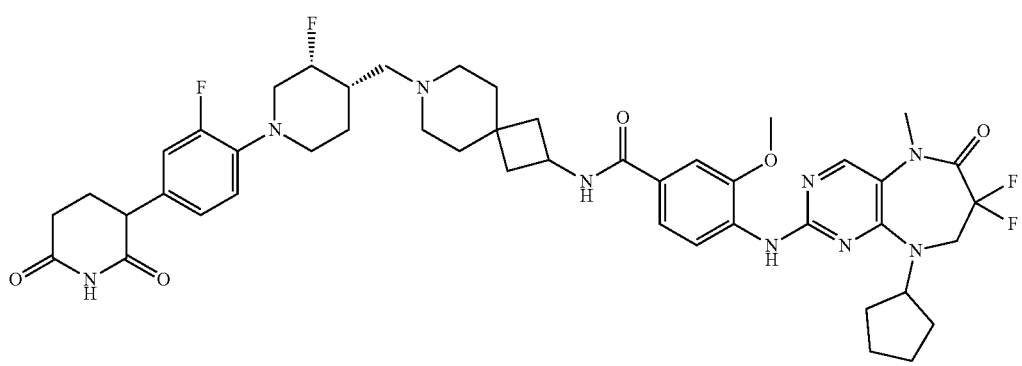 [SMILES: COc1cc(C(=O)NC2CC3(CCN(C[C@@H]4CCN(c5ccc(C6CCC(=O)NC6=O)cc5F)C[C@@H]4F)CC3)C2)ccc1Nc1ncc2c(n1)N(C1CCCC1)CC(F)(F)C(=O)N2C] |

The compounds of the present invention were purified according to the following method and the structure was analyzed.

Instruments
LCMS: Shimadzu LCMS-2020, Agilent 1200/G6110A, Agilent 1200/G1956A
HPLC: Agilent 1260 II LC, Agilent 1200/G640B
NMR: BRUKER AVANCE/400 MHZ
SFC: SHIMADZU LC-30ADsf, Agilent 1260

LCMS Analysis

LCMS data were recorded with Shimadzu LCMS-2020 or Agilent 1200/G6110A or Agilent 1200/G1956A equipped with an ESI (Electron Spray Ionization) device. 0.0375% TFA in water (solvent A) and 0.01875% TFA in ACN (solvent B) or 0.025% $NH_3·H_2O$ in water (solvent A) and ACN (solvent B) were used as mobile phases. As a column, Kinetex EVO C18 (2.1×30 mm, 5 μm) or HALO C18 (3.0×30 mm, 2.7 μm) were used.

HPLC Analysis

In HPLC analysis, Agilent 1260 II LC or Agilent 1200/G6410B were used. 0.0375% TFA in water (solvent A) and 0.01875% TFA in ACN (solvent B) were used as the mobile phase. As a column, Zobrax Eclipse Plus C18 (4.6×150 mm, 3.5 μm) or YMC ODS A (4.6×150 mm, 3 μm) were used.

NMR Analysis $^1$H NMR spectrum was recorded with Bruker AVANCE III 400 MHz/5 mm Probe (BBO).

SFC Analysis

In SFC analysis, SHIMADZU LC-30ADsf or Agilent 1260 were used. $CO_2$ (solvent A) and 0.05% DEA in IPA+ACN (solvent B) or $CO_2$ (solvent A) and 0.05% DEA in MeOH+ACN (solvent B) or 0.05% DEA in ACN (solvent A) and 0.05% DEA in EtOH (solvent B) were used as the mobile phase. As a column, Chiralpak AD-3 (50×4.6 mm, 3 μm) or Chiralpak AS-3 (50×4.6 mm, 3 μm) or Chiralpak OJ-3 (50×4.6 mm, 3 μm) or Chiralpak IA-3 (50×4.6 mm, 3 μm) or Chiralpak OD (50×4.6 mm, 3 μm) or Chiralpak IC-3 (50×4.6 mm, 3 μm) or (S,S) Whelk-O1 (100×4.6 mm, 3.5 μm) were used.

Example 1. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(14-((4-(2,6-dioxopiperidin-3-yl)phenyl)amino)-3,6,9,12-tetraoxatetradecyl)piperidin-4-yl)-2-fluoro-5-methoxybenzamide (Compound 1)
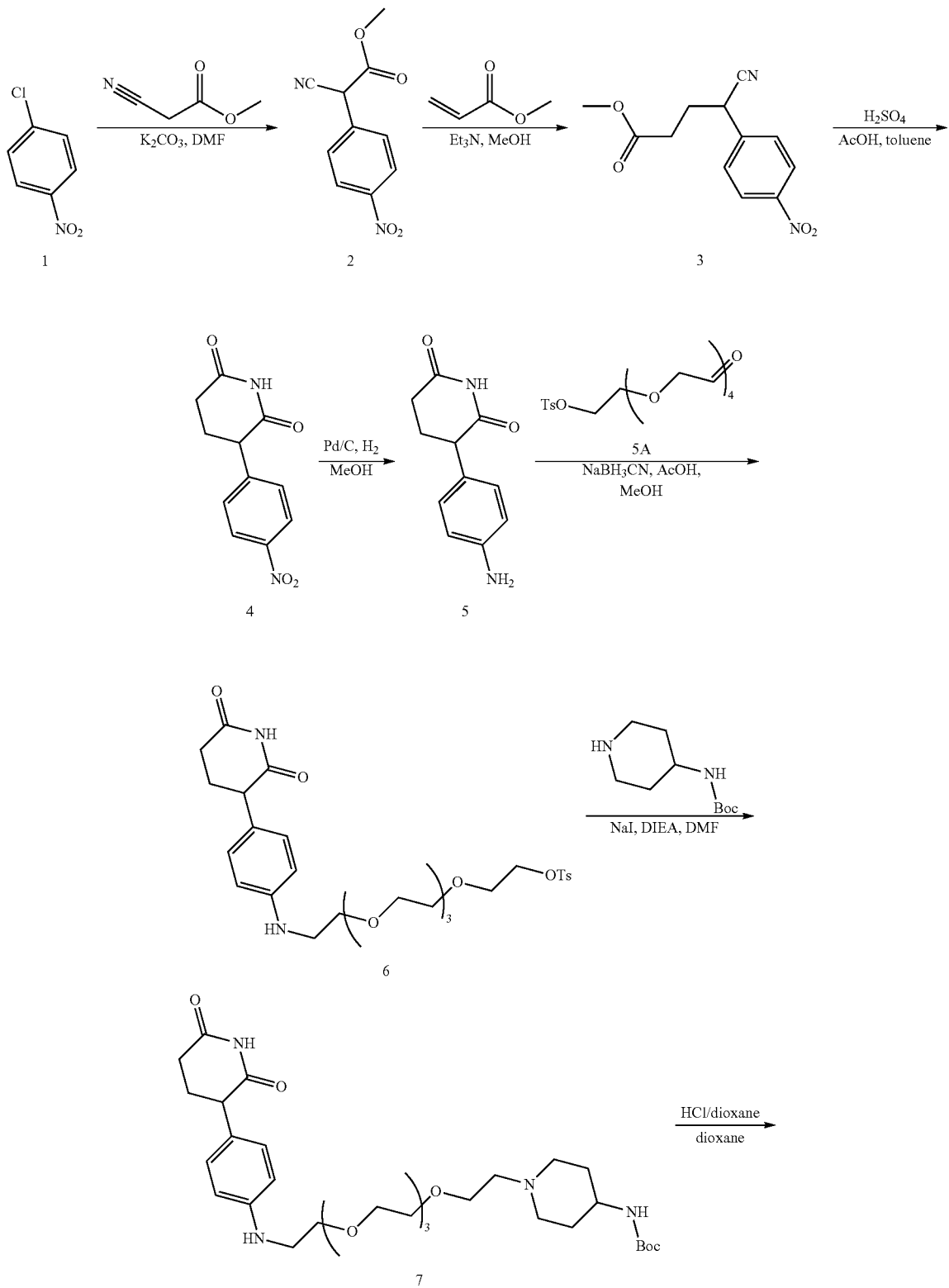

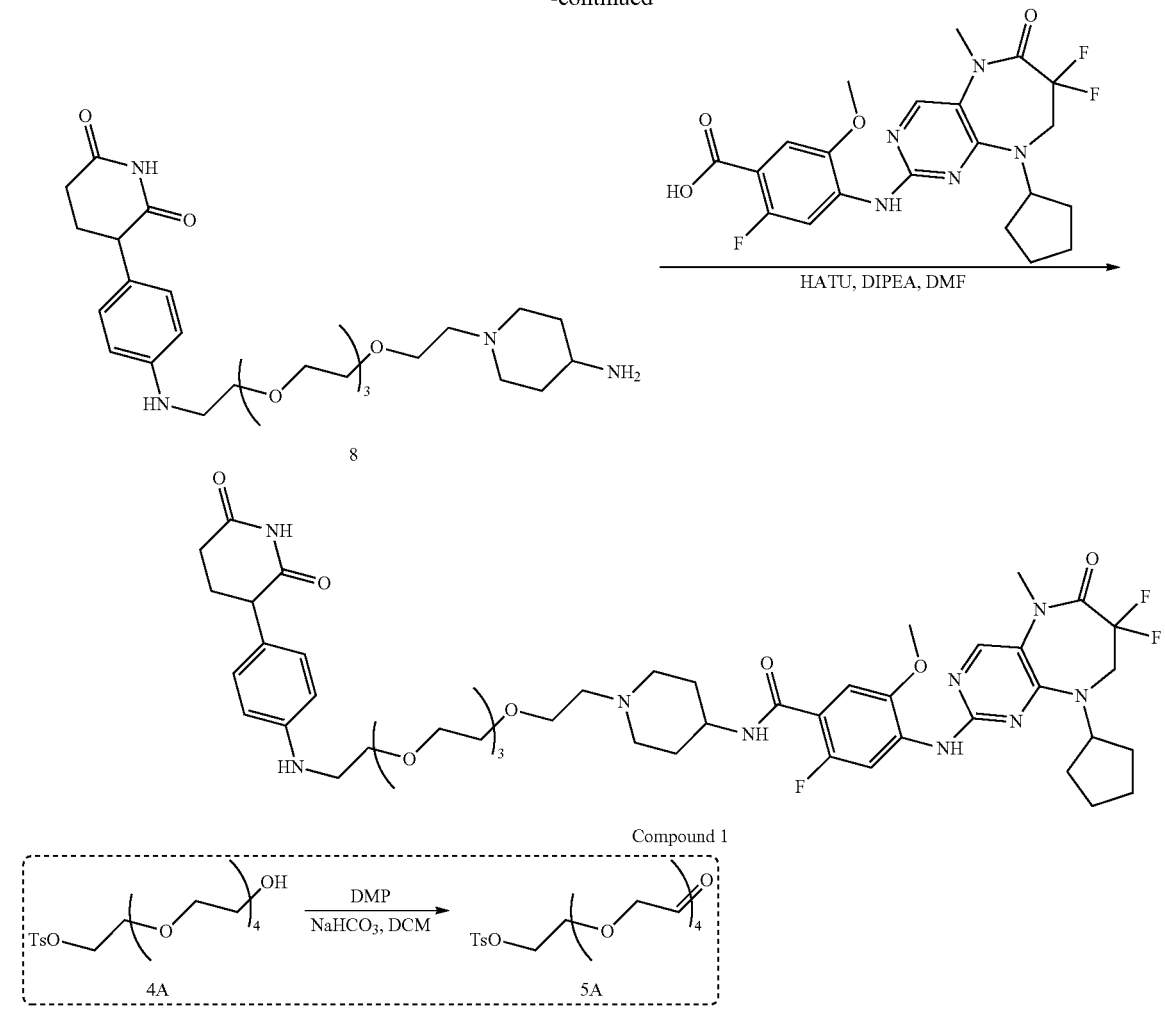

Step 1. Synthesis of methyl 2-cyano-2-(4-nitrophenyl)acetate (2)

To the mixture of 1-chloro-4-nitro-benzene (15 g, 95.21 mmol) and K$_2$CO$_3$ (26.32 g, 190.41 mmol) in DMF (150 mL) was added methyl 2-cyanoacetate (18.87 g, 190.41 mmol) at 120° C. and the mixture was stirred at 120° C. for 12 h. TLC (Petroleum ether/EtOAc=3/1) showed that the reaction was completed, the reaction mixture was diluted with H$_2$O (1000 mL), and extracted with EtOAc (300 mL×3). The organic layer was washed with brine (800 mL×3), dried over Na$_2$SO$_4$, filtrated and concentrated. The residue was purified by flash silica gel chromatography (120 g SepaFlash Silica Flash Column, Eluent of 0~20% EtOAc/Petroleum ethergradient @ 80 mL/min) to afford methyl 2-cyano-2-(4-nitrophenyl)acetate (27 g, crude) as yellow solid. MS (M+H)$^+$=221.2

$^1$H NMR (400 MHz, CDCl$_3$) δ=8.33-8.31 (m, 2H), 7.72-7.69 (m, 2H), 4.90 (s, 1H), 3.87 (s, 3H).

Step 2. Synthesis of methyl 4-cyano-4-(4-nitrophenyl)butanoate (3)

To the solution of methyl 2-cyano-2-(4-nitrophenyl)acetate (10 g, 45.42 mmol) in MeOH (100 mL) was added Et$_3$N (9.19 g, 90.83 mmol, 12.64 mL) and methyl prop-2-enoate (3.91 g, 45.42 mmol, 4.09 mL) and the resulting mixture was stirred at 60° C. for 12 h. TLC (Petroleum ether/EtOAc=1/1) showed that the reaction was completed, the reaction mixture was diluted with water (200 mL), followed by distillation under vacuum to removed MeOH, aqueous layers was extracted with EtOAc (100 mL×3), the combined organic was washed with water (200 mL×2), dried by Na$_2$SO$_4$, filtered and concentrated. The residue was purified by flash silica gel chromatography (80 g SepaFlash Silica Flash Column, Eluent of 0~50% EtOAc/Petroleum ethergradient @ 100 mL/min) to afford methyl 4-cyano-4-(4-nitrophenyl) butanoate (10 g, crude) as red liquid.

MS (M+H)$^+$=249.2

Step 3. Synthesis of 3-(4-nitrophenyl)piperidine-2,6-dione (4)

To the solution of methyl 4-cyano-4-(4-nitrophenyl) butanoate (10 g, 40.28 mmol) in toluene (100 mL) was added H$_2$SO$_4$ (9.87 g, 100.63 mmol, 5.36 mL) and AcOH (6.04 g, 100.58 mmol, 5.75 mL) and the resulting mixture was stirred at 110° C. for 12 h. TLC (EtOAc/Petroleum ether=2/1) showed that the reaction was completed, the reaction mixture was diluted with H$_2$O (10 mL) and extracted with EtOAc (10 mL×3). The organic layer was washed with brine (30 mL×3), dried over $Na_2SO_4$, filtrated and concentrated. The residue was purified by flash silica gel chromatography (ISCO; 80 g SepaFlash Silica Flash Column, Eluent of 0~50% EtOAc/Petroleum ether gradient @ 100 mL/min) to afford 3-(4-nitrophenyl)piperidine-2,6-dione (1.6 g, 6.83 mmol, 16.96% yield) as red solid. MS $(M+H)^+=235.2$ $^1$H NMR (400 MHz, DMSO-$d_6$) δ=8.21-8.06 (m, 2H), 7.57-7.38 (m, 2H), 3.70 (t, J=7.3 Hz, 1H), 2.27-1.99 (m, 3H), 1.90-1.73 (m, 1H).

Step 4. Synthesis of
3-(4-aminophenyl)piperidine-2,6-dione (5)

To the solution of 3-(4-nitrophenyl)piperidine-2,6-dione (1.6 g, 6.83 mmol) in MeOH (20 mL) was added Pd/C (200 mg, 10% purity) under $N_2$ atmosphere and the resulting mixture was stirred under $H_2$ (15 psi) at 20° C. for 12 h. TLC (Petroleum ether/EtOAc=1/2) showed that the reaction was completed, the mixture was filtered and the filtrate was concentrated. The residue was purified by flash silica gel chromatography (12 g SepaFlash Silica Flash Column, Eluent of 0~60% EtOAc/Petroleum ethergradient @ 80 mL/min) to afford 3-(4-aminophenyl)piperidine-2,6-dione (0.6 g, 2.94 mmol, 43.01% yield) as white solid. MS $(M+H)^+=205.2$ Step 5. Synthesis of
14-oxo-3,6,9,12-tetraoxatetradecyl
4-methylbenzenesulfonate (5A)

To the solution of 14-hydroxy-3,6,9,12-tetraoxatetradecyl 4-methylbenzenesulfonate (1 g, 2.55 mmol) in DCM (20 mL) was added DMP (1.40 g, 3.31 mmol) and $NaHCO_3$ (2.14 g, 25.48 mmol) and the resulting mixture was stirred at 20° C. for 2 h. LCMS showed that that the reaction was completed, the mixture was filtered and the filtrate was concentrated. The residue was purified by flash silica gel chromatography (ISCO; 20 g SepaFlash Silica Flash Column, Eluent of 0~10% Methanol/EtOAc gradient @ 50 mL/min) to afford 14-oxo-3,6,9,12-tetraoxatetradecyl 4-methylbenzenesulfonate (0.65 g, 1.66 mmol, 65.34% yield) as yellow oil. MS $(M+H)^+=391.1$ Step 6. Synthesis of 14-((4-(2,6-dioxopiperidin-3-yl)phenyl)amino)-3,6,9,12-tetraoxatetradecyl
4-methylbenzenesulfonate (6)

To the solution of 3-(4-aminophenyl) piperidine-2, 6-dione (250 mg, 1.22 mmol) and 14-oxo-3,6,9,12-tetraoxatetradecyl 4-methylbenzenesulfonate (621.35 mg, 1.59 mmol) in MeOH (5 mL) was added $NaBH_3CN$ (230.78 mg, 3.67 mmol) and AcOH (7.35 mg, 122.41 µmol) and the resulting mixture was stirred at 20° C. for 12 h. LCMS showed that the reaction was completed. The mixture was poured into the water (50 mL) and extracted with EtOAc (20 mL×3), the combined organic layer was washed by brine (50 mL), dried over $Na_2SO_4$, filtered and concentrated. The residue was purified by flash silica gel chromatography (ISCO; 20 g SepaFlash Silica Flash Column, Eluent of 0~100% EtOAc/Petroleum ether gradient @ 80 mL/min) to afford 14-((4-(2,6-dioxopiperidin-3-yl)phenyl)amino)-3,6,9,12-tetraoxatetradecyl 4-methylbenzenesulfonate (0.55 g, 741.35 µmol, 60.56% yield, 78% purity) as yellow oil. MS $(M+H)^+=579.1$ Step 7. Synthesis of tert-butyl (1-(14-((4-(2,6-dioxopiperidin-3-yl)phenyl)amino)-3,6,9,12-tetraoxatetradecyl)piperidin-4-yl)carbamate (7)

To the solution of 14-((4-(2,6-dioxopiperidin-3-yl)phenyl)amino)-3,6,9,12-tetraoxatetradecyl 4-methylbenzenesulfonate (0.45 g, 777.64 µmol) and tert-butyl N-(4-piperidyl) carbamate (233.62 mg, 1.17 mmol) in DMF (5 mL) was added NaI (11.66 mg, 77.76 µmol) and DIPEA (201.01 mg, 1.56 mmol) and the resulting mixture was stirred at 100° C. for 12 h. LCMS showed that the reaction was consumed, the mixture was poured into water (20 mL) and extracted with EtOAc (20 mL×3), the combined organic layer was washed with brine (50 mL), dried over $Na_2SO_4$, filtered and concentrated, the residue was purified by prep-TLC (EtOAc) to afford tert-butyl (1-(14-((4-(2,6-dioxopiperidin-3-yl)phenyl)amino)-3,6,9,12-tetraoxatetradecyl)piperidin-4-yl)carbamate (260 mg, 407.09 umol, 52.35% yield, 95% purity) as yellow oil. MS $(M+H)^+=607.4$ Step 8. Synthesis of 3-(4-((14-(4-aminopiperidin-1-yl)-3,6,9,12-tetraoxatetradecyl)amino)phenyl)piperidine-2,6-dione (8)

To the solution of tert-butyl (1-(14-((4-(2,6-dioxopiperidin-3-yl)phenyl)amino)-3,6,9,12-tetraoxatetradecyl)piperidin-4-yl)carbamate (130 mg, 214.26 µmol) in dioxane (2 mL) was added HCl/dioxane (4 M, 2 mL) and the resulting mixture was stirred at 20° C. for 1 h. LCMS showed that the reaction was completed, the reaction was concentrated to afford 3-(4-((14-(4-aminopiperidin-1-yl)-3,6,9,12-tetraoxatetradecyl)amino)phenyl)piperidine-2,6-dione (120 mg, crude, HCl) as yellow oil. MS $(M+H)^+=507.3$ Step 9. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(14-((4-(2,6-dioxopiperidin-3-yl)phenyl)amino)-3,6,9,12-tetraoxatetradecyl)piperidin-4-yl)-2-fluoro-5-methoxybenzamide (Compound 1)

To the solution of 3-(4-((14-(4-aminopiperidin-1-yl)-3,6,9,12-tetraoxatetradecyl)amino)phenyl)piperidine-2,6-dione (0.12 g, 220.96 µmol, HCl) and 4-((9-cyclopentyl-7,7-difluoro-5-methyl-6-oxo-6,7,8,9-tetrahydro-5H-pyrimido[4,5-b][1,4]diazepin-2-yl)amino)-2-fluoro-5-methoxybenzoic acid (113.12 mg, 243.05 µmol) in DMF (2 mL) were added HATU (126.02 mg, 331.43 µmol) and DIPEA (114.23 mg, 883.82 µmol) and the resulting mixture was stirred at 20° C. for 12 h. LCMS showed that the reaction was completed, the mixture was poured into water (20 mL) and extracted with EtOAc (20 mL×3), the combined organic layer was washed by brine (50 mL), dried over $Na_2SO_4$, filtered and concentrated, the residue was purified by prep-HPLC (column: Phenomenex Synergi $C_{18}$ 150*25 mm*10 µm; mobile phase: [water (0.225% FA)—ACN]; B %: 16%-46%, 10 min) and the eluant was lyophilized to afford 4-((9-cyclopentyl-7,7-difluoro-5-methyl-6-oxo-6,7,8,9-tetrahydro-5H-pyrimido[4,5-b][1,4]diazepin-2-yl)amino)-N-(1-(14-((4-(2,6-dioxopiperidin-3-yl)phenyl)amino)-3,6,9,12-tetraoxatetradecyl)piperidin-4-yl)-2-fluoro-5-methoxybenzamide (52.9 mg, 52.68 µmol, 23.84% yield, 95% purity) as white solid. MS $(M+H)^+=954.5$ $^1$H NMR (400 MHz, DMSO-$d_6$) δ=10.74 (s, 1H), 8.31 (s, 1H), 8.25 (d, J=13.3 Hz, 1H), 8.19 (s, 1H), 8.04 (s, 1H), 7.93-7.86 (m, 1H), 7.20 (d, J=6.6 Hz, 1H), 6.91 (d, J=8.5 Hz, 2H), 6.55 (d, J=8.5 Hz, 2H), 5.48 (s, 1H), 4.83 (t, J=7.9 Hz, 1H), 4.08 (t, J=13.8 Hz, 2H), 3.92 (s, 3H), 3.76-3.74 (m, 2H), 3.64 (dd, J=5.1, 10.4 Hz, 2H), 3.59-3.55 (m, 6H), 3.53-3.52 (m, 10H), 3.18 (s, 2H), 2.90-2.87 (m, 2H), 2.61-2.55 (m, 2H), 2.47-2.43 (m, 1H), 2.18-2.05 (m, 4H), 2.03-1.91 (m, 4H), 1.83-1.72 (m, 3H), 1.63-1.47 (m, 6H).
Example 2. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(4-(3-(2,6-dioxopiperidin-3-yl)phenoxy)butanoyl)piperidin-4-yl)-2-fluoro-5-methoxybenzamide (Compound 2)
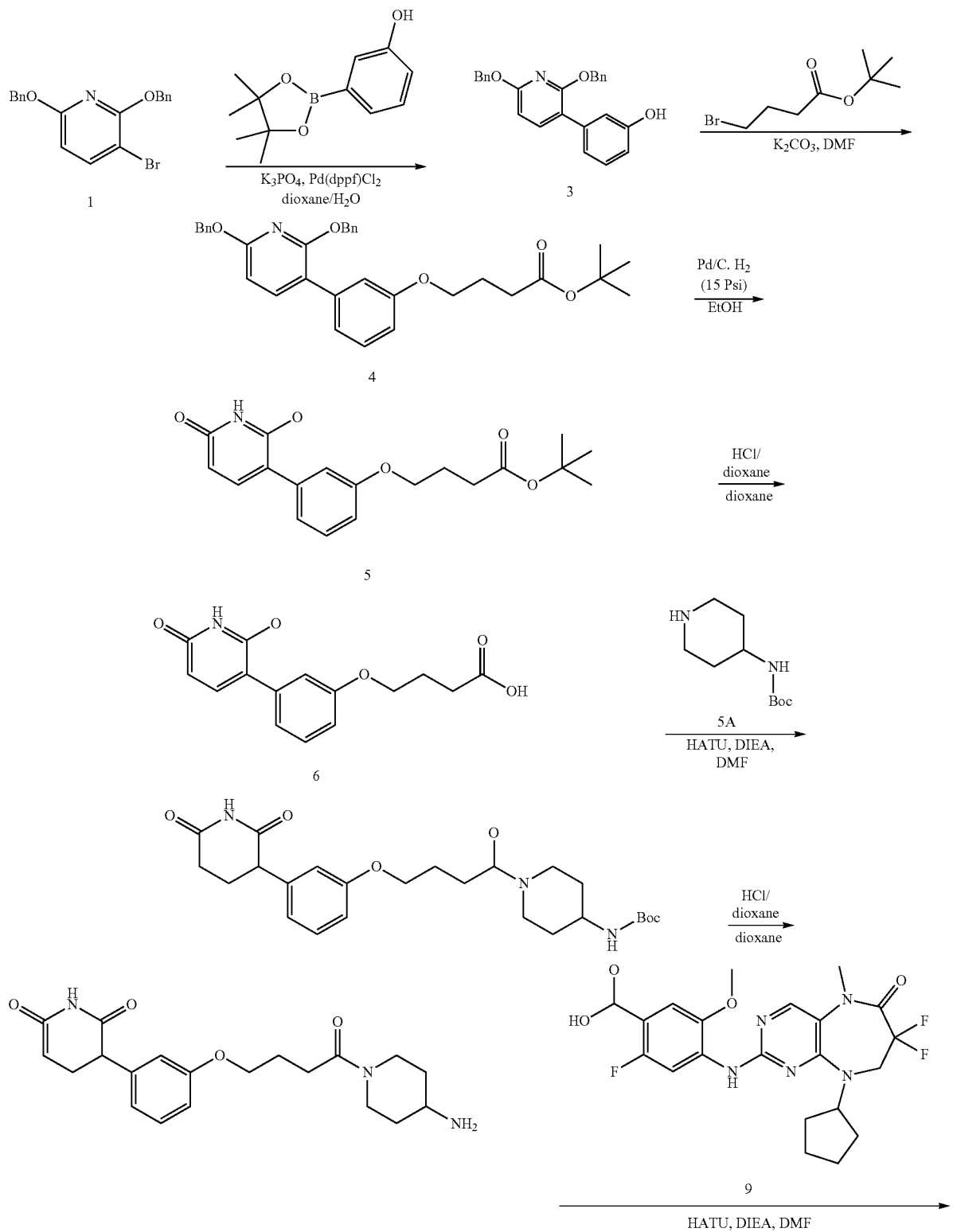

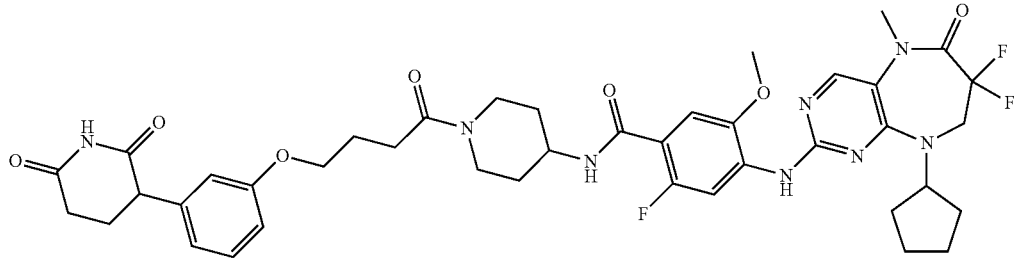

Compound 2

Step 1. Synthesis of 3-(2,6-bis(benzyloxy)pyridin-3-yl)phenol (3)

To a mixture of 3-(4,4,5,5-tetramethyl-1,3,2-dioxaborolan-2-yl)phenol (1 g, 4.54 mmol), 2,6-bis(benzyloxy)-3-bromopyridine (1.68 g, 4.54 mmol) and $K_3PO_4$ (2.89 g, 13.63 mmol) in $H_2O$ (4 mL) and dioxane (20 mL) was added Pd(dppf)$Cl_2$ (332.48 mg, 454.40 µmol) and the resulting mixture was degassed and purged with $N_2$ for three times, and heated to 110° C. and stirred for 14 h. LCMS showed the starting material was consumed and a peak (85%) with desired mass. The mixture was poured into water (100 mL) and extracted with EtOAc (50 mL×3). The combined organic layer was washed with brine (100 mL), dried over $Na_2SO_4$, filtered and concentrated in vacuo. The residue was purified by flash silica gel chromatography (ISCO; 20 g SepaFlash Silica Flash Column, Eluent of 0~30% EtOAc/Petroleum ether gradient @ 80 mL/min) to afford 3-(2,6-bis(benzyloxy)pyridin-3-yl)phenol (1.8 g, crude) as yellow oil. MS (M+H)$^+$=384.1

Step 2. Synthesis of tert-butyl 4-(3-(2,6-bis(benzyloxy)pyridin-3-yl)phenoxy)butanoate (4)

To the solution of 3-(2,6-bis(benzyloxy)pyridin-3-yl)phenol (1.8 g, 4.69 mmol) and tert-butyl 4-bromobutanoate (1.15 g, 5.16 mmol) in DMF (30 mL) was added $K_2CO_3$ (1.95 g, 14.08 mmol) and the resulting mixture was stirred at 60° C. for 12 h. LCMS showed the starting material was consumed and a peak (97%) with desired mass. The mixture was poured into water (100 mL) and extracted with EtOAc (50 mL×3). The combined organic layer was washed with brine (100 mL), dried over $Na_2SO_4$, filtered and concentrated in vacuo to afford tert-butyl 4-(3-(2,6-bis(benzyloxy)pyridin-3-yl)phenoxy)butanoate (2.5 g, crude) as yellow oil. MS (M+H)$^+$=526.2

Step 3. Synthesis of tert-butyl 4-(3-(2,6-dioxopiperidin-3-yl)phenoxy)butanoate (5)

To the solution of tert-butyl 4-(3-(2,6-bis(benzyloxy)pyridin-3-yl)phenoxy)butanoate (2 g, 3.80 mmol) in EtOH (40 mL) was added Pd/C (200 mg, 10% purity) under $N_2$ atmosphere and the resulting mixture was stirred at 20° C. under $H_2$ (15 psi) for 12 h. LCMS showed that starting material was consumed and 77% desired mass was detected. The reaction was filtered and the filtrate was concentrated to afford tert-butyl 4-(3-(2,6-dioxopiperidin-3-yl)phenoxy)butanoate (1 g, 2.88 mmol, 75.65% yield) as yellow oil. MS (M+Na)+=370.2

Step 4. Synthesis of 4-(3-(2,6-dioxopiperidin-3-yl)phenoxy)butanoic acid (6)

To the solution of tert-butyl 4-(3-(2,6-dioxopiperidin-3-yl)phenoxy)butanoate (1 g, 2.88 mmol) in dioxane (10 mL) was added HCl/dioxane (4 M, 10 mL) and the resulting mixture was stirred at 25° C. for 12 h. LCMS showed starting material was consumed, the reaction mixture was concentrated in vacuo to afford 4-(3-(2,6-dioxopiperidin-3-yl)phenoxy)butanoic acid (1.0 g, crude) as yellow oil. MS (M+H)$^+$=293.3

Step 5. Synthesis of tert-butyl (1-(4-(3-(2,6-dioxopiperidin-3-yl)phenoxy)butanoyl)piperidin-4-yl) carbamate (7)

To the solution of 4-(3-(2,6-dioxopiperidin-3-yl)phenoxy) butanoic acid (500 mg, 1.72 mmol) and tert-butyl piperidin-4-ylcarbamate (343.77 mg, 1.72 mmol) in DMF (5 mL) were added HATU (978.97 mg, 2.57 mmol) and DIPEA (665.52 mg, 5.15 mmol, 896.93 µL) and the resulting mixture was stirred at 20° C. for 12 h. LCMS showed the starting material was consumed and a peak (29%) with desired mass. The mixture was poured into water (100 mL) and extracted with EtOAc (50 mL×3). The combined organic layer was washed with brine (100 mL), dried over $Na_2SO_4$, filtered and concentrated. The residue was purified by flash silica gel chromatography (20 g SepaFlash Silica Flash Column, Eluent of 0~90% EtOAc/Petroleum ether gradient @ 80 mL/min) to afford tert-butyl (1-(4-(3-(2,6-dioxopiperidin-3-yl)phenoxy)butanoyl)piperidin-4-yl)carbamate (0.3 g, 633.50 µmol, 36.91% yield) as yellow oil. MS (M+H)$^+$= 474.1

Step 6. Synthesis of 3-(3-(4-(4-aminopiperidin-1-yl)-4-oxobutoxy)phenyl)piperidine-2,6-dione (8)

To the solution of tert-butyl (1-(4-(3-(2,6-dioxopiperidin-3-yl)phenoxy)butanoyl)piperidin-4-yl)carbamate (0.3 g, 633.50 µmol) in dioxane (5 mL) was added HCl/dioxane (4 M, 5 mL) and the resulting mixture was stirred at 25° C. for 0.5 h. LCMS showed the starting material was consumed and a peak (81%) with desired mass. The reaction was filtered and the filtrate was concentrated to afford 3-(3-(4-(4-aminopiperidin-1-yl)-4-oxobutoxy)phenyl)piperidine-2,6-dione (0.3 g, crude, HCl salt) as yellow oil. MS (M+H)$^+$= 374.1

Step 7. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(4-(3-(2,6-dioxopiperidin-3-yl)phenoxy)butanoyl)piperidin-4-yl)-2-fluoro-5-methoxybenzamide (Compound 2)

To the solution of 3-(3-(4-(4-aminopiperidin-1-yl)-4-oxobutoxy)phenyl)piperidine-2,6-dione (260 mg, 634.29

μmol, HCl salt) and 4-((9-cyclopentyl-7,7-difluoro-5-methyl-6-oxo-6,7,8,9-tetrahydro-5H-pyrimido[4,5-b][1,4]diazepin-2-yl)amino)-2-fluoro-5-methoxybenzoic acid (295.22 mg, 634.29 μmol) in DMF (5 mL) were added HATU (361.77 mg, 951.44 μmol) and DIPEA (245.93 mg, 1.90 mmol, 331.45 μL) and the resulting mixture was stirred at 25° C. for 12 h. LCMS showed the starting material was consumed and a peak (59%) with desired mass. The mixture was poured into water (20 mL) and extracted with EtOAc (20 mL×3), the combined organic layer was washed with brine (50 mL), dried over $Na_2SO_4$, filtered and concentrated. The resulting mixture was purified by prep-HPLC (column: Waters Xbridge C18 150*50 mm*10 μm; mobile phase: [water ($NH_4HCO_3$)—ACN]; B %: 36%-66%, 11 min) and the eluent was lyophilized to afford 4-((9-cyclopentyl-7,7-difluoro-5-methyl-6-oxo-6,7,8,9-tetrahydro-5H-pyrimido[4,5-b][1,4]diazepin-2-yl)amino)-N-(1-(4-(3-(2,6-dioxopiperidin-3-yl)phenoxy)butanoyl)piperidin-4-yl)-2-fluoro-5-methoxybenzamide (66.3 mg, 79.15 μmol, 12.48% yield, 98% purity) as a white solid.

MS $(M+H)^+$=821.4

$^1H$ NMR (400 MHz, DMSO-$d_6$) δ=10.88 (s, 1H), 8.36 (s, 1H), 8.31 (d, J=13.4 Hz, 1H), 8.10 (s, 1H), 8.02 (dd, J=2.9, 7.6 Hz, 1H), 7.34-7.23 (m, 2H), 6.90 (dd, J=2.1, 8.1 Hz, 1H), 6.87-6.82 (m, 2H), 4.94-4.83 (m, 1H), 4.39 (br d, J=12.9 Hz, 1H), 4.19-4.08 (m, 3H), 4.04 (br t, J=6.4 Hz, 3H), 3.98 (s, 3H), 3.95-3.85 (m, 2H), 3.39 (s, 3H), 3.20 (br t, J=11.6 Hz, 1H), 2.84-2.66 (m, 2H), 2.54-2.50 (m, 2H), 2.33-2.20 (m, 1H), 2.11-1.99 (m, 4H), 1.94-1.90 (m, 2H), 1.82-1.96 (m, 2H), 1.74-1.61 (m, 4H), 1.57-1.37 (m, 2H).

Example 3. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(4-(4-(2,6-dioxopiperidin-3-yl)phenoxy)butanoyl)piperidin-4-yl)-2-fluoro-5-methoxybenzamide (Compound 3)

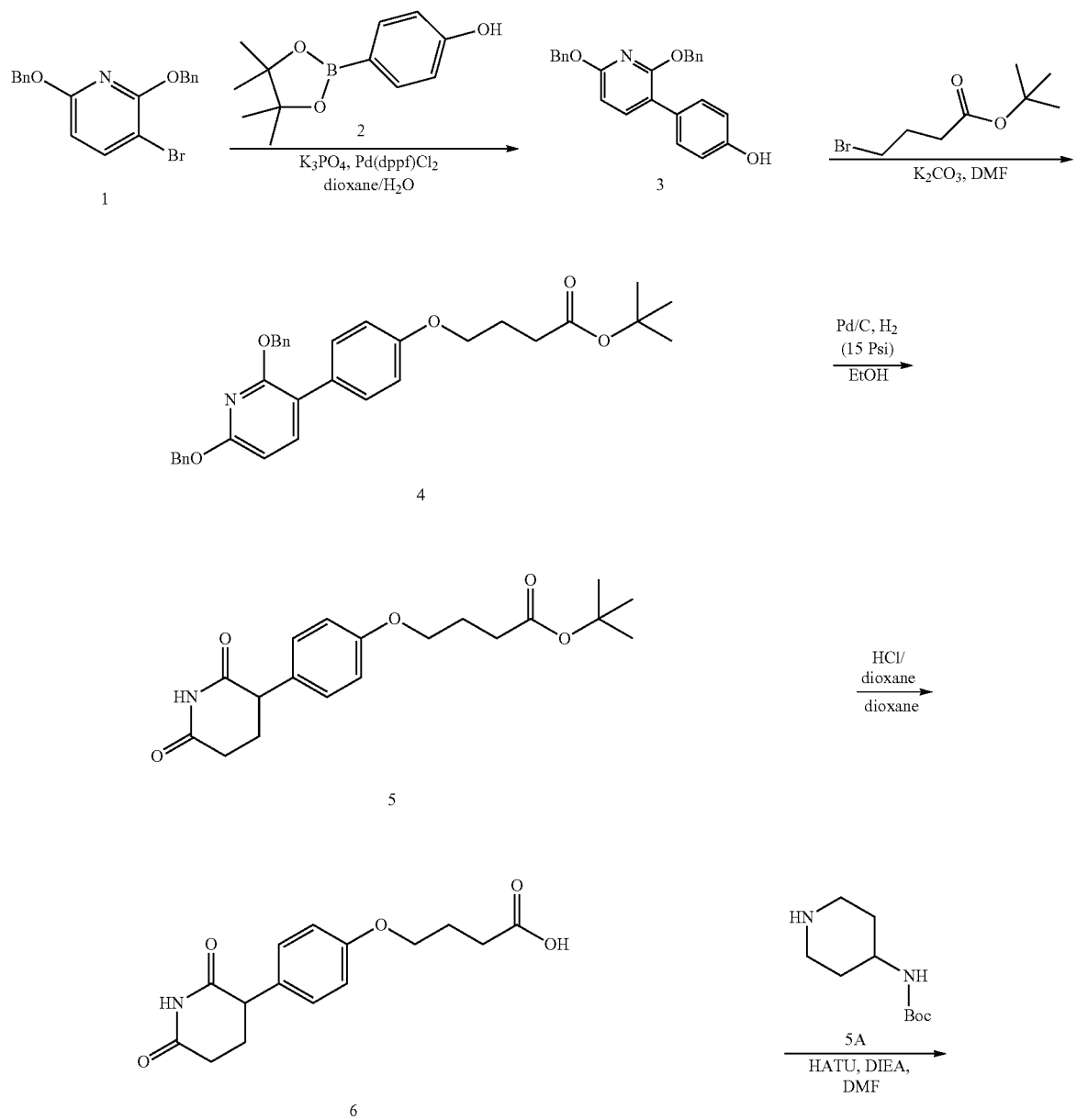

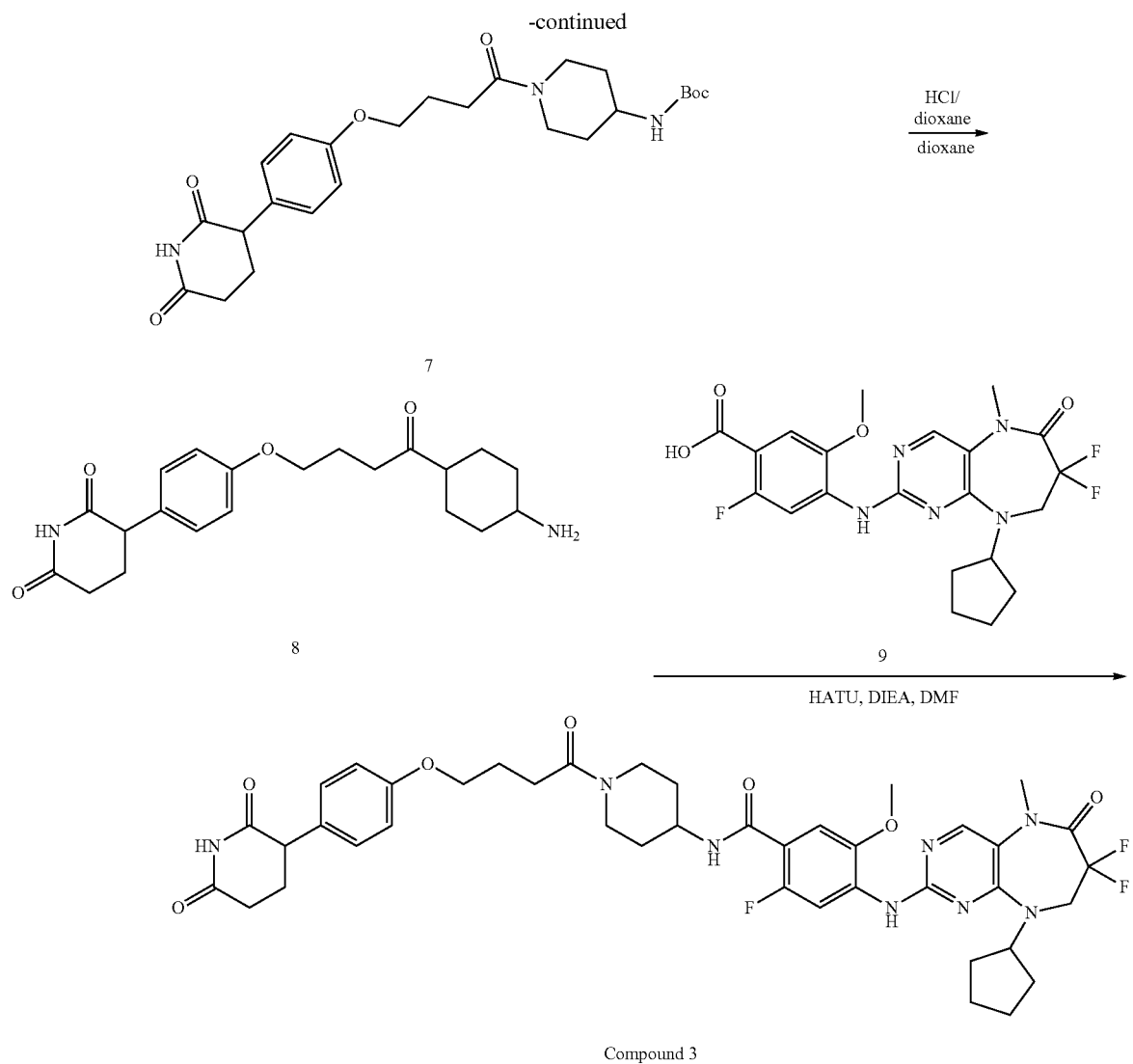

Compound 3

Step 1. Synthesis of 4-(2,6-bis(benzyloxy)pyridin-3-yl)phenol (3)

To a mixture of 4-(4,4,5,5-tetramethyl-1,3,2-dioxaborolan-2-yl)phenol (594.40 mg, 2.70 mmol), 2,6-bis(benzyloxy)-3-bromopyridine (1 g, 2.70 mmol) and $K_3PO_4$ (1.72 g, 8.10 mmol) in dioxane (15 mL) and $H_2O$ (3 mL) was added Pd(dppf)$Cl_2$ (197.63 mg, 270.10 µmol) and the resulting mixture was degassed and purged with $N_2$ for three times, and heated to 110° C. and stirred for 14 h. LCMS showed that starting material was consumed and 89% desired mass was detected. The mixture was poured into water (100 mL) and extracted with EtOAc (50 mL×3). The combined organic layer was washed with brine (100 mL), dried over $Na_2SO_4$, filtered and concentrated. The residue was purified by flash silica gel chromatography (20 g SepaFlash Silica Flash Column, Eluent of 0~30% EtOAc/Petroleum ether gradient @ 80 mL/min) to afford 4-(2,6-bis(benzyloxy)pyridin-3-yl)phenol (1 g, 2.61 mmol, 96.56% yield) as yellow oil. MS (M+H)$^+$=384.1

Step 2. Synthesis of tert-butyl 4-(4-(2,6-bis(benzyloxy)pyridin-3-yl)phenoxy)butanoate (4)

To the solution of 4-(2,6-bis(benzyloxy)pyridin-3-yl)phenol (1 g, 2.61 mmol) and tert-butyl 4-bromobutanoate (640.04 mg, 2.87 mmol) in DMF (20 mL) was added $K_2CO_3$ (1.08 g, 7.82 mmol) and the resulting mixture was stirred at 60° C. for 12 h. LCMS showed the starting material was consumed and a major peak (98%) with desired mass. The mixture was poured into water (100 mL) and extracted with EtOAc (50 mL×3). The combined organic layer was washed with brine (100 mL), dried over $Na_2SO_4$, filtered and concentrated to afford tert-butyl 4-(4-(2,6-bis(benzyloxy)pyridin-3-yl)phenoxy)butanoate (1.5 g, crude) as yellow oil. MS (M+H)$^+$=526.2

Step 3. Synthesis of tert-butyl 4-(4-(2,6-dioxopiperidin-3-yl)phenoxy)butanoate (5)

To the solution of tert-butyl 4-(4-(2,6-bis(benzyloxy)pyridin-3-yl)phenoxy)butanoate (1.5 g, 2.85 mmol) in EtOH (20 mL) was added Pd/C (150 mg, 10% purity) under $N_2$ atmosphere and the resulting mixture was stirred at 20° C.

under H₂ (15 psi) for 12 h. LCMS showed the starting material was consumed and a peak (81%) with desired mass. The reaction mixture was filtered and the filtrate was concentrated to afford tert-butyl 4-(4-(2,6-dioxopiperidin-3-yl)phenoxy)butanoate (0.8 g, 2.30 mmol, 80.69% yield) as yellow oil. MS (M+Na)+=370.2

Step 4. Synthesis of 4-(4-(2,6-dioxopiperidin-3-yl)phenoxy)butanoic acid (6)

To the solution of tert-butyl 4-(4-(2,6-dioxopiperidin-3-yl)phenoxy)butanoate (0.8 g, 2.30 mmol) in dioxane (10 mL) was added HCl/dioxane (4 M, 8.00 mL) and the resulting mixture was stirred at 25° C. for 12 h. LCMS showed the starting material was consumed. The reaction was filtered and the filtrate was concentrated to afford 4-(4-(2,6-dioxopiperidin-3-yl)phenoxy)butanoic acid (1 g, crude) as yellow oil. MS (M+H)⁺=292.3

Step 5. Synthesis of tert-butyl (1-(4-(4-(2,6-dioxopiperidin-3-yl)phenoxy)butanoyl)piperidin-4-yl)carbamate (7)

To the solution of 4-(4-(2,6-dioxopiperidin-3-yl)phenoxy)butanoic acid (500.00 mg, 1.72 mmol) and tert-butyl piperidin-4-ylcarbamate (343.77 mg, 1.72 mmol) in DMF (5 mL) were added HATU (978.97 mg, 2.57 mmol) and DIPEA (665.50 mg, 5.15 mmol, 896.90 µL) and the resulting mixture was stirred at 20° C. for 1 h. LCMS showed the starting material was consumed and a peak (63%) with desired mass. The mixture was poured into water (100 mL) and extracted with EtOAc (50 mL×3). The combined organic layer was washed with brine (100 mL), dried over Na₂SO₄, filtered and concentrated. The residue was purified by flash silica gel chromatography (20 g SepaFlash Silica Flash Column, Eluent of 0~90% EtOAc/Petroleum ether gradient @ 80 mL/min) to afford tert-butyl (1-(4-(4-(2,6-dioxopiperidin-3-yl)phenoxy)butanoyl)piperidin-4-yl)carbamate (0.3 g, 589.15 µmol, 34.32% yield, 93% purity) as yellow oil. MS (M+H)⁺=474.3

Step 6. Synthesis of 3-(4-(4-(4-aminopiperidin-1-yl)-4-oxobutoxy)phenyl)piperidine-2,6-dione (8)

To the solution of tert-butyl (1-(4-(4-(2,6-dioxopiperidin-3-yl)phenoxy)butanoyl)piperidin-4-yl)carbamate (300.00 mg, 633.50 µmol) in dioxane (5 mL) was added HCl/dioxane (4 M, 5 mL) and the resulting mixture was stirred at 25° C. for 0.5 h. LCMS showed the starting material was consumed and desired mass was detected. The reaction was filtered and the filtrate was concentrated to afford 3-(4-(4-(4-aminopiperidin-1-yl)-4-oxobutoxy)phenyl)piperidine-2,6-dione (0.3 g, crude, HCl salt) as yellow oil. MS (M+H)⁺=374.2

Step 7. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(4-(4-(2,6-dioxopiperidin-3-yl)phenoxy)butanoyl)piperidin-4-yl)-2-fluoro-5-methoxybenzamide (Compound 3)

To the solution of 3-(4-(4-(4-aminopiperidin-1-yl)-4-oxobutoxy)phenyl)piperidine-2,6-dione (150.00 mg, 365.94 µmol, HCl salt) and 4-((9-cyclopentyl-7,7-difluoro-5-methyl-6-oxo-6,7,8,9-tetrahydro-5H-pyrimido[4,5-b][1,4]diazepin-2-yl)amino)-2-fluoro-5-methoxybenzoic acid (170.32 mg, 365.94 µmol) in DMF (5 mL) were added HATU (208.71 mg, 548.91 µmol) and DIPEA (141.88 mg, 1.10 mmol, 191.22 µL) and the resulting mixture was stirred at 25° C. for 12 h. LCMS showed the starting material was consumed and a peak (73%) with desired mass. The mixture was poured into water (20 mL) and extracted with EtOAc (20 mL×3). The combined organic layer was washed with brine (50 mL), dried over Na₂SO₄, filtered and concentrated. The resulting mixture was purified by prep-HPLC (column: Waters Xbridge C18 150*50 mm*10 µm; mobile phase: [water (NH₄HCO₃)—ACN]; B %: 35%-65%, 11 min) and the eluent was lyophilized to afford 4-((9-cyclopentyl-7,7-difluoro-5-methyl-6-oxo-6,7,8,9-tetrahydro-5H-pyrimido[4,5-b][1,4]diazepin-2-yl)amino)-N-(1-(4-(4-(2,6-dioxopiperidin-3-yl)phenoxy)butanoyl)piperidin-4-yl)-2-fluoro-5-methoxybenzamide (69 mg, 82.38 µmol, 22.51% yield, 98% purity) as a white solid.

MS (M+H)⁺=821.4

¹H NMR (400 MHz, DMSO-d₆) δ=10.79 (s, 1H), 8.30 (s, 1H), 8.25 (d, J=13.4 Hz, 1H), 8.04 (s, 1H), 7.96 (dd, J=3.1, 7.6 Hz, 1H), 7.20 (d, J=6.6 Hz, 1H), 7.12 (d, J=8.6 Hz, 2H), 6.89 (d, J=8.8 Hz, 2H), 4.90-4.75 (m, 1H), 4.32 (br d, J=12.9 Hz, 1H), 4.15-4.01 (m, 3H), 4.07-3.96 (m, 3H), 3.91 (s, 3H), 3.89-3.81 (m, 1H), 3.78-3.76 (m, 1H), 3.33 (br s, 3H), 3.13 (br t, J=11.7 Hz, 1H), 2.77-2.60 (m, 2H), 2.52-2.46 (m, 2H), 2.47-2.43 (m, 1H), 2.22-2.09 (m, 1H), 2.01-1.92 (m, 4H), 1.85-1.80 (m, 2H), 1.75-1.71 (m, 2H), 1.64-1.60 (m, 4H), 1.52-1.30 (m, 2H).

Example 4. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(4-(3-(2,6-dioxopiperidin-3-yl)phenoxy)butanoyl)piperidin-4-yl)-3-methoxybenzamide (Compound 4)

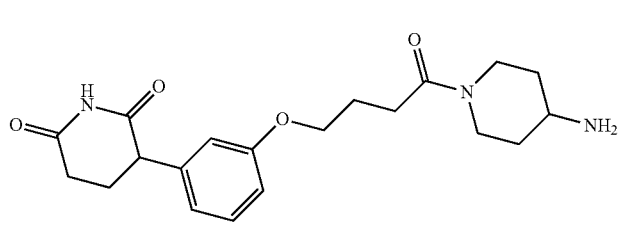

1

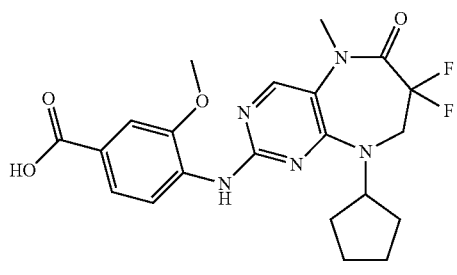

2

HATU, DIPEA, DMF

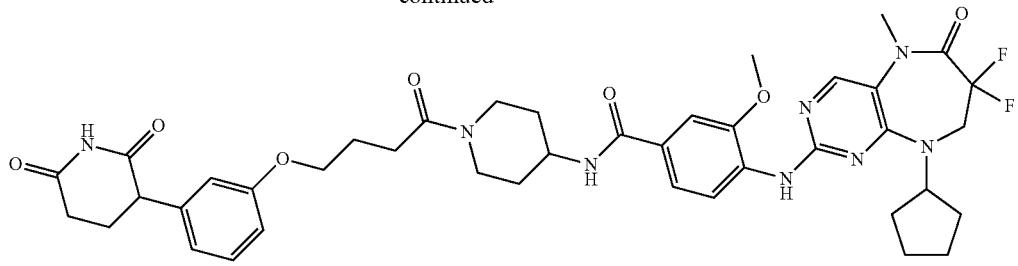

Compound 4

To a solution of 4-((9-cyclopentyl-7,7-difluoro-5-methyl-6-oxo-6,7,8,9-tetrahydro-5H-pyrimido[4,5-b][1,4]diazepin-2-yl)amino)-3-methoxybenzoic acid (800 mg, 1.79 mmol) in DMF (6 mL) were added HATU (747.82 mg, 1.97 mmol) and DIPEA (462.17 mg, 3.58 mmol, 622.86 μL), the mixture was stirred at 20° C. for 10 min and a solution of 3-(3-(4-(4-aminopiperidin-1-yl)-4-oxobutoxy)phenyl)piperidine-2,6-dione (952.77 mg, 2.32 mmol, HCl) in DMF (6 mL) with DIPEA (462.17 mg, 3.58 mmol, 622.86 μL) was added and the resulting mixture was stirred at 20° C. for 1 h. LCMS showed all starting material was consumed completely and a peak (74%) with desired mass. The reaction mixture was diluted with H$_2$O (60 mL) and extracted with EtOAc (60 mL×5). The organic layer was dried over Na$_2$SO$_4$, filtered and concentrated. The residue was purified by prep-HPLC (column: Phenomenex luna C18 150*40 mm*15 μm; mobile phase: [water (FA)-ACN]; B %: 38%-68%, 10 min) and the eluent was lyophilized to afford 2 batches of title compound, batch 1: (438.5 mg, 543.98 μmol, 30.42% yield, 97.7% purity) as a white solid, batch 2: (302 mg, 92% purity), the batch 2 was re-purified by prep-HPLC (column: Unisil 3-100 C18 Ultra 150*50 mm*3 μm; mobile phase:[water (FA)—ACN]; B %: 35%-65%, 10 min) and the eluent was lyophilized to afford 4-((9-cyclopentyl-7,7-difluoro-5-methyl-6-oxo-6,7,8,9-tetrahydro-5H-pyrimido[4,5-b][1,4]diazepin-2-yl)amino)-N-(1-(4-(3-(2,6-dioxopiperidin-3-yl)phenoxy)butanoyl)piperidin-4-yl)-3-methoxybenzamide (184.3 mg, 229.09 μmol, 12.81% yield, 99.8% purity) as a white solid. MS (M+H)$^+$=803.1

Batch 1 (438.5 mg): $^1$H NMR (400 MHz, DMSO-d$_6$) δ=10.82 (s, 1H), 8.30-8.23 (m, 2H), 8.14 (d, J=7.4 Hz, 1H), 8.01 (s, 1H), 7.51-7.44 (m, 2H), 7.23 (t, J=7.9 Hz, 1H), 6.84 (dd, J=2.1, 7.9 Hz, 1H), 6.81-6.75 (m, 2H), 4.77 (quin, J=8.1 Hz, 1H), 4.41 (br d, J=13.1 Hz, 1H), 4.13-3.86 (m, 10H), 3.81 (dd, J=4.9, 11.4 Hz, 1H), 3.32 (s, 3H), 3.12 (br t, J=12.1 Hz, 1H), 2.72-2.60 (m, 2H), 2.53-2.51 (m, 1H), 2.45 (br t, J=4.3 Hz, 1H), 2.27-2.14 (m, 1H), 2.06-1.99 (m, 1H), 1.99-1.90 (m, 4H), 1.89-1.78 (m, 2H), 1.76-1.66 (m, 2H), 1.66-1.55 (m, 4H), 1.52-1.33 (m, 2H).

Batch 2 (184 mg): $^1$H NMR (400 MHz, DMSO-d$_6$) δ=10.82 (s, 1H), 8.30-8.24 (m, 2H), 8.14 (br d, J=7.8 Hz, 1H), 7.97 (s, 1H), 7.50-7.46 (m, 2H), 7.23 (t, J=7.8 Hz, 1H), 6.84 (dd, J=2.1, 8.0 Hz, 1H), 6.81-6.75 (m, 2H), 4.82-4.70 (m, 1H), 4.40 (br d, J=14.0 Hz, 1H), 4.14-3.85 (m, 10H), 3.81 (dd, J=4.9, 11.4 Hz, 1H), 3.32 (br s, 3H), 3.17-3.07 (m, 1H), 2.69-2.60 (m, 2H), 2.48-2.40 (m, 2H), 2.21 (dq, J=4.3, 12.1 Hz, 1H), 2.06-1.99 (m, 1H), 1.99-1.90 (m, 4H), 1.89-1.78 (m, 2H), 1.75-1.66 (m, 2H), 1.65-1.54 (m, 4H), 1.52-1.33 (m, 2H).

Example 5. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(3-(4-(4-(2,6-dioxopiperidin-3-yl)phenyl)piperazin-1-yl)propanoyl)piperidin-4-yl)-3-methoxybenzamide (Compound 5)

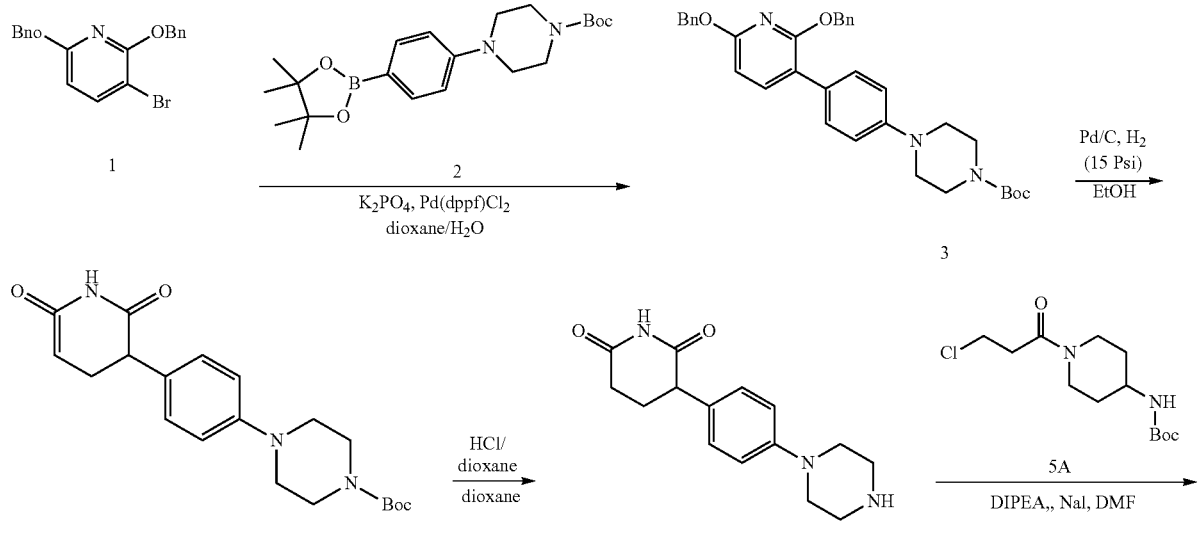

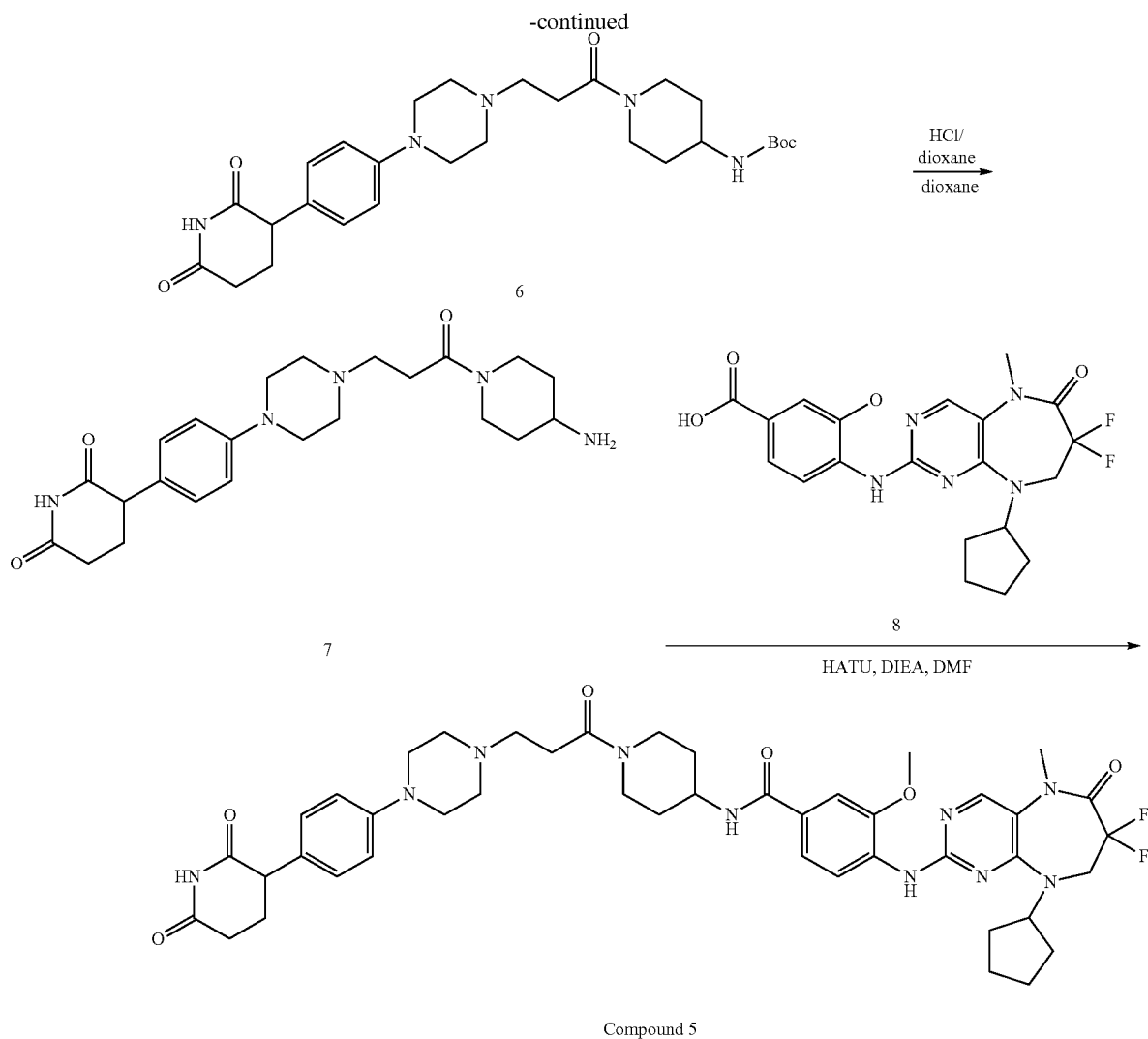

Compound 5

Step 1. Synthesis of tert-butyl 4-(4-(2,6-bis(benzyloxy)pyridin-3-yl)phenyl)piperazine-1-carboxylate (3)

To a mixture of 2,6-bis(benzyloxy)-3-bromopyridine (500 mg, 1.35 mmol), tert-butyl 4-(4-(4,4,5,5-tetramethyl-1,3,2-dioxaborolan-2-yl)phenyl)piperazine-1-carboxylate (524.40 mg, 1.35 mmol) and $K_3PO_4$ (859.98 mg, 4.05 mmol) in dioxane (12 mL) and $H_2O$ (2 mL) was added Pd(dppf)Cl$_2$ (98.82 mg, 135.05 µmol) at 25° C. The resulting mixture was purged and degassed with $N_2$ for three times, heated to 100° C. and stirred for 14 hrs. LCMS showed a main peak with desired mass. The reaction mixture was diluted with EtOAc (40 mL), dried over $Na_2SO_4$ and filtered. The filtrate was concentrated to give the crude product, which was purified by flash silica gel chromatography (4 g silica gel column, EtOAc/petroleum ether=0-5%, 40 mL/min) to afford tert-butyl 4-(4-(2,6-bis(benzyloxy)pyridin-3-yl)phenyl)piperazine-1-carboxylate (700 mg, 1.27 mmol, 93.96% yield, 100% purity) as yellow oil. MS (M+H)$^+$=552.3

Step 2. Synthesis of tert-butyl 4-(4-(2,6-dioxopiperidin-3-yl)phenyl)piperazine-1-carboxylate (4)

A mixture of tert-butyl 4-(4-(2,6-bis(benzyloxy)pyridin-3-yl)phenyl)piperazine-1-carboxylate (700 mg, 1.27 mmol) and Pd/C (200 mg, 10% purity) in EtOH (20 mL) was stirred purged and degassed with $H_2$ for three times and then stirred under $H_2$ (15 Psi) at 25° C. for 14 hrs. LCMS showed the starting material was consumed completely and a main peak with desired mass. The reaction mixture was filtered and washed with EtOH (20 mL). The filtrate was concentrated to afford tert-butyl 4-(4-(2,6-dioxopiperidin-3-yl)phenyl)piperazine-1-carboxylate (250 mg, 669.44 µmol, 52.76% yield) as white solid. MS (M+H)$^+$=374.5

Step 3. Synthesis of 3-(4-(piperazin-1-yl)phenyl)piperidine-2,6-dione (5)

A solution of tert-butyl 4-(4-(2,6-dioxopiperidin-3-yl)phenyl)piperazine-1-carboxylate (250 mg, 669.44 µmol) and HCl/dioxane (4 M, 5 mL) in dioxane (5 mL) was stirred at 25° C. for 1 h. LCMS showed the starting material was consumed completely and the desired mass. The reaction mixture was concentrated to afford 3-(4-(piperazin-1-yl)

phenyl)piperidine-2,6-dione (200 mg, 645.60 μmol, 96.44% yield, HCl) as white solid. MS (M+H)+=274.1

Step 4. Synthesis of tert-butyl (1-(3-(4-(4-(2,6-dioxopiperidin-3-yl)phenyl)piperazin-1-yl)propanoyl)piperidin-4-yl)carbamate (6)

To a solution of 3-(4-(piperazin-1-yl)phenyl)piperidine-2,6-dione (200 mg, 645.60 μmol, HCl) and tert-butyl N-[1-(3-chloropropanoyl)-4-piperidyl]carbamate (244.05 mg, 839.28 μmol) in DMF (6 mL) were added DIPEA (250.32 mg, 1.94 mmol, 337.35 uL) and NaI (9.68 mg, 64.56 μmol) at 25° C. The resulting mixture was stirred at 80° C. for 14 hrs. LCMS showed the starting material was consumed completely and the desired mass. The reaction mixture was poured into brine (50 mL). The mixture was extracted with EtOAc (20 mL×3). The combined organic layers were washed with brine (10 mL×2), dried over Na$_2$SO$_4$ and concentrated to afford the crude product. The crude product was purified by flash silica gel chromatography (4 g silica gel column, EtOAc/petroleum ether=10-100% and then EtOAc/methanol=10/1, 40 mL/min) to afford tert-butyl (1-(3-(4-(4-(2,6-dioxopiperidin-3-yl)phenyl)piperazin-1-yl)propanoyl)piperidin-4-yl)carbamate (130 mg, 246.37 μmol, 38.16% yield) as yellow solid. MS (M+H)+=528.4

Step 5. Synthesis of 3-(4-(4-(3-(4-aminopiperidin-1-yl)-3-oxopropyl)piperazin-1-yl)phenyl)piperidine-2,6-dione (7)

A solution of tert-butyl (1-(3-(4-(4-(2,6-dioxopiperidin-3-yl)phenyl)piperazin-1-yl)propanoyl)piperidin-4-yl)carbamate (120 mg, 227.42 μmol) and HCl/dioxane (4 M, 3 mL) in dioxane (1 mL) was stirred at 25° C. for 1 h. LCMS showed the starting material was consumed completely and the desired mass. The reaction mixture was concentrated to afford 3-(4-(4-(3-(4-aminopiperidin-1-yl)-3-oxopropyl)piperazin-1-yl)phenyl)piperidine-2,6-dione (100 mg, crude, HCl) as a yellow solid. The crude product was used for the next step directly. MS (M+H)+=428.1

Step 6. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(3-(4-(4-(2,6-dioxopiperidin-3-yl)phenyl)piperazin-1-yl)propanoyl)piperidin-4-yl)-3-methoxybenzamide (Compound 5)

To a solution of 3-(4-(4-(3-(4-aminopiperidin-1-yl)-3-oxopropyl)piperazin-1-yl)phenyl)piperidine-2,6-dione (100 mg, 215.52 μmol, HCl), 4-((9-cyclopentyl-7,7-difluoro-5-methyl-6-oxo-6,7,8,9-tetrahydro-5H-pyrimido[4,5-b][1,4]diazepin-2-yl)amino)-3-methoxybenzoic acid (96.43 mg, 215.52 μmol) and DIPEA (111.42 mg, 862.07 μmol, 150.16 uL) in DMF (3 mL) was added HATU (106.53 mg, 280.17 μmol) at 25° C. The resulting mixture was stirred at 25° C. for 12 hrs. LCMS showed the starting material was consumed completely and the desired mass. The reaction mixture was poured into brine (30 mL) and extracted with EtOAc (10 mL×4). The combined organic layers were washed with brine (10 mL×2), dried over Na$_2$SO$_4$ and concentrated to give the crude product. The crude product was purified by flash silica gel chromatography (4 g silica gel column, EtOAc/petroleum ether=20-100% and then methanol/EtOAc=10-30%, 40 mL/min) to afford the product (70 mg). The crude product was further purified by prep-HPLC (column: Waters Xbridge 150*25 mm*5 μm; mobile phase: [water (NH$_4$HCO$_3$)—ACN]; B %: 38%-68%, 10 min) and lyophilized to afford 4-((9-cyclopentyl-7,7-difluoro-5-methyl-6-oxo-6,7,8,9-tetrahydro-5H-pyrimido[4,5-b][1,4]diazepin-2-yl)amino)-N-(1-(3-(4-(4-(2,6-dioxopiperidin-3-yl)phenyl)piperazin-1-yl)propanoyl)piperidin-4-yl)-3-methoxybenzamide (13.8 mg, 15.59 μmol, 7.23% yield, 96.8% purity) as a white solid. MS (M+H)+=857.0
$^1$H NMR (400 MHz, DMSO-d$_6$) δ=10.77 (s, 1H), 8.28-8.26 (m, 2H), 8.16 (d, J=8.0 Hz, 1H), 7.97 (s, 1H), 7.49-7.47 (m, 2H), 7.04 (d, J=8.0 Hz, 2H), 6.89 (d, J=8.0 Hz, 2H), 4.78-4.74 (m, 1H), 4.40-4.37 (m, 1H), 4.07-3.96 (m, 4H), 3.93 (s, 3H), 3.73-3.70 (m, 1H), 3.32 (s, 3H), 3.15-3.10 (m, 5H), 2.70-2.62 (m, 3H), 2.60-2.54 (m, 7H), 2.44-2.42 (m, 1H), 2.13-2.10 (m, 1H), 2.01-1.79 (m, 5H), 1.74-1.68 (m, 2H), 1.64-1.52 (m, 4H), 1.50-1.37 (m, 2H).

Example 6. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(3-(4-(3-(2,6-dioxopiperidin-3-yl)phenyl)piperazin-1-yl)propanoyl)piperidin-4-yl)-3-methoxybenzamide (Compound 6)

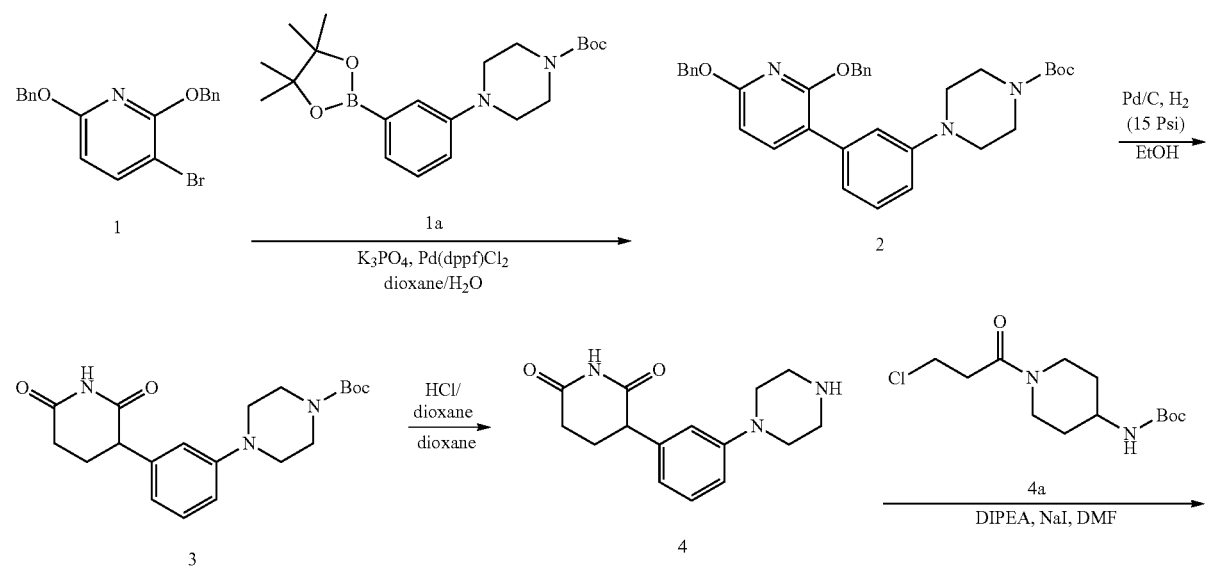

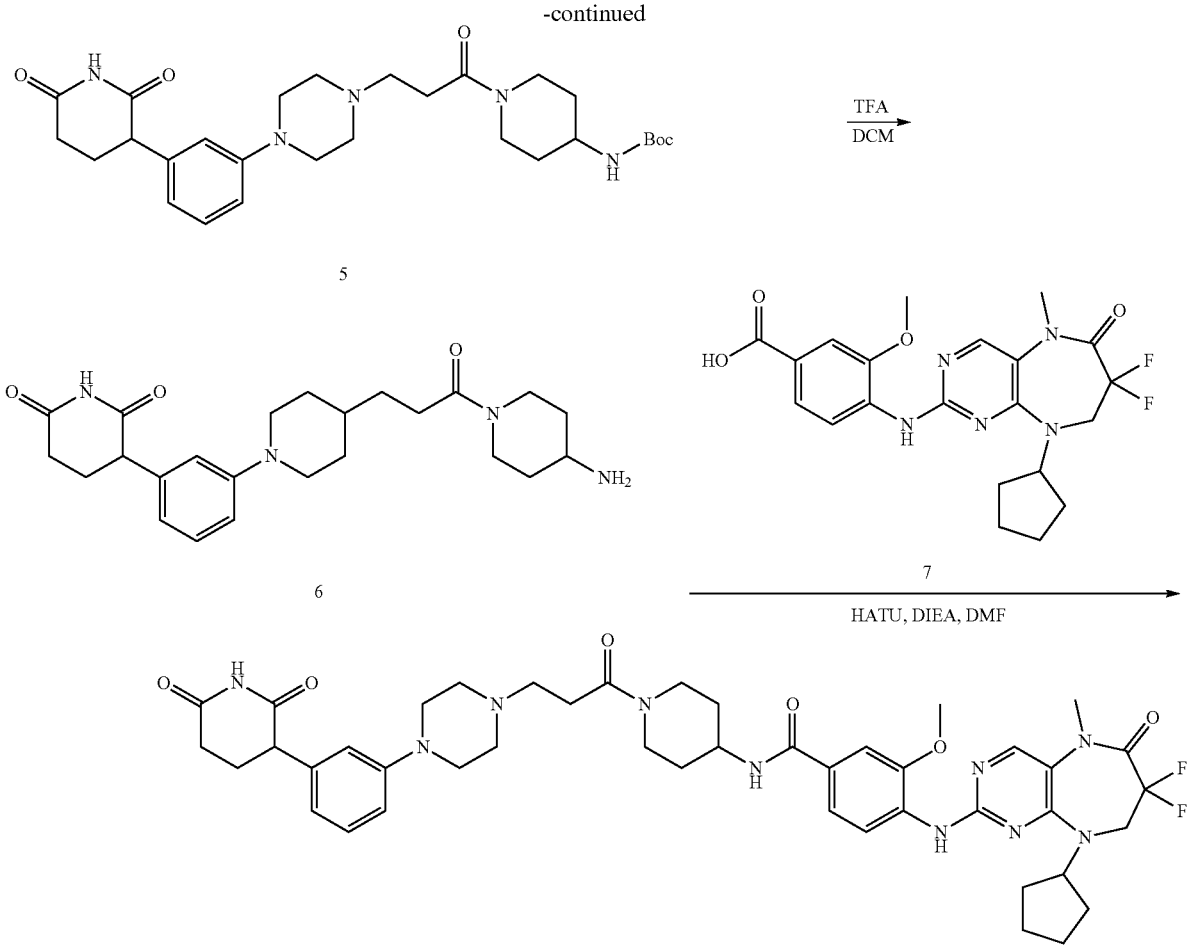

Compound 6

Step 1. Synthesis of tert-butyl 4-(3-(2,6-bis(benzyloxy)pyridin-3-yl)phenyl)piperazine-1-carboxylate (2)

To a mixture of 2,6-bis(benzyloxy)-3-bromopyridine (0.5 g, 1.35 mmol), tert-butyl 4-(3-(4,4,5,5-tetramethyl-1,3,2-dioxaborolan-2-yl)phenyl)piperazine-1-carboxylate (524.40 mg, 1.35 mmol) and $K_3PO_4$ (859.98 mg, 4.05 mmol) in dioxane (10 mL) and $H_2O$ (2 mL) was added Pd(dppf)Cl$_2$ (98.82 mg, 135.05 µmol) at 25° C. The resulting mixture was purged and degassed with $N_2$ for three times, heated to 100° C. and stirred for 14 hrs. LCMS showed the 2,6-bis(benzyloxy)-3-bromopyridine was consumed completely and a main peak with desired mass. The mixture was diluted with EtOAc (30 mL) dried over $Na_2SO_4$ and concentrated to give the residue. The residue was purified by flash silica gel chromatography (10 g SepaFlash Silica Flash Column, Eluent of 0~50% EtOAc/Petroleum ether gradient @ 50 mL/min) to afford tert-butyl 4-(3-(2,6-bis(benzyloxy)pyridin-3-yl)phenyl)piperazine-1-carboxylate (0.7 g, 1.17 mmol, 86.44% yield, 92% purity) as yellow solid. MS $(M+H)^+=552.1$ Step 2. Synthesis of tert-butyl 4-(3-(2,6-dioxopiperidin-3-yl)phenyl)piperazine-1-carboxylate (3)

To a solution of tert-butyl 4-(3-(2,6-bis(benzyloxy)pyridin-3-yl)phenyl)piperazine-1-carboxylate (0.7 g, 1.27 mmol) in EtOH (20 mL) was added Pd/C (0.5 g, 1.27 mmol, 10% purity). The mixture was stirred at 30° C. under $H_2$ (15 PSI) for 12 hr. LCMS showed the starting material was consumed completely and a main peak with desired mass. The reaction mixture was filtered through a celite pad and the filtrate was concentrated under vacuum to afford tert-butyl 4-(3-(2,6-dioxopiperidin-3-yl)phenyl)piperazine-1-carboxylate (0.5 g, crude) as yellow oil, which was used for the next step directly. MS $(M+H)^+=374.2$ Step 3 Synthesis of 3-(3-(piperazin-1-yl)phenyl)piperidine-2,6-dione (4)

To a solution of t tert-butyl 4-(3-(2,6-dioxopiperidin-3-yl)phenyl)piperazine-1-carboxylate (0.5 g, 1.34 mmol) in dioxane (2 mL) was added HCl/dioxane (4 M, 10 mL) at 25° C. The resulting mixture was stirred at 25° C. for 0.5 hr. TLC (petroleum ether:EtOAc=1:1; Rf=0) showed the starting material was consumed completely and found new spot. The mixture solution was concentrated under reduced pressure to afford 3-(3-(piperazin-1-yl)phenyl)piperidine-2,6-dione (0.5 g, crude, HCl) as yellow solid, which was used for the next step directly. MS $(M+H)^+=274.1$ Step 4. Synthesis of tert-butyl (1-(3-(4-(3-(2,6-di-oxopiperidin-3-yl)phenyl)piperazin-1-yl)propanoyl)piperidin-4-yl)carbamate (5)

To a solution of tert-butyl (1-(3-chloropropanoyl)piperidin-4-yl)carbamate (844.79 mg, 2.91 mmol) and 3-(3-(piperazin-1-yl)phenyl)piperidine-2,6-dione (450 mg, 1.45 mmol, HCl) in DMF (5 mL) was added NaI (21.77 mg, 145.26 μmol) and DIEA (563.20 mg, 4.36 mmol, 759.03 μL) at 25° C., the mixture was stirred at 80° C. for 16 hr. LCMS showed the 3-(3-(piperazin-1-yl)phenyl)piperidine-2,6-dione was consumed completely and a peak (27%) with desired mass. The mixture solution was concentrated under reduced pressure to give the crude product. The crude product was purified by flash silica gel chromatography (5 g SepaFlash Silica Flash Column, Eluent of 0~100% EtOAc/Petroleum ether gradient @ 60 mL/min; Eluent of 0~50% Methanol/EtOAc @ 60 mL/min) to afford tert-butyl (1-(3-(4-(3-(2,6-dioxopiperidin-3-yl)phenyl)piperazin-1-yl)propanoyl)piperidin-4-yl)carbamate (0.8 g, crude) as brown oil, which was used for the next step directly. MS (M+H)$^+$= 528.3

Step 5. Synthesis of 3-(3-(4-(3-(4-aminopiperidin-1-yl)-3-oxopropyl)piperazin-1-yl)phenyl)piperidine-2,6-dione (6)

To a solution of tert-butyl (1-(3-(4-(3-(2,6-dioxopiperidin-3-yl)phenyl)piperazin-1-yl)propanoyl)piperidin-4-yl)carbamate (0.8 g, 1.52 mmol) in DCM (10 mL) was added TFA (3.08 g, 27.01 mmol, 2 mL) at 25° C. The resulting mixture was stirred at 25° C. for 0.5 hr. LCMS showed the starting material was consumed completely and a peak (41%) with desired mass. The mixture solution was concentrated under reduced pressure to afford 3-(3-(4-(3-(4-aminopiperidin-1-yl)-3-oxopropyl)piperazin-1-yl)phenyl)piperidine-2,6-dione (0.8 g, crude, TFA) as brown oil, which was used for the next step directly. MS (M+H)$^+$=428.2

Step 6. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(3-(4-(3-(2,6-dioxopiperidin-3-yl)phenyl)piperazin-1-yl)propanoyl)piperidin-4-yl)-3-methoxybenzamide (Compound 6)

To a solution of 4-((9-cyclopentyl-7,7-difluoro-5-methyl-6-oxo-6,7,8,9-tetrahydro-5H-pyrimido[4,5-b][1,4]diazepin-2-yl)amino)-3-methoxybenzoic acid (90 mg, 201.15 μmol) in DMF (3 mL) was added HATU (91.78 mg, 241.38 μmol) and DIPEA (155.98 mg, 1.21 mmol, 210.21 μL). The mixture was stirred at 25° C. for 10 min. To mixture was added 3-(3-(4-(3-(4-aminopiperidin-1-yl)-3-oxopropyl)piperazin-1-yl)phenyl)piperidine-2,6-dione (217.87 mg, 402.30 μmol, TFA). The mixture was stirred at 25° C. for 2 h. LCMS showed the 3-(3-(4-(3-(4-aminopiperidin-1-yl)-3-oxopropyl)piperazin-1-yl)phenyl)piperidine-2,6-dione was consumed completely and a peak (62%) with desired mass. The mixture was concentrated under reduced pressure to give the residue. The residue was purified by flash silica gel chromatography (5 g SepaFlash Silica Flash Column, Eluent of 0~100% EtOAc/Petroleum ether gradient @ 60 mL/min; Eluent of 0~50% Methanol/EtOAc @ 60 mL/min) to give crude product. The crude product was purified by prep-TLC (Dichloromethane:Methanol=10:1; Rf=0.4) and prep-HPLC (column: Waters Xbridge 150×25 mmx 5 um; mobile phase: [water (NH$_4$HCO$_3$)—ACN]; B %: 36%-66%, 8 min) and lyophilized to afford 4-((9-cyclopentyl-7,7-difluoro-5-methyl-6-oxo-6,7,8,9-tetrahydro-5H-pyrimido[4,5-b][1,4]diazepin-2-yl)amino)-N-(1-(3-(4-(3-(2,6-dioxopiperidin-3-yl)phenyl)piperazin-1-yl)propanoyl)piperidin-4-yl)-3-methoxybenzamide (26.5 mg, 30.30 μmol, 15.07% yield, 98% purity) as white solid. MS (M+H)$^+$=857.3

$^1$H NMR (400 MHz, DMSO-d$_6$) δ=10.79 (s, 1H), 8.31-8.23 (m, 2H), 8.15 (d, J=7.6 Hz, 1H), 7.96 (s, 1H), 7.53-7.43 (m, 2H), 7.15 (t, J=7.8 Hz, 1H), 6.87-6.74 (m, 2H), 6.61 (d, J=7.6 Hz, 1H), 4.76 (q, J=8.3 Hz, 1H), 4.39 (d, J=13.1 Hz, 1H), 4.12-3.94 (m, 4H), 3.93 (s, 3H), 3.75 (dd, J=4.9, 11.2 Hz, 1H), 3.30 (s, 3H), 3.19-3.05 (m, 5H), 2.75-2.53 (m, 10H), 2.46-2.39 (m, 1H), 2.25-2.12 (m, 1H), 2.06-1.78 (m, 5H), 1.73-1.34 (m, 8H).

Example 7. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-((1r,4r)-4-(((1-(4-(2,6-dioxopiperidin-3-yl)-2-fluorophenyl)piperidin-4-yl)methyl)(methyl)amino)cyclohexyl)-3-methoxybenzamide (trans) (Compound 7)

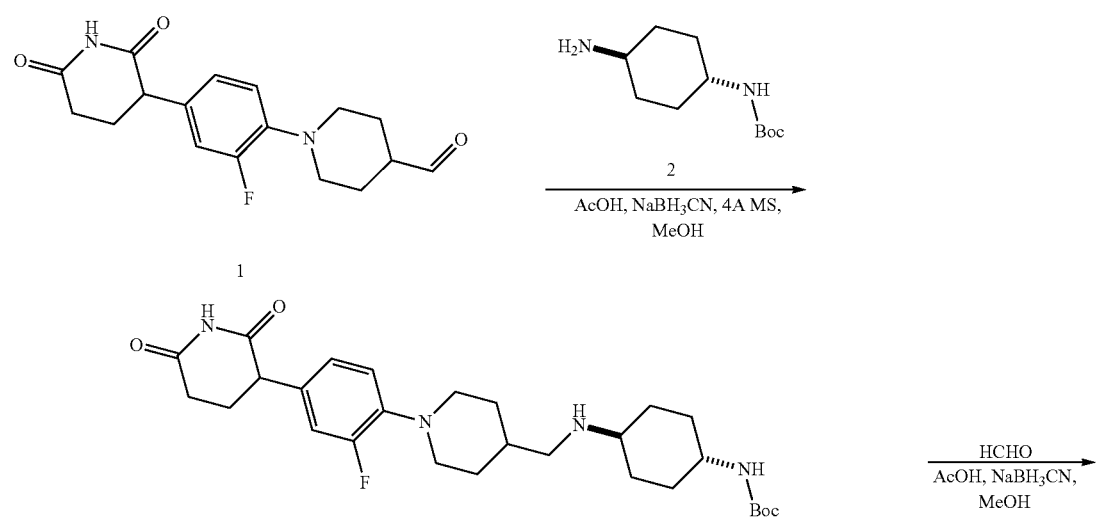

-continued

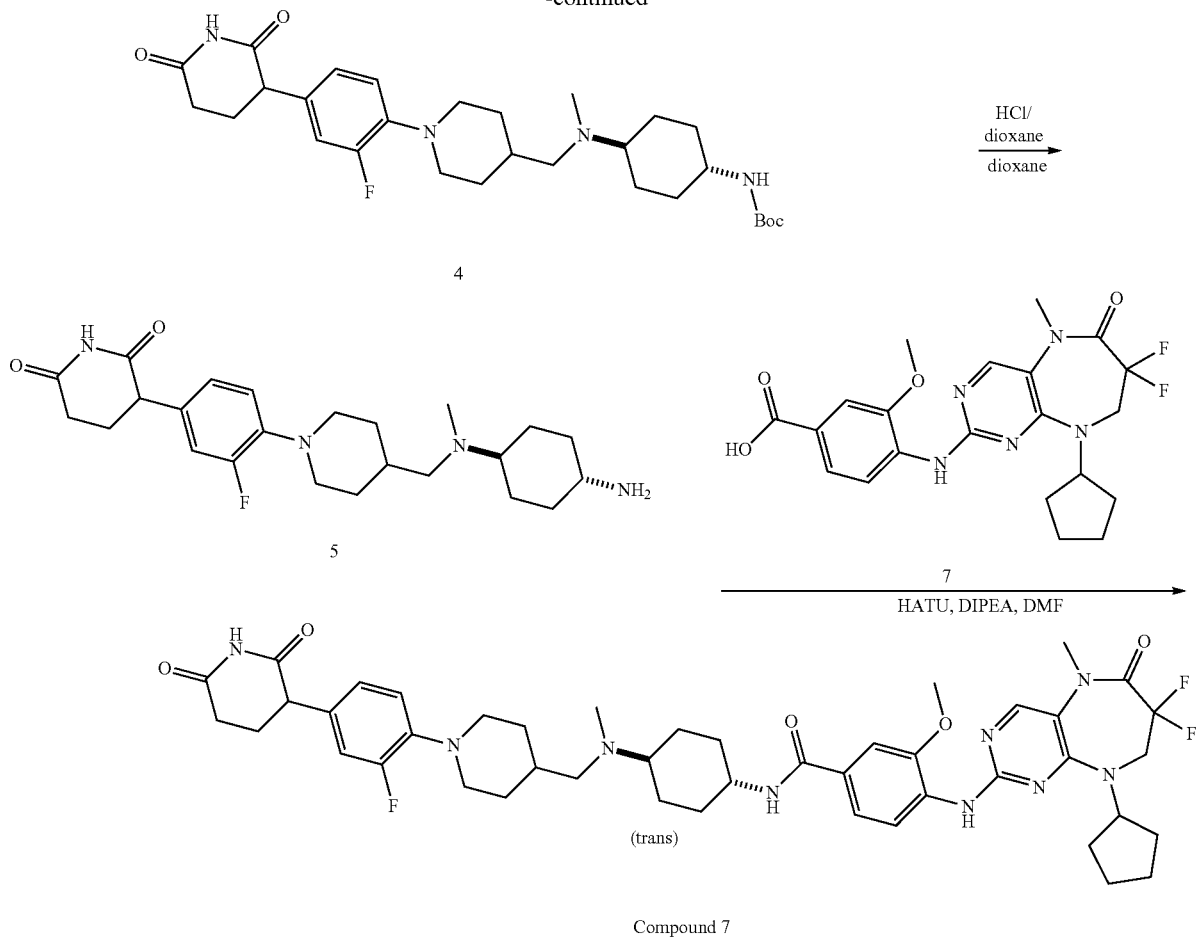

Compound 7

Step 1. Synthesis of tert-butyl ((1r,4r)-4-(((1-(4-(2,6-dioxopiperidin-3-yl)-2-fluorophenyl)piperidin-4-yl)methyl)amino)cyclohexyl)carbamate (trans) (3)

To a solution of 1-(4-(2,6-dioxopiperidin-3-yl)-2-fluorophenyl)piperidine-4-carbaldehyde (1 g, 3.14 mmol) and tert-butyl (1r,4r)-4-aminocyclohexyl)carbamate (trans) (673.19 mg, 3.14 mmol) in MeOH (10 mL) were added AcOH (188.64 mg, 3.14 mmol, 179.66 µL) and 4A MS (100 mg). Then NaBH$_3$CN (592.21 mg, 9.42 mmol) was added slowly at 20° C. and the resulting mixture was stirred at 20° C. for 1 h. LCMS showed starting material was consumed completely and 76% peak with desired mass. The reaction mixture was filtered and the filtrate was concentrated to afford tert-butyl ((1r,4r)-4-(((1-(4-(2,6-dioxopiperidin-3-yl)-2-fluorophenyl)piperidin-4-yl)methyl)amino)cyclohexyl)carbamate (trans) (1.6 g, crude) as a yellow oil. MS (M+H)$^+$= 517.3

Step 2. Synthesis of tert-butyl ((1r,4r)-4-(((1-(4-(2,6-dioxopiperidin-3-yl)-2-fluorophenyl)piperidin-4-yl)methyl)(methyl)amino)cyclohexyl)carbamate (trans) (4)

To a solution of tert-butyl ((1r,4r)-4-(((1-(4-(2,6-dioxopiperidin-3-yl)-2-fluorophenyl)piperidin-4-yl)methyl)amino)cyclohexyl)carbamate (trans) (1.6 g, 3.10 mmol) and HCHO (502.63 mg, 6.19 mmol, 461.13 µL, 37% purity) in MeOH (20 mL) was added AcOH (185.97 mg, 3.10 mmol, 177.12 µL). Then NaBH$_3$CN (583.85 mg, 9.29 mmol,) was added slowly at 20° C. and the resulting mixture was stirred at 20° C. for 12 h. LCMS showed starting material was consumed completely and 82% peak with desired mass. The reaction mixture was diluted with H$_2$O (60 mL) and extracted with EtOAc (60 mL×3). The organic layer was washed with saturated NaHCO$_3$ (60 mL×3), dried over Na$_2$SO$_4$, filtered and concentrated. The residue was purified by flash silica gel chromatography (20 g SepaFlash Silica Flash Column, Eluent of 0~100% EtOAc/Petroleum ether gradient @ 100 mL/min) to afford tert-butyl ((1r,4r)-4-(((1-(4-(2,6-dioxopiperidin-3-yl)-2-fluorophenyl)piperidin-4-yl)methyl)(methyl)amino)cyclohexyl)carbamate (trans) (0.5 g, 942.20 µmol, 30.42% yield, 100% purity) as a white solid. MS (M+H)$^+$=531.3

Step 3. Synthesis of 3-(4-(4-((((1r,4r)-4-aminocyclohexyl)(methyl)amino)methyl)piperidin-1-yl)-3-fluorophenyl)piperidine-2,6-dione (trans) (5)

To a solution of tert-butyl ((1r,4r)-4-(((1-(4-(2,6-dioxopiperidin-3-yl)-2-fluorophenyl)piperidin-4-yl)methyl)(methyl)amino)cyclohexyl)carbamate (trans) (0.5 g, 942.20 µmol) in dioxane (5 mL) was added HCl/dioxane (4 M, 10 mL) at 20° C. and the resulting mixture was stirred at 20° C. for 1 h. LCMS showed starting material was consumed completely and 91% peak with desired mass. The reaction mixture was concentrated in vacuum to afford 3-(4-(4-((((1r,4r)-4-aminocyclohexyl)(methyl)amino)methyl)piperidin-1-yl)-3-fluorophenyl)piperidine-2,6-dione (trans) (451 mg, crude, HCl) as a white solid. MS (M+H)$^+$=431.3

Step 4. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-((1r,4r)-4-(((1-(4-(2,6-dioxopiperidin-3-yl)-2-fluorophenyl)piperidin-4-yl)methyl)(methyl)amino)cyclohexyl)-3-methoxybenzamide (trans) (Compound 7)

To a solution of 4-((9-cyclopentyl-7,7-difluoro-5-methyl-6-oxo-6,7,8,9-tetrahydro-5H-pyrimido[4,5-b][1,4]diazepin-2-yl)amino)-3-methoxybenzoic acid (90 mg, 201.15 μmol) in DMF (2 mL) were added HATU (84.13 mg, 221.26 μmol) and DIPEA (51.99 mg, 402.29 μmol, 70.07 μL). The mixture was stirred at 20° C. for 10 min and a solution of 3-(4-(4-((((1r,4r)-4-aminocyclohexyl)(methyl)amino)methyl)piperidin-1-yl)-3-fluorophenyl)piperidine-2,6-dione (trans) (103.33 mg, 221.26 μmol, HCl) in DMF (2 mL) with DIPEA (51.99 mg, 402.29 μmol, 70.07 μL) was added and the resulting mixture was stirred at 20° C. for 1 h. LCMS showed all starting material was consumed completely and 50% peak with desired mass. The reaction mixture was diluted with H$_2$O (15 mL) and extracted with EtOAc (15 mL×3). The organic layer was dried over Na$_2$SO$_4$, filtered and concentrated. The residue was purified by flash silica gel chromatography (4 g SepaFlash Silica Flash Column, Eluent of 0~100% EtOAc/Petroleum ether 0~10% Dichloromethane/Methanol gradient @ 100 mL/min) and re-purified by prep-HPLC (column: Waters Xbridge 150*25 mm*5 μm; mobile phase: [water (NH$_4$HCO$_3$)—ACN]; B %: 49%-79%, 8 min) and lyophilization to afford 4-((9-cyclopentyl-7,7-difluoro-5-methyl-6-oxo-6,7,8,9-tetrahydro-5H-pyrimido[4,5-b][1,4]diazepin-2-yl)amino)-N-((1r,4r)-4-(((1-(4-(2,6-dioxopiperidin-3-yl)-2-fluorophenyl)piperidin-4-yl)methyl)(methyl)amino)cyclohexyl)-3-methoxybenzamide (trans) (31.3 mg, 35.30 μmol, 17.55% yield, 97% purity) as a white solid. MS (M+H)$^+$=860.4

$^1$H NMR (400 MHz, DMSO-d$_6$) δ=10.80 (s, 1H), 8.29-8.23 (m, 2H), 8.06 (d, J=7.8 Hz, 1H), 7.95 (s, 1H), 7.52-7.44 (m, 2H), 7.04-6.90 (m, 3H), 4.83-4.70 (m, 1H), 4.04 (t, J=14.0 Hz, 2H), 3.93 (s, 3H), 3.83-3.68 (m, 2H), 3.38 (s, 2H), 3.30 (s, 3H), 2.65-2.53 (m, 4H), 2.47-2.46 (m, 1H), 2.28 (d, J=6.4 Hz, 2H), 2.25-2.13 (m, 4H), 2.05-1.88 (m, 5H), 1.83-1.67 (m, 6H), 1.65-1.49 (m, 5H), 1.44-1.31 (m, 4H), 1.30-1.19 (m, 2H)

Example 8. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-((1r,4r)-4-(((1-(4-(2,6-dioxopiperidin-3-yl)-2-fluorophenyl)piperidin-4-yl)(methyl)amino)methyl)cyclohexyl)-3-methoxybenzamide (Compound 8)

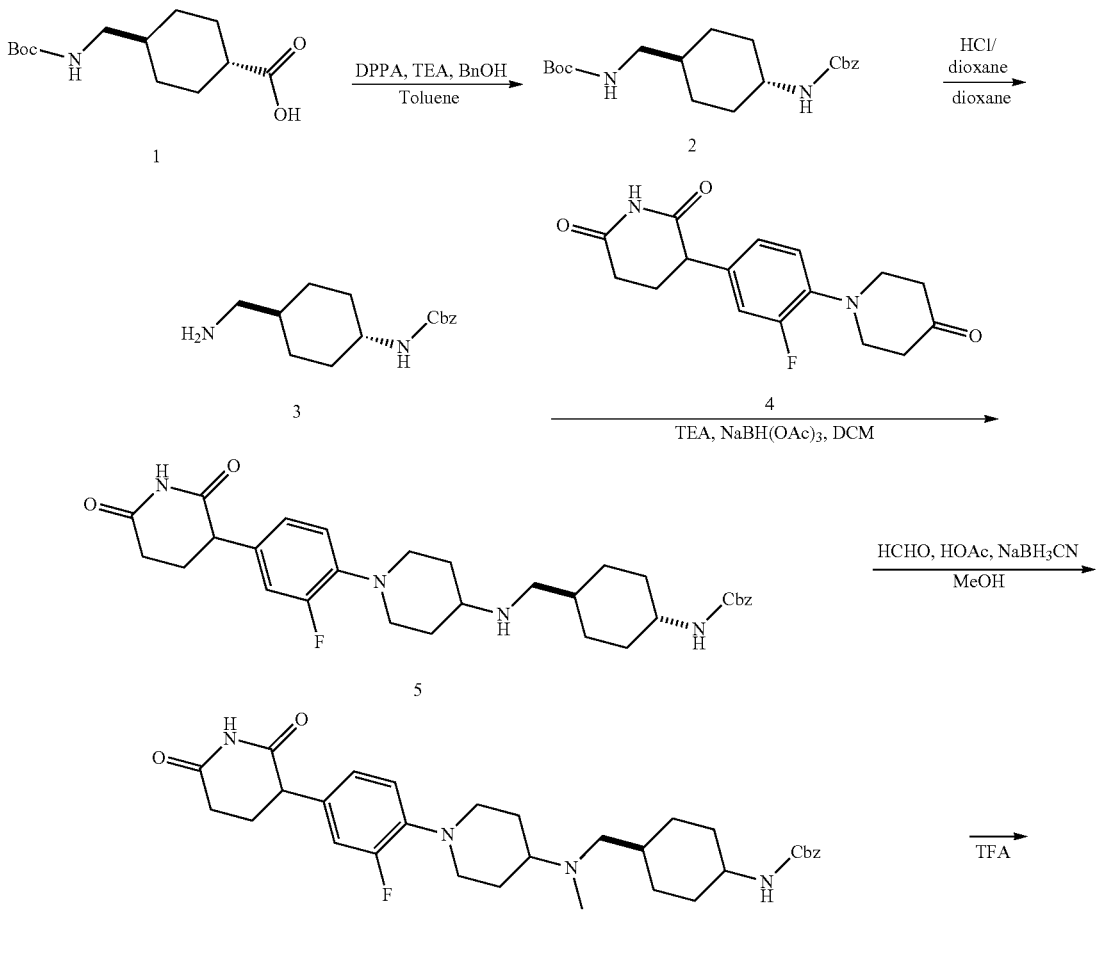

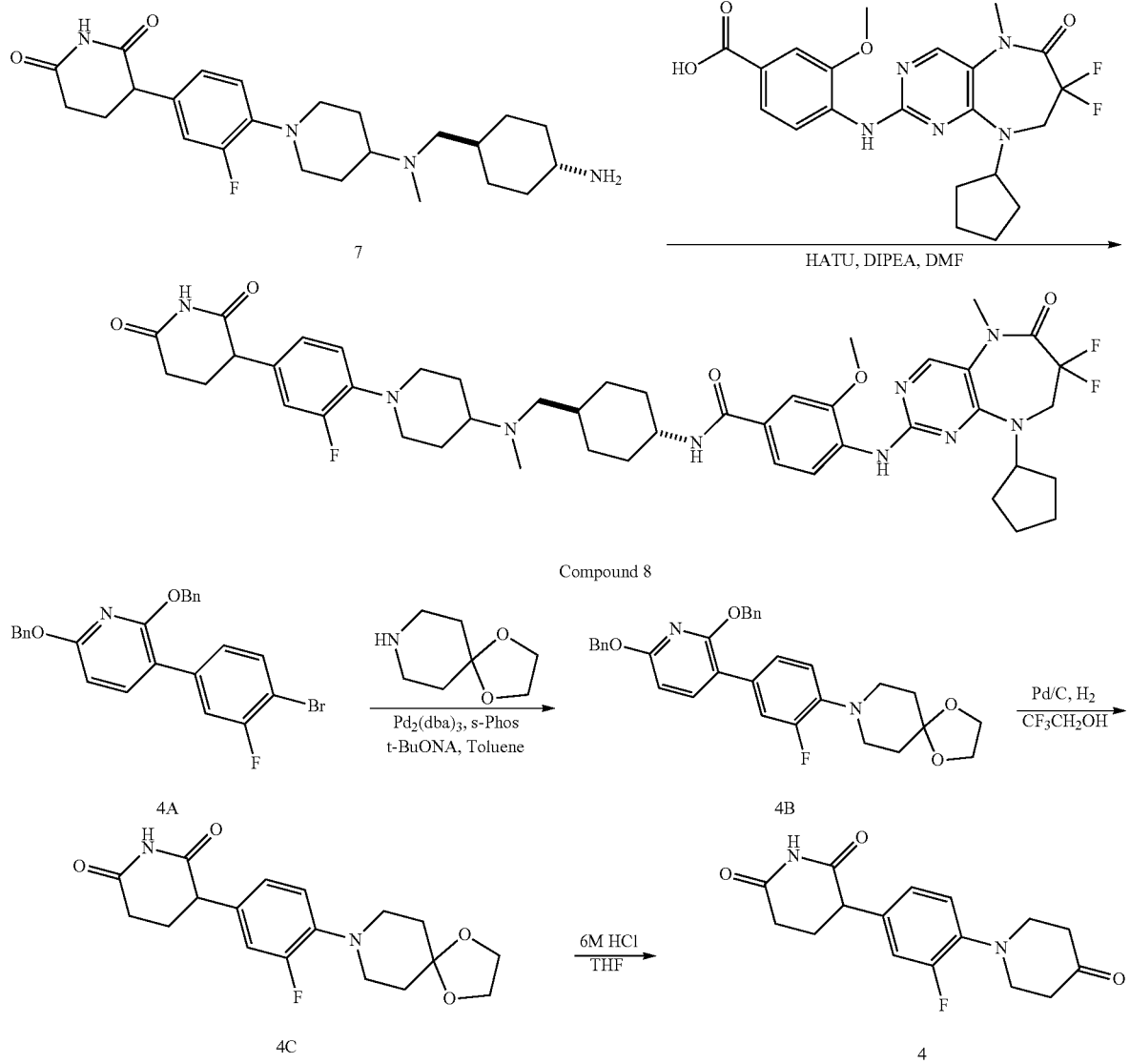

Compound 8

Step 1. Synthesis of tert-butyl (((1r,4r)-4-(((benzyloxy)carbonyl)amino)cyclohexyl)methyl)carbamate (2)

To a solution of (1r,4r)-4-(((tert-butoxycarbonyl)amino)methyl)cyclohexane-1-carboxylic acid (2 g, 7.77 mmol) in toluene (40 mL) was added TEA (1.18 g, 11.66 mmol, 1.62 mL) at −10° C. in a dry ice bath, then DPPA (2.14 g, 7.77 mmol, 1.68 mL) was added dropwise over 10 minutes. The mixture was warmed to 10° C., and then slowly heated to 70° C. After 16 hours, the mixture was cooled to 47° C. and BnOH (2.52 g, 23.32 mmol, 2.42 mL) was added, the resulting mixture was heated to 110° C. for another 16 hours. LCMS showed the (1r,4r)-4-(((tert-butoxycarbonyl)amino)methyl)cyclohexane-1-carboxylic acid was consumed completely and 11% of desired mass. The mixture was diluted with H$_2$O (80 mL), HCl solution (1 N) was added until pH=5-6, the resulting mixture was extracted with EtOAc (50 mL×3), the combined organic layers were washed with NaHCO$_3$ solution (50 mL×2), dried over Na$_2$SO$_4$, filtered and concentrated in vacuum. The residue was triturated with a mixture of MTBE (7 mL) and Petroleum ether (15 mL) for 5 minutes, the suspension was filtered and the filter cake was washed with MTBE (5 mL) and Petroleum ether (20 mL), the filter cake was collected and dried under vacuum to afford tert-butyl (((1r,4r)-4-(((benzyloxy)carbonyl)amino)cyclohexyl)methyl)carbamate (1.94 g, 5.35 mmol, 68.86% yield) as a light brown solid. MS (M−Boc+H)$^+$=263.2

Step 2. Synthesis of benzyl ((1r,4r)-4-(aminomethyl)cyclohexyl)carbamate (3)

To a solution of tert-butyl (((1r,4r)-4-(((benzyloxy)carbonyl)amino)cyclohexyl)methyl)carbamate (300 mg, 827.67 μmol) in dioxane (6 mL) was added HCl/dioxane (4 M, 6 mL). The mixture was stirred at 20° C. for 2 hr. LCMS showed 68% peak with the desired mass. The reaction mixture was concentrated to afford benzyl ((1r,4r)-4-(aminomethyl)cyclohexyl)carbamate (240 mg, crude, HCl) as a light yellow solid. MS (M+H)$^+$=263.0

Step 3. Synthesis of 8-(4-(2,6-bis(benzyloxy)pyridin-3-yl)-2-fluorophenyl)-1,4-dioxa-8-azaspiro[4.5]decane (4B)

A mixture of 2,6-bis(benzyloxy)-3-(4-bromo-3-fluorophenyl)pyridine (1 g, 2.15 mmol), 1,4-dioxa-8-azaspiro[4.5]decane (1 g, 6.98 mmol, 892.86 µL), $Pd_2(dba)_3$ (200.00 mg, 218.41 µmol,), s-Phos (80.00 mg, 194.87 µmol) and t-BuONa (1 M, 6.00 mL) in Toluene (30 mL) was degassed and purged with $N_2$ for 3 times, and then the mixture was stirred at 100° C. for 16 h under $N_2$ atmosphere. LCMS showed 34% peak with desired mas. The reaction mixture was filtered and the filtrate was diluted with $H_2O$ (30 mL), the mixture was extracted with EtOAc (50 mL×2), the combined organic layers were washed with brine (25 mL×2), dried over $Na_2SO_4$, filtered and the filtrate was concentrated under reduced pressure. The residue was purified by flash silica gel chromatography (Biotage; 20 g SepaFlash Silica Flash Column, Eluent of 2-20% EtOAc: Petroleum ether gradient, 60 mL/min) to afford 8-(4-(2,6-bis(benzyloxy)pyridin-3-yl)-2-fluorophenyl)-1,4-dioxa-8-azaspiro[4.5]decane (320 mg, 607.68 µmol, 28.22% yield) as a yellow oil. MS $(M+H)^+=527.1$

Step 4. Synthesis of 3-(3-fluoro-4-(1,4-dioxa-8-azaspiro[4.5]decan-8-yl)phenyl)piperidine-2,6-dione (4C)

To a solution of 8-(4-(2,6-bis(benzyloxy)pyridin-3-yl)-2-fluorophenyl)-1,4-dioxa-8-azaspiro[4.5]decane (320 mg, 607.68 µmol) in $CF_3CH_2OH$ (10 mL) was added Pd/C (100 mg, 10% purity) under $N_2$ atmosphere, Then the mixture was stirred at 20° C. for 16 h under $H_2$ atmosphere (15 Psi). LCMS showed 48% peak with the desired mass. The reaction mixture was filtered and the filtrate was concentrated under reduced pressure. The residue was purified by flash silica gel chromatography (Biotage; 10 g SepaFlash Silica Flash Column, Eluent of 20~100% EtOAc:Petroleum ether gradient, 60 mL/min) to afford 3-(3-fluoro-4-(1,4-dioxa-8-azaspiro[4.5]decan-8-yl)phenyl)piperidine-2,6-dione (130 mg, 373.17 µmol, 61.41% yield) as a light yellow solid. MS $(M+H)^+=349.0$

Step 5. Synthesis of 3-(3-fluoro-4-(4-oxopiperidin-1-yl)phenyl)piperidine-2,6-dione (4)

To a solution of 3-(3-fluoro-4-(1,4-dioxa-8-azaspiro[4.5]decan-8-yl)phenyl)piperidine-2,6-dione (150 mg, 430.58 µmol) in THF (3 mL) was added HCl (6 M, 3.00 mL). The resulting mixture was stirred at 20° C. for 16 hr. LCMS showed 51% peak with desired mass. The reaction mixture was diluted with EtOAc (15 mL), then saturated $NaHCO_3$ solution was added to the mixture until pH=8-9 at 0° C., the resulting mixture was extracted with EtOAc (20 mL×3), then the combined organic layers were washed with brine (25 mL×2), dried over $Na_2SO_4$, filtered and the filtrate was concentrated under reduced pressure to afford 3-(3-fluoro-4-(4-oxopiperidin-1-yl)phenyl)piperidine-2,6-dione (130 mg, crude) as a white solid. MS $(M+H)^+=305.0$

Step 6. Synthesis of benzyl ((1r,4r)-4-(((1-(4-(2,6-dioxopiperidin-3-yl)-2-fluorophenyl)piperidin-4-yl)amino)methyl)cyclohexyl)carbamate (5)

To a solution of 3-(3-fluoro-4-(4-oxopiperidin-1-yl)phenyl)piperidine-2,6-dione (130 mg, 427.19 µmol) in DCM (10 mL) was added benzyl ((1r,4r)-4-(aminomethyl)cyclohexyl)carbamate (130.00 mg, 435.06 µmol, HCl) and TEA (436.20 mg, 4.31 mmol, 600 µL). The mixture was stirred at 25° C. for 1 hr. Then $NaBH(OAc)_3$ (350 mg, 1.65 mmol) was added to the mixture at 25° C., the resulting mixture was stirred at 25° C. for 15 hr. LCMS showed 3-(3-fluoro-4-(4-oxopiperidin-1-yl)phenyl)piperidine-2,6-dione was consumed completely and 70% peak with desired mass. The reaction mixture was filtered and the filtrate was diluted with $H_2O$ (2 mL) at 0° C., then saturated $NaHCO_3$ solution was added to the mixture until pH=8-9 at 0° C. The resulting mixture was extracted with EtOAc (15 mL×3), then the combined organic layers were washed with brine (10 mL×2), dried over $Na_2SO_4$, filtered and the filtrate was concentrated under reduced pressure. The residue was purified by flash silica gel chromatography (Biotage; 4 g SepaFlash Silica Flash Column, Eluent of 2-20% Methanol: Dichloromethane ether gradient, 50 mL/min) to afford benzyl ((1r,4r)-4-(((1-(4-(2,6-dioxopiperidin-3-yl)-2-fluorophenyl)piperidin-4-yl)amino)methyl)cyclohexyl)carbamate (80 mg, 145.28 µmol, 34.01% yield) as a light yellow solid.
MS $(M+H)^+=551.1$

Step 7. Synthesis of benzyl ((1r,4r)-4-(((1-(4-(2,6-dioxopiperidin-3-yl)-2-fluorophenyl)piperidin-4-yl)(methyl)amino)methyl)cyclohexyl)carbamate (6)

To a solution of benzyl ((1r,4r)-4-(((1-(4-(2,6-dioxopiperidin-3-yl)-2-fluorophenyl)piperidin-4-yl)amino)methyl) cyclohexyl)carbamate (100 mg, 181.60 µmol) in MeOH (10 mL) was added HOAc (10.91 mg, 181.60 µmol, 10.39 µL) and HCHO (136.32 mg, 1.82 mmol, 125.06 µL, 40% purity). The mixture was stirred at 20° C. for 1 hr. Then $NaBH_3CN$ (100.00 mg, 1.59 mmol) was added to the mixture at 0° C., the resulting mixture was stirred at 20° C. for 15 hr. LCMS showed one main peak with desired mass was detected. The reaction mixture was diluted with $H_2O$ (10 mL), then it was concentrated to remove MeOH, the mixture was diluted with EtOAc (30 mL) and then saturated $NaHCO_3$ solution was added to the mixture until pH=8-9 at 0° C., The resulting mixture was extracted with EtOAc (30 mL×2), then the combined organic layers were washed with brine (30 mL×2), dried over $Na_2SO_4$, filtered and the filtrate was concentrated under reduced pressure. The residue was purified by flash silica gel chromatography (Biotage; 10 g SepaFlash Silica Flash Column, Eluent of 0~20% Methanol: Dichloromethane gradient, 60 mL/min) to afford benzyl ((1r,4r)-4-(((1-(4-(2,6-dioxopiperidin-3-yl)-2-fluorophenyl)piperidin-4-yl)(methyl)amino)methyl)cyclohexyl)carbamate (102 mg, 180.63 µmol, 99.47% yield) as a light yellow solid. MS $(M+H)^+=565.1$

Step 8. Synthesis of 3-(4-(4-((((1r,4r)-4-aminocyclohexyl)methyl)(methyl)amino)piperidin-1-yl)-3-fluorophenyl)piperidine-2,6-dione (7)

A solution of benzyl ((1r,4r)-4-(((1-(4-(2,6-dioxopiperidin-3-yl)-2-fluorophenyl)piperidin-4-yl)(methyl)amino) methyl)cyclohexyl)carbamate (80 mg, 141.67 µmol) in TFA (2.46 g, 21.61 mmol, 1.60 mL) was stirred at 40° C. for 2.5 h under $N_2$ atmosphere. LCMS showed 43% peak with desired mass. The reaction mixture was concentrated under reduced pressure to afford 3-(4-(4-((((1r,4r)-4-aminocyclohexyl)methyl)(methyl)amino)piperidin-1-yl)-3-fluorophenyl)piperidine-2,6-dione (77 mg, crude, TFA) as a light yellow oil. MS $(M+H)^+=431.1$ Step 9. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-((1r,4r)-4-(((1-(4-(2,6-dioxopiperidin-3-yl)-2-fluorophenyl)piperidin-4-yl)(methyl)amino)methyl)cyclohexyl)-3-methoxybenzamide (Compound 8)

To a solution of 4-((9-cyclopentyl-7,7-difluoro-5-methyl-6-oxo-6,7,8,9-tetrahydro-5H-pyrimido[4,5-b][1,4]diazepin-2-yl)amino)-3-methoxybenzoic acid (80 mg, 178.80 µmol) in DMF (3 mL) were added HATU (120.00 mg, 315.60 µmol), DIPEA (178.08 mg, 1.38 mmol, 240.00 µL) and 3-(4-(4-((((1r,4r)-4-aminocyclohexyl)methyl)(methyl)amino)piperidin-1-yl)-3-fluorophenyl)piperidine-2,6-dione (80.00 mg, crude, TFA) at 20° C. The resulting mixture was stirred at 20° C. for 16 h under N₂ atmosphere. LCMS showed 4-((9-cyclopentyl-7,7-difluoro-5-methyl-6-oxo-6,7,8,9-tetrahydro-5H-pyrimido[4,5-b][1,4]diazepin-2-yl)amino)-3-methoxybenzoic acid was consumed completely and 61% peak with desired mass. The reaction mixture was diluted with H₂O (8 mL), the mixture was extracted with EtOAc (25 mL×2), the combined organic layers were washed with brine (20 mL×3), dried over Na₂SO₄, filtered and the filtrate was concentrated under reduced pressure. The residue was purified by flash silica gel chromatography (Biotage; 10 g SepaFlash Silica Flash Column, Eluent of 0~25% Methanol: Dichloromethane gradient, 60 mL/min) and re-purified prep-HPLC (column: 3_Phenomenex Luna C18 75×30 mm×3 µm; mobile phase: [water (TFA)—ACN]; B %: 28%-48%, 10 min, 7 min; Column Temp: 30° C.) followed by lyophilization. to afford 4-((9-cyclopentyl-7,7-difluoro-5-methyl-6-oxo-6,7,8,9-tetrahydro-5H-pyrimido[4,5-b][1,4]diazepin-2-yl)amino)-N-((1r,4r)-4-(((1-(4-(2,6-dioxopiperidin-3-yl)-2-fluorophenyl)piperidin-4-yl)(methyl)amino)methyl)cyclohexyl)-3-methoxybenzamide (62.3 mg, 54.97 µmol, 30.74% yield, 96% purity, 2TFA) as a white solid. MS (M+H)$^+$=860.2

$^1$H NMR (400 MHz, DMSO-d$_6$) δ=10.83 (s, 1H), 8.97-8.75 (m, 1H), 8.28-8.22 (m, 2H), 8.17-8.13 (m, 1H), 7.54-7.44 (m, 2H), 7.12-6.94 (m, 3H), 4.83-4.73 (m, 1H), 4.11-4.05 (m, 2H), 3.94 (s, 3H), 3.53-3.37 (m, 4H), 3.33 (s, 3H), 3.20-3.12 (m, 1H), 2.94-2.87 (m, 1H), 2.86-2.79 (m, 3H), 2.78-2.68 (m, 2H), 2.44-2.38 (m, 1H), 2.25-2.08 (m, 3H), 2.07-1.79 (m, 11H), 1.77-1.68 (m, 3H), 1.66-1.54 (m, 4H), 1.47-1.35 (m, 2H), 1.24-1.10 (m, 2H).

Example 9. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(3-((3-(2,6-dioxopiperidin-3-yl)benzyl)amino)propanoyl)piperidin-4-yl)-3-methoxybenzamide (Compound 9)

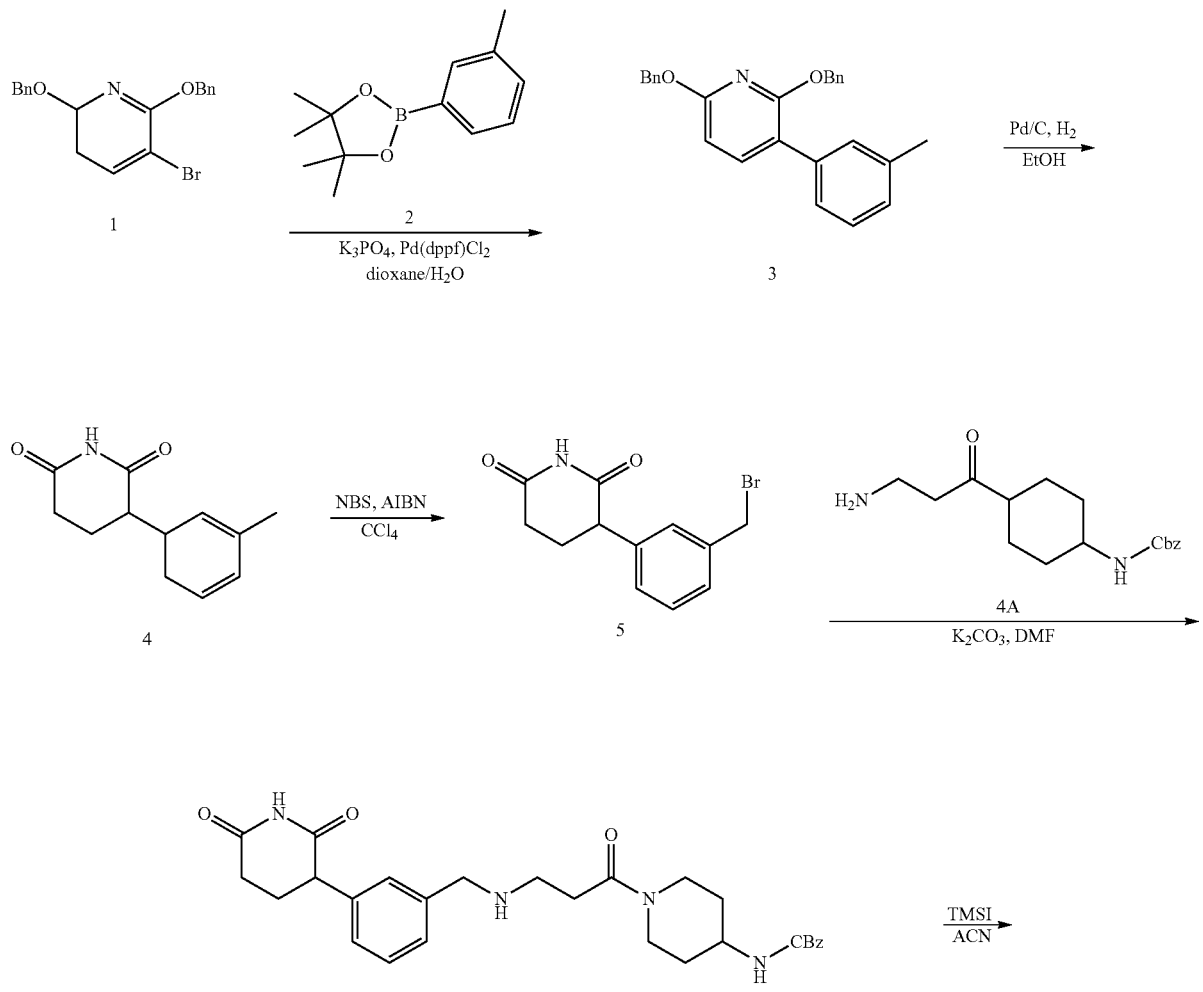

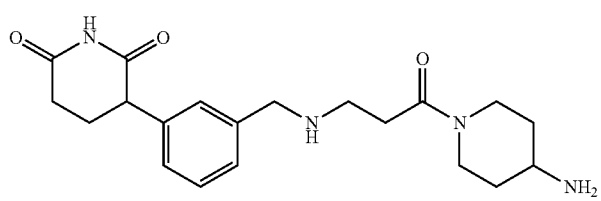

7

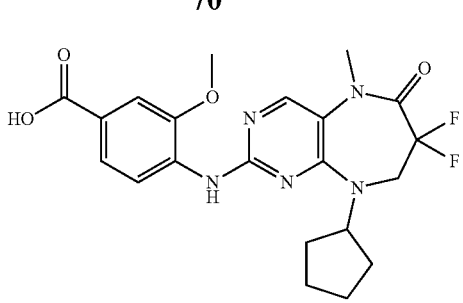

8

→ HATU, DIPEA, DMF

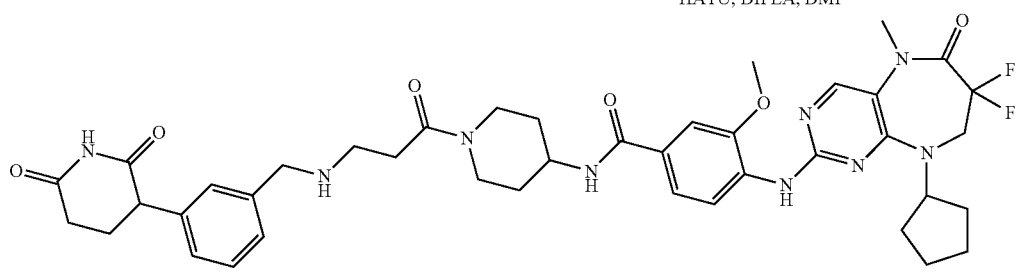

Compound 9

Step 1. Synthesis of 2,6-bis(benzyloxy)-3-(m-tolyl)pyridine (3)

To a solution of 2,6-bis(benzyloxy)-3-bromopyridine (5 g, 13.50 mmol) and 4,4,5,5-tetramethyl-2-(m-tolyl)-1,3,2-dioxaborolane (3.09 g, 14.18 mmol) in dioxane (100 mL) and $H_2O$ (20 mL) were added $K_3PO_4$ (8.60 g, 40.51 mmol) and Pd(dppf)$Cl_2$ (494 mg, 675.14 µmol) and the mixture was stirred at 100° C. for 14 h under $N_2$ atmosphere. TLC (Petroleum ether:EtOAc=20:1) showed new spot was formed. The mixture was dried over $Na_2SO_4$ and then filtered, the filter cake was washed with EtOAc (100 mL). The filtrate was concentrated under reduced pressure. The residue was purified by flash silica gel chromatography (40 g SepaFlash Silica Flash Column, Eluent of 0% EtOAc/Petroleum ether gradient @ 60 mL/min) to afford 2,6-bis(benzyloxy)-3-(m-tolyl)pyridine (5.3 g, 13.48 mmol, 99.79% yield, 97% purity) as yellow oil. MS (M+H)$^+$=382.1

Step 2. Synthesis of 3-(m-tolyl)piperidine-2,6-dione (4)

To a solution of 2,6-bis(benzyloxy)-3-(m-tolyl)pyridine (5.3 g, 13.89 mmol) in EtOH (70 mL) was added Pd/C (0.7 g, 10% purity) under $N_2$ atmosphere, the suspension was degassed and purged with $H_2$ for 3 times, the resulting mixture was stirred at 25° C. under $H_2$ (15 Psi) for 14 h. LCMS showed a peak (60%) with desired mass. The mixture was diluted with THF (50 mL), filtered and the filter cake was washed with THF (60 mL) and MeOH (80 mL). The filtrate was concentrated under reduced pressure to afford 3-(m-tolyl)piperidine-2,6-dione (2.7 g, 12.62 mmol, 90.86% yield, 95% purity) as a white solid. MS (M+H)$^+$=204.0

Step 3. Synthesis of 3-(3-(bromomethyl)phenyl)piperidine-2,6-dione (5)

To a solution of 3-(m-tolyl)piperidine-2,6-dione (0.5 g, 2.46 mmol) and NBS (482 mg, 2.71 mmol) in $CCl_4$ (8 mL) was added AIBN (40.40 mg, 246.02 µmol) and the mixture was stirred at 80° C. for 14 h. LCMS showed the desired mass was detected. The mixture was concentrated under reduced pressure. The residue was purified by flash silica gel chromatography (5 g SepaFlash Silica Flash Column, Eluent of 30~50% EtOAc/Petroleum ether gradient @ 50 mL/min) to afford 3-(3-(bromomethyl)phenyl)piperidine-2,6-dione (650 mg, 2.30 mmol, 93.65% yield) as a yellow solid.

MS (M+H)$^+$=281.8

Step 4. Synthesis of tert-butyl (3-(4-(((benzyloxy)carbonyl)amino)piperidin-1-yl)-3-oxopropyl)carbamate (3A)

A mixture of 3-((tert-butoxycarbonyl)amino)propanoic acid (2 g, 10.57 mmol), benzyl piperidin-4-ylcarbamate (2.48 g, 10.57 mmol), HBTU (4.81 g, 12.68 mmol), and DIPEA (4.10 g, 31.71 mmol, 5.52 mL) in DCM (30 mL) was degassed and purged with $N_2$ for 3 times, and then the mixture was stirred at 25° C. for 16 h under $N_2$ atmosphere. LCMS showed a peak (70%) with desired mass. The reaction mixture was diluted with water (200 mL) and extracted with EtOAc (200 mL). The combined organic layers were washed with brine (100 mL×2), dried over $Na_2SO_4$, filtered and concentrated under reduced pressure. The residue was purified by flash silica gel chromatography (40 g SepaFlash Silica Flash Column, Eluent of 20~60% EtOAc/Petroleum ether gradient @ 60 mL/min) to afford tert-butyl (3-(4-(((benzyloxy)carbonyl)amino)piperidin-1-yl)-3-oxopropyl)carbamate (4.5 g, crude) as a white solid. MS (M+H)$^+$=406.3

Step 5. Synthesis of benzyl (1-(3-aminopropanoyl)piperidin-4-yl)carbamate (4A)

To a solution of tert-butyl (3-(4-(((benzyloxy)carbonyl)amino)piperidin-1-yl)-3-oxopropyl)carbamate (4.5 g, 11.10 mmol) in DCM (40 mL) was added TFA (7.59 g, 66.59 mmol, 4.93 mL) and the mixture was stirred at 25° C. for 14 h. LCMS showed the desired mass was detected. The mixture was concentrated under reduced pressure to afford benzyl (1-(3-aminopropanoyl)piperidin-4-yl)carbamate (10 g, crude, TFA) as yellow oil. MS (M+H)$^+$=306.2

Step 6. Synthesis of benzyl (1-(3-((3-(2,6-dioxopiperidin-3-yl)benzyl)amino)propanoyl)piperidin-4-yl) carbamate (6)

To a solution of benzyl (1-(3-aminopropanoyl)piperidin-4-yl)carbamate (1.78 g, 4.25 mmol, TFA salt) in DMF (8 mL) were added K$_2$CO$_3$ (1.37 g, 9.93 mmol) and 3-(3-(bromomethyl)phenyl)piperidine-2,6-dione (0.4 g, 1.42 mmol) and the mixture was stirred at 80° C. for 14 h. LCMS showed 31% of the desired mass was detected. The mixture was diluted with H$_2$O (10 mL) and extracted with EtOAc (10 mL×3), the combined organic layer was washed with brine (10 mL×3), dried over Na$_2$SO$_4$ and filtered. The filtrate was concentrated under reduced pressure. The crude was purified by prep-HPLC (column: Phenomenex luna C18 150×40 mm×15 μm; mobile phase: [water (FA)—ACN]; B %: 12%-42%, 10 min) and the eluent was lyophilized to afford 2 batches of benzyl (1-(3-((3-(2,6-dioxopiperidin-3-yl)benzyl)amino)propanoyl)piperidin-4-yl)carbamate. Batch 1: (39 mg, 70.57 μmol, 4.98% yield, 100% purity, FA salt) as a yellow solid and batch 2: (45 mg, crude, FA salt) as a yellow solid. MS (M+H)$^+$=507.1

Step 7. Synthesis of 3-(3-(((3-(4-aminopiperidin-1-yl)-3-oxopropyl)amino)methyl)phenyl) piperidine-2,6-dione (7)

To a solution of benzyl (1-(3-((3-(2,6-dioxopiperidin-3-yl)benzyl)amino)propanoyl)piperidin-4-yl)carbamate (39 mg, 76.99 μmol) in ACN (0.4 mL) was added TMSI (58.80 mg, 293.87 μmol, 40 μL) and the mixture was stirred at 20° C. for 1 h. LCMS showed the starting material was consumed. The mixture was quenched with H$_2$O (10 mL), then washed with MTBE (10 mL×3), the combined organic layer was extracted with H$_2$O (10 mL). The combined aqueous phase was lyophilized to afford 3-(3-(((3-(4-aminopiperidin-1-yl)-3-oxopropyl)amino)methyl)phenyl)piperidine-2,6-dione (50 mg, crude, 2HI salt) as a yellow solid.
MS (M+H)$^+$=373.2

Step 8. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(3-((3-(2,6-dioxopiperidin-3-yl)benzyl)amino)propanoyl) piperidin-4-yl)-3-methoxybenzamide (Compound 9)

To a solution of 4-((9-cyclopentyl-7,7-difluoro-5-methyl-6-oxo-6,7,8,9-tetrahydro-5H-pyrimido[4,5-b][1,4]diazepin-2-yl)amino)-3-methoxybenzoic acid (37 mg, 82.69 μmol) in DMF (0.5 mL) were added HATU (37.73 mg, 99.23 μmol) and DIPEA (7.42 mg, 57.41 μmol, 10 μL) and the mixture was stirred at 20° C. for 15 min. Then a solution of 3-(3-(((3-(4-aminopiperidin-1-yl)-3-oxopropyl)amino) methyl)phenyl)piperidine-2,6-dione (60 mg, 95.50 μmol, 2HI salt) and DIPEA (59.36 mg, 459.29 μmol, 80 μL) in DMF (1.5 mL) was added and the resulting mixture was stirred at 20° C. for 1 h. LCMS showed a peak (80%) with desired mass. The mixture was diluted with H$_2$O (10 mL) and extracted with EtOAc (10 mL×3). The combined organic layer was washed with brine (10 mL×3), dried over Na$_2$SO$_4$ and filtered. The filtrate was concentrated under reduced pressure. The crude was purified by prep-HPLC (column: Waters Xbridge 150×25 mm×5 μm; mobile phase: [water (NH$_4$HCO$_3$)—ACN]; B %: 38%-68%, 8 min) followed by prep-HPLC (column: Phenomenex C18 75×30 mm×3 μm; mobile phase: [water (FA)—ACN]; B %: 15%-45%, 7 min) and the eluent was lyophilized to afford 4-((9-cyclopentyl-7,7-difluoro-5-methyl-6-oxo-6,7,8,9-tetrahydro-5H-pyrimido[4,5-b][1,4]diazepin-2-yl)amino)-N-(1-(3-((3-(2,6-dioxopiperidin-3-yl)benzyl)amino)propanoyl)piperidin-4-yl)-3-methoxybenzamide (11.4 mg, 13.36 μmol, 16.16% yield, 94% purity) as a white solid. MS (M+H)$^+$=802.5

$^1$H NMR (400 MHz, DMSO-d$_6$) δ=10.84 (s, 1H), 8.30-8.24 (m, 2H), 8.17-8.12 (m, 1H), 7.97 (s, 1H), 7.51-7.45 (m, 2H), 7.30-7.20 (m, 2H), 7.18 (s, 1H), 7.08 (br d, J=7.6 Hz, 1H), 4.79-4.74 (m, 1H), 4.44-4.33 (m, 1H), 4.10-3.99 (m, 3H), 3.93 (s, 3H), 3.91-3.81 (m, 2H), 3.71 (s, 2H), 3.33-3.32 (m, 3H), 3.14-3.05 (m, 1H), 2.76-2.61 (m, 8H), 2.22-2.11 (m, 1H), 2.09-2.00 (m, 1H), 1.99-1.89 (m, 2H), 1.88-1.76 (m, 2H), 1.74-1.66 (m, 2H), 1.65-1.54 (m, 3H), 1.50-1.34 (m, 2H).

Example 10. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(2-(1-(4-(2,6-dioxopiperidin-3-yl)-2-fluorophenyl) piperidin-4-yl)acetyl)piperidin-4-yl)-3-methoxybenzamide (Compound 10)

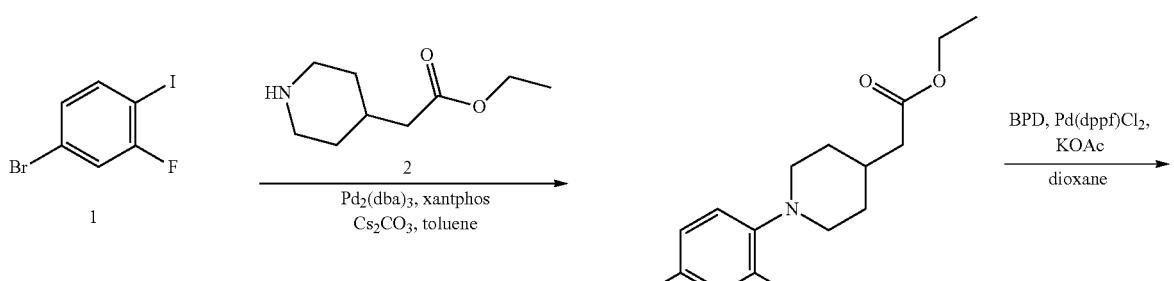

-continued
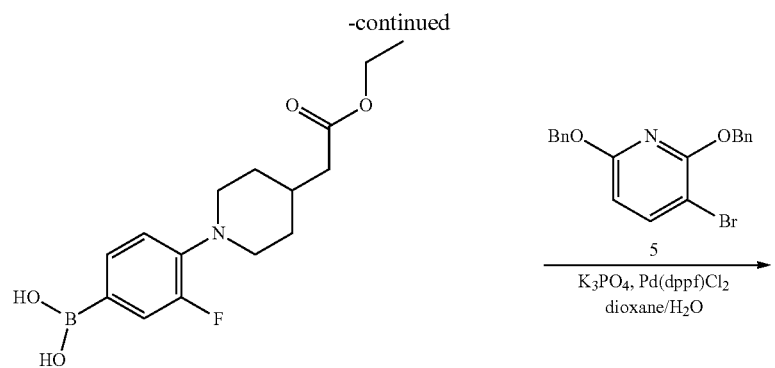
4
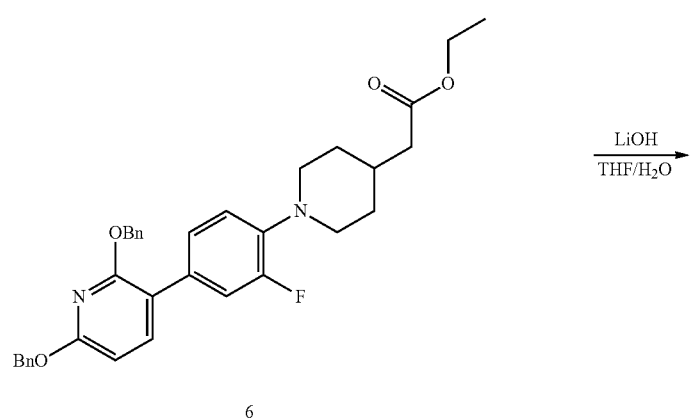
6
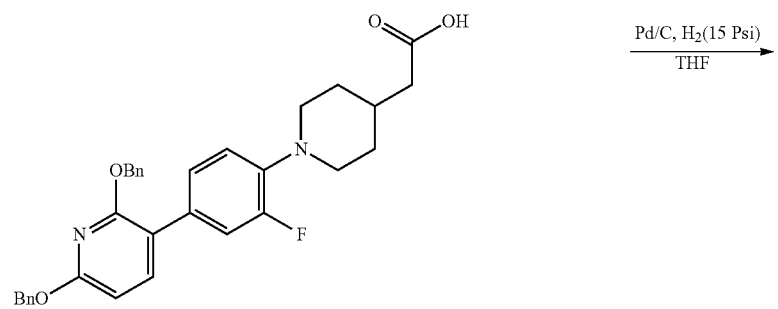
7
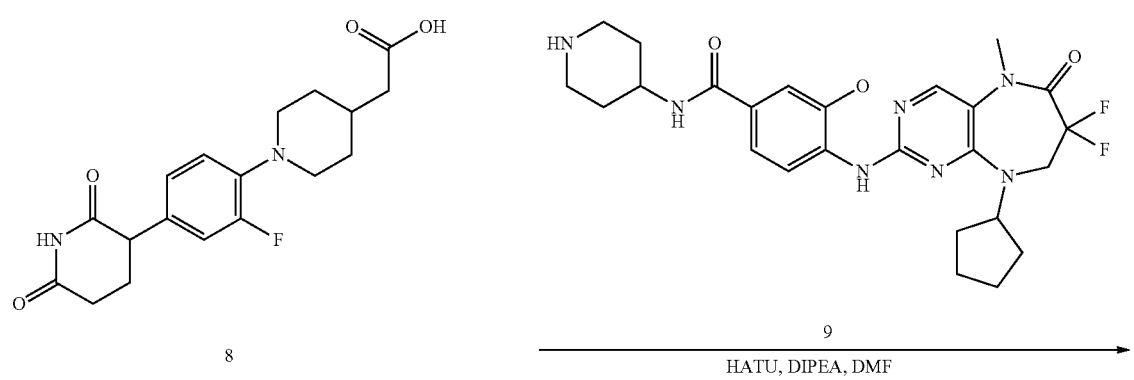

-continued

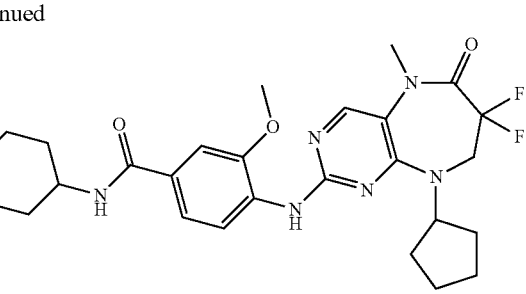

Compound 10

Step 1. Synthesis of ethyl 2-(1-(4-bromo-2-fluorophenyl)piperidin-4-yl)acetate (3)

To a solution of 4-bromo-2-fluoro-1-iodobenzene (1 g, 3.32 mmol) and ethyl 2-(piperidin-4-yl)acetate (682.91 mg, 3.99 mmol) in toluene (10 mL) were added $Cs_2CO_3$ (3.25 g, 9.97 mmol), $Pd_2(dba)_3$ (61 mg, 66.61 μmol) and Xantphos (58 mg, 100.24 μmol) and the mixture was stirred at 100° C. for 14 h. LCMS showed the starting material was consumed and the desired mass was detected. The mixture was filtered and the filter cake was washed with EtOAc (30 mL). The filtrate was concentrated under reduced pressure. The residue was purified by flash silica gel chromatography (12 g SepaFlash Silica Flash Column, Eluent of 2-3% EtOAc/Petroleum ether gradient @ 50 mL/min) to afford ethyl 2-(1-(4-bromo-2-fluorophenyl)piperidin-4-yl)acetate (670 mg, 1.83 mmol, 55.05% yield, 94% purity) as yellow oil. MS $(M+H)^+=344.2$

Step 2. Synthesis of (4-(4-(2-ethoxy-2-oxoethyl)piperidin-1-yl)-3-fluorophenyl)boronic acid (4)

To a solution of ethyl 2-(1-(4-bromo-2-fluorophenyl)piperidin-4-yl)acetate (670 mg, 1.95 mmol) and BPD (643 mg, 2.53 mmol) in dioxane (10 mL) were added KOAc (573.08 mg, 5.84 mmol) and $Pd(dppf)Cl_2$ (28.48 mg, 38.93 μmol) and the resulting mixture was stirred at 80° C. for 14 h. LCMS showed a peak (60%) with desired mass. The mixture was filtered and the filter cake was washed with EtOAc (20 mL). The filtrate was concentrated under reduced pressure. The residue was purified by flash silica gel chromatography (5 g SepaFlash Silica Flash Column, Eluent of 2-3% EtOAc/Petroleum ether gradient @ 50 mL/min) to afford (4-(4-(2-ethoxy-2-oxoethyl)piperidin-1-yl)-3-fluorophenyl)boronic acid (690 mg, crude) as a white solid. MS $(M+H)^+=309.9$

Step 3. Synthesis of ethyl 2-(1-(4-(2,6-bis(benzyloxy)pyridin-3-yl)-2-fluorophenyl)piperidin-4-yl)acetate (6)

To a solution of (4-(4-(2-ethoxy-2-oxoethyl)piperidin-1-yl)-3-fluorophenyl)boronic acid (640 mg, 2.07 mmol), 2,6-bis(benzyloxy)-3-bromopyridine (1.54 g, 4.15 mmol) and $K_3PO_4$ (1.32 g, 6.21 mmol) in dioxane (15 mL) and $H_2O$ (3 mL) was added $Pd(dppf)Cl_2$ (46 mg, 62.87 μmol) under $N_2$ atmosphere and the mixture was stirred at 80° C. for 14 h under $N_2$ atmosphere. LCMS showed a peak (68%) with desired mass. The mixture was dried over $Na_2SO_4$ and filtered. The filter cake was washed with EtOAc (30 mL). The filtrate was concentrated under reduced pressure. The residue was purified by column chromatography ($SiO_2$, Petroleum ether/EtOAc=50/1 to 30/1) to afford ethyl 2-(1-(4-(2,6-bis(benzyloxy)pyridin-3-yl)-2-fluorophenyl)piperidin-4-yl)acetate (730 mg, 1.20 mmol, 57.85% yield, 91% purity) as a yellow solid. MS $(M+H)^+=555.4$

Step 4. Synthesis of 2-(1-(4-(2,6-bis(benzyloxy)pyridin-3-yl)-2-fluorophenyl)piperidin-4-yl)acetic acid (7)

To a solution of ethyl 2-(1-(4-(2,6-bis(benzyloxy)pyridin-3-yl)-2-fluorophenyl)piperidin-4-yl)acetate (730 mg, 1.32 mmol) in THF (10 mL) was added $LiOH·H_2O$ (3 M, 880 μL) and the mixture was stirred at 20° C. for 14 h. LCMS showed 29% of the desired mass and 65% of the starting material remained. Additional $LiOH·H_2O$ (3 M, 880 μL) was added and the mixture was stirred at 60° C. for 14 h. LCMS showed the starting material was consumed and a main peak (91%) with desired mass. The mixture was adjusted the pH=3 with 1 N HCl and diluted with $H_2O$ (10 mL), then extracted with EtOAc (10 mL×3), the combined organic layer was washed with $H_2O$ (10 mL), dried over $Na_2SO_4$ and filtered. The filtrate was concentrated under reduced pressure to afford 2-(1-(4-(2,6-bis(benzyloxy)pyridin-3-yl)-2-fluorophenyl)piperidin-4-yl)acetic acid (660 mg, crude) as a yellow solid. MS $(M+H)^+=527.3$

Step 5. Synthesis of 2-(1-(4-(2,6-dioxopiperidin-3-yl)-2-fluorophenyl)piperidin-4-yl)acetic acid (8)

To a solution of 2-(1-(4-(2,6-bis(benzyloxy)pyridin-3-yl)-2-fluorophenyl)piperidin-4-yl)acetic acid (0.2 g, 379.80 μmol) in THF (5 mL) was added Pd/C (30 mg, 10% purity) under $N_2$ atmosphere, the reaction mixture was degassed and purged with $H_2$ for 3 times. The mixture was stirred at 20° C. for 18 h under $H_2$ (15 Psi). LCMS showed the starting material was consumed and the desired mass was detected. The mixture was filtered and the filter cake was washed with THF (20 mL). The filtrate was concentrated under reduced pressure to afford 2-(1-(4-(2,6-dioxopiperidin-3-yl)-2-fluorophenyl)piperidin-4-yl)acetic acid (110 mg, crude) as a brown solid. MS $(M+H)^+=348.9$

Step 6. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(2-(1-(4-(2,6-dioxopiperidin-3-yl)-2-fluorophenyl)piperidin-4-yl)acetyl)piperidin-4-yl)-3-methoxybenzamide (Compound 10)

To a solution of 2-(1-(4-(2,6-dioxopiperidin-3-yl)-2-fluorophenyl)piperidin-4-yl)acetic acid (50 mg, 143.53 μmol) in DMF (0.8 mL) were added HATU (66 mg, 173.58 µmol) and DIPEA (22.26 mg, 172.23 µmol, 30 µL) and the mixture was stirred at 20° C. for 15 min. Then a solution of 4-((9-cyclopentyl-7,7-difluoro-5-methyl-6-oxo-6,7,8,9-tetrahydro-5H-pyrimido[4,5-b][1,4]diazepin-2-yl)amino)-3-methoxy-N-(piperidin-4-yl)benzamide (50.00 mg, 88.33 µmol, HCl salt) and DIPEA (37.10 mg, 287.05 µmol, 50.00 µL) in DMF (0.7 mL) was added and the mixture was stirred at 20° C. for 0.5 h. LCMS showed a peak (66%) with desired mass. The mixture was diluted with H₂O (10 mL) and extracted with EtOAc (10 mL×3), the combined organic layer was washed with brine (10 mL), dried over Na₂SO₄ and filtered. The filtrate was concentrated under reduced pressure. The crude was purified by prep-HPLC (column: Waters Xbridge 150×25 mm×5 µm; mobile phase: [water (NH₄HCO₃)—ACN]; B %: 41%-71%, 8 min) and prep-HPLC (column: Phenomenex luna C18 150×25 mm×10 µm; mobile phase: [water (FA)—ACN]; B %: 37%-67%, 10 min) and the eluent was lyophilized to afford 4-((9-cyclopentyl-7,7-difluoro-5-methyl-6-oxo-6,7,8,9-tetrahydro-5H-pyrimido[4,5-b][1,4]diazepin-2-yl)amino)-N-(1-(2-(1-(4-(2,6-dioxopiperidin-3-yl)-2-fluorophenyl)piperidin-4-yl)acetyl)piperidin-4-yl)-3-methoxybenzamide (26.8 mg, 29.92 µmol, 20.85% yield, 96% purity) as a brown solid. MS (M+H)⁺= 860.5

¹H NMR (400 MHz, DMSO-d₆) δ=10.81 (s, 1H), 8.30-8.25 (m, 2H), 8.16 (br d, J=7.9 Hz, 1H), 7.97 (s, 1H), 7.51-7.46 (m, 2H), 7.03-6.92 (m, 3H), 4.85-4.69 (m, 1H), 4.49-4.37 (m, 1H), 4.12-3.89 (m, 7H), 3.83-3.73 (m, 1H), 3.32-3.28 (m, 5H), 3.18-3.08 (m, 1H), 2.72-2.61 (m, 5H), 2.35-2.31 (m, 2H), 2.25-2.11 (m, 1H), 2.03-1.88 (m, 4H), 1.86-1.67 (m, 6H), 1.65-1.53 (m, 4H), 1.50-1.31 (m, 4H).

Example 11. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(3-(4-(4-(2,6-dioxopiperidin-3-yl)-2-fluorophenyl)piperazin-1-yl)propanoyl)piperidin-4-yl)-3-methoxybenzamide (Compound 11)

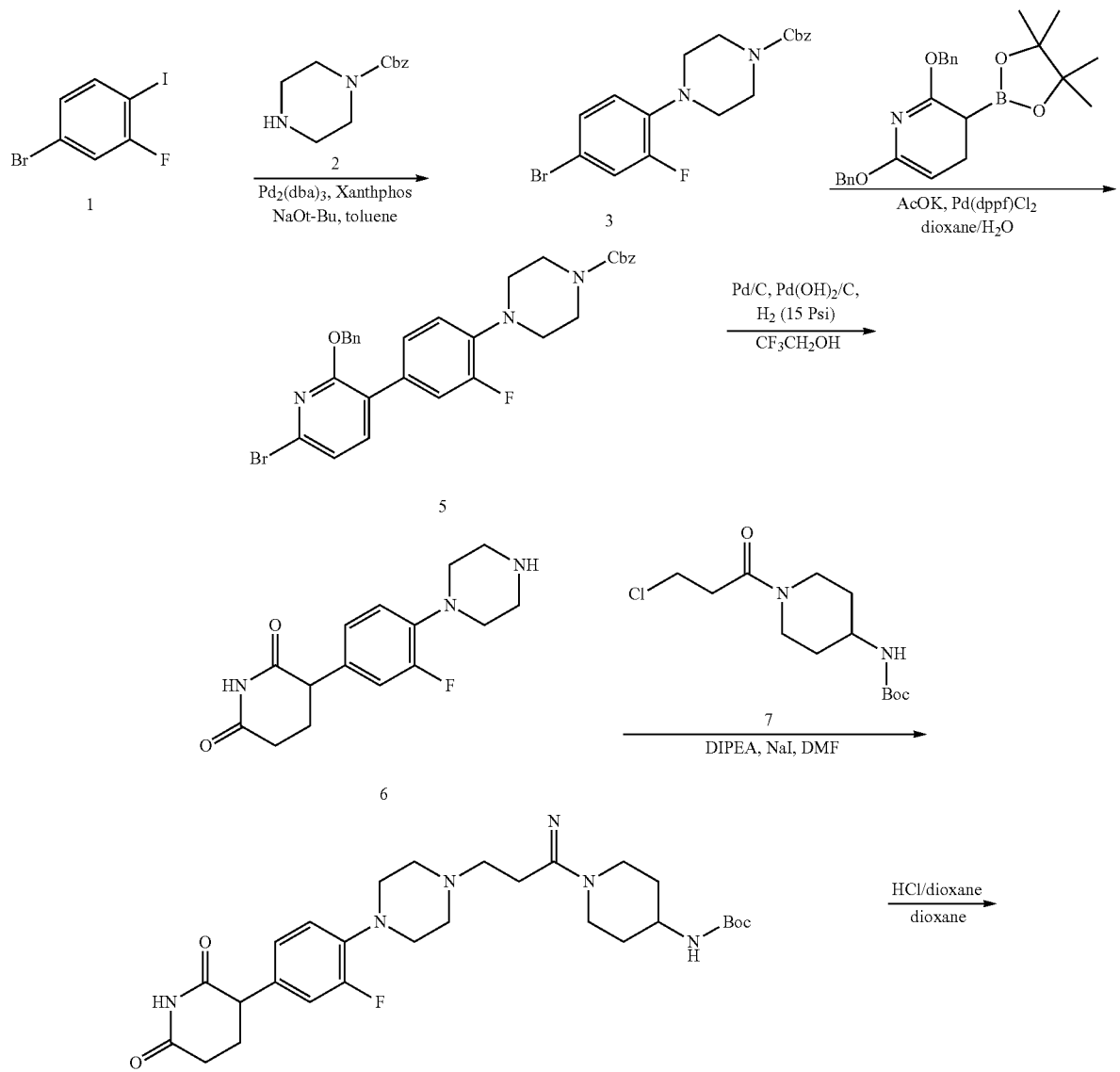

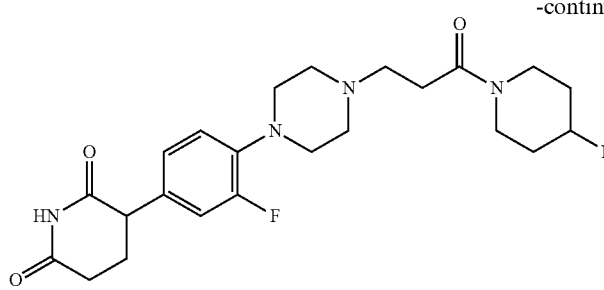

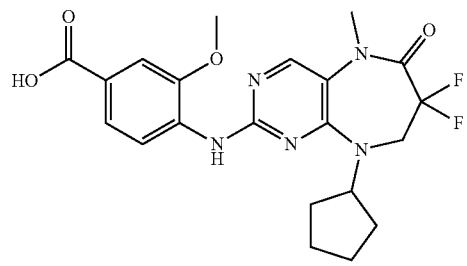

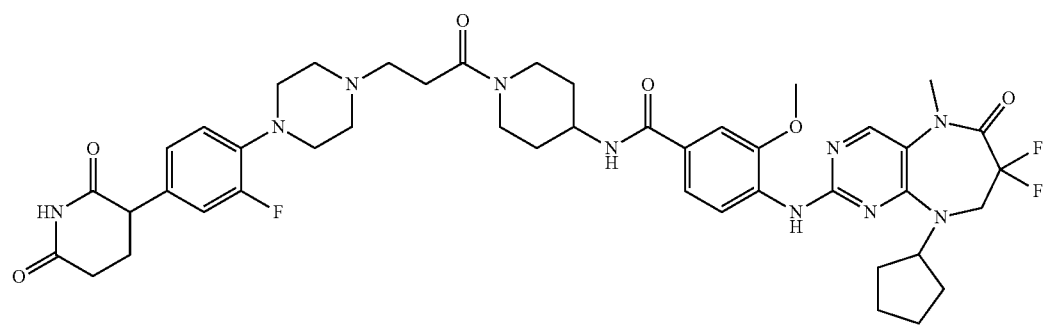

Compound 11

Step 1. Synthesis of benzyl 4-(4-bromo-2-fluorophenyl)piperazine-1-carboxylate (3)

To a mixture of 4-bromo-2-fluoro-1-iodo-benzene (5 g, 16.62 mmol), benzyl piperazine-1-carboxylate (4.39 g, 19.94 mmol, 3.85 mL) and t-BuONa (2 M in THF, 24.93 mL) in toluene (100 mL) were added $Pd_2(dba)_3$ (760.83 mg, 830.86 µmol) and Xantphos (961.50 mg, 1.66 mmol) at 25° C. The resulting mixture was degassed and purged with $N_2$ for three times, then heated to 80° C. and stirred for 2 h under $N_2$ atmosphere. LCMS showed the starting material was consumed completely and the desired mass. The reaction mixture was concentrated. The crude product was purified by flash silica gel chromatography (40 g silica gel column, EtOAc/petroleum ether=0-5%, 100 mL/min) to afford benzyl 4-(4-bromo-2-fluorophenyl)piperazine-1-carboxylate (4 g, 10.17 mmol, 61.21% yield) as yellow oil. MS $(M+H)^+=394.3$

Step 2. Synthesis of benzyl 4-(4-(2,6-bis(benzyloxy)pyridin-3-yl)-2-fluorophenyl)piperazine-1-carboxylate (5)

A mixture of benzyl 4-(4-bromo-2-fluorophenyl)piperazine-1-carboxylate (3.5 g, 8.90 mmol), 2,6-bis(benzyloxy)-3-(4,4,5,5-tetramethyl-1,3,2-dioxaborolan-2-yl)pyridine (4.46 g, 10.68 mmol), KOAc (2.62 g, 26.70 mmol) and $Pd(dppf)Cl_2$ (325.62 mg, 445.01 µmol) in dioxane (40 mL) and $H_2O$ (7 mL) was stirred at 100° C. for 14 h under the protection of $N_2$. LCMS showed the starting material was consumed completely and the desired mass. The reaction mixture was diluted with EtOAc (100 mL). The resulting mixture was dried over $Na_2SO_4$, filtered and concentrated. The crude product was purified by flash silica gel chromatography (40 g silica gel column, EtOAc/petroleum ether=0-10%, 100 mL/min) to afford benzyl 4-(4-(2,6-bis(benzyloxy)pyridin-3-yl)-2-fluorophenyl)piperazine-1-carboxylate (2.9 g, 4.80 mmol, 53.97% yield) as yellow oil.
MS $(M+H)^+=604.7$

Step 3. Synthesis of 3-(3-fluoro-4-(piperazin-1-yl)phenyl)piperidine-2,6-dione (6)

To a solution of benzyl 4-(4-(2,6-bis(benzyloxy)pyridin-3-yl)-2-fluorophenyl)piperazine-1-carboxylate (2.9 g, 4.80 mmol) in $CF_3CH_2OH$ (50 mL) was added Pd/C (300 mg, 10% purity) at 25° C. under the protection of $N_2$. The resulting mixture was purged and degassed with $H_2$ for three times, then stirred at 25° C. for 14 h under $H_2$ (15 Psi). LCMS showed major peak with mass of intermediate (3-(3-fluoro-4-(piperazin-1-yl)phenyl)pyridine-2,6-diol). Then $Pd(OH)_2/C$ (400 mg, 20% purity) was added and the resulting mixture was stirred at 45° C. for another 4 h under $H_2$ (15 Psi). LCMS showed desired mass. The reaction mixture was filtered and washed with EtOH (50 mL). The filtrate was concentrated to afford 3-(3-fluoro-4-(piperazin-1-yl)phenyl)piperidine-2,6-dione (1.2 g, crude) as a white solid. The crude product was used for the next step directly.
MS $(M+H)^+=292.3$

Step 4. Synthesis of tert-butyl (1-(3-(4-(4-(2,6-dioxopiperidin-3-yl)-2-fluorophenyl)piperazin-1-yl)propanoyl)piperidin-4-yl)carbamate (8)

To a mixture of 3-(3-fluoro-4-(piperazin-1-yl)phenyl)piperidine-2,6-dione (1.2 g, 4.12 mmol) and tert-butyl (1-(3-chloropropanoyl)piperidin-4-yl)carbamate (1.92 g, 6.59 mmol) in DMF (20 mL) were added DIPEA (1.60 g, 12.36 mmol, 2.15 mL) and NaI (61.74 mg, 411.92 µmol) at 25° C. The resulting mixture was stirred at 25° C. for 1 h, then heated to 80° C. and stirred at 80° C. for 13 h. LCMS showed the starting material was consumed completely and the desired mass. After cooling to 25° C., the reaction mixture was poured into H$_2$O (60 mL). The resulting mixture was extracted with EtOAc (20 mL×5). The combined organic layers were washed with brine (15 mL×3), dried over Na$_2$SO$_4$ and concentrated. The crude product was triturated with petroleum ether/EtOAc (30 mL, 3:1) to afford tert-butyl (1-(3-(4-(4-(2,6-dioxopiperidin-3-yl)-2-fluorophenyl)piperazin-1-yl)propanoyl)piperidin-4-yl)carbamate (2 g, crude) as a white solid.

MS (M+H)$^+$=546.7

$^1$H NMR (400 MHz, DMSO-d$_6$) δ=10.81 (s, 1H), 7.08-6.91 (m, 2H), 6.90-6.84 (m, 1H), 6.07 (dd, J=2.4, 16.7 Hz, 1H), 4.23-4.19 (m, 1H), 3.88-3.72 (m, 3H), 3.58-3.37 (m, 2H), 3.12-2.94 (m, 4H), 2.71-2.61 (m, 2H), 2.59-2.52 (m, 7H), 2.06-1.94 (m, 1H), 1.77-1.68 (m, 2H), 1.38 (s, 9H), 1.28-1.15 (m, 2H).

Step 5. Synthesis of 3-(4-(4-(3-(4-aminopiperidin-1-yl)-3-oxopropyl)piperazin-1-yl)-3-fluorophenyl)piperidine-2,6-dione (9)

To a solution of tert-butyl (1-(3-(4-(4-(2,6-dioxopiperidin-3-yl)-2-fluorophenyl)piperazin-1-yl)propanoyl)piperidin-4-yl)carbamate (2 g, 3.67 mmol) in dioxane (10 mL) was added HCl/dioxane (4 M, 10 mL) at 20° C. The resulting mixture was stirred at 20° C. for 1 h. LCMS showed the reaction was completed. The reaction mixture was concentrated to afford 3-(4-(4-(3-(4-aminopiperidin-1-yl)-3-oxopropyl)piperazin-1-yl)-3-fluorophenyl)piperidine-2,6-dione (1.9 g, crude, 2HCl salt) as yellow solid. MS (M+H)$^+$=446.0

Step 6. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(3-(4-(4-(2,6-dioxopiperidin-3-yl)-2-fluorophenyl)piperazin-1-yl)propanoyl)piperidin-4-yl)-3-methoxybenzamide (Compound 11)

To a mixture of 3-(4-(4-(3-(4-aminopiperidin-1-yl)-3-oxopropyl)piperazin-1-yl)-3-fluorophenyl)piperidine-2,6-dione (1.4 g, 2.70 mmol, 2HCl salt), 4-((9-cyclopentyl-7,7-difluoro-5-methyl-6-oxo-6,7,8,9-tetrahydro-5H-pyrimido[4,5-b][1,4]diazepin-2-yl)amino)-3-methoxybenzoic acid (1.03 g, 2.30 mmol) and DIPEA (1.40 g, 10.80 mmol) in DMF (8 mL) was added HATU (1.13 g, 2.97 mmol) at 20° C. The resulting mixture was stirred at 20° C. for 1 h. LCMS showed the starting material was consumed completely and the desired mass. The reaction mixture was neutralized by AcOH to pH=6. The resulting mixture was purified by prep-HPLC (column: Phenomenex luna C18 (250×70 mm, 10 μm); mobile phase: [water (TFA)—ACN]; B %: 15%-45%, 20 min) followed by prep-HPLC (column: Waters Xbridge C18 150×50 mm×10 μm; mobile phase: [water (NH$_4$HCO$_3$)—ACN]; B %: 30%-60%, 10 min) and the eluent was lyophilized to afford 4-((9-cyclopentyl-7,7-difluoro-5-methyl-6-oxo-6,7,8,9-tetrahydro-5H-pyrimido[4,5-b][1,4]diazepin-2-yl)amino)-N-(1-(3-(4-(4-(2,6-dioxopiperidin-3-yl)-2-fluorophenyl)piperazin-1-yl)propanoyl)piperidin-4-yl)-3-methoxybenzamide (543.2 mg, 607.80 μmol, 22.51% yield, 97.9% purity) as a white solid. MS (M+H)$^+$=875.5

$^1$H NMR (400 MHz, DMSO-d$_6$) δ=10.80 (s, 1H), 8.30-8.24 (m, 2H), 8.14 (br d, J=7.5 Hz, 1H), 7.96 (s, 1H), 7.53-7.46 (m, 2H), 7.06-6.92 (m, 3H), 4.80-4.70 (m, 1H), 4.46-4.33 (m, 1H), 4.10-3.94 (m, 4H), 3.93 (s, 3H), 3.79 (br dd, J=4.8, 11.4 Hz, 1H), 3.32-3.31 (m, 3H), 3.18-3.09 (m, 1H), 3.05-2.91 (m, 4H), 2.65-2.53 (m, 10H), 2.26-2.14 (m, 1H), 2.04-1.73 (m, 6H), 1.71-1.65 (m, 2H), 1.65-1.55 (m, 4H), 1.50-1.35 (m, 2H).

Example 12. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(4-(2-(4-(4-(2,6-dioxopiperidin-3-yl)-2-fluorophenyl)piperazin-1-yl)ethyl)piperidin-1-yl)-3-methoxybenzamide (Compound 12)

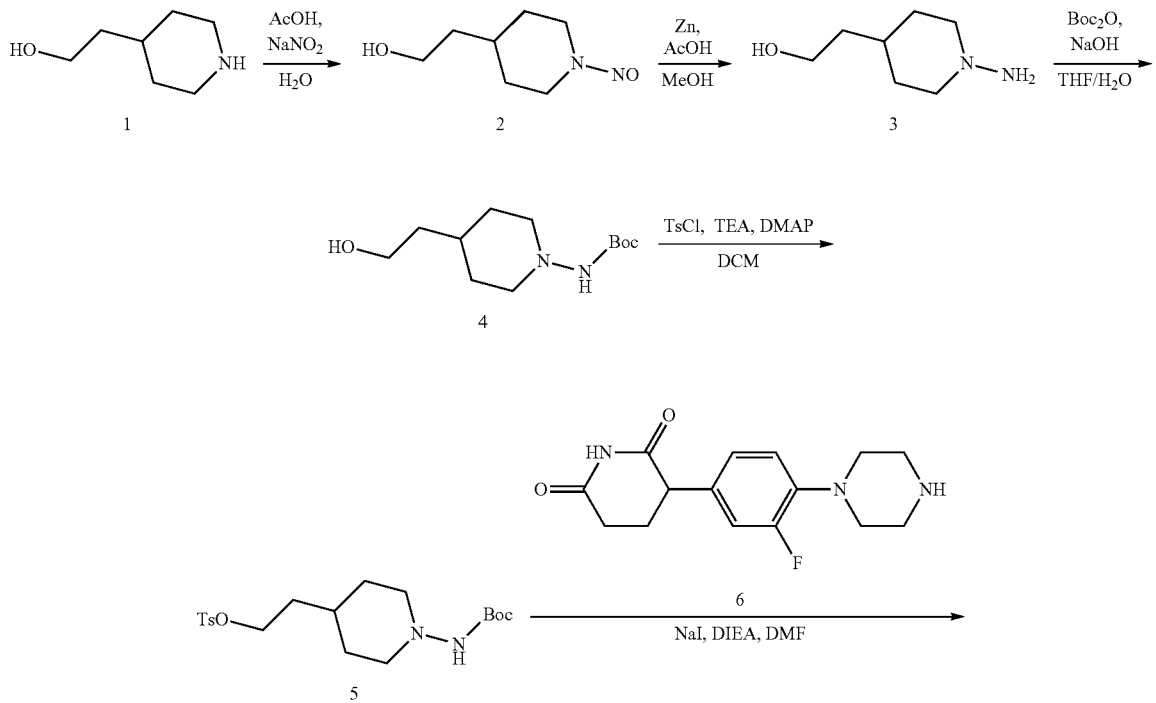

-continued
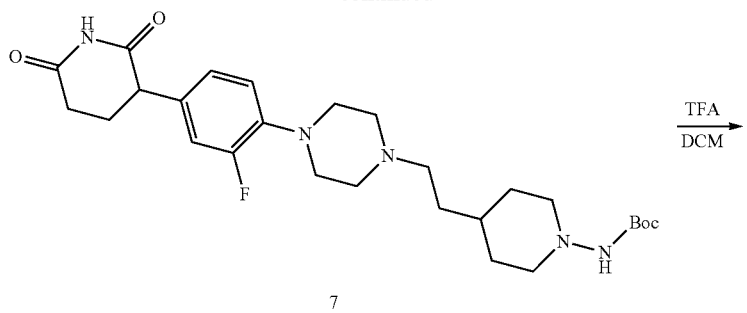
7
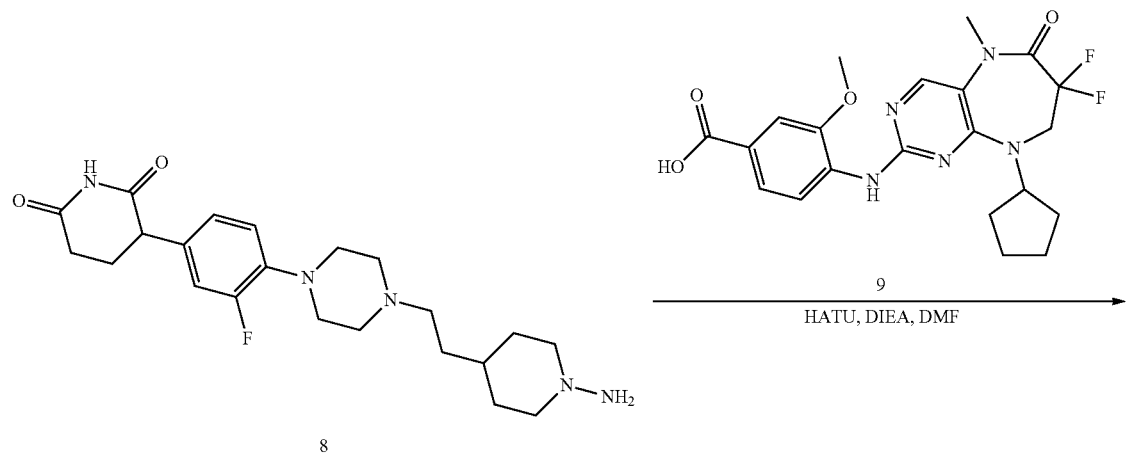
8
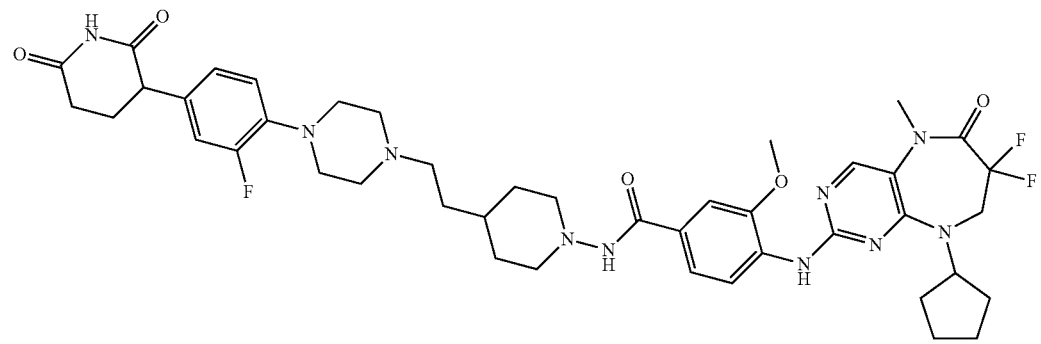
Compound 12
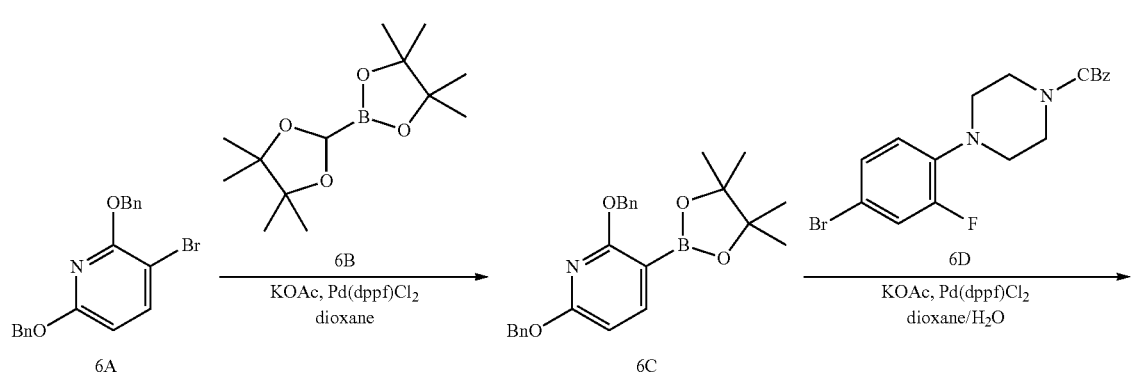

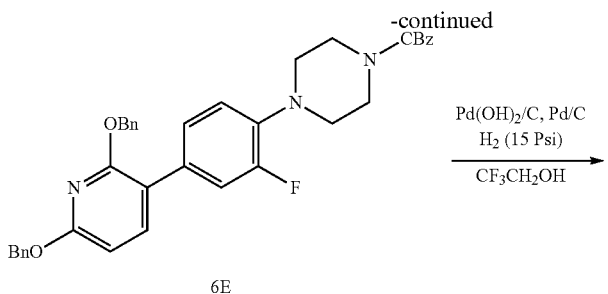 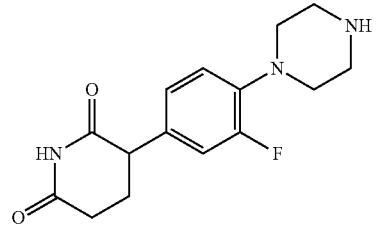

Step 1. Synthesis of 2-(1-nitrosopiperidin-4-yl)ethan-1-ol (2)

To a solution of 2-(piperidin-4-yl)ethan-1-ol (6 g, 46.44 mmol) in H₂O (120 mL) was added NaNO₂ (6.41 g, 92.88 mmol) in portions at 0° C. Then AcOH (8.37 g, 139.32 mmol, 7.97 mL) was added drop-wise at 0° C. The resulting mixture was allowed to warm to 15° C. slowly and stirred at 15° C. for 16 hours. LCMS showed 23% of starting material remained and 75% of desired mass was detected. The reaction mixture was stirred at 15° C. for further 16 hours, LCMS showed 12% of starting material remained and 81% of desired mass was detected. To the reaction mixture was added saturated NaHCO₃ solution to adjust pH >7, the resulting mixture was extracted with a solution (EtOAc:MeOH=10:1, 250 mL×11), the combined organic layers were dried over Na₂SO₄, filtered and concentrated to afford 2-(1-nitrosopiperidin-4-yl)ethan-1-ol (7.98 g) as a yellow oil, which was used in the next step directly. MS (M+H)⁺=159.2

Step 2. Synthesis of 2-(1-aminopiperidin-4-yl)ethan-1-ol (3)

To a solution of 2-(1-nitrosopiperidin-4-yl)ethan-1-ol (7.98 g, 50.44 mmol) in MeOH (70 mL) was added Zn (16.49 g, 252.22 mmol) at 0° C., than AcOH (45.44 g, 756.65 mmol, 43.27 mL) was added dropwise at 0° C. The resulting mixture was allowed to warm to 15° C. slowly and stirred at 15° C. for 2 h. LCMS showed the starting material was consumed completely and a main peak (92%) with desired mass. The mixture was filtered and the filter cake was washed with MeOH (200 mL). The filtrate was concentrated in vacuum. The yellow solid was treated with MeOH (80 mL) and stirred for 10 minutes, filtered, the filter cake was discard. The filtrate was concentrated in vacuum to afford 2-(1-aminopiperidin-4-yl)ethan-1-ol (29.7 g) as a yellow gum, which was used in the next step directly. MS (M+H)⁺=145.2

Step 3. Synthesis of tert-butyl (4-(2-hydroxyethyl)piperidin-1-yl)carbamate (4)

To a solution of 2-(1-aminopiperidin-4-yl)ethan-1-ol (29.7 g, 205.94 mmol) in THF (80 mL) was added a solution of NaOH (24.71 g, 617.83 mmol) in H₂O (40 mL), followed by the addition of Boc₂O (44.95 g, 205.94 mmol, 47.31 mL), the resulting mixture was stirred at 15° C. for 16 hours. TLC showed the starting material was consumed completely. The reaction mixture was filtered and the filter cake was washed with EtOAc (100 mL), the filtrate was diluted with H₂O (200 mL) and extracted with EtOAc (150 mL×3). The combined organic layers were dried over Na₂SO₄, filtered and concentrated in vacuum. The residue was purified by flash silica gel chromatography (40 g SepaFlash Silica Flash Column, Eluent of 14-40% EtOAc/Petroleum ether gradient @ 100 mL/min) to afford tert-butyl (4-(2-hydroxyethyl)piperidin-1-yl)carbamate (3.58 g, 14.65 mmol, 7.11% yield) as an off-white solid. MS (M−56+H)⁺=189.1

Step 4. Synthesis of 2-(1-((tert-butoxycarbonyl)amino)piperidin-4-yl)ethyl 4-methylbenzenesulfonate (5)

To a solution of tert-butyl (4-(2-hydroxyethyl)piperidin-1-yl)carbamate (3.58 g, 14.65 mmol) in DCM (50 mL) were added TEA (2.97 g, 29.30 mmol, 4.08 mL), DMAP (17.90 mg, 146.52 μmol) and TosCl (4.19 g, 21.98 mmol), the mixture was stirred at 15° C. for 16 hours. TLC (SiO₂, Petroleum ether:EtOAc=3:1) indicated reactant was consumed completely and one major new spot with lower polarity was detected. The reaction was concentrated in vacuum. The residue was purified by flash silica gel chromatography (20 g SepaFlash Silica Flash Column, Eluent of 16-50% EtOAc/Petroleum ether gradient @ 100 mL/min) to afford 2-(1-((tert-butoxycarbonyl)amino)piperidin-4-yl) ethyl 4-methylbenzenesulfonate (5.05 g, 12.67 mmol, 86.48% yield) as a white solid. MS (M+H)⁺=399.1

Step 5. Synthesis of 2,6-bis(benzyloxy)-3-(4,4,5,5-tetramethyl-1,3,2-dioxaborolan-2-yl)pyridine (6C)

A mixture of 2,6-bis(benzyloxy)-3-bromopyridine (20 g, 54.02 mmol), 4,4,5,5-tetramethyl-2-(4,4,5,5-tetramethyl-1,3-dioxolan-2-yl)-1,3,2-dioxaborolane (17.99 g, 70.22 mmol), KOAc (10.60 g, 108.04 mmol), Pd(dppf)Cl₂ (1.98 g, 2.70 mmol) in dioxane (300 mL) was degassed and purged with N₂ for 3 times, and then the mixture was stirred at 100° C. for 16 hours under N₂ atmosphere. LCMS showed 2,6-bis(benzyloxy)-3-bromopyridine was consumed completely and 26% of desired mass was detected. The reaction mixture was filtered and the filter cake was washed with EtOAc (30 mL). The filtrate was concentrated in vacuum. The residue was purified by flash silica gel chromatography (330 g SepaFlash Silica Flash Column, Eluent of 0~90% EtOAc/Petroleum ether gradient @ 100 mL/min) to afford 2,6-bis(benzyloxy)-3-(4,4,5,5-tetramethyl-1,3,2-dioxaborolan-2-yl)pyridine (14.05 g, 33.67 mmol, 62.33% yield) as a brown gum.

MS (M+H)⁺=417.9

Step 6. Synthesis of benzyl 4-(4-(2,6-bis(benzyloxy)pyridin-3-yl)-2-fluorophenyl)piperazine-1-carboxylate (6E)

A mixture of 2,6-bis(benzyloxy)-3-(4,4,5,5-tetramethyl-1,3,2-dioxaborolan-2-yl)pyridine (6 g, 14.38 mmol), benzyl 4-(4-bromo-2-fluorophenyl)piperazine-1-carboxylate (3.96 g, 10.06 mmol), KOAc (4.23 g, 43.13 mmol) and Pd(dppf)Cl$_2$ (526.02 mg, 718.90 µmol) in dioxane (90 mL) and H$_2$O (15 mL) was stirred at 100° C. for 16 hours under the protection of N$_2$. LCMS showed 10% of 2,6-bis(benzyloxy)-3-(4,4,5,5-tetramethyl-1,3,2-dioxaborolan-2-yl)pyridine remained and 53% of the desired mass was detected. The reaction mixture was concentrated. The residue was diluted with H$_2$O (100 mL) and extracted with EtOAc (80 mL×3). The combined organic layers were dried over Na$_2$SO$_4$, filtered and concentrated in vacuum. The residue was purified by flash silica gel chromatography (80 g SepaFlash Silica Flash Column, Eluent of 4-5% EtOAc/Petroleum ether gradient @ 100 mL/min) to afford benzyl 4-(4-(2,6-bis(benzyloxy)pyridin-3-yl)-2-fluorophenyl)piperazine-1-carboxylate (3.98 g, 6.59 mmol, 45.85% yield) as a light yellow oil.

MS (M+H)$^+$=604.1

Step 7. Synthesis of 3-(3-fluoro-4-(piperazin-1-yl)phenyl)piperidine-2,6-dione (6)

To a solution of benzyl 4-(4-(2,6-bis(benzyloxy)pyridin-3-yl)-2-fluorophenyl)piperazine-1-carboxylate (3.95 g, 6.54 mmol) in CF$_3$CH$_2$OH (100 mL) were added Pd/C (1 g, 10% purity) and Pd(OH)$_2$/C (1 g, 10% purity) at 15° C. under the protection of N$_2$. The resulting mixture was degassed and purged with H$_2$ for three times, then stirred at 45° C. for 16 h under H$_2$ (15 Psi) atmosphere. LCMS showed the starting material was consumed completely and 63% of desired mass was detected. The reaction mixture was filtered and washed with CF$_3$CH$_2$OH (100 mL). The filtrate was concentrated to afford 3-(3-fluoro-4-(piperazin-1-yl)phenyl)piperidine-2,6-dione (2.53 g) as a light brown gum, which was used in the next step directly. MS (M+H)$^+$=292.1

Step 8. Synthesis of tert-butyl (4-(2-(4-(4-(2,6-dioxopiperidin-3-yl)-2-fluorophenyl)piperazin-1-yl)ethyl)piperidin-1-yl)carbamate (7)

To a solution of 3-(3-fluoro-4-(piperazin-1-yl)phenyl)piperidine-2,6-dione (300 mg, 1.03 mmol) and 2-(1-((tert-butoxycarbonyl)amino)piperidin-4-yl)ethyl 4-methylbenzenesulfonate (615.58 mg, 1.54 mmol) in DMF (7 mL) were added DIPEA (399.28 mg, 3.09 mmol, 538.12 µL) and NaI (15.44 mg, 102.98 µmol), the mixture was stirred at 60° C. for 16 hours. LCMS showed 3-(3-fluoro-4-(piperazin-1-yl)phenyl)piperidine-2,6-dione was consumed completely and 63% of the desired mass under 254 nm was detected. The reaction mixture was diluted with H$_2$O (100 mL) and extracted with DCM (60 mL×3). The combined organic layers were washed with brine (100 mL×4), dried over Na$_2$SO$_4$, filtered. The filtrate was concentrated in vacuum. The residue was triturated with a mixture (MTBE: EtOAc=10 mL:10 mL) for 10 minutes, the suspension was filtered and the filter cake was washed with MTBE (20 mL). The filter cake was collected and dried in vacuo to afford tert-butyl (4-(2-(4-(4-(2,6-dioxopiperidin-3-yl)-2-fluorophenyl)piperazin-1-yl)ethyl)piperidin-1-yl)carbamate (250 mg, 482.97 µmol, 46.90% yield) as a brown solid. MS (M+H)$^+$=518.2

Step 9. Synthesis of 3-(4-(4-(2-(1-aminopiperidin-4-yl)ethyl)piperazin-1-yl)-3-fluorophenyl)piperidine-2,6-dione (8)

To a solution of tert-butyl (4-(2-(4-(4-(2,6-dioxopiperidin-3-yl)-2-fluorophenyl)piperazin-1-yl)ethyl)piperidin-1-yl)carbamate (100 mg, 193.19 µmol) in DCM (3 mL) was added TFA (220.28 mg, 1.93 mmol, 143.04 µL), the mixture was stirred at 15° C. for 12 hours. LCMS showed the starting material was consumed completely and 77% of desired mass was detected. The reaction mixture was concentrated in vacuum to afford 3-(4-(4-(2-(1-aminopiperidin-4-yl)ethyl)piperazin-1-yl)-3-fluorophenyl)piperidine-2,6-dione (105 mg, TFA salt) as a brown gum, which was used in the next step directly. MS (M+H)$^+$=418.2

Step 10. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(4-(2-(4-(4-(2,6-dioxopiperidin-3-yl)-2-fluorophenyl)piperazin-1-yl)ethyl)piperidin-1-yl)-3-methoxybenzamide (Compound 12)

To a solution of 4-((9-cyclopentyl-7,7-difluoro-5-methyl-6-oxo-6,7,8,9-tetrahydro-5H-pyrimido[4,5-b][1,4]diazepin-2-yl)amino)-3-methoxybenzoic acid (90 mg, 201.15 µmol) in DMF (2 mL) were added HATU (114.72 mg, 301.72 µmol) and DIPEA (259.97 mg, 2.01 mmol, 350.36 µL), the mixture was stirred at 15° C. for 15 minutes, then 3-(4-(4-(2-(1-aminopiperidin-4-yl)ethyl)piperazin-1-yl)-3-fluorophenyl)piperidine-2,6-dione (100.45 mg, 221.26 µmol, HCl salt) was added and the resulting mixture was stirred at 15° C. for 1 hours. LCMS showed the starting material was consumed completely and 47% of desired mass was detected. To the mixture was added CH$_3$COOH to adjust pH<7 and purified by prep-HPLC (column: Phenomenex C18 75×30 mm×3 µm; mobile phase: [water (FA)—ACN]; B %: 15%-45%, 7 min) followed by prep-HPLC (column: Waters Xbridge 150×25 mm×5 µm; mobile phase: [water (NH$_4$CO$_3$)—ACN]; B %: 43%-73%, 8 min), the eluent was freeze-dried to afford 4-((9-cyclopentyl-7,7-difluoro-5-methyl-6-oxo-6,7,8,9-tetrahydro-5H-pyrimido[4,5-b][1,4]diazepin-2-yl)amino)-N-(4-(2-(4-(4-(2,6-dioxopiperidin-3-yl)-2-fluorophenyl)piperazin-1-yl)ethyl)piperidin-1-yl)-3-methoxybenzamide (12.6 mg, 14.58 µmol, 7.25% yield, 98% purity) as a white solid. MS (M+H)$^+$=847.3

$^1$H NMR (400 MHz, DMSO-d$_6$) δ=10.81 (s, 1H), 9.27 (s, 1H), 8.36-8.18 (m, 2H), 7.96 (s, 1H), 7.54-7.34 (m, 2H), 7.11-6.83 (m, 3H), 4.85-4.69 (m, 1H), 4.04 (br t, J=14.0 Hz, 2H), 3.93 (s, 3H), 3.80 (br dd, J=4.6, 11.8 Hz, 1H), 3.30 (br s, 3H), 3.00 (br s, 6H), 2.79-2.73 (m, 2H), 2.70-2.57 (m, 6H), 2.39-2.33 (m, 2H), 2.24-2.15 (m, 1H), 2.04-1.98 (m, 1H), 1.94 (br s, 2H), 1.71 (br s, 4H), 1.59 (br s, 4H), 1.43 (br d, J=2.8 Hz, 2H), 1.30 (br s, 3H).

Example 13. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(2-(4-(4-(2,6-dioxopiperidin-3-yl)-2-fluorophenyl)piperazin-1-yl)acetyl)piperidin-3-yl)-3-methoxybenzamide (Compound 13)

Step 1. Synthesis of tert-butyl (1-(2-chloroacetyl)piperidin-3-yl)carbamate (3)

To a solution of tert-butyl piperidin-3-ylcarbamate (4 g, 19.97 mmol) and TEA (4.04 g, 39.94 mmol, 5.56 mL) in DCM (50 mL) was added 2-chloroacetyl chloride (2.26 g,

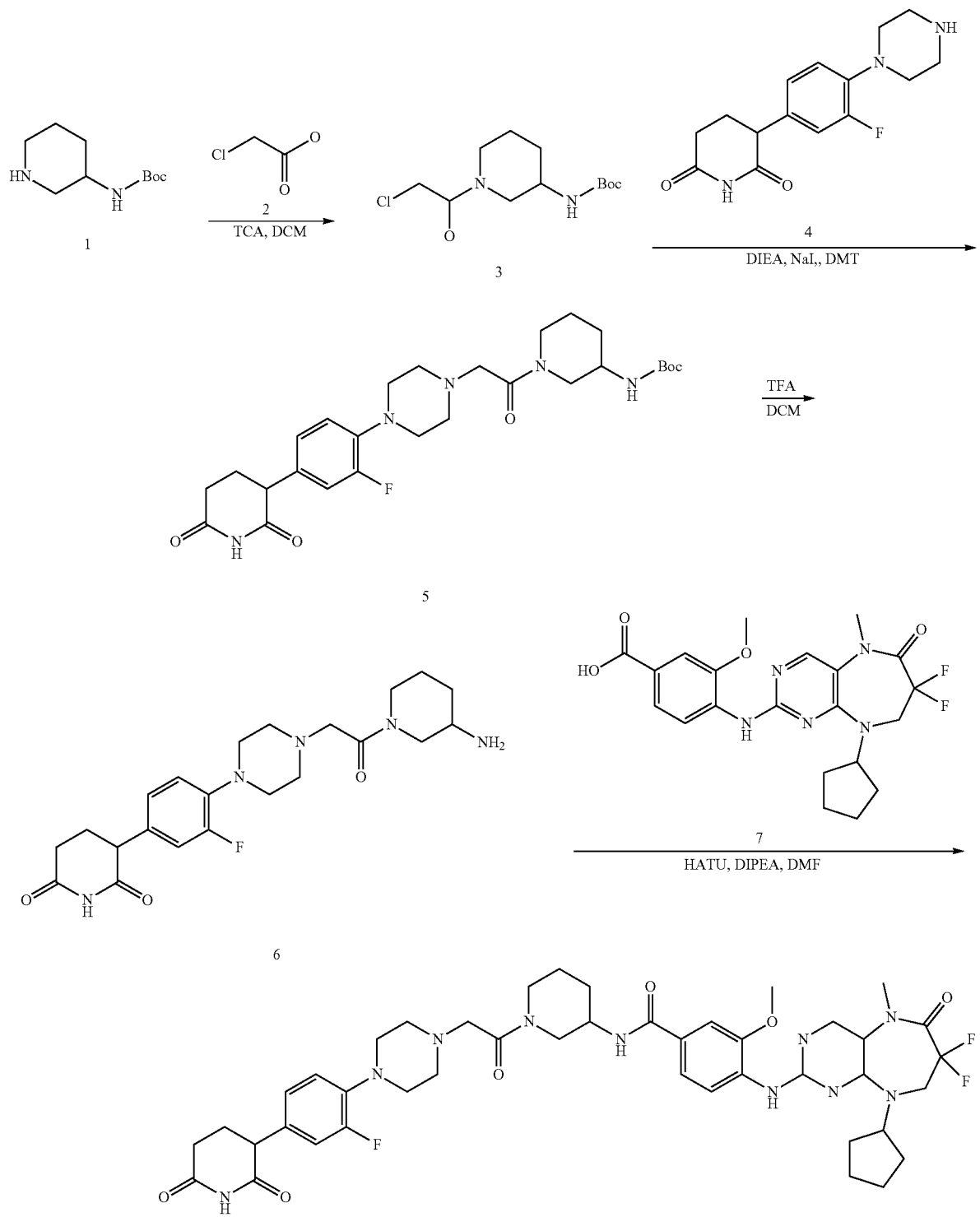

Compound 13

19.97 mmol, 1.59 mL) dropwise at 0° C., after addition, the resulting material was stirred at 15° C. for 2 hours. TLC (SiO$_2$, Petroleum ether:EtOAc=1:2) showed trace of tert-butyl piperidin-3-ylcarbamate remained and one major spot with lower polarity was detected. The mixture was concentrated in vacuum. The residue was purified by flash silica gel chromatography (20 g SepaFlash Silica Flash Column, Eluent of 12-18% EtOAc/Petroleum ether gradient @ 100 mL/min) to afford tert-butyl (1-(2-chloroacetyl)piperidin-3-yl)carbamate (3.15 g, 11.38 mmol, 56.99% yield) as a brown solid.

MS (M−100+H)$^+$=177.1

Step 2. Synthesis of tert-butyl (1-(2-(4-(4-(2,6-dioxopiperidin-3-yl)-2-fluorophenyl)piperazin-1-yl)acetyl)piperidin-3-yl)carbamate (5)

To a solution of 3-(3-fluoro-4-(piperazin-1-yl)phenyl)piperidine-2,6-dione (300 mg, 1.03 mmol) and tert-butyl (1-(2-chloroacetyl)piperidin-3-yl)carbamate (228.00 mg, 823.84 μmol) in DMF (10 mL) were added DIPEA (399.28 mg, 3.09 mmol, 538.12 μL) and NaI (15.44 mg, 102.98 μmol), the mixture was stirred at 60° C. for 16 hours. LCMS showed a peak (79%) with desired mass under 254 nm. The reaction mixture was diluted with H$_2$O (100 mL) and extracted with EtOAc (50 mL×3). The combined organic layers were washed with brine (100 mL×3), dried over Na$_2$SO$_4$, filtered and concentrated in vacuum. The residue was purified by prep-HPLC (column: Phenomenex luna C18 150×40 mm×15 μm; mobile phase: [water (FA)—ACN]; B %: 10%-40%, 10 min), the eluent was freeze-dried to afford tert-butyl (1-(2-(4-(4-(2,6-dioxopiperidin-3-yl)-2-fluorophenyl)piperazin-1-yl)acetyl)piperidin-3-yl)carbamate (150 mg, 282.16 μmol, 27.40% yield) as a white solid. MS (M+H)$^+$=532.2

Step 3. Synthesis of 3-(4-(4-(2-(3-aminopiperidin-1-yl)-2-oxoethyl)piperazin-1-yl)-3-fluorophenyl)piperidine-2,6-dione (6)

To a solution of tert-butyl (1-(2-(4-(4-(2,6-dioxopiperidin-3-yl)-2-fluorophenyl)piperazin-1-yl)acetyl)piperidin-3-yl)carbamate (150 mg, 282.16 μmol) in DCM (3 mL) was added TFA (308.00 mg, 2.70 mmol, 200 μL), the mixture was stirred at 15° C. for 16 hours. LCMS showed the starting material was consumed completely and a major peak (100% of) with desired mass. The reaction mixture was concentrated in vacuum to afford 3-(4-(4-(2-(3-aminopiperidin-1-yl)-2-oxoethyl)piperazin-1-yl)-3-fluorophenyl)piperidine-2,6-dione (155 mg, TFA salt) as a brown oil.

MS (M+H)$^+$=432.2

Step 4. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(2-(4-(4-(2,6-dioxopiperidin-3-yl)-2-fluorophenyl)piperazin-1-yl)acetyl)piperidin-3-yl)-3-methoxybenzamide (Compound 13)

To a solution of 4-((9-cyclopentyl-7,7-difluoro-5-methyl-6-oxo-6,7,8,9-tetrahydro-5H-pyrimido[4,5-b][1,4]diazepin-2-yl)amino)-3-methoxybenzoic acid (120 mg, 268.20 μmol) in DMF (3 mL) were added HATU (132.57 mg, 348.65 μmol) and DIPEA (207.97 mg, 1.61 mmol, 280.29 μL), the mixture was stirred at 15° C. for 15 minutes, then 3-(4-(4-(2-(3-aminopiperidin-1-yl)-2-oxoethyl)piperazin-1-yl)-3-fluorophenyl)piperidine-2,6-dione (146.31 mg, 268.20 μmol, TFA salt) was added and the resulting mixture was stirred at 15° C. for 1 hour. LCMS showed a main peak (94%) with desired mass. To the mixture was added CH$_3$COOH to adjust pH<7 and the resulting mixture was purified by prep-HPLC (column: Phenomenex luna C18 150×25 mm×10 μm; mobile phase: [water (FA)—ACN]; B %: 26%-56%, 10 min) followed by prep-HPLC (column: Waters Xbridge 150×25 mm×5 μm; mobile phase: [water (NH$_4$HCO$_3$)—ACN]; B %: 40%-70%, 8 min), the eluent was freeze-dried to afford 4-((9-cyclopentyl-7,7-difluoro-5-methyl-6-oxo-6,7,8,9-tetrahydro-5H-pyrimido[4,5-b][1,4]diazepin-2-yl)amino)-N-(1-(2-(4-(4-(2,6-dioxopiperidin-3-yl)-2-fluorophenyl)piperazin-1-yl)acetyl)piperidin-3-yl)-3-methoxybenzamide (56.7 mg, 64.54 μmol, 24.07% yield, 98% purity) as a white solid. MS (M+H)$^+$=861.3

$^1$H NMR (400 MHz, DMSO-d$_6$) δ=10.81 (s, 1H), 8.32-8.23 (m, 2H), 8.17 (br t, J=8.6 Hz, 1H), 7.98 (s, 1H), 7.54-7.43 (m, 2H), 7.08-6.87 (m, 3H), 4.83-4.68 (m, 1H), 4.44-4.11 (m, 1H), 4.04 (br t, J=14.0 Hz, 3H), 3.93 (d, J=8.6 Hz, 3H), 3.80 (br dd, J=5.4, 11.1 Hz, 2H), 3.36-3.25 (m, 5H), 3.21-2.92 (m, 6H), 2.77-2.55 (m, 6H), 2.27-2.12 (m, 1H), 2.06-1.86 (m, 4H), 1.84-1.67 (m, 3H), 1.66-1.45 (m, 6H).

Example 14. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(3-(4-(4-(2,6-dioxopiperidin-3-yl)-2-fluorophenyl)piperazin-1-yl)propanoyl)piperidin-3-yl)-3-methoxybenzamide (Compound 14)

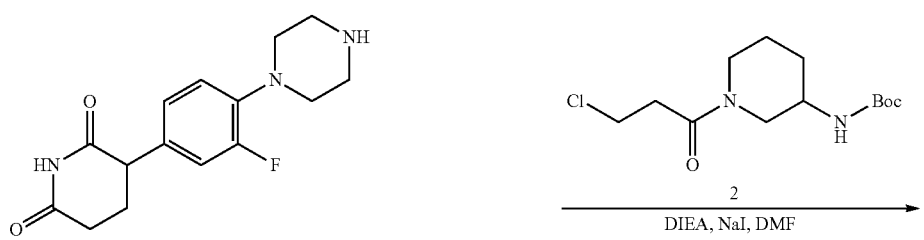

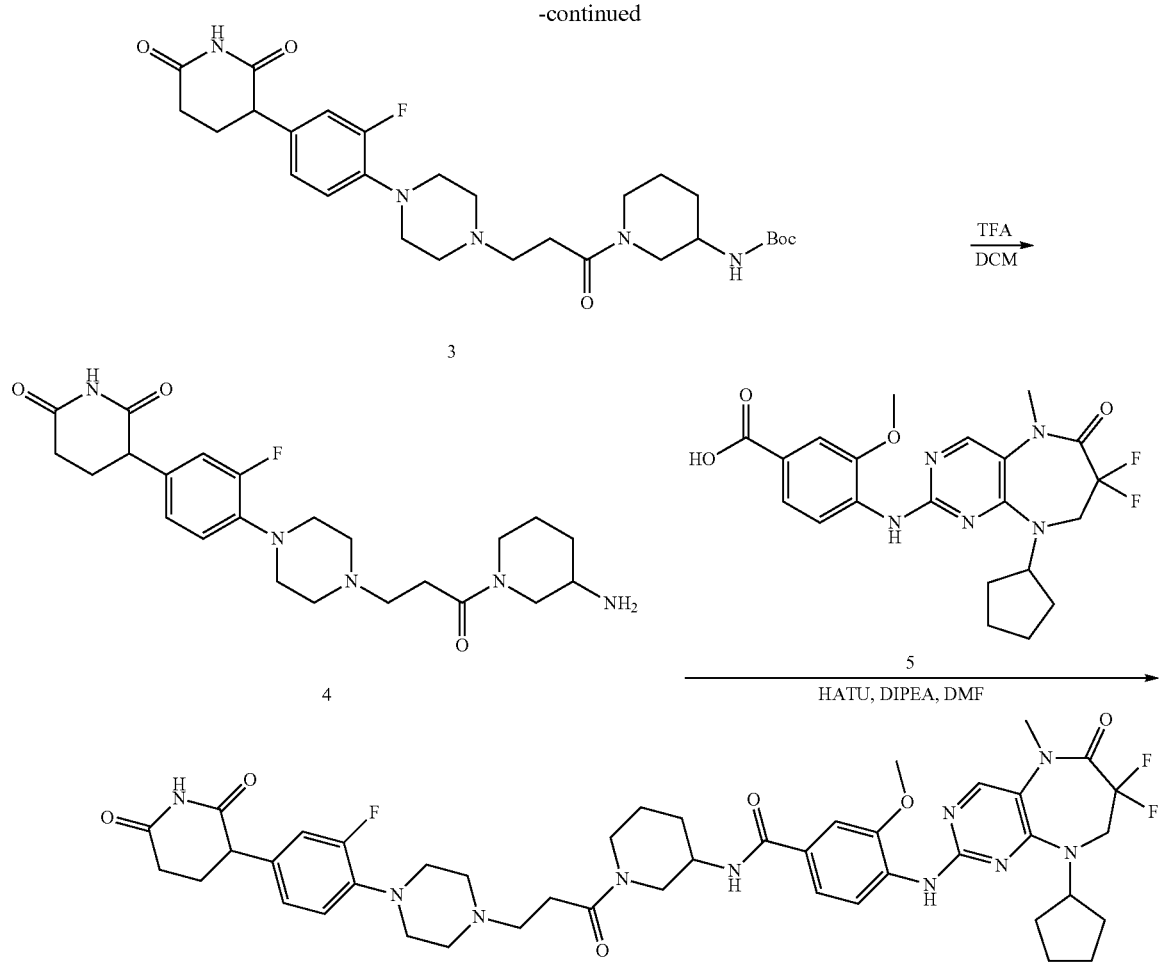

Compound 14

Step 1. Synthesis of tert-butyl (1-(3-(4-(4-(2,6-di-oxopiperidin-3-yl)-2-fluorophenyl)piperazin-1-yl) propanoyl)piperidin-3-yl)carbamate (3)

To a solution of 3-(3-fluoro-4-(piperazin-1-yl)phenyl)piperidine-2,6-dione (300 mg, 1.03 mmol) and tert-butyl (1-(3-chloropropanoyl)piperidin-3-yl)carbamate (449.17 mg, 1.54 mmol) in DMF (10 mL) were added DIPEA (399.28 mg, 3.09 mmol, 538.12 µL) and NaI (15.44 mg, 102.98 µmol), the mixture was stirred at 60° C. for 16 hours. LCMS showed 3-(3-fluoro-4-(piperazin-1-yl)phenyl)piperidine-2,6-dione was consumed completely and 65% of desired mass under 254 nm was detected. The reaction mixture was diluted with H$_2$O (100 mL) and extracted with EtOAc (50 mL×3). The combined organic layers were washed with brine (100 mL×3), dried over Na$_2$SO$_4$, filtered and concentrated in vacuum. The residue was purified by prep-HPLC (column: Phenomenex luna C18 150×40 mm×15 µm; mobile phase: [water (FA)—ACN]; B %: 10%-40%, 10 min), the eluent was freeze-dried to afford tert-butyl (1-(3-(4-(4-(2,6-dioxopiperidin-3-yl)-2-fluorophenyl)piperazin-1-yl)propanoyl)piperidin-3-yl)carbamate (100 mg, 183.27 µmol, 17.80% yield) as a white solid. MS (M+H)$^+$=546.2

Step 2. Synthesis of 3-(4-(4-(3-(3-aminopiperidin-1-yl)-3-oxopropyl)piperazin-1-yl)-3-fluorophenyl) piperidine-2,6-dione (4)

To a solution of tert-butyl (1-(3-(4-(4-(2,6-dioxopiperidin-3-yl)-2-fluorophenyl)piperazin-1-yl)propanoyl)piperidin-3-yl)carbamate (100 mg, 183.27 µmol) in DCM (4 mL) was added TFA (150 µL), the mixture was stirred at 15° C. for 4 hours. LCMS showed 3% of the starting material remained and 86% of desired mass was detected. The reaction mixture was concentrated in vacuum to afford 3-(4-(4-(3-(3-aminopiperidin-1-yl)-3-oxopropyl)piperazin-1-yl)-3-fluorophenyl)piperidine-2,6-dione (105 mg, TFA salt) as a brown oil, which was used directly. MS (M+H)$^+$= 446.2

Step 3. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(3-(4-(4-(2,6-dioxopiperidin-3-yl)-2-fluorophenyl)piperazin-1-yl) propanoyl)piperidin-3-yl)-3-methoxybenzamide (Compound 14)

To a solution of 4-((9-cyclopentyl-7,7-difluoro-5-methyl-6-oxo-6,7,8,9-tetrahydro-5H-pyrimido[4,5-b][1,4]diazepin- 2-yl)amino)-3-methoxybenzoic acid (80 mg, 178.80 μmol) in DMF (2 mL) were added HATU (88.38 mg, 232.44 μmol) and DIPEA (138.65 mg, 1.07 mmol, 186.86 μL), the mixture was stirred at 15° C. for 15 minutes, then 3-(4-(4-(3-(3-aminopiperidin-1-yl)-3-oxopropyl)piperazin-1-yl)-3-fluorophenyl)piperidine-2,6-dione (100.05 mg, 178.80 μmol, TFA salt) and the resulting mixture was stirred at 15° C. for 1 hour. LCMS showed the starting material was consumed completely and 95% of desired mass was detected. To the mixture was added $CH_3COOH$ to adjust pH<7. The resulting mixture was purified by prep-HPLC (column: Phenomenex Luna C18 150×25 mm×10 μm; mobile phase: [water (FA)—ACN]; B %: 26%-56%, 10 min) followed by prep-HPLC (column: Waters Xbridge 150×25 mm×5 μm; mobile phase: [water ($NH_4HCO_3$)—ACN]; B %: 38%-68%, 8 min), the eluent was freeze-dried to afford 4-((9-cyclopentyl-7,7-difluoro-5-methyl-6-oxo-6,7,8,9-tetrahydro-5H-pyrimido[4,5-b][1,4]diazepin-2-yl)amino)-N-(1-(3-(4-(4-(2,6-dioxopiperidin-3-yl)-2-fluorophenyl)piperazin-1-yl)propanoyl) piperidin-3-yl)-3-methoxybenzamide (35.7 mg, 39.99 μmol, 22.36% yield, 98% purity) as a white solid. MS (M+H)$^+$= 875.8

$^1$H NMR (400 MHz, DMSO-d$_6$) δ=10.93-10.75 (m, 1H), 8.43-8.11 (m, 3H), 7.98 (s, 1H), 7.67-7.44 (m, 2H), 7.17-6.85 (m, 3H), 4.88-4.69 (m, 1H), 4.48-4.10 (m, 1H), 4.04 (br t, J=13.9 Hz, 3H), 3.94 (s, 3H), 3.85-3.74 (m, 2H), 3.53-3.36 (m, 5H), 3.11-2.89 (m, 5H), 2.79-2.57 (m, 9H), 2.28-2.11 (m, 1H), 2.06-1.87 (m, 4H), 1.85-1.49 (m, 9H).

Example 15. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(7-((1-(4-(2,6-dioxopiperidin-3-yl)-2-fluorophenyl)piperidin-4-yl)methyl)-7-azaspiro[3.5]nonan-2-yl)-3-methoxybenzamide (Compound 15)

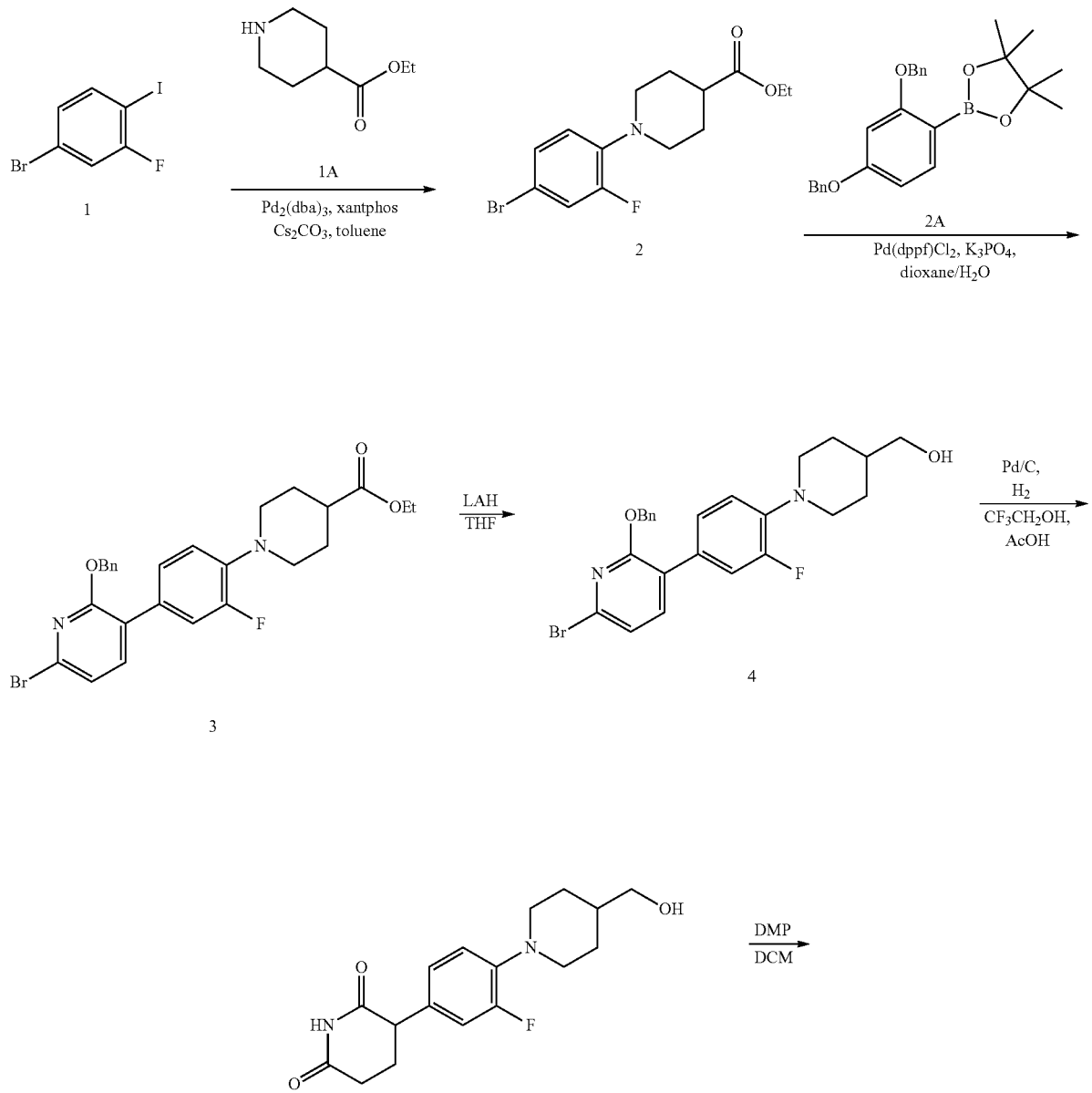

-continued
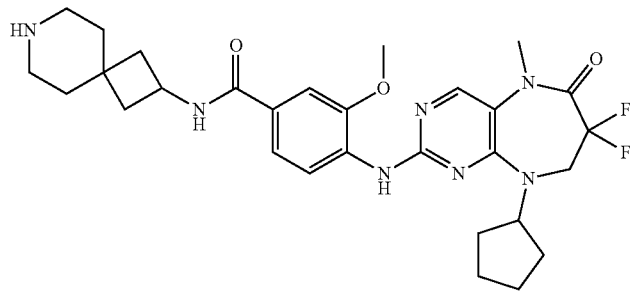
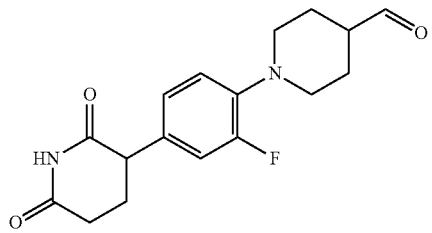
6
↓ 6A
NaOAc, NaBH(OAc)₃, DCM
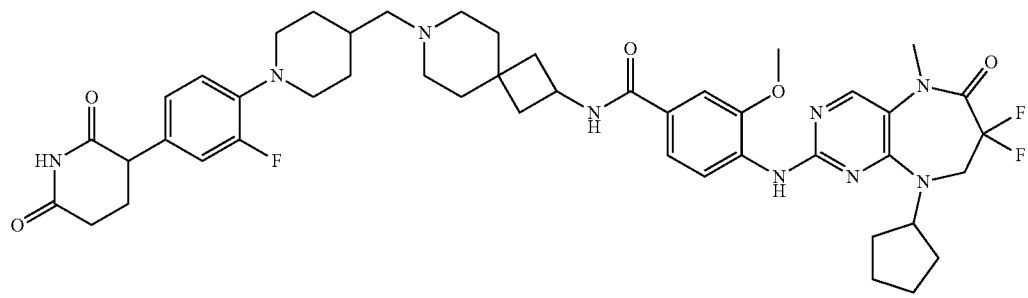
Compound 15
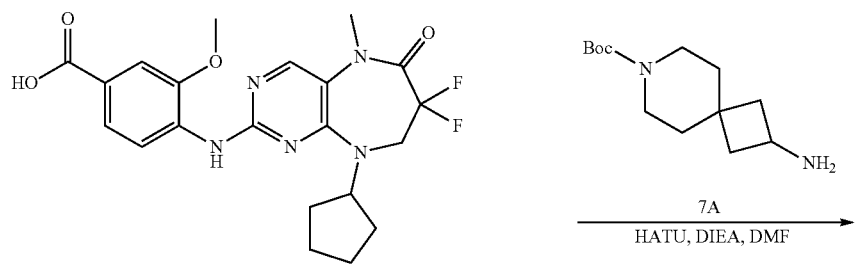
7
↓ 7A
HATU, DIEA, DMF
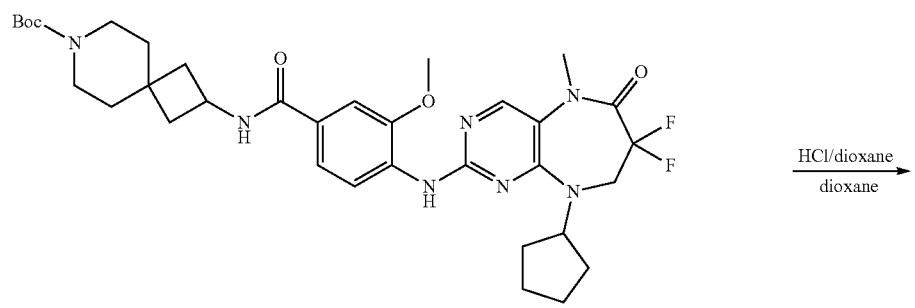
8
↓ HCl/dioxane
dioxane -continued

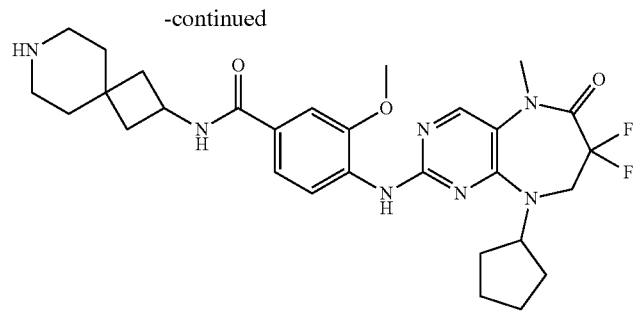

6a

Step 1. Synthesis of ethyl 1-(4-bromo-2-fluorophenyl)piperidine-4-carboxylate (2)

To a solution of 4-bromo-2-fluoro-1-iodobenzene (10 g, 33.23 mmol) and ethyl piperidine-4-carboxylate (5.22 g, 33.23 mmol, 5.12 mL) in toluene (200 mL) were added $Cs_2CO_3$ (32.49 g, 99.70 mmol), $Pd_2(dba)_3$ (608.66 mg, 664.69 μmol) and Xantphos (576.90 mg, 997.03 μmol) and the mixture was stirred at 100° C. for 14 h under $N_2$. LCMS showed a peak (17%) with desired mass. The reaction mixture was diluted with $H_2O$ (500 mL), extracted with EtOAc (50 mL×3). The combined organic layers were washed with brine (100 mL×2), dried over $Na_2SO_4$, filtered and concentrated under reduced pressure. The residue was purified by flash silica gel chromatography (20 g SepaFlash Silica Flash Column, Eluent of 0~15% EtOAc/Petroleum ether gradient @ 40 mL/min) to afford ethyl 1-(4-bromo-2-fluorophenyl)piperidine-4-carboxylate (2.6 g, 7.40 mmol, 22.27% yield, 94% purity) as yellow oil. MS $(M+H)^+$=330.0

Step 2. Synthesis of ethyl 1-(4-(2,6-bis(benzyloxy)pyridin-3-yl)-2-fluorophenyl)piperidine-4-carboxylate (3)

To a solution of ethyl 1-(4-bromo-2-fluorophenyl)piperidine-4-carboxylate (2.1 g, 6.36 mmol) and 2,6-bis(benzyloxy)-3-(4,4,5,5-tetramethyl-1,3,2-dioxaborolan-2-yl)pyridine (5.31 g, 12.72 mmol) in dioxane (40 mL) and $H_2O$ (8 mL) were added $K_3PO_4$ (4.05 g, 19.08 mmol) and Pd(dppf)$Cl_2$ (465.36 mg, 635.99 μmol) and the resulting mixture was stirred at 90° C. for 12 h. LCMS showed a peak (58%) with desired mass, the mixture was concentrated in vacuum. The residue was purified by flash silica gel chromatography (40 g SepaFlash Silica Flash Column, Eluent of 0~10% EtOAc/Petroleum ether gradient @ 100 mL/min) to afford ethyl 1-(4-(2,6-bis(benzyloxy)pyridin-3-yl)-2-fluorophenyl) piperidine-4-carboxylate (1.5 g, 2.77 mmol, 43.63% yield, 100% purity) as a white solid. MS $(M+H)^+$=541.2

Step 3. Synthesis of (1-(4-(2,6-bis(benzyloxy)pyridin-3-yl)-2-fluorophenyl)piperidin-4-yl)methanol (4)

To the suspension of LAH (315.92 mg, 8.32 mmol) in THF (30 mL) was added ethyl 1-(4-(2,6-bis(benzyloxy)pyridin-3-yl)-2-fluorophenyl) piperidine-4-carboxylate (3 g, 5.55 mmol) in THF (20 mL) at 20° C. and the resulting mixture was stirred at 20° C. for 2 h. LCMS showed a peak (97%) with desired mass. The reaction mixture was quenched with $H_2O$ (0.3 mL), NaOH solution (15%, 0.3 mL) and $H_2O$ (0.9 mL) at 0° C., then the mixture was filtered and the filtrate was concentrated under reduced pressured to afford (1-(4-(2,6-bis(benzyloxy)pyridin-3-yl)-2-fluorophenyl)piperidin-4-yl)methanol (2.9 g, crude) as a white solid. MS $(M+H)^+$=499.3

Step 4. Synthesis of 3-(3-fluoro-4-(4-(hydroxymethyl)piperidin-1-yl)phenyl)piperidine-2,6-dione (5)

To a solution of (1-(4-(2,6-bis(benzyloxy)pyridin-3-yl)-2-fluorophenyl)piperidin-4-yl)methanol (2.9 g, 5.82 mmol) in $CF_3CH_2OH$ (100 mL) were added AcOH (349.29 mg, 5.82 mmol, 332.66 μL) and Pd/C (0.3 g, 10% purity) under $N_2$ atmosphere, the mixture was degassed and purged with $H_2$ 3 times and the mixture was stirred at 20° C. for 16 h under $H_2$ atmosphere (15 Psi). LCMS showed a peak (80%) with desired mass, the mixture was filtered and concentrated to afford 3-(3-fluoro-4-(4-(hydroxymethyl)piperidin-1-yl) phenyl) piperidine-2,6-dione (1.8 g, 4.94 mmol, 85.01% yield, 88% purity) as a white solid. MS $(M+H)^+$=321.2

Step 5. Synthesis of 1-(4-(2,6-dioxopiperidin-3-yl)-2-fluorophenyl)piperidine-4-carbaldehyde (6)

To a solution of 3-(3-fluoro-4-(4-(hydroxymethyl)piperidin-1-yl)phenyl)piperidine-2,6-dione (0.8 g, 2.50 mmol) in DCM (30 mL) was added DMP (1.59 g, 3.75 mmol, 1.16 mL) and the mixture was stirred at 20° C. for 2 h. LCMS showed that 3-(3-fluoro-4-(4-(hydroxymethyl)piperidin-1-yl) phenyl)piperidine-2,6-dione was consumed completely and desired mass was detected, the mixture was filtered and the filtrate was concentrated under reduced pressure to afford 1-(4-(2,6-dioxopiperidin-3-yl)-2-fluorophenyl)piperidine-4-carbaldehyde (0.8 g, crude) as yellow oil.
MS $(M+H)^+$=319.0

Step 6. Synthesis of tert-butyl 2-(4-((9-cyclopentyl-7,7-difluoro-5-methyl-6-oxo-6,7,8,9-tetrahydro-5H-pyrimido[4,5-b][1,4]diazepin-2-yl)amino)-3-methoxybenzamido)-7-azaspiro[3.5]nonane-7-carboxylate (8)

To the solution of 4-((9-cyclopentyl-7,7-difluoro-5-methyl-6-oxo-6,7,8,9-tetrahydro-5H-pyrimido[4,5-b][1,4] diazepin-2-yl)amino)-3-methoxybenzoic acid (2 g, 4.47 mmol) and tert-butyl 2-amino-7-azaspiro[3.5]nonane-7-carboxylate (1.07 g, 4.47 mmol) in DMF (20 mL) were added HATU (2.04 g, 5.36 mmol) and DIPEA (1.73 g, 13.41 mmol, 2.34 mL) and the resulting mixture was stirred at 20° C. for 2 h. LCMS showed a peak (72%) with desired mass. The mixture was poured into water (100 mL) and extracted with EtOAc (50 mL×3). The combined organic layer was washed with brine (50 mL), dried over Na$_2$SO$_4$, filtered and concentrated. The residue was purified by flash silica gel chromatography (20 g SepaFlash Silica Flash Column, Eluent of 0~100% EtOAc/Petroleum ether gradient @ 80 mL/min) to afford tert-butyl 2-(4-((9-cyclopentyl-7,7-difluoro-5-methyl-6-oxo-6,7,8,9-tetrahydro-5H-pyrimido[4,5-b][1,4]diazepin-2-yl)amino)-3-methoxybenzamido)-7-azaspiro[3.5]nonane-7-carboxylate (1.7 g, 2.51 mmol, 56.22% yield, 99% purity) as a yellow solid. MS (M+H)$^+$= 670.6

Step 7. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-3-methoxy-N-(7-azaspiro[3.5]nonan-2-yl)benzamide (6a)

To the solution of tert-butyl 2-(4-((9-cyclopentyl-7,7-difluoro-5-methyl-6-oxo-6,7,8,9-tetrahydro-5H-pyrimido[4,5-b][1,4]diazepin-2-yl)amino)-3-methoxybenzamido)-7-azaspiro[3.5]nonane-7-carboxylate (1.7 g, 2.54 mmol) in dioxane (20 mL) was added HCl/dioxane (4 M, 17.00 mL) and the resulting mixture was stirred at 20° C. for 2 h. LCMS showed a peak (100%) with desired mass the mixture was concentrated under reduced pressure to afford 4-((9-cyclopentyl-7,7-difluoro-5-methyl-6-oxo-6,7,8,9-tetrahydro-5H-pyrimido[4,5-b][1,4]diazepin-2-yl)amino)-3-methoxy-N-(7-azaspiro[3.5]nonan-2-yl)benzamide (1.5 g, 2.47 mmol, 97.50% yield, HCl) as a yellow solid. MS (M+H)$^+$=570.3

Step 8. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(7-((1-(4-(2,6-dioxopiperidin-3-yl)-2-fluorophenyl)piperidin-4-yl)methyl)-7-azaspiro[3.5]nonan-2-yl)-3-methoxybenzamide (Compound 15)

To a solution of 1-(4-(2,6-dioxopiperidin-3-yl)-2-fluorophenyl)piperidine-4-carbaldehyde (0.8 g, 2.51 mmol) in DCM (50 mL) was added 4-((9-cyclopentyl-7,7-difluoro-5-methyl-6-oxo-6,7,8,9-tetrahydro-5H-pyrimido[4,5-b][1,4]diazepin-2-yl)amino)-3-methoxy-N-(7-azaspiro[3.5]nonan-2-yl)benzamide (1.22 g, 2.01 mmol, HCl salt) and NaOAc (309.23 mg, 3.77 mmol), the mixture was stirred at 20° C. for 1 h. Then NaBH(OAc)$_3$ (2.66 g, 12.57 mmol) was added to the mixture at 20° C. and the resulting mixture was stirred at 20° C. for 15 h. LCMS showed a peak (38%) with desired mass. The mixture was poured into water (100 mL) and extracted with DCM (50 mL×3). The combined organic layer was washed with brine (50 mL), dried over Na$_2$SO$_4$, filtered and concentrated. The residue was purified by flash silica gel chromatography (20 g SepaFlash Silica Flash Column, Eluent of 0~30% MeOH/EtOAc gradient @ 80 mL/min) to afford 0.7 g of crude product, the crude product was triturated with EtOAc (20 mL) to afford 0.6 g of desired product (95% purity), the desired product was triturated with ACN (10 mL) and MeOH (10 mL) to afford 560 mg of desired product (96% purity), 560 mg of desired product was triturated with DMF (5 mL) and MeOH (2 mL) to afford 4-((9-cyclopentyl-7,7-difluoro-5-methyl-6-oxo-6,7,8,9-tetrahydro-5H-pyrimido[4,5-b][1,4]diazepin-2-yl)amino)-N-(7-((1-(4-(2,6-dioxopiperidin-3-yl)-2-fluorophenyl)piperidin-4-yl)methyl)-7-azaspiro[3.5]nonan-2-yl)-3-methoxybenzamide (230 mg, 258.49 µmol, 10.29% yield, 98% purity) as a white solid. All mother liquor was concentrated and re-purified by prep-HPLC (column: Waters Xbridge C18 150*50 mm*10 µm; mobile phase: [water (NH$_4$HCO$_3$)—ACN]; B %: 45%-75%, 10 min) and the eluent was lyophilized to afford 4-((9-cyclopentyl-7,7-difluoro-5-methyl-6-oxo-6,7,8,9-tetrahydro-5H-pyrimido[4,5-b][1,4]diazepin-2-yl)amino)-N-(7-((1-(4-(2,6-dioxopiperidin-3-yl)-2-fluorophenyl)piperidin-4-yl)methyl)-7-azaspiro[3.5]nonan-2-yl)-3-methoxybenzamide (281.4 mg, 316.26 µmol, 12.58% yield, 98% purity) as a white solid. MS (M+H)$^+$=872.5

$^1$H NMR (400 MHz, DMSO-d$_6$) δ=10.80 (s, 1H), 8.43 (br d, J=7.3 Hz, 1H), 8.29-8.24 (m, 2H), 7.96 (s, 1H), 7.50-7.46 (m, 2H), 7.02-6.92 (m, 3H), 4.83-4.71 (m, 1H), 4.45-4.33 (m, 1H), 4.04 (br t, J=14.1 Hz, 2H), 3.94 (s, 3H), 3.79 (dd, J=4.9, 11.6 Hz, 1H), 3.31 (br s, 5H), 2.68-2.59 (m, 3H), 2.33-2.12 (m, 9H), 2.04-1.92 (m, 3H), 1.85-1.70 (m, 6H), 1.65-1.51 (m, 10H), 1.31-1.20 (m, 2H).

Example 16. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(7-((1-(4-(2,6-dioxopiperidin-3-yl)phenyl)piperidin-4-yl)methyl)-7-azaspiro[3.5]nonan-2-yl)-3-methoxybenzamide (Compound 16)

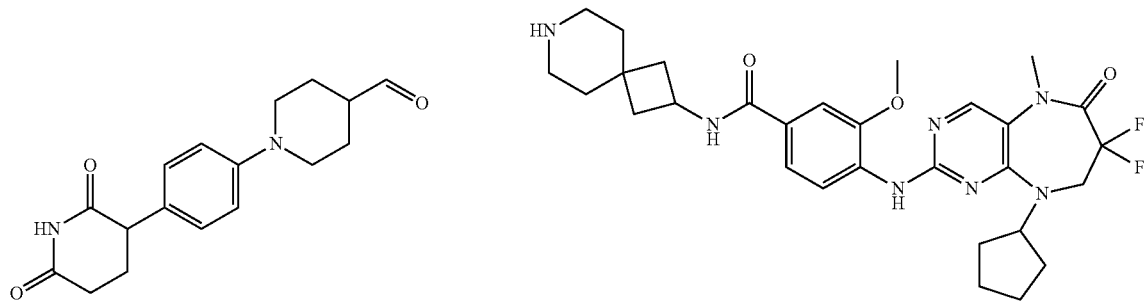

9 → 10

NaOAc, NaBH(Oac)$_3$, DCE

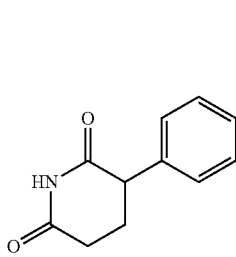 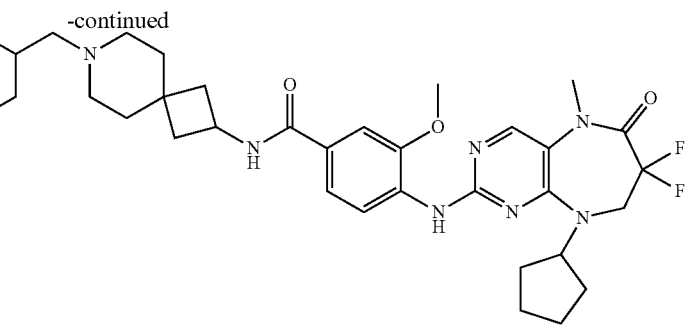

Compound 16

To a solution of 1-[4-(2,6-dioxo-3-piperidyl)phenyl]piperidine-4-carbaldehyde (94.15 mg, 313.48 μmol) in DCE (5 mL) was added 4-((9-cyclopentyl-7,7-difluoro-5-methyl-6-oxo-6,7,8,9-tetrahydro-5H-pyrimido[4,5-b][1,4]diazepin-2-yl)amino)-3-methoxy-N-(7-azaspiro[3.5]nonan-2-yl)benzamide (190 mg, 313.48 μmol, HCl salt) and NaOAc (38.57 mg, 470.22 μmol). The mixture was stirred at 20° C. for 1 h. Then NaBH(OAc)$_3$ (332.19 mg, 1.57 mmol) was added at 20° C. and the resulting mixture was stirred at 20° C. for 16 h. LCMS showed the desired Mass. The reaction mixture was washed with H$_2$O (15 mL×3). The combined organic layer was dried over Na$_2$SO$_4$, filtered and concentrated under reduced pressure. The residue was purified by prep-HPLC (column: 3_Phenomenex Luna C18 75×30 mm×3 μm; mobile phase: [water (TFA)—ACN]; B %: 20%-40%, 9 min) followed by prep-TLC (SiO$_2$, Dichloromethane:Methanol=10:1) to afford 4-((9-cyclopentyl-7,7-difluoro-5-methyl-6-oxo-6,7,8,9-tetrahydro-5H-pyrimido[4,5-b][1,4]diazepin-2-yl)amino)-N-(7-((1-(4-(2,6-dioxopiperidin-3-yl)phenyl)piperidin-4-yl)methyl)-7-azaspiro[3.5]nonan-2-yl)-3-methoxybenzamide (28.7 mg, 32.60 μmol, 10.40% yield, 97% purity) as a white solid. MS (M+H)$^+$=854.7

$^1$H NMR (400 MHz, DMSO-d$_6$) δ=10.76 (s, 1H), 8.42 (d, J=7.5 Hz, 1H), 8.31-8.23 (m, 2H), 7.96 (s, 1H), 7.52-7.45 (m, 2H), 7.02 (d, J=8.7 Hz, 2H), 6.87 (d, J=8.8 Hz, 2H), 4.82-4.71 (m, 1H), 4.39 (sxt, J=7.6 Hz, 1H), 4.04 (br t, J=14.1 Hz, 2H), 3.94 (s, 3H), 3.71 (dd, J=5.0, 10.8 Hz, 1H), 3.64 (br d, J=12.1 Hz, 2H), 3.32 (br s, 3H), 2.65-2.57 (m, 3H), 2.48-2.41 (m, 2H), 2.32-2.20 (m, 3H), 2.18-2.09 (m, 5H), 2.04-1.91 (m, 3H), 1.85-1.68 (m, 6H), 1.66-1.51 (m, 9H), 1.23-1.11 (m, 2H).

Example 17. Synthesis of 3-(4-(4-((2-((4-((9-cyclopentyl-7,7-difluoro-5-methyl-6-oxo-6,7,8,9-tetrahydro-5H-pyrimido[4,5-b][1,4]diazepin-2-yl)amino)-3-methoxyphenoxy)methyl)-7-azaspiro[3.5]nonan-7-yl)methyl)piperidin-1-yl)-3-fluorophenyl)piperidine-2,6-dione (Compound 17)

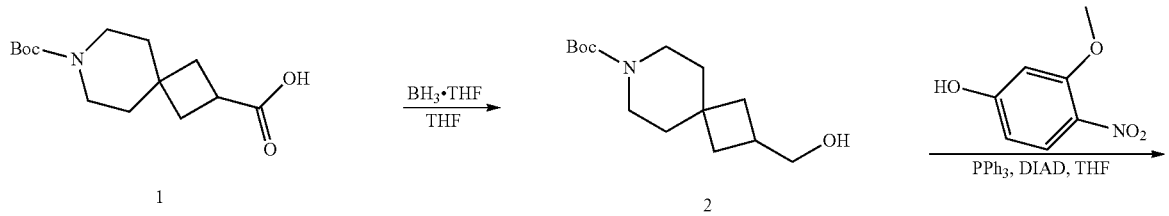

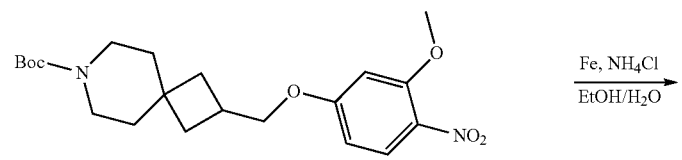

-continued

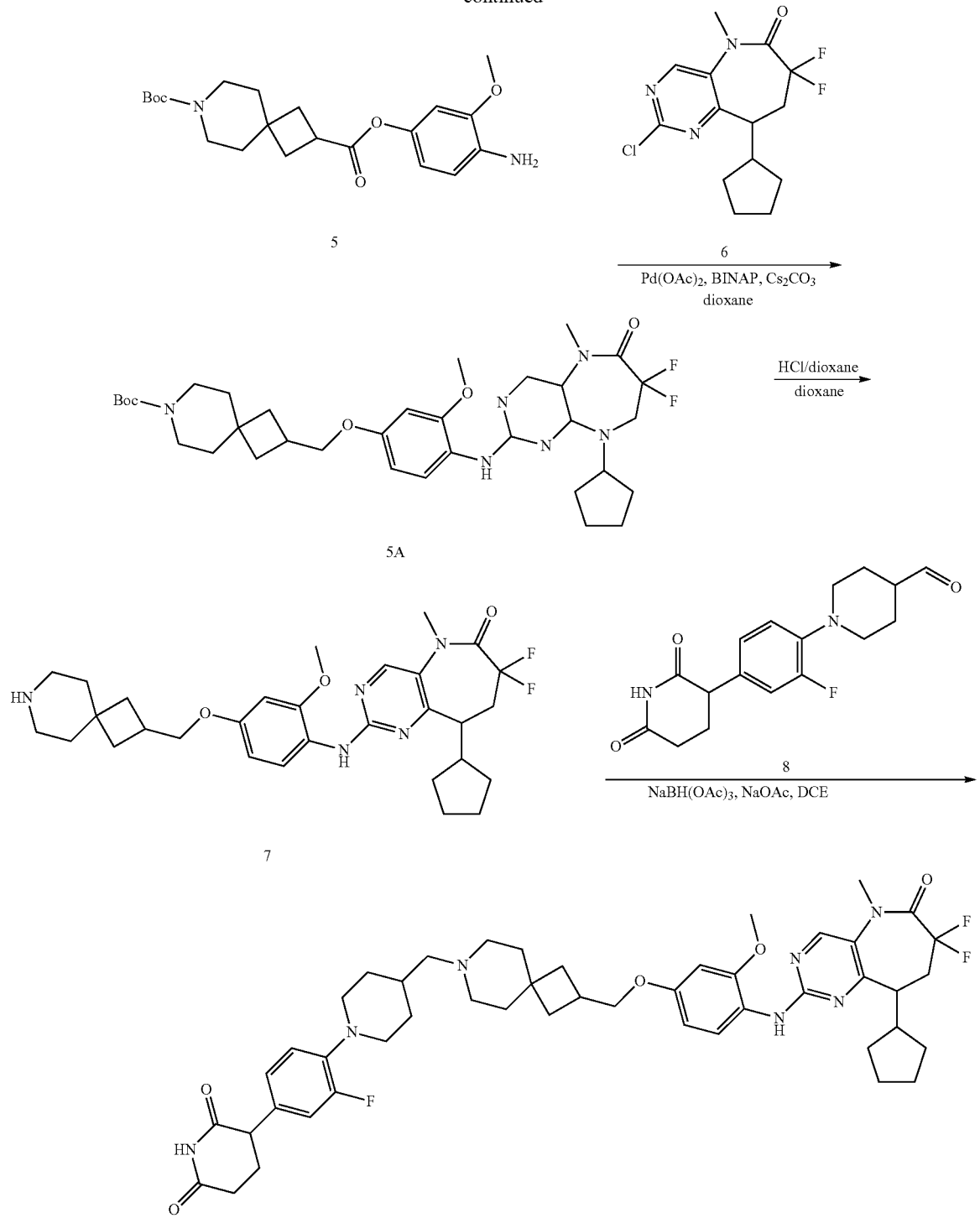

Compound 17

Step 1. Synthesis of tert-butyl 2-(hydroxymethyl)-7-azaspiro[3.5]nonane-7-carboxylate (2)

To a solution of 7-(tert-butoxycarbonyl)-7-azaspiro[3.5]nonane-2-carboxylic acid (1 g, 3.71 mmol) in THF (20 mL) was added BH$_3$THF (1 M, 10 mL) at 0° C. The mixture was stirred at 20° C. for 2 hr under N$_2$ atmosphere. TLC (Petroleum ether:EtOAc=1:1; 12) indicated Reactant 1 was consumed completely and one new spot (Rf=0.28) was formed. The mixture was quenched with Methanol (30 mL) at 0° C. Then the mixture was concentrated under reduced pressure. The residue was diluted with water (100 mL) and extracted with EtOAc (50 mL×3). The combined organic layers were washed with brine (50 mL), dried over sodium sulfate, filtered and concentrated under reduced pressure to afford tert-butyl 2-(hydroxymethyl)-7-azaspiro[3.5]nonane-7-carboxylate (940 mg, crude) as a light yellow oil. MS (M+H)$^+$=256.4

Step 2. Synthesis of tert-butyl 2-((3-methoxy-4-nitrophenoxy)methyl)-7-azaspiro[3.5]nonane-7-carboxylate (4)

To a solution of tert-butyl 2-(hydroxymethyl)-7-azaspiro[3.5]nonane-7-carboxylate (740 mg, 2.90 mmol) in THF (6 mL) were added PPh$_3$ (1.15 g, 4.37 mmol), 3-methoxy-4-nitrophenol (500 mg, 2.96 mmol) and DIAD (936.00 mg, 4.63 mmol, 900 μL) at 0° C. The mixture was stirred at 20° C. for 16 hr under N$_2$ atmosphere. LCMS showed a peak (31%) with desired mass. The reaction mixture was concentrated under reduced pressure. The residue was purified by flash silica gel chromatography (Biotage; 20 g SepaFlash Silica Flash Column, Eluent of 10~33% EtOAc:Petroleum ether gradient, 60 mL/min) to afford tert-butyl 2-((3-methoxy-4-nitrophenoxy)methyl)-7-azaspiro[3.5]nonane-7-carboxylate (1.16 g, 2.85 mmol, 98.48% yield) as a light yellow oil. MS (M+Na)+=429.3

Step 3. Synthesis of tert-butyl 2-((4-amino-3-methoxyphenoxy)methyl)-7-azaspiro[3.5]nonane-7-carboxylate (5)

To a solution of tert-butyl 2-((3-methoxy-4-nitrophenoxy)methyl)-7-azaspiro[3.5]nonane-7-carboxylate (700 mg, 1.72 mmol) in EtOH (10 mL) and H$_2$O (10 mL) were added Fe (700 mg, 12.53 mmol) and NH$_4$Cl (700 mg, 13.09 mmol). The mixture was stirred at 80° C. for 2 hr. TLC (Petroleum ether:EtOAc=1:1) indicated the starting material was consumed completely and one new spot was formed. The reaction mixture was filtered, the filtrate was concentrated to remove the EtOH. Then Na$_2$CO$_3$ (sat. aq, 8 mL) was added to adjust pH=9, and extracted with EtOAc (40 mL×3). The combined organic layers were washed with brine 100 mL (50 mL×2), dried over Na$_2$SO$_4$, filtered and the filtrate was concentrated under reduced pressure. The residue was purified by flash silica gel chromatography (Biotage; 20 g SepaFlash Silica Flash Column, Eluent of 20~50% EtOAc:Petroleum ether gradient, 60 mL/min) to afford tert-butyl 2-((4-amino-3-methoxyphenoxy)methyl)-7-azaspiro[3.5]nonane-7-carboxylate (630 mg, 1.67 mmol, 97.17% yield) as a yellow oil. MS (M+H)$^+$=377.3

Step 4. Synthesis of tert-butyl 2-((4-((9-cyclopentyl-7,7-difluoro-5-methyl-6-oxo-6,7,8,9-tetrahydro-5H-pyrimido[4,5-b][1,4]diazepin-2-yl)amino)-3-methoxyphenoxy)methyl)-7-azaspiro[3.5]nonane-7-carboxylate (5A)

A mixture of 2-chloro-9-cyclopentyl-7,7-difluoro-5-methyl-5,7,8,9-tetrahydro-6H-pyrimido[4,5-b][1,4]diazepin-6-one (350 mg, 1.11 mmol), tert-butyl 2-((4-amino-3-methoxyphenoxy)methyl)-7-azaspiro[3.5]nonane-7-carboxylate (420 mg, 1.12 mmol), Pd(OAc)$_2$ (56.00 mg, 249.43 μmol), BINAP (140.00 mg, 224.84 μmol) and Cs$_2$CO$_3$ (1.40 g, 4.30 mmol) in dioxane (30 mL) was degassed and purged with N$_2$ for 3 times, then the mixture was stirred at 100° C. for 16 hr under N$_2$ atmosphere. LCMS showed a peak (21%) with desired mass. The reaction mixture was concentrated under reduced pressure. The residue was purified by flash silica gel chromatography (Biotage; 10 g SepaFlash Silica Flash Column, Eluent of 20~50% EtOAc:Petroleum ether gradient, 60 mL/min) and repurified by prep-HPLC (column: Unisil 3-100 C18 Ultra 150×50 mm×3 μm; mobile phase: [water (FA)—ACN]; B %: 59%-89%, 7 min; Column Temp: 30° C.), the eluent was lyophilized to afford tert-butyl 2-((4-((9-cyclopentyl-7,7-difluoro-5-methyl-6-oxo-6,7,8,9-tetrahydro-5H-pyrimido[4,5-b][1,4]diazepin-2-yl)amino)-3-methoxyphenoxy)methyl)-7-azaspiro[3.5]nonane-7-carboxylate (240 mg, 365.43 μmol, 33.07% yield) as a yellow oil. MS (M+H)$^+$=657.6

Step 5. Synthesis of 2-((4-((7-azaspiro[3.5]nonan-2-yl)methoxy)-2-methoxyphenyl)amino)-9-cyclopentyl-7,7-difluoro-5-methyl-5,7,8,9-tetrahydro-6H-pyrimido[4,5-b][1,4]diazepin-6-one (7)

To a solution of tert-butyl 2-((4-((9-cyclopentyl-7,7-difluoro-5-methyl-6-oxo-6,7,8,9-tetrahydro-5H-pyrimido[4,5-b][1,4]diazepin-2-yl)amino)-3-methoxyphenoxy)methyl)-7-azaspiro[3.5]nonane-7-carboxylate (240 mg, 365.43 μmol) in dioxane (3 mL) was added HCl/dioxane (4 M, 12.00 mL), the mixture was stirred at 20° C. for 1 hr. LCMS showed the starting material was consumed completely and a peak (81%) with desired mass. The reaction mixture was concentrated under reduced pressure to afford 2-((4-((7-azaspiro[3.5]nonan-2-yl)methoxy)-2-methoxyphenyl)amino)-9-cyclopentyl-7,7-difluoro-5-methyl-5,7,8,9-tetrahydro-6H-pyrimido[4,5-b][1,4]diazepin-6-one (210 mg, crude, HCl salt) as a yellow oil. MS (M+H)$^+$=557.5

Step 6. Synthesis of 3-(4-(4-((2-((4-((9-cyclopentyl-7,7-difluoro-5-methyl-6-oxo-6,7,8,9-tetrahydro-5H-pyrimido[4,5-b][1,4]diazepin-2-yl)amino)-3-methoxyphenoxy)methyl)-7-azaspiro[3.5]nonan-7-yl)methyl)piperidin-1-yl)-3-fluorophenyl)piperidine-2,6-dione (Compound 17)

To a solution of 1-(4-(2,6-dioxopiperidin-3-yl)-2-fluorophenyl)piperidine-4-carbaldehyde (128 mg, 402.08 μmol) in DCE (8 mL) was added 2-((4-((7-azaspiro[3.5]nonan-2-yl)methoxy)-2-methoxyphenyl)amino)-9-cyclopentyl-7,7-difluoro-5-methyl-5,7,8,9-tetrahydro-6H-pyrimido[4,5-b][1,4]diazepin-6-one (210 mg, 354.07 μmol, HCl salt) and NaOAc (110 mg, 1.34 mmol). The mixture was stirred at 20° C. for 1 hr. Then NaBH(OAc)$_3$ (355 mg, 1.67 mmol) was added to the mixture at 0° C., the mixture was stirred at 20° C. for 15 hr. LCMS showed a peak (33%) with the desired mass. The reaction mixture was diluted with H$_2$O (5 mL) at 0° C., and adjusted the pH=9 by using saturated NaHCO$_3$ solution at 0° C., then the resulting mixture was extracted with EtOAc (20 mL×3). the combined organic layers were washed with brine (20 mL×2), dried over Na$_2$SO$_4$, filtered and the filtrate was concentrated under reduced pressure. The residue was purified by flash silica gel chromatography (Biotage; 10 g SepaFlash Silica Flash Column, Eluent of 0~25% Methanol:Dichloromethane gradient, 60 mL/min) followed by prep-HPLC (column: Unisil 3-100 C18 Ultra 150×50 mm×3 μm; mobile phase: [water (FA)—ACN]; B %: 19%-49%, 7 min, Column Temp: 30° C.), the eluent was lyophilized to afford 3-(4-(4-((2-((4-((9-cyclopentyl-7,7-difluoro-5-methyl-6-oxo-6,7,8,9-tetrahydro-5H-pyrimido[4,5-b][1,4]diazepin-2-yl)amino)-3-methoxyphenoxy)methyl)-7-azaspiro[3.5]nonan-7-yl)methyl)piperidin-1-yl)-3-fluorophenyl)piperidine-2,6-dione (66.3 mg, 74.10 μmol, 18.43% yield, 96% purity) as a white solid. MS (M+H)$^+$=859.2

$^1$H NMR (400 MHz, DMSO-d$_6$) δ=10.80 (s, 1H), 8.17 (s, 0.3H), 8.14 (s, 1H), 7.82 (s, 1H), 7.71-7.64 (m, 1H), 7.03-6.90 (m, 3H), 6.60 (d, J=2.4 Hz, 1H), 6.50-6.42 (m, 1H), 4.69-4.43 (m, 1H), 4.00-3.88 (m, 4H), 3.79 (s, 3H), 3.79-3.75 (m, 1H), 3.36-3.29 (m, 5H), 2.66-2.60 (m, 4H), 2.34-2.28 (m, 2H), 2.25-2.10 (m, 5H), 2.02-1.96 (m, 1H), 1.93-1.73 (m, 7H), 1.66-1.48 (m, 13H), 1.30-1.19 (m, 2H).

Example 18. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(4-(7-(4-(2,6-dioxopiperidin-3-yl)-2-fluorophenyl)-2,7-diazaspiro[3.5]nonan-2-yl)piperidin-1-yl)-3-methoxybenzamide (Compound 18)
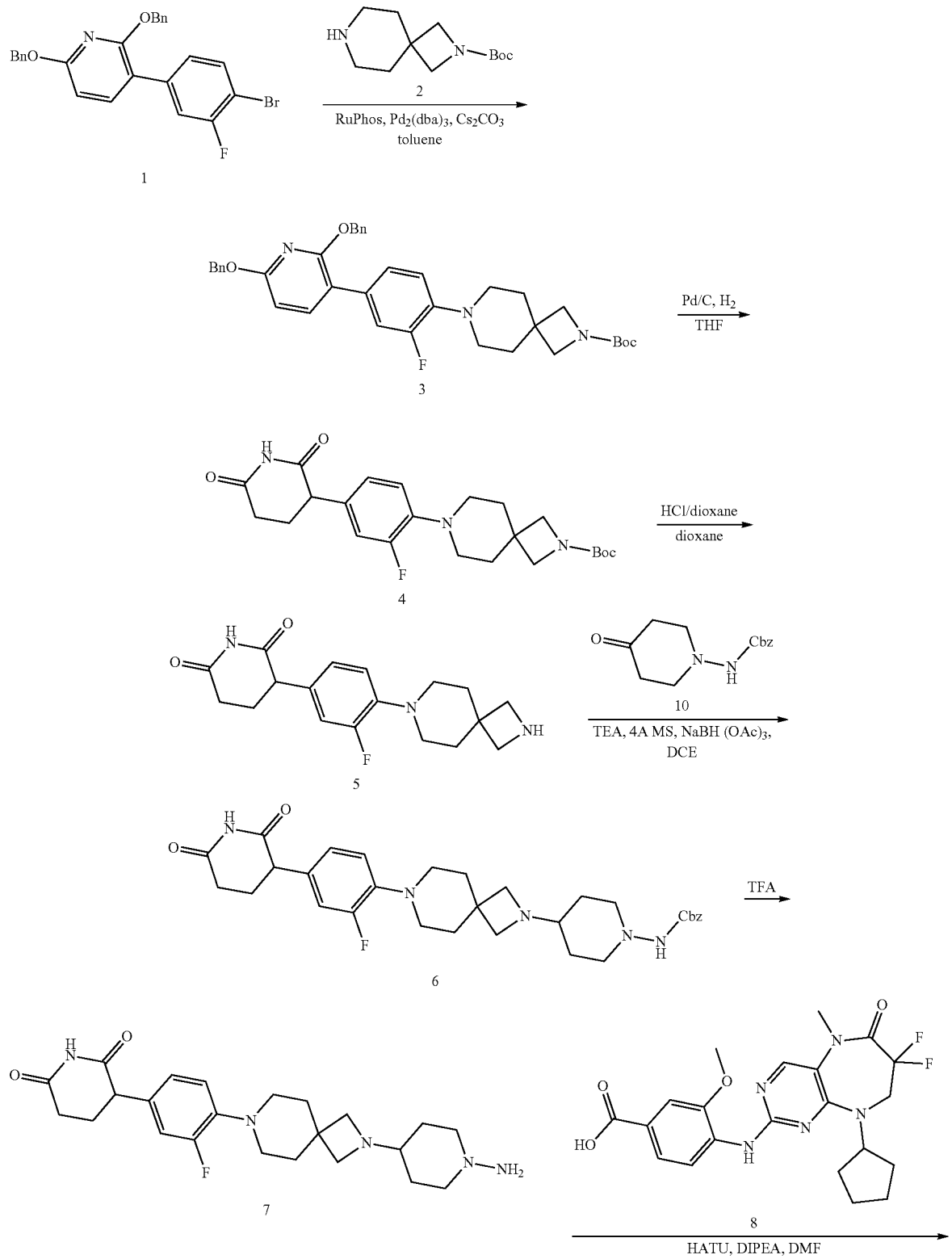

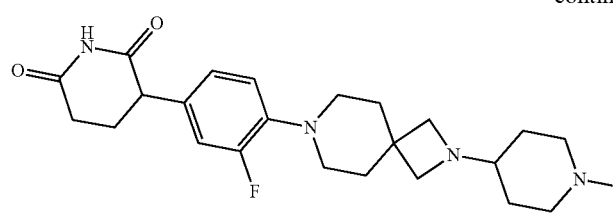

Compound 18

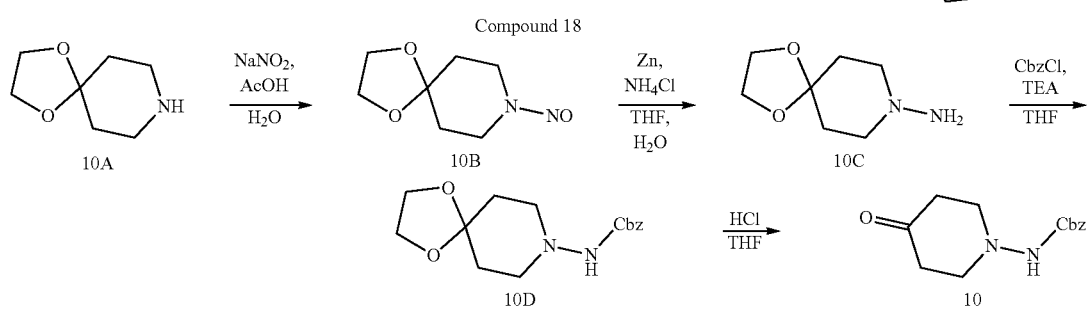

Step 1. Synthesis of tert-butyl 7-(4-(2,6-bis(benzyloxy)pyridin-3-yl)-2-fluorophenyl)-2,7-diazaspiro[3.5]nonane-2-carboxylate (3)

To a solution of 2,6-dibenzyloxy-3-(4-bromo-3-fluorophenyl) pyridine (1.5 g, 3.23 mmol) and tert-butyl 2,7-diazaspiro[3.5]nonane-2-carboxylate (804.22 mg, 3.55 mmol) in toluene (50 mL) were added $Cs_2CO_3$ (3.16 g, 9.69 mmol), $Pd_2(dba)_3$ (147.91 mg, 161.52 μmol) and RuPhos (150.75 mg, 323.05 μmol) at 20° C. under $N_2$ and the resulting mixture was stirred at 100° C. for 12 h. LCMS showed all starting material was consumed completely and 28% peak with desired mass. The reaction mixture was combined with another batch (0.5 g scale) for work-up. The reaction mixture was filtered and the filtrate was concentrated in vacuum. The residue was purified by flash silica gel chromatography (20 g SepaFlash Silica Flash Column, Eluent of 0~15% EtOAc/Petroleum ether gradient @ 100 mL/min) to afford tert-butyl 7-(4-(2,6-bis(benzyloxy)pyridin-3-yl)-2-fluorophenyl)-2,7-diazaspiro[3.5]nonane-2-carboxylate (1.5 g, 1.48 mmol, 52.69% yield, 90% purity) as a white solid. MS $(M+H)^+$=610.3

Step 2. Synthesis of tert-butyl 7-(4-(2,6-dioxopiperidin-3-yl)-2-fluorophenyl)-2,7-diazaspiro[3.5]nonane-2-carboxylate (4)

To a solution of tert-butyl 7-(4-(2,6-bis(benzyloxy)pyridin-3-yl)-2-fluorophenyl)-2,7-diazaspiro[3.5]nonane-2-carboxylate (1.5 g, 2.46 mmol) in THF (20 mL) was added Pd/C (1 g, 10% purity) under $N_2$ atmosphere. The suspension was degassed and purged with $H_2$ for 3 times. The mixture was stirred under $H_2$ (15 Psi) at 20° C. for 12 h. LCMS showed 46% of starting material remained and a peak with desired mass and added Pd/C (1 g, 10% purity) to this reaction mixture under $N_2$ atmosphere the reaction mixture was stirred at 20° C. for 24 h under $H_2$ (15 Psi). LCMS showed starting material was consumed completely and 67% peak with desired mass. The reaction mixture was diluted with THF (15 mL) and filtered. The filtrate was concentrated in vacuum to afford tert-butyl 7-(4-(2,6-dioxopiperidin-3-yl)-2-fluorophenyl)-2,7-diazaspiro[3.5]nonane-2-carboxylate (917 mg, 2.13 mmol, 86.38% yield) as a yellow solid. MS $(M+H)^+$=432.2

Step 3. Synthesis of 3-(3-fluoro-4-(2,7-diazaspiro[3.5]nonan-7-yl)phenyl)piperidine-2,6-dione (5)

To a solution of tert-butyl 7-(4-(2,6-dioxopiperidin-3-yl)-2-fluorophenyl)-2,7-diazaspiro[3.5]nonane-2-carboxylate (917 mg, 2.13 mmol) in dioxane (6 mL) was added HCl/dioxane (4 M, 12 mL) at 20° C. and the resulting mixture was stirred at 20° C. for 1 h. LCMS showed starting material was consumed completely and 58% peak with desired mass. The reaction mixture was concentrated in vacuum to afford 3-(3-fluoro-4-(2,7-diazaspiro[3.5]nonan-7-yl)phenyl)piperidine-2,6-dione (782 mg, crude, HCl) as an off-white solid. MS $(M+H)^+$=332.4

Step 4. Synthesis of 8-nitroso-1,4-dioxa-8-azaspiro[4.5]decane (10B)

To a solution of 1,4-dioxa-8-azaspiro[4.5]decane (26 g, 181.59 mmol, 23.21 mL) in $H_2O$ (300 mL) was added $NaNO_2$ (37.59 g, 544.76 mmol) at 0° C. Then AcOH (43.62 g, 726.34 mmol, 41.54 mL) was added drop-wise at 0° C. and the resulting mixture was stirred at 20° C. for 12 h. LCMS showed starting material was consumed completely and 98% peak with desired mass. TLC ($SiO_2$, Petroleum ether:EtOAc=3:1) indicated starting material was consumed completely and one new spot was detected. Saturated $NaHCO_3$ (400 mL) was added to this reaction mixture at 20° C. to adjust the pH=7 and extracted with EtOAc (400 mL×4). The organic layer was washed with saturated $NaHCO_3$ (200 mL×3), dried over $Na_2SO_4$, filtered and concentrated to afford 8-nitroso-1,4-dioxa-8-azaspiro[4.5]decane (25.5 g, 148.10 mmol, 81.56% yield) as a yellow solid.

MS $(M+H)^+$=173.3

Step 5. Synthesis of 1,4-dioxa-8-azaspiro[4.5]decan-8-amine (10C)

To a solution of 8-nitroso-1,4-dioxa-8-azaspiro[4.5]decane (25.5 g, 148.10 mmol) in THF (200 mL) and $H_2O$ (100 mL) was added NH$_4$Cl (23.77 g, 444.30 mmol), then Zn (29.05 g, 444.30 mmol) was added portion wise at 0° C. and the resulting mixture was stirred at 20° C. for 12 h. LCMS showed starting material was consumed completely and a peak with desired mass. The reaction mixture was diluted with THF (500 mL) and filtered. The filtrate was concentrated in vacuum to afford crude product. The crude product was triturated with THF:EtOAc=1:1 (200 mL×4) at 20° C. for 15 min and filtered. The filtrate was concentrated in vacuum to afford 1,4-dioxa-8-azaspiro[4.5]decan-8-amine (9.8 g, 61.95 mmol, 41.83% yield) as a yellow oil. MS (M+H)$^+$=159.1

Step 6. Synthesis of benzyl (1,4-dioxa-8-azaspiro[4.5]decan-8-yl)carbamate (10D)

To a solution of 1,4-dioxa-8-azaspiro[4.5]decan-8-amine (7 g, 44.25 mmol) in THF (80 mL) were added TEA (22.26 g, 220.03 mmol, 30.63 mL) and CbzCl (7.56 g, 44.32 mmol, 6.30 mL) at 0° C. and the mixture was stirred at 20° C. for 14 h. LCMS showed the desired mass was detected. The mixture was diluted with H$_2$O (100 mL) and extracted with EtOAc (30 mL×3), the combined organic layer was washed with brine (100 mL), dried over Na$_2$SO$_4$ and filtered. The filtrate was concentrated under reduced pressure. The residue was purified by flash silica gel chromatography (80 g SepaFlash Silica Flash Column, Eluent of 40~50% EtOAc/Petroleum ether gradient @ 100 mL/min) to afford crude product. The crude product was re-purified by flash silica gel chromatography (12 g SepaFlash Silica Flash Column, Eluent of 40~50% EtOAc/Petroleum ether gradient @ 70 mL/min) to afford benzyl (1,4-dioxa-8-azaspiro[4.5]decan-8-yl)carbamate (850 mg, 2.38 mmol, 5.39% yield, 82% purity) as yellow solid. MS (M+H)$^+$=293.1

Step 7. Synthesis of benzyl N-(4-oxo-1-piperidyl)carbamate (10)

To a solution of benzyl N-(1,4-dioxa-8-azaspiro[4.5]decan-8-yl) carbamate (930 mg, 3.18 mmol) in THF (20 mL) was added HCl (1 M, 12 mL) and the mixture was stirred at 50° C. for 1 h. LCMS showed 38% of the starting material remained and 50% of the desired mass. The mixture was stirred at 50° C. for 1 h. LCMS showed 18% of the starting material remained and 70% of the desired mass was detected. The mixture was stirred at 50° C. for 1 h. The mixture was quenched with NaHCO$_3$ (60 mL) and then extracted with EtOAc (20 mL×3), the combined organic layer was washed with water (10 mL), dried over Na$_2$SO$_4$ and filtered. The filtrate was concentrated under reduced pressure to afford benzyl N-(4-oxo-1-piperidyl) carbamate (740 mg, crude) as yellow solid.
MS (M+H)$^+$=249.2

Step 8. Synthesis of benzyl (4-(7-(4-(2,6-dioxopiperidin-3-yl)-2-fluorophenyl)-2,7-diazaspiro[3.5]nonan-2-yl)piperidin-1-yl)carbamate (6)

To a solution of 3-(3-fluoro-4-(2,7-diazaspiro[3.5]nonan-7-yl)phenyl)piperidine-2,6-dione (355.58 mg, 966.66 μmol, HCl) in DCE (10 mL) were added TEA (815.13 mg, 8.06 mmol, 1.12 mL), 4A MS (300 mg) and benzyl N-(4-oxo-1-piperidyl) carbamate (200 mg, 805.55 μmol) at 20° C. Then NaBH(OAc)$_3$ (512.19 mg, 2.42 mmol) was slowly added at 20° C. and the resulting mixture was stirred at 20° C. for 12 h. LCMS showed starting material was consumed completely and 67% peak with desired mass was detected. The reaction mixture was filtered and the filtrate was concentrated in vacuum. The residue was purified by flash silica gel chromatography (10 g SepaFlash Silica Flash Column, Eluent of 0~100% EtOAc/Petroleum ether to 0~10% Dichloromethane/Methanol gradient @ 100 mL/min) to afford benzyl (4-(7-(4-(2,6-dioxopiperidin-3-yl)-2-fluorophenyl)-2,7-diazaspiro[3.5]nonan-2-yl)piperidin-1-yl)carbamate (342 mg, 582.48 μmol, 72.31% yield, 96% purity) as a light yellow solid. MS (M+H)$^+$=564.3

Step 9. Synthesis of 3-(4-(2-(1-aminopiperidin-4-yl)-2,7-diazaspiro[3.5]nonan-7-yl)-3-fluorophenyl)piperidine-2,6-dione (7)

A mixture of benzyl (4-(7-(4-(2,6-dioxopiperidin-3-yl)-2-fluorophenyl)-2,7-diazaspiro[3.5]nonan-2-yl)piperidin-1-yl)carbamate (325 mg, 576.59 μmol) in TFA (3 mL) at 20° C. and the resulting mixture was stirred at 60° C. for 3 h. LCMS showed 26% of starting material remained and 35% peak with desired mass was detected and the mixture was stirred at 60° C. for 1 h. LCMS showed 5% of starting material remained and 47% peak with desired mass was detected. The reaction mixture was concentrated in vacuum to afford 3-(4-(2-(1-aminopiperidin-4-yl)-2,7-diazaspiro[3.5]nonan-7-yl)-3-fluorophenyl)piperidine-2,6-dione (314 mg, crude, TFA) as a yellow oil. MS (M+H)$^+$=430.3

Step 10. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(4-(7-(4-(2,6-dioxopiperidin-3-yl)-2-fluorophenyl)-2,7-diazaspiro[3.5]nonan-2-yl)piperidin-1-yl)-3-methoxybenzamide (Compound 18)

To a solution of 4-((9-cyclopentyl-7,7-difluoro-5-methyl-6-oxo-6,7,8,9-tetrahydro-5H-pyrimido[4,5-b][1,4]diazepin-2-yl)amino)-3-methoxybenzoic acid (100 mg, 223.50 μmol) in DMF (3 mL) were added HATU (93.48 mg, 245.85 μmol) and DIPEA (57.77 mg, 446.99 μmol, 77.86 μL). The mixture was stirred at 20° C. for 10 min and a solution of 3-(4-(2-(1-aminopiperidin-4-yl)-2,7-diazaspiro[3.5]nonan-7-yl)-3-fluorophenyl)piperidine-2,6-dione (182.22 mg, 335.24 μmol, TFA) in DMF (3 mL) with DIPEA (86.66 mg, 670.49 μmol, 116.79 μL) was added and the resulting mixture was stirred at 20° C. for 1 h. LCMS showed starting material was consumed completely and 93% peak with desired mass. The reaction mixture was diluted with H$_2$O (12 mL) and extracted with EtOAc (12 mL×3). The organic layer was washed with brine (12 mL×3), dried over Na$_2$SO$_4$, filtered and concentrated. The residue was purified by prep-HPLC (column: Phenomenex Synergi Polar-RP 100*25 mm*4 μm; mobile phase: [water (TFA)—ACN]; B %: 31%-51%, 7 min) and lyophilization to afford product (160 mg). The product was dissolved in mix solution CH$_3$CN:H$_2$O=1:1 (10 mL). Saturated NaHCO$_3$ (2 mL) was added to this mixture solution to adjust the pH=7. The reaction mixture was extracted with DCM (10 mL×3), dried over Na$_2$SO$_4$, filtered and concentrated to give the residue. The residue was re-purified by prep-HPLC (column: Phenomenex C18 75*30 mm*3 μm; mobile phase: [water (FA)—ACN]; B %: 15%-45%, 7 min) and lyophilization to afford 4-((9-cyclopentyl-7,7-difluoro-5-methyl-6-oxo-6,7,8,9-tetrahydro-5H-pyrimido[4,5-b][1,4]diazepin-2-yl)amino)-N-(4-(7-(4-(2,6-dioxopiperidin-3-yl)-2-fluorophenyl)-2,7-diazaspiro[3.5]nonan-2-yl)piperidin-1-yl)-3-methoxybenzamide (68.6 mg, 73.89 μmol, 33.06% yield, 95% purity, 0.5 FA) as a white solid. MS (M+H)$^+$=859.4

$^1$H NMR (400 MHz, DMSO-d$_6$) δ=10.82 (s, 1H), 9.34 (s, 1H), 8.30-8.20 (m, 2H), 7.96 (s, 1H), 7.47-7.38 (m, 2H), 7.06-6.90 (m, 3H), 4.82-4.70 (m, 1H), 4.11-3.98 (m, 2H), 3.92 (s, 3H), 3.79 (dd, J=4.7, 11.7 Hz, 1H), 3.34-3.28 (m, 4H), 3.07-2.96 (m, 6H), 2.95-2.84 (m, 4H), 2.79 (t, J=9.1 Hz, 2H), 2.70-2.58 (m, 1H), 2.25-2.12 (m, 2H), 2.04-1.88 (m, 3H), 1.86-1.76 (m, 4H), 1.76-1.65 (m, 4H), 1.65-1.54 (m, 4H), 1.39-1.26 (m, 2H).
Example 19. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(4-((2R)-1-(4-(4-(2,6-dioxopiperidin-3-yl)-2-fluorophenyl)piperazin-1-yl)propan-2-yl)piperidin-1-yl)-3-methoxybenzamide (Compound 19)
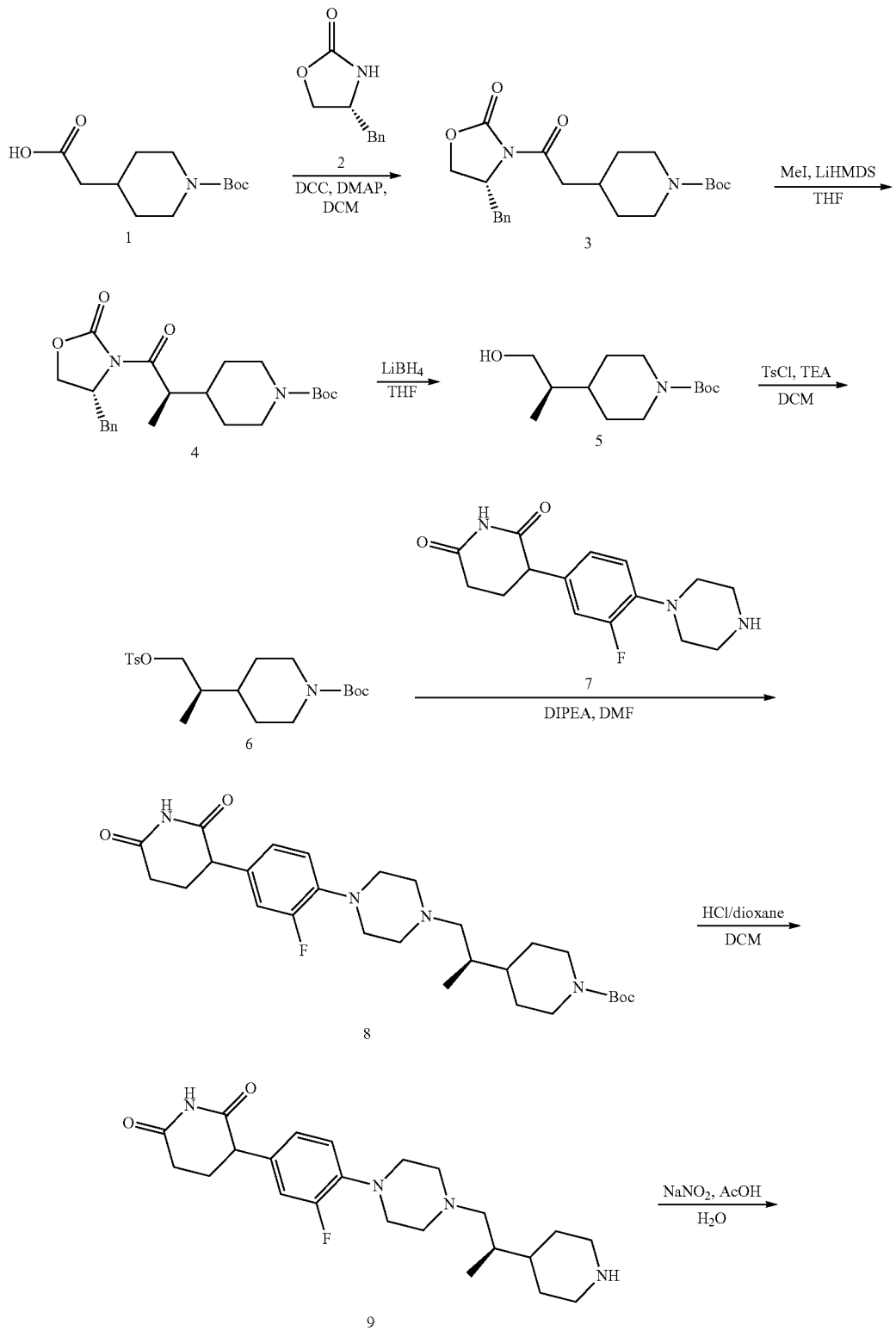

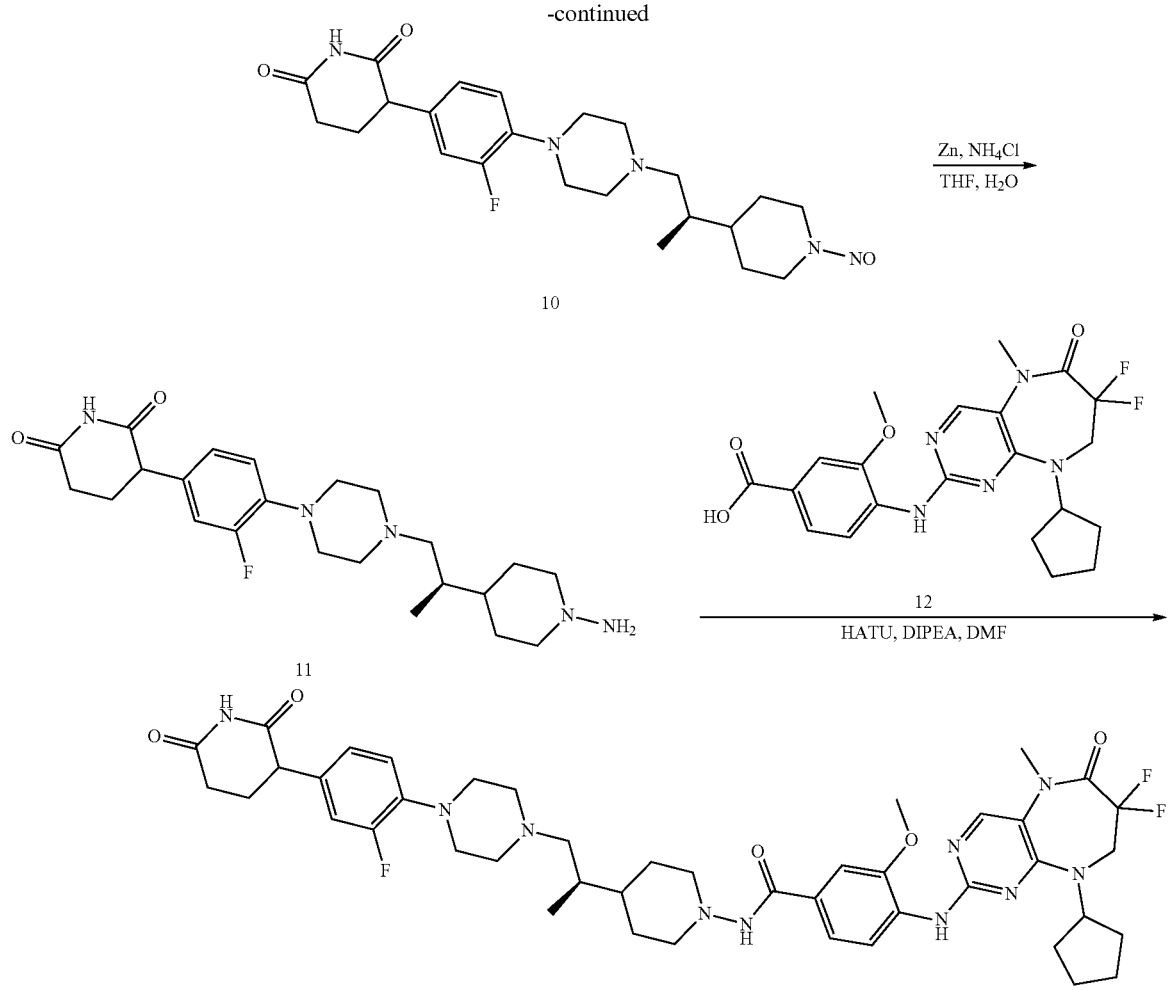

Compound 19

Step 1. Synthesis of tert-butyl (R)-4-(2-(4-benzyl-2-oxooxazolidin-3-yl)-2-oxoethyl)piperidine-1-carboxylate (3)

To a solution of 2-(1-(tert-butoxycarbonyl)piperidin-4-yl)acetic acid (6 g, 24.66 mmol) and (R)-4-benzyloxazolidin-2-one (4.4 g, 24.83 mmol) in DCM (60 mL) were added DMAP (1.51 g, 12.33 mmol) and DCC (5.09 g, 24.66 mmol, 4.99 mL) and the mixture was stirred at 20° C. for 14 h. LCMS showed the desired mass was detected. The mixture was filtered and the filter cake was washed with MTBE (30 mL). The filtrate was washed with $H_2O$ (50 mL×3), the combined organic layer was dried over $Na_2SO_4$ and filtered. The filtrate was concentrated under reduced pressure. The crude was diluted with Petroleum ether (50 mL) and stirred at 20° C. for 0.5 h. The mixture was filtered and the filter cake was washed with Petroleum ether (20 mL). The filtrate was concentrated under reduced pressure. The product was purified by flash silica gel chromatography (120 g SepaFlash Silica Flash Column, Eluent of 50~80% EtOAc/Petroleum ether gradient @ 100 mL/min) to afford tert-butyl (R)-4-(2-(4-benzyl-2-oxooxazolidin-3-yl)-2-oxoethyl)piperidine-1-carboxylate (10 g, 24.10 mmol, 97.73% yield, 97% purity) as a yellow oil. MS (M−56+H)$^+$=347.4

Step 2. Synthesis of tert-butyl 4-((R)-1-((R)-4-benzyl-2-oxooxazolidin-3-yl)-1-oxopropan-2-yl)piperidine-1-carboxylate (4)

To a solution of tert-butyl (R)-4-(2-(4-benzyl-2-oxooxazolidin-3-yl)-2-oxoethyl)piperidine-1-carboxylate (10 g, 24.85 mmol) in THF (200 mL) was slowly added LiHMDS (2 M, 25.00 mL) at 0° C. and the mixture stirred at 0° C. for 30 min. Then MeI (7.07 g, 49.80 mmol, 3.10 mL) was added at −40° C. and the mixture was stirred at −40° C. for 2 h, then the reaction mixture was warmed to 20° C. and stirred at 20° C. for 14 h. LCMS showed a peak (52%) with desired mass. The mixture was quenched with $NH_4Cl$ (100 mL) and extracted with EtOAc (100 mL×3). The combined organic layer was washed with brine (50 mL), dried over $Na_2SO_4$ and filtered. The filtrate was concentrated under reduced pressure. The residue was purified by flash silica gel chromatography (120 g SepaFlash Silica Flash Column, Eluent of 20% EtOAc/Petroleum ether gradient @ 50 mL/min) to afford tert-butyl 4-((R)-1-((R)-4-benzyl-2-oxooxazolidin-3-yl)-1-oxopropan-2-yl)piperidine-1-carboxylate (5.42 g, 13.01 mmol, 52.36% yield) as a yellow oil. MS (M−56+H)$^+$=361.1

Step 3. Synthesis of tert-butyl (R)-4-(1-hydroxypropan-2-yl)piperidine-1-carboxylate (5)

To a solution of tert-butyl 4-((R)-1-((R)-4-benzyl-2-oxooxazolidin-3-yl)-1-oxopropan-2-yl)piperidine-1-carboxylate (5.42 g, 13.01 mmol) in THF (100 mL) was slowly added LiBH$_4$ (460 mg, 21.12 mmol) at 20° C. and the mixture was stirred at 20° C. for 30 h. LCMS showed trace of the starting material remained. The mixture was quenched with NH$_4$Cl (50 mL) and extracted with EtOAc (50 mL×3). The combined organic layer was washed with water (50 mL), dried over Na$_2$SO$_4$ and filtered. The filtrate was concentrated under reduced pressure to afford tert-butyl (R)-4-(1-hydroxypropan-2-yl)piperidine-1-carboxylate (5 g, crude) as a yellow oil. MS (M+H)$^+$=244.4

Step 4. Synthesis of tert-butyl (R)-4-(1-(tosyloxy)propan-2-yl)piperidine-1-carboxylate (6)

To a solution of tert-butyl (R)-4-(1-hydroxypropan-2-yl)piperidine-1-carboxylate (5 g, 20.55 mmol) in DCM (80 mL) were added TEA (6.25 g, 61.79 mmol, 8.6 mL) and TosCl (3.92 g, 20.55 mmol) and the mixture was stirred at 20° C. for 14 h. LCMS showed the desired mass. The mixture was diluted with water (50 mL), extracted with EtOAc (20 mL×2). The combined organic layer was dried over Na$_2$SO$_4$, filtered and concentrated under vacuum. The residue was purified by flash silica gel chromatography (20 g SepaFlash Silica Flash Column, Eluent of 17-20% EtOAc/Petroleum ether gradient @ 100 mL/min) to afford tert-butyl (R)-4-(1-(tosyloxy)propan-2-yl)piperidine-1-carboxylate (2.19 g, 3.75 mmol, 18.23% yield, 68% purity) as a yellow oil. MS (M−100+H)$^+$=298.3

Step 5. Synthesis of tert-butyl 4-((2R)-1-(4-(4-(2,6-dioxopiperidin-3-yl)-2-fluorophenyl)piperazin-1-yl)propan-2-yl)piperidine-1-carboxylate (8)

To a solution of 3-(3-fluoro-4-(piperazin-1-yl)phenyl)piperidine-2,6-dione (0.5 g, 1.23 mmol, TFA salt) and tert-butyl (R)-4-(1-(tosyloxy)propan-2-yl)piperidine-1-carboxylate (1.08 g, 1.85 mmol, 68% purity) in DMF (8 mL) were added DIPEA (797.10 mg, 6.17 mmol, 1.07 mL) and NaI (18.49 mg, 123.35 μmol) and the mixture was stirred at 60° C. for 14 h. LCMS showed the desired mass was detected. The reaction mixture was diluted with water (20 mL) and extracted with EtOAc (10 mL×3). The combined organic layer was washed with brine (10 mL×3), dried over Na$_2$SO$_4$ and filtered. The filtrate was concentrated under reduced pressure. The residue was purified by flash silica gel chromatography (12 g SepaFlash Silica Flash Column, Eluent of 60% EtOAc/Petroleum ether gradient @ 80 mL/min) to afford tert-butyl 4-((2R)-1-(4-(4-(2,6-dioxopiperidin-3-yl)-2-fluorophenyl)piperazin-1-yl)propan-2-yl)piperidine-1-carboxylate (330 mg, 606.80 μmol, 49.19% yield, 95% purity) as a white solid. MS (M+H)$^+$=517.5

SFC: Method Details: "Column: (S. S) Whelk-O$_1$ 50×4.6 mm I. D., 3.5 μm Mobile phase: Phase A for CO$_2$, and Phase B for MeOH+ACN=4:1 (0.05% DEA); Gradient elution: 40% MeOH+ACN=4:1 (0.05% DEA) in CO$_2$ Flow rate: 3 mL/min; Detector: PDA Column Temp: 35° C.; Back Pressure: 100 Bar".

Step 6. Synthesis of 3-(3-fluoro-4-(4-((R)-2-(piperidin-4-yl)propyl)piperazin-1-yl)phenyl)piperidine-2,6-dione (9)

To a solution of tert-butyl 4-((2R)-1-(4-(4-(2,6-dioxopiperidin-3-yl)-2-fluorophenyl)piperazin-1-yl)propan-2-yl)piperidine-1-carboxylate (330 mg, 638.73 μmol) in DCM (5 mL) was added HCl/dioxane (4 M, 6 mL) and the mixture was stirred at 20° C. for 1 h. LCMS showed a major peak (100%) with desired mass after work-up. The mixture was concentrated under reduced pressure to afford 3-(3-fluoro-4-(4-((R)-2-(piperidin-4-yl)propyl)piperazin-1-yl)phenyl)piperidine-2,6-dione (290 mg, crude, HCl salt) as a white solid. MS (M+H)$^+$=417.4

Step 7. Synthesis of 3-(3-fluoro-4-(4-((R)-2-(1-nitrosopiperidin-4-yl)propyl)piperazin-1-yl)phenyl)piperidine-2,6-dione (10)

To a solution of 3-(3-fluoro-4-(4-((R)-2-(piperidin-4-yl)propyl)piperazin-1-yl)phenyl)piperidine-2,6-dione (290 mg, 640.19 μmol, HCl salt) in H$_2$O (6 mL) was added NaNO$_2$ (132.51 mg, 1.92 mmol), then AcOH (147.00 mg, 2.45 mmol, 140 μL) was added slowly and the resulting mixture was stirred at 20° C. for 14 h. LCMS showed a peak (21%) with desired mass and 70% of the starting material remained. Additional NaNO$_2$ (132.51 mg, 1.92 mmol) and AcOH (147.00 mg, 2.45 mmol, 140 μL) were added and the mixture was stirred at 20° C. for another 1 h. LCMS showed 43% of the desired mass and 43% of the starting material remained. Another batch of NaNO$_2$ (132.51 mg, 1.92 mmol) was added and the mixture was stirred at 20° C. for 12.5 h. LCMS showed 75% of the desired mass and 23% of the starting material remained. The mixture was quenched with NaHCO$_3$ (20 mL) and extracted with EtOAc (10 mL×3). The combined organic layer was washed with NaHCO$_3$ (10 mL) and water (10 mL), dried over Na$_2$SO$_4$ and filtered. The filtrate was concentrated under reduced pressure to afford 3-(3-fluoro-4-(4-((R)-2-(1-nitrosopiperidin-4-yl)propyl)piperazin-1-yl)phenyl)piperidine-2,6-dione (250 mg, crude) as a yellow solid. MS (M+H)$^+$=446.5.

Step 8. Synthesis of 3-(4-(4-((R)-2-(1-aminopiperidin-4-yl)propyl)piperazin-1-yl)-3-fluorophenyl)piperidine-2,6-dione (11)

To a solution of 3-(3-fluoro-4-(4-((R)-2-(1-nitrosopiperidin-4-yl)propyl)piperazin-1-yl)phenyl)piperidine-2,6-dione (250 mg, 561.13 μmol) and NH$_4$Cl (92 mg, 1.72 mmol) in THF (5 mL) and H$_2$O (2.5 mL) was added Zn (111 mg, 1.70 mmol) at 0° C. and the mixture was stirred at 20° C. for 4 h. LCMS showed 17% of the starting material remained and 79% of the desired mass. The mixture was filtered and the filter cake was washed with THF (30 mL). The filtrated was concentrated under reduced pressure to afford 3-(4-(4-((R)-2-(1-aminopiperidin-4-yl)propyl)piperazin-1-yl)-3-fluorophenyl)piperidine-2,6-dione (250 mg, crude) as a white solid.
MS (M+H)$^+$=432.1.

Step 9. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(4-((2R)-1-(4-(4-(2,6-dioxopiperidin-3-yl)-2-fluorophenyl)piperazin-1-yl)propan-2-yl)piperidin-1-yl)-3-methoxybenzamide (Compound 19)

To a solution of 4-((9-cyclopentyl-7,7-difluoro-5-methyl-6-oxo-6,7,8,9-tetrahydro-5H-pyrimido[4,5-b][1,4]diazepin-2-yl)amino)-3-methoxybenzoic acid (0.2 g, 446.99 μmol) in DMF (3 mL) were added HATU (203 mg, 533.89 μmol) and DIPEA (371.00 mg, 2.87 mmol, 0.5 mL) and the mixture was stirred at 20° C. for 15 min. Then a solution of 3-(4-(4-((R)-2-(1-aminopiperidin-4-yl)propyl)piperazin-1-yl)-3-fluorophenyl)piperidine-2,6-dione (250 mg, 579.31 μmol) in DMF (3 mL) was added and the mixture was stirred at 20° C. for 45 min. LCMS showed 64% of the desired mass. The reaction mixture was diluted with water (15 mL) and extracted with EtOAc (10 mL×3). The combined organic layer was washed with brine (15 mL×2), dried over $Na_2SO_4$ and filtered. The filtrate was concentrated under reduced pressure. The residue was purified by flash silica gel chromatography (12 g SepaFlash Silica Flash Column, Eluent of 8-15% MeOH/EtOAc gradient @ 80 mL/min) and re-purified by prep-TLC (EtOAc:Dichloromethane:Methanol=5:5:1). The product was lyophilized to afford 4-((9-cyclopentyl-7,7-difluoro-5-methyl-6-oxo-6,7,8,9-tetrahydro-5H-pyrimido[4,5-b][1,4]diazepin-2-yl)amino)-N-(4-((2R)-1-(4-(4-(2,6-dioxopiperidin-3-yl)-2-fluorophenyl)piperazin-1-yl)propan-2-yl)piperidin-1-yl)-3-methoxybenzamide (95.5 mg, 104.82 μmol, 23.45% yield, 94.5% purity) as a white solid. MS (M+H)$^+$=861.0 SFC Method details: "Column: (S, S) Whelk-O$_1$ 100×4.6 mm I. D., 3.5 μm Mobile phase: Phase A for $CO_2$, and Phase B for MeOH+ACN (0.05% DEA); Gradient elution: 60% MeOH+ACN (0.05% DEA) in $CO_2$ Flow rate: 3 mL/min; Detector: PDA Column Temp: 35° C.; Back Pressure: 100 Bar"

$^1$H NMR (400 MHz, DMSO-d$_6$) δ=10.81 (s, 1H), 9.26 (s, 1H), 8.29-8.24 (m, 2H), 7.95 (s, 1H), 7.45-7.38 (m, 2H), 7.06-6.93 (m, 3H), 4.81-4.71 (m, 1H), 4.04 (br t, J=14.1 Hz, 2H), 3.93 (s, 3H), 3.80 (dd, J=4.9, 12.0 Hz, 1H), 3.30 (s, 3H), 3.07-2.96 (m, 5H), 2.81-2.71 (m, 2H), 2.64-2.59 (m, 1H), 2.56-2.52 (m, 6H), 2.31-2.08 (m, 3H), 2.03-1.89 (m, 3H), 1.75-1.54 (m, 9H), 1.50-1.29 (m, 3H), 0.86 (br d, J=6.6 Hz, 3H).

Example 20. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(4-((2S)-1-(4-(4-(2,6-dioxopiperidin-3-yl)-2-fluorophenyl)piperazin-1-yl)propan-2-yl)piperidin-1-yl)-3-methoxybenzamide (Compound 20)

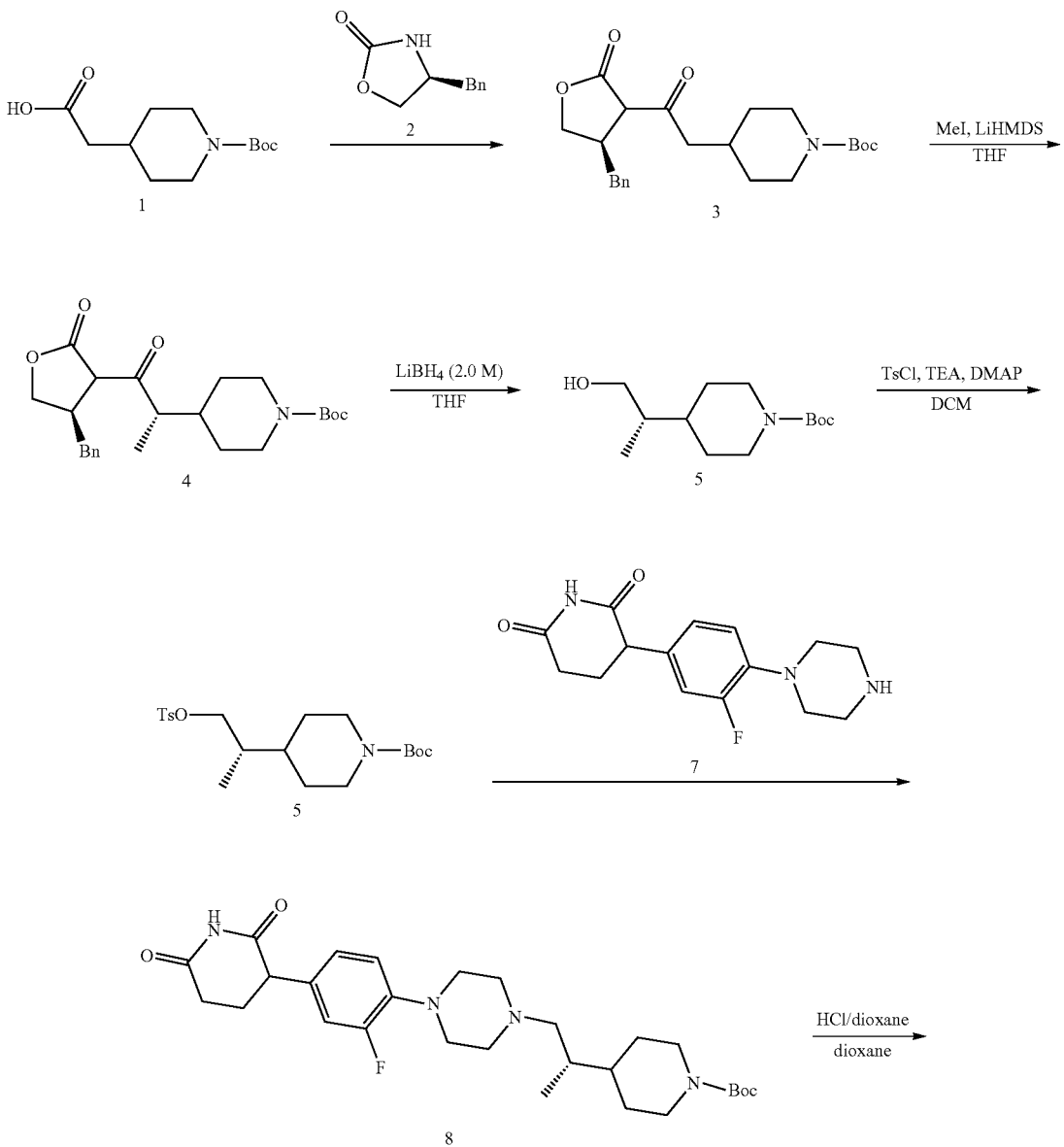

123

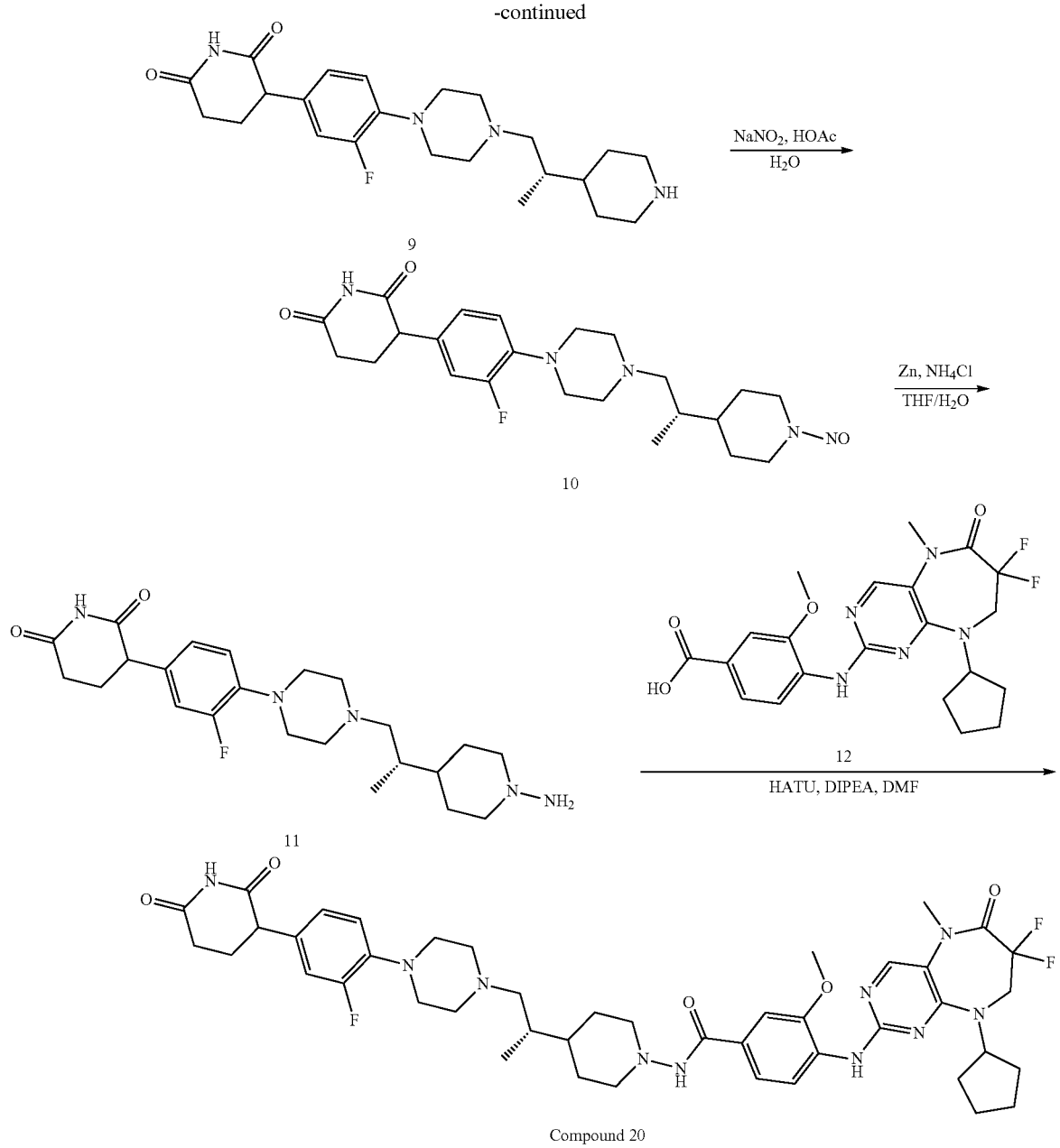

Compound 20

Step 1. Synthesis of tert-butyl (S)-4-(2-(4-benzyl-2-oxooxazolidin-3-yl)-2-oxoethyl)piperidine-1-carboxylate (3)

To a solution of 2-(1-(tert-butoxycarbonyl)piperidin-4-yl)acetic acid (4 g, 16.44 mmol) in DCM (40 mL) were added DCC (3.73 g, 18.08 mmol, 3.66 mL) and DMAP (1.00 g, 8.22 mmol), and after stirring for 0.5 h, (S)-4-benzyloxazolidin-2-one (3.20 g, 18.08 mmol) was added and the resulting mixture was stirred at 25° C. for 12 h. LCMS showed a peak (~57%) with desired mass. The mixture was filtered to remove the solid. The filtrate was diluted with water (100 ml) and extracted with DCM (50 mL×3). The combined organic layers were washed with brine (50 mL), dried over anhydrous sodium sulfate, filtered and concentrated under reduced pressure. The residue was purified by flash silica gel chromatography (ISCO; 40 g SepaFlash Silica Flash Column, Eluent of 0~40% petroleum ether:EtOAc gradient @ 80 mL/min) to afford tert-butyl (S)-4-(2-(4-benzyl-2-oxooxazolidin-3-yl)-2-oxoethyl)piperidine-1-carboxylate (7 g, 13.22 mmol, 80.40% yield, 76% purity) as yellow oil. MS (M−56+H)$^+$=347.1

Step 2. Synthesis of tert-butyl 4-((S)-1-((S)-4-benzyl-2-oxooxazolidin-3-yl)-1-oxopropan-2-yl)piperidine-1-carboxylate (4)

To a solution of tert-butyl (S)-4-(2-(4-benzyl-2-oxooxazolidin-3-yl)-2-oxoethyl)piperidine-1-carboxylate (7 g, 17.39 mmol) in THF (30 mL) was added LiHMDS (1 M, 26.09 mL) at 0° C., and after stirring for 0.5 h, MeI (4.94 g, 34.78 mmol, 2.17 mL) was added at −40° C. and the resulting mixture was stirred at 25° C. for 12 h. LCMS showed a peak (57%) with desired mass. The mixture was quenched with NH₄Cl (50 mL) and extracted with EtOAc (30 mL×3). The combined organic layer was washed with brine (50 mL), dried over Na$_2$SO$_4$ and filtered. The filtrate was concentrated under reduced pressure. The residue was purified by flash silica gel chromatography (ISCO; 80 g SepaFlash Silica Flash Column, Eluent of 0~40% petroleum ether:EtOAc gradient @ 80 mL/min) to afford tert-butyl 4-((S)-1-((S)-4-benzyl-2-oxooxazolidin-3-yl)-1-oxopropan-2-yl)piperidine-1-carboxylate (3.3 g, 7.46 mmol, 42.91% yield, 94.2% purity) as yellow oil. MS (M−56+H)$^+$=361.2

Step 3. Synthesis of tert-butyl (S)-4-(1-hydroxypropan-2-yl)piperidine-1-carboxylate (5)

To a solution of tert-butyl 4-((S)-1-((S)-4-benzyl-2-oxooxazolidin-3-yl)-1-oxopropan-2-yl)piperidine-1-carboxylate (3.3 g, 7.92 mmol) in THF (20 mL) was added LiBH$_4$ (2 M, 5.94 mL) at 0° C. The mixture was stirred at 25° C. for 12 h. LCMS showed the starting material was consumed completely. The mixture was quenched with NH$_4$Cl (50 mL) and extracted with EtOAc (50 mL×3). The combined organic layer was washed with brine (50 mL), dried over Na$_2$SO$_4$ and filtered. The filtrate was concentrated under reduced pressure to afford tert-butyl (S)-4-(1-hydroxypropan-2-yl)piperidine-1-carboxylate (2.7 g, crude) as yellow oil. MS (M+H)$^+$=244.4

Step 4. Synthesis of tert-butyl (S)-4-(1-(tosyloxy)propan-2-yl)piperidine-1-carboxylate (6)

To a solution of tert-butyl (S)-4-(1-hydroxypropan-2-yl)piperidine-1-carboxylate (2.7 g, 11.10 mmol) in DCM (20 mL) were added TosCl (2.12 g, 11.10 mmol), DMAP (271.10 mg, 2.22 mmol) and TEA (2.25 g, 22.19 mmol, 3.09 mL). The mixture was stirred at 25° C. for 12 h. LCMS showed a peak (15%) with desired mass. The reaction mixture was diluted with water (50 mL) and extracted with DCM (50 mL×3). The combined organic layers were washed with saturated brine (50 mL), dried over anhydrous sodium sulfate, filtered and concentrated under reduced pressure. The residue was purified by silica gel chromatography (SiO$_2$, 1000 mesh, petroleum ether:EtOAc=1:0 then 20:1) to afford tert-butyl (S)-4-(1-(tosyloxy)propan-2-yl)piperidine-1-carboxylate (1.8 g, 4.53 mmol, 40.81% yield) as yellow oil. MS (M−56+H)$^+$=342.0

Step 5. Synthesis of tert-butyl 4-((2S)-1-(4-(4-(2,6-dioxopiperidin-3-yl)-2-fluorophenyl)piperazin-1-yl)propan-2-yl)piperidine-1-carboxylate (8)

To a solution of tert-butyl (S)-4-(1-(tosyloxy)propan-2-yl)piperidine-1-carboxylate (1.8 g, 4.53 mmol) in DMF (10 mL) were added DIEA (877.82 mg, 6.79 mmol, 1.18 mL) and 3-(3-fluoro-4-(piperazin-1-yl)phenyl)piperidine-2,6-dione (1.06 g, 3.62 mmol). The mixture was stirred at 50° C. for 12 h. LCMS showed a peak (10%) with desired mass. The reaction mixture was diluted with water (50 mL) and extracted with EtOAc (50 mL×3). The combined organic layers were washed with brine (50 mL), dried over anhydrous sodium sulfate, filtered and concentrated under reduced pressure. The residue was purified by flash silica gel chromatography (ISCO; 40 g SepaFlash Silica Flash Column, Eluent of 0~30% petroleum ether/EtOAc:ethanol (v:v=3:1) gradient @60 mL/min) to afford tert-butyl 4-((2S)-1-(4-(4-(2,6-dioxopiperidin-3-yl)-2-fluorophenyl)piperazin-1-yl)propan-2-yl)piperidine-1-carboxylate (1.2 g, 2.32 mmol, 51.30% yield) as a yellow solid.
MS (M+H)$^+$=517.5

Step 6. Synthesis of 3-(3-fluoro-4-(4-((S)-2-(piperidin-4-yl)propyl)piperazin-1-yl)phenyl)piperidine-2,6-dione (9)

To a solution of tert-butyl 4-((2S)-1-(4-(4-(2,6-dioxopiperidin-3-yl)-2-fluorophenyl)piperazin-1-yl)propan-2-yl)piperidine-1-carboxylate (1.2 g, 2.32 mmol) in dioxane (5 mL) was added HCl/dioxane (4 M, 10 mL). The mixture was stirred at 20° C. for 1 h. LCMS showed a peak (40%) with desired mass. The mixture was concentrated under reduced pressure to afford 3-(3-fluoro-4-(4-((S)-2-(piperidin-4-yl)propyl)piperazin-1-yl)phenyl)piperidine-2,6-dione (1 g, crude, HCl salt) as yellow oil. MS (M+H)$^+$=417.2

Step 7. Synthesis of 3-(3-fluoro-4-(4-((S)-2-(1-nitrosopiperidin-4-yl)propyl)piperazin-1-yl)phenyl)piperidine-2,6-dione (10)

To a solution of 3-(3-fluoro-4-(4-((S)-2-(piperidin-4-yl)propyl)piperazin-1-yl)phenyl)piperidine-2,6-dione (0.8 g, 1.77 mmol, HCl salt) in H$_2$O (15 mL) was added NaNO$_2$ (609.24 mg, 8.83 mmol). Then HOAc (530.27 mg, 8.83 mmol, 505.02 µL) was added dropwise to the mixture at 0° C. The mixture was stirred at 20° C. for 12 h. LCMS showed a main peak with desired mass. The reaction mixture was quenched with saturated sodium bicarbonate solution (50 mL) and extracted with EtOAc (50 mL×3). The combined organic layers were washed with brine (50 mL), dried over anhydrous sodium sulfate, filtered and concentrated under reduced pressure to afford 3-(3-fluoro-4-(4-((S)-2-(1-nitrosopiperidin-4-yl)propyl)piperazin-1-yl)phenyl)piperidine-2,6-dione (0.3 g, crude) as yellow oil. MS (M+H)$^+$=446.2.

Step 8. Synthesis of 3-(4-(4-((S)-2-(1-aminopiperidin-4-yl)propyl)piperazin-1-yl)-3-fluorophenyl)piperidine-2,6-dione (11)

To a solution of 3-(3-fluoro-4-(4-((S)-2-(1-nitrosopiperidin-4-yl)propyl)piperazin-1-yl)phenyl)piperidine-2,6-dione (0.3 g, 673.36 µmol) in THF (10 mL) was added Zn (220.15 mg, 3.37 mmol) at 0° C. Then a solution of NH$_4$Cl (108.05 mg, 2.02 mmol) in H$_2$O (5 mL) was added to the mixture at 0° C. The mixture was stirred at 20° C. for 2 h. LCMS showed a peak (60%) with desired mass. The mixture was filtered to remove the solid. The filter cake was washed with THF (50 mL). The filtrate was concentrated under reduced pressure to afford 3-(4-(4-((S)-2-(1-aminopiperidin-4-yl)propyl)piperazin-1-yl)-3-fluorophenyl)piperidine-2,6-dione (240 mg, crude) as a yellow solid. MS (M+H)$^+$=432.2

Step 9. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(4-((2S)-1-(4-(4-(2,6-dioxopiperidin-3-yl)-2-fluorophenyl)piperazin-1-yl)propan-2-yl)piperidin-1-yl)-3-methoxybenzamide (Compound 20)

To a solution of 4-((9-cyclopentyl-7,7-difluoro-5-methyl-6-oxo-6,7,8,9-tetrahydro-5H-pyrimido[4,5-b][1,4]diazepin-2-yl)amino)-3-methoxybenzoic acid (150 mg, 335.24 µmol) in DMF (2 mL) were added HATU (152.96 mg, 402.29 µmol) and DIEA (216.64 mg, 1.68 mmol, 291.97 µL), the mixture was stirred for 0.5 h, then a solution of 3-(4-(4-

((S)-2-(1-aminopiperidin-4-yl)propyl)piperazin-1-yl)-3-fluorophenyl)piperidine-2,6-dione (144.67 mg, 335.24 μmol) in DMF (2 mL) was added to the mixture and the resulting mixture was stirred at 20° C. for 12 h. LCMS showed a peak (36%) with desired mass. The reaction mixture was diluted with water (20 mL) and extracted with EtOAc (30 mL×3). The combined organic layers were washed with brine (50 mL), dried over anhydrous sodium sulfate, filtered and concentrated under reduced pressure. The residue was purified by flash silica gel chromatography (ISCO; 20 g SepaFlash Silica Flash Column, Eluent of 0~60% petroleum ether:EtOAc/ethanol (v/v=2/1) gradient @ 60 mL/min) and prep-HPLC (column: Welch Ultimate C18 150×25 mm×5 μm; mobile phase: [water (FA)—ACN]; B %: 15%-45%, 10 min), the eluent was lyophilized to afford 4-((9-cyclopentyl-7,7-difluoro-5-methyl-6-oxo-6,7,8,9-tetrahydro-5H-pyrimido[4,5-b][1,4]diazepin-2-yl)amino)-N-(4-((2S)-1-(4-(4-(2,6-dioxopiperidin-3-yl)-2-fluorophenyl)piperazin-1-yl)propan-2-yl)piperidin-1-yl)-3-methoxybenzamide (13.1 mg, 14.79 μmol, 4.35% yield, 96.3% purity) as a white solid.

MS (M+H)$^+$=861.4

$^1$H NMR (400 MHz, DMSO-d$_6$) δ=10.81 (s, 1H), 9.25 (s, 1H), 8.41-8.17 (m, 2H), 7.96 (s, 1H), 7.47-7.36 (m, 2H), 7.08-6.82 (m, 3H), 4.84-4.67 (m, 1H), 4.12-3.97 (m, 2H), 3.93 (s, 3H), 3.80 (dd, J=4.8, 11.8 Hz, 1H), 3.32 (s, 3H), 3.06-2.93 (m, 6H), 2.81-2.61 (m, 8H), 2.28-2.08 (m, 3H), 2.05-1.88 (m, 3H), 1.80-1.54 (m, 9H), 1.51-1.27 (m, 3H), 0.86 (d, J=6.8 Hz, 3H).

Example 21. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-((7-(4-(2,6-dioxopiperidin-3-yl)-2-fluorophenyl)-7-azaspiro[3.5]nonan-2-yl)methyl)piperidin-4-yl)-3-methoxybenzamide (Compound 21)

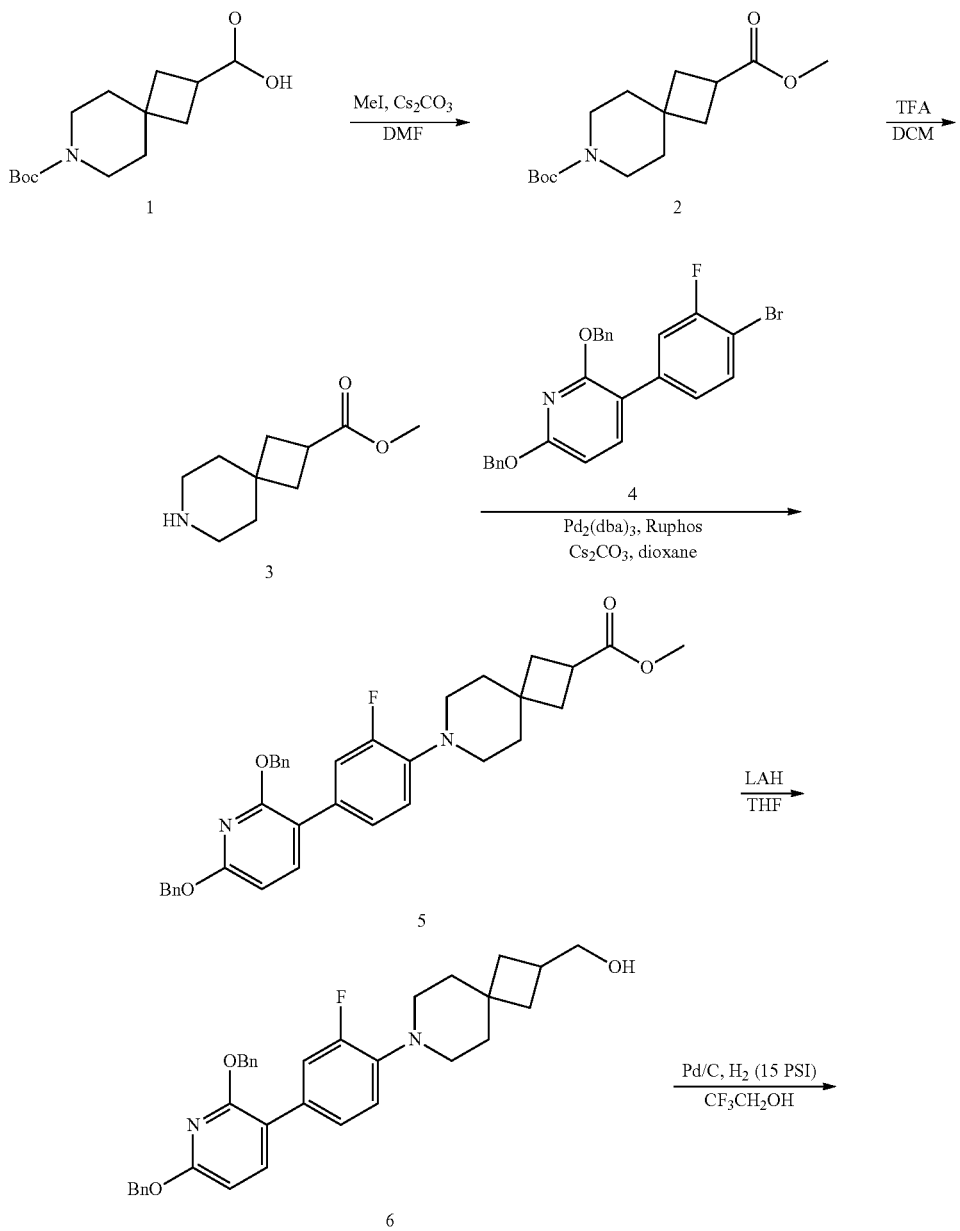

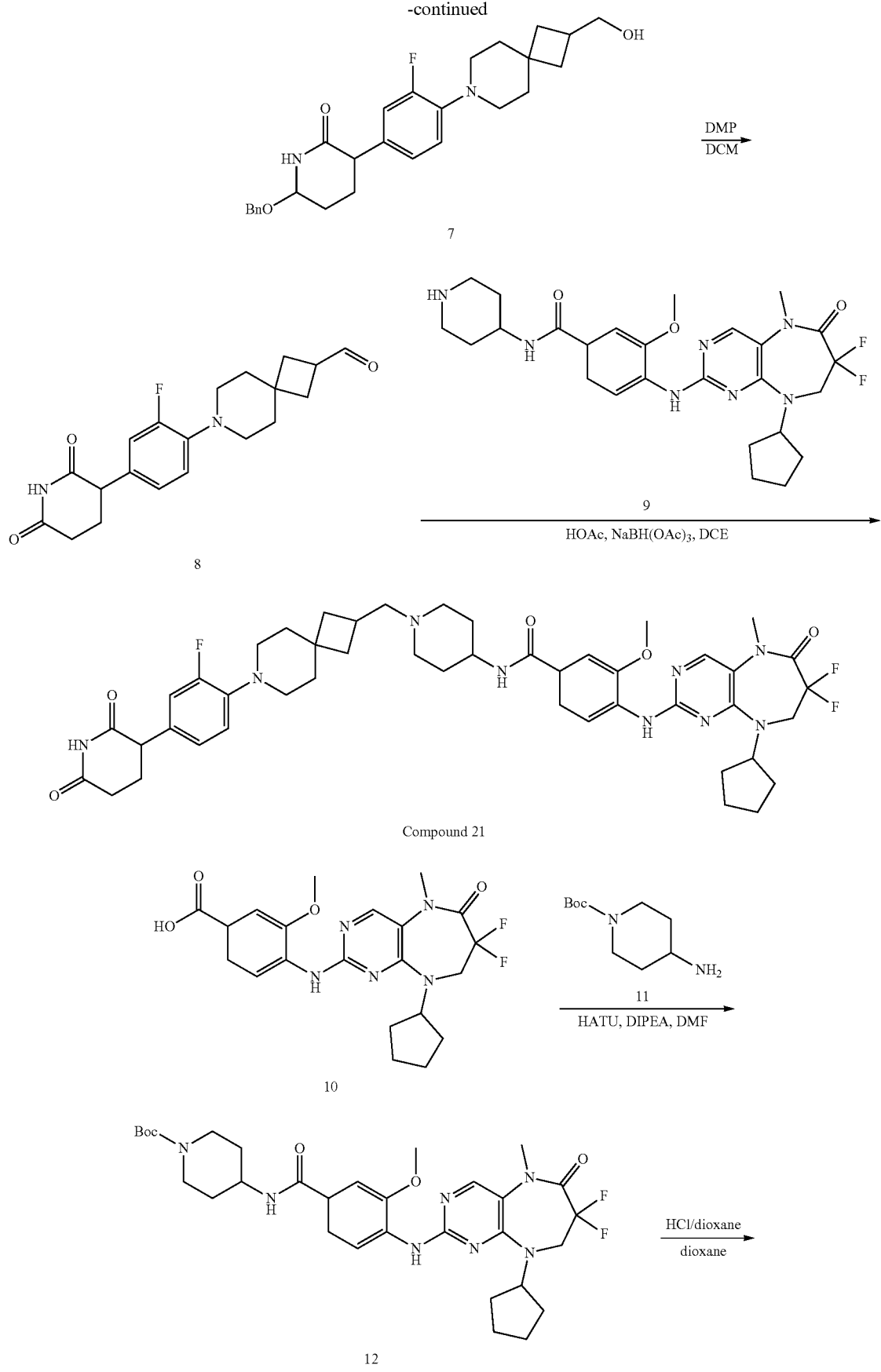

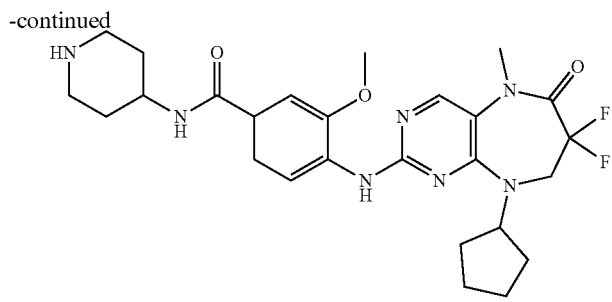

9

Step 1. Synthesis of 7-(tert-butyl) 2-methyl 7-azaspiro[3.5]nonane-2,7-dicarboxylate (2)

To a solution of 7-(tert-butoxycarbonyl)-7-azaspiro[3.5]nonane-2-carboxylic acid (3 g, 11.14 mmol) in DMF (20 mL) were added MeI (2.37 g, 16.71 mmol, 1.04 mL) and $Cs_2CO_3$ (5.44 g, 16.71 mmol). The mixture was stirred at 25° C. for 12 h. LCMS showed a main peak with desired mass. The reaction mixture was diluted with water (50 mL) and extracted with EtOAc (50 mL×3). The combined organic layers were washed with saturated brine (50 mL), dried over anhydrous sodium sulfate, filtered and concentrated under reduced pressure to afford 7-(tert-butyl) 2-methyl 7-azaspiro[3.5]nonane-2,7-dicarboxylate (5.1 g, crude) as yellow oil.
MS $(M-56+H)^+=228.1$

Step 2. Synthesis of methyl 7-azaspiro[3.5]nonane-2-carboxylate (3)

To a solution of 7-(tert-butyl) 2-methyl 7-azaspiro[3.5]nonane-2,7-dicarboxylate (4.6 g, 16.23 mmol) in DCM (20 mL) was added TFA (7.70 g, 67.53 mmol, 5 mL) at 0° C. The mixture was stirred at 20° C. for 2 h. LCMS showed 7-(tert-butyl) 2-methyl 7-azaspiro[3.5]nonane-2,7-dicarboxylate was remained. Additional TFA (7.70 g, 67.53 mmol, 5 mL) was added and the resulting mixture was stirred at 20° C. for 12 h. LCMS showed a main peak with desired mass. The mixture was concentrated under reduced pressure to afford methyl 7-azaspiro[3.5]nonane-2-carboxylate (5 g, crude, TFA salt) as yellow oil. MS $(M+H)^+=184.1$

Step 3. Synthesis of methyl 7-(4-(2,6-bis(benzyloxy)pyridin-3-yl)-2-fluorophenyl)-7-azaspiro[3.5]nonane-2-carboxylate (5)

To a solution of methyl 7-azaspiro[3.5]nonane-2-carboxylate (3 g, 10.09 mmol, TFA salt) in dioxane (20 mL) were added 2,6-bis(benzyloxy)-3-(4-bromo-3-fluorophenyl)pyridine (3.75 g, 8.07 mmol), $Cs_2CO_3$ (9.86 g, 30.28 mmol), $Pd_2(dba)_3$ (462.06 mg, 504.59 µmol) and RuPhos (470.92 mg, 1.01 mmol). The mixture was stirred at 100° C. for 12 h. LCMS showed a peak (~16%) with desired mass. The reaction mixture was filtered to remove the solid. The filtrate was diluted with water (100 mL) and extracted with EtOAc (60 mL×3). The combined organic layers were washed with brine (100 mL), dried over anhydrous sodium sulfate, filtered and concentrated under reduced pressure. The residue was purified by flash silica gel chromatography (ISCO; 120 g SepaFlash Silica Flash Column, Eluent of 0~10% petroleum ether:EtOAc gradient @ 80 mL/min) to afford methyl 7-(4-(2,6-bis(benzyloxy)pyridin-3-yl)-2-fluorophenyl)-7-azaspiro[3.5]nonane-2-carboxylate (1 g, 1.45 mmol, 14.34% yield, 82% purity) as yellow oil. MS $(M+H)^+=567.3$

Step 4. Synthesis of (7-(4-(2,6-bis(benzyloxy)pyridin-3-yl)-2-fluorophenyl)-7-azaspiro[3.5]nonan-2-yl)methanol (6)

To a suspension of $LiAlH_4$ (133.96 mg, 3.53 mmol) in THF (5 mL) was added a solution of methyl 7-(4-(2,6-bis(benzyloxy)pyridin-3-yl)-2-fluorophenyl)-7-azaspiro[3.5]nonane-2-carboxylate (1 g, 1.76 mmol) in THF (5 mL) drop-wise. The mixture was stirred at 20° C. for 2 h under $N_2$. LCMS showed a major peak (100%) with desired mass. The reaction mixture was quenched with $H_2O$ (0.15 mL), NaOH (15% aq, 0.15 mL) and $H_2O$ (0.4 mL). The reaction mixture was dried over $Na_2SO_4$ and filtered. The filtrate was concentrated under reduced pressure. The residue was purified by flash silica gel chromatography (ISCO; 20 g SepaFlash Silica Flash Column, Eluent of 0~30% petroleum ether:EtOAc gradient @ 80 mL/min) to afford (7-(4-(2,6-bis(benzyloxy)pyridin-3-yl)-2-fluorophenyl)-7-azaspiro[3.5]nonan-2-yl)methanol (0.7 g, 1.22 mmol, 69.37% yield, 94.2% purity) as yellow oil. MS $(M+H)^+=539.6$

Step 5. Synthesis of 3-(3-fluoro-4-(2-(hydroxymethyl)-7-azaspiro[3.5]nonan-7-yl)phenyl)piperidine-2,6-dione (7)

To a solution of (7-(4-(2,6-bis(benzyloxy)pyridin-3-yl)-2-fluorophenyl)-7-azaspiro[3.5]nonan-2-yl)methanol (0.6 g, 1.11 mmol) in $CF_3CH_2OH$ (10 mL) was added Pd/C (0.2 g, 556.95 µmol, 10% purity) in $CF_3CH_2OH$ (10 mL) under $N_2$ atmosphere. The mixture was degassed and purged with $H_2$ for several times, then the suspension was stirred at 20° C. for 12 h under $H_2$ (15 psi) atmosphere. LCMS showed a main peak with desired mass. The mixture was filtered to remove the catalyst. The filtrate was concentrated under reduced pressure to afford 3-(3-fluoro-4-(2-(hydroxymethyl)-7-azaspiro[3.5]nonan-7-yl)phenyl)piperidine-2,6-dione (380 mg, 992.12 µmol, 89.07% yield, 94.1% purity) as a gray solid. MS $(M+H)^+=361.4$.

Step 6. Synthesis of 7-(4-(2,6-dioxopiperidin-3-yl)-2-fluorophenyl)-7-azaspiro[3.5]nonane-2-carbaldehyde (8)

To a solution of 3-(3-fluoro-4-(2-(hydroxymethyl)-7-azaspiro[3.5]nonan-7-yl)phenyl)piperidine-2,6-dione (150 mg, 416.18 µmol) in DCM (10 mL) was added DMP (211.82 mg, 499.42 µmol, 154.62 µL). The mixture was stirred at 25° C. for 14 h. LCMS showed a main peak with desired mass. The reaction mixture was diluted with water (10 mL) and extracted with DCM (10 mL×3). The combined organic layers were washed with brine (50 mL), dried over anhydrous sodium sulfate, filtered and concentrated under reduced pressure to afford 7-(4-(2,6-dioxopiperidin-3-yl)-2-fluorophenyl)-7-azaspiro[3.5]nonane-2-carbaldehyde (0.2 g, crude) as yellow oil. MS (M+H)$^+$=359.0

Step 7. Synthesis of tert-butyl 4-(4-((9-cyclopentyl-7,7-difluoro-5-methyl-6-oxo-6,7,8,9-tetrahydro-5H-pyrimido[4,5-b][1,4]diazepin-2-yl)amino)-3-methoxybenzamido)piperidine-1-carboxylate (12)

To a solution of 4-((9-cyclopentyl-7,7-difluoro-5-methyl-6-oxo-6,7,8,9-tetrahydro-5H-pyrimido[4,5-b][1,4]diazepin-2-yl)amino)-3-methoxybenzoic acid (0.5 g, 1.12 mmol) in DMF (5 mL) were added HATU (509.88 mg, 1.34 mmol) and DIPEA (288.85 mg, 2.23 mmol, 389.29 µL), the mixture was stirred for 0.5 h, then tert-butyl 4-aminopiperidine-1-carboxylate (235.00 mg, 1.17 mmol) was added and the resulting mixture was stirred at 25° C. for 12 h LCMS showed a peak (~62%) with desired mass. The reaction mixture was diluted with water (20 mL) and extracted with EtOAc (30 mL×3). The combined organic layers were washed with brine (50 mL), dried over anhydrous sodium sulfate, filtered and concentrated under reduced pressure. The residue was purified by flash silica gel chromatography (ISCO; 40 g SepaFlash Silica Flash Column, Eluent of 0~80% petroleum ether:EtOAc gradient @ 80 mL/min) to afford tert-butyl 4-(4-((9-cyclopentyl-7,7-difluoro-5-methyl-6-oxo-6,7,8,9-tetrahydro-5H-pyrimido[4,5-b][1,4]diazepin-2-yl)amino)-3-methoxybenzamido)piperidine-1-carboxylate (0.64 g, 990.95 µmol, 88.68% yield, 97.5% purity) as a yellow solid. MS (M+H)$^+$=630.3

Step 8. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-3-methoxy-N-(piperidin-4-yl)benzamide (9)

To a solution of tert-butyl 4-(4-((9-cyclopentyl-7,7-difluoro-5-methyl-6-oxo-6,7,8,9-tetrahydro-5H-pyrimido[4,5-b][1,4]diazepin-2-yl)amino)-3-methoxybenzamido)piperidine-1-carboxylate (0.64 g, 1.02 mmol) in dioxane (5 mL) was added HCl/dioxane (4 M, 10 mL). The mixture was stirred at 20° C. for 2 h. TLC (petroleum ether:EtOAc=0:1) indicated one new spot was formed. The mixture was concentrated under reduced pressure to afford 4-((9-cyclopentyl-7,7-difluoro-5-methyl-6-oxo-6,7,8,9-tetrahydro-5H-pyrimido[4,5-b][1,4]diazepin-2-yl)amino)-3-methoxy-N-(piperidin-4-yl)benzamide (0.8 g, crude, HCl salt) as a white solid. MS (M+H)$^+$=530.3

Step 9. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-((7-(4-(2,6-dioxopiperidin-3-yl)-2-fluorophenyl)-7-azaspiro[3.5]nonan-2-yl)methyl)piperidin-4-yl)-3-methoxybenzamide (Compound 21)

To a solution of 7-(4-(2,6-dioxopiperidin-3-yl)-2-fluorophenyl)-7-azaspiro[3.5]nonane-2-carbaldehyde (0.2 g, 558.03 µmol) in DCE (10 mL) were added 4-((9-cyclopentyl-7,7-difluoro-5-methyl-6-oxo-6,7,8,9-tetrahydro-5H-pyrimido[4,5-b][1,4]diazepin-2-yl)amino)-3-methoxy-N-(piperidin-4-yl)benzamide (252.69 mg, 446.42 µmol, HCl salt) and HOAc (100.53 mg, 1.67 mmol, 95.74 µL), the mixture was stirred at 20° C. for 0.5 h, then NaBH(OAc)$_3$ (354.81 mg, 1.67 mmol) was added and the resulting mixture was stirred at 20° C. for 12 h. LCMS showed a peak (~24%) with desired mass. The reaction mixture was diluted with saturated sodium bicarbonate solution (50 mL) and extracted with DCM (30 mL×3). The combined organic layers were washed with brine (50 mL), dried over anhydrous sodium sulfate, filtered and concentrated under reduced pressure. The residue was purified by prep-HPLC (column: Phenomenex luna C18 150×25 mm×10 µm; mobile phase: [water (FA)—ACN]; B %: 15%-45%, 8 min), the eluent was lyophilized to afford 4-((9-cyclopentyl-7,7-difluoro-5-methyl-6-oxo-6,7,8,9-tetrahydro-5H-pyrimido[4,5-b][1,4]diazepin-2-yl)amino)-N-(1-((7-(4-(2,6-dioxopiperidin-3-yl)-2-fluorophenyl)-7-azaspiro[3.5]nonan-2-yl)methyl)piperidin-4-yl)-3-methoxybenzamide (29.9 mg, 31.16 µmol, 5.58% yield, 91.6% purity) as a white solid. MS (M+H)$^+$=872.3

$^1$H NMR (400 MHz, DMSO-d$_6$) δ=10.80 (s, 1H), 8.30-8.21 (m, 2H), 8.09 (d, J=7.9 Hz, 1H), 7.96 (s, 1H), 7.53-7.45 (m, 2H), 7.04-6.89 (m, 3H), 4.81-4.72 (m, 1H), 4.05 (t, J=14.1 Hz, 2H), 3.94 (s, 3H), 3.80-3.76 (m, 2H), 3.30-3.27 (m, 3H), 2.95-2.91 (m, 2H), 2.88-2.80 (m, 4H), 2.68-2.59 (m, 3H), 2.48-2.33 (m, 4H), 2.22-2.13 (m, 1H), 2.03-1.91 (m, 7H), 1.80-1.69 (m, 6H), 1.64-1.56 (m, 6H), 1.50-1.38 (m, 2H).

Example 22. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-((1-((1-(4-(2,6-dioxopiperidin-3-yl)-2-fluorophenyl)piperidin-4-yl)methyl)piperidin-4-yl)methyl)-3-methoxybenzamide (Compound 22)

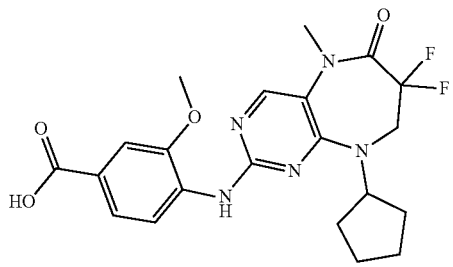
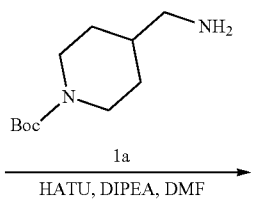

HATU, DIPEA, DMF

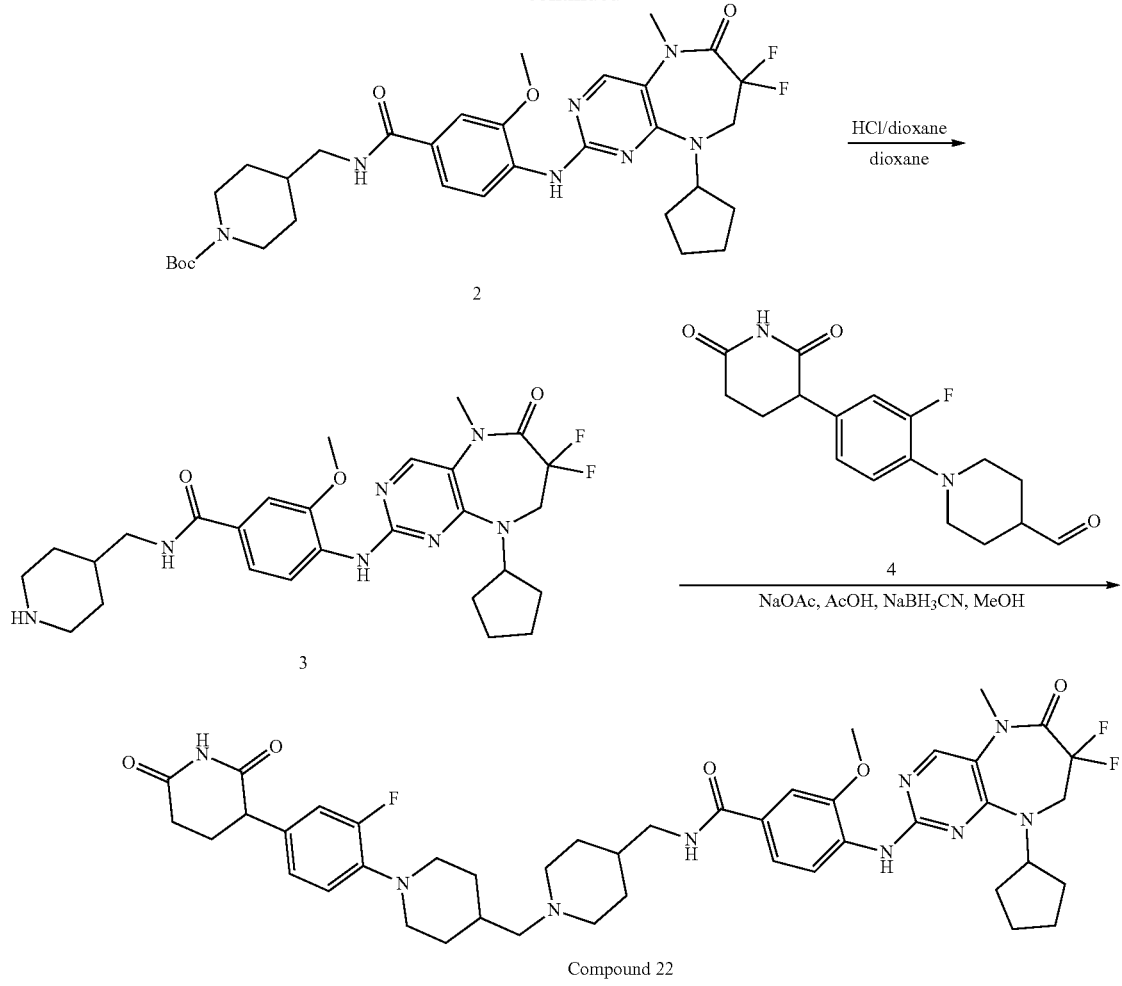

Step 1. Synthesis of tert-butyl 4-((4-((9-cyclopentyl-7,7-difluoro-5-methyl-6-oxo-6,7,8,9-tetrahydro-5H-pyrimido[4,5-b][1,4]diazepin-2-yl)amino)-3-methoxybenzamido)methyl)piperidine-1-carboxylate (2)

To a solution of 4-((9-cyclopentyl-7,7-difluoro-5-methyl-6-oxo-6,7,8,9-tetrahydro-5H-pyrimido[4,5-b][1,4]diazepin-2-yl)amino)-3-methoxybenzoic acid (0.3 g, 670.49 μmol) in DMF (5 mL) was added HATU (305.93 mg, 804.59 μmol) and DIPEA (259.96 mg, 2.01 mmol, 350.35 μL). The mixture was stirred at 25° C. for 10 min. To mixture was added tert-butyl 4-(aminomethyl)piperidine-1-carboxylate (143.69 mg, 670.49 μmol). The mixture was stirred at 25° C. for 1 h. LCMS showed the starting material was consumed completely and a main peak with desired mass. The mixture was poured into water (30 mL) and extracted with EtOAc (15 mL×4). The combined organic phase was washed with brine (15 mL×3), dried over Na$_2$SO$_4$, filtered and concentrated under reduced pressure to give a residue. The residue was purified by flash silica gel chromatography (4 g Sepa-Flash Silica Flash Column, Eluent of 0~100% EtOAc/Petroleum ether gradient @ 100 mL/min) to afford tert-butyl 4-((4-((9-cyclopentyl-7,7-difluoro-5-methyl-6-oxo-6,7,8,9-tetrahydro-5H-pyrimido[4,5-b][1,4]diazepin-2-yl)amino)-3-methoxybenzamido)methyl)piperidine-1-carboxylate (0.6 g, crude) as brown solid, which was used for the next step directly. MS (M+H)$^+$=644.4

Step 2. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-3-methoxy-N-(piperidin-4-ylmethyl)benzamide (3)

To a solution of tert-butyl 4-((4-((9-cyclopentyl-7,7-difluoro-5-methyl-6-oxo-6,7,8,9-tetrahydro-5H-pyrimido[4,5-b][1,4]diazepin-2-yl)amino)-3-methoxybenzamido)methyl)piperidine-1-carboxylate (0.6 g, crude) in dioxane (2 mL) was added HCl/dioxane (4 M, 15 mL) at 25° C. The resulting mixture was stirred at 25° C. for 0.5 hr. LCMS showed the starting material was consumed completely and a main peak with desired mass. The mixture solution was concentrated under reduced pressure, to afford 4-((9-cyclopentyl-7,7-difluoro-5-methyl-6-oxo-6,7,8,9-tetrahydro-5H-pyrimido[4,5-b][1,4]diazepin-2-yl)amino)-3-methoxy-N-(piperidin-4-ylmethyl)benzamide (0.5 g, crude) as brown solid, which was used for the next step directly. MS (M+H)$^+$=544.3

Step 3. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-((1-((1-(4-(2,6-dioxopiperidin-3-yl)-2-fluorophenyl)piperidin-4-yl)methyl)piperidin-4-yl)methyl)-3-methoxybenzamide (Compound 22)

A mixture of 4-((9-cyclopentyl-7,7-difluoro-5-methyl-6-oxo-6,7,8,9-tetrahydro-5H-pyrimido[4,5-b][1,4]diazepin-2-yl)amino)-3-methoxy-N-(piperidin-4-ylmethyl)benzamide (160 mg, 275.83 µmol, HCl) and NaOAc (22.63 mg, 275.83 µmol) in MeOH (2 mL) was stirred at 25° C. for 20 min. To the above mixture was added 1-(4-(2,6-dioxopiperidin-3-yl)-2-fluorophenyl)piperidine-4-carbaldehyde (131.71 mg, 413.74 µmol) and AcOH (16.56 mg, 275.83 µmol, 15.77 µL) at 25° C. The resulting mixture was stirred at 25° C. for 30 min. To the reaction mixture was added NaBH₃CN (52.00 mg, 827.49 µmol) at 25° C., The mixture was stirred at 25° C. for 1 h. LCMS showed the starting material was consumed completely and a main peak with desired mass. The reaction solution was concentrated to remove the organic solvent. The crude product was dissolved with EtOAc (30 mL) washed with saturated NaHCO₃ (10 mL), dried over Na₂SO₄, filtered and concentrated under reduced pressure to give a residue. The residue was purified by flash silica gel chromatography (4 g SepaFlash Silica Flash Column, Eluent of 0~100% EtOAc/Petroleum ether gradient @ 100 mL/min; Eluent of 0~50% Methanol/EtOAc @ 100 mL/min) and re-purified by prep-HPLC (column: Waters □bridge 150×25 mm×5 um; mobile phase: [water (NH₄HCO₃)—ACN]; B %: 45%-75%, 8 min) and lyophilized to afford 4-((9-cyclopentyl-7,7-difluoro-5-methyl-6-oxo-6,7,8,9-tetrahydro-5H-pyrimido[4,5-b][1,4]diazepin-2-yl)amino)-N-((1-((1-(4-(2,6-dioxopiperidin-3-yl)-2-fluorophenyl)piperidin-4-yl)methyl)piperidin-4-yl)methyl)-3-methoxybenzamide (27.5 mg, 31.21 µmol, 11.31% yield, 96% purity) as white solid. MS (M+H)⁺=846.5

¹H NMR (400 MHz, DMSO-d₆) δ=10.81 (s, 1H), 8.38 (t, J=4.9 Hz, 1H), 8.32-8.19 (m, 2H), 7.97 (s, 1H), 7.60-7.44 (m, 2H), 7.08-6.87 (m, 3H), 4.89-4.67 (m, 1H), 4.14-3.98 (m, 2H), 3.92 (s, 3H), 3.85-3.72 (m, 1H), 3.32 (s, 3H), 3.31-3.25 (m, 2H), 3.18-3.15 (m, 2H), 2.91-2.79 (m, 2H), 2.72-2.57 (m, 4H), 2.26-2.11 (m, 3H), 2.04-1.89 (m, 3H), 1.88-1.44 (m, 14H), 1.34-1.10 (m, 4H).

Example 23. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(6-((1-(4-(2,6-dioxopiperidin-3-yl)-2-fluorophenyl)piperidin-4-yl)methyl)-6-azaspiro[2.5]octan-1-yl)-3-methoxybenzamide (Compound 23)

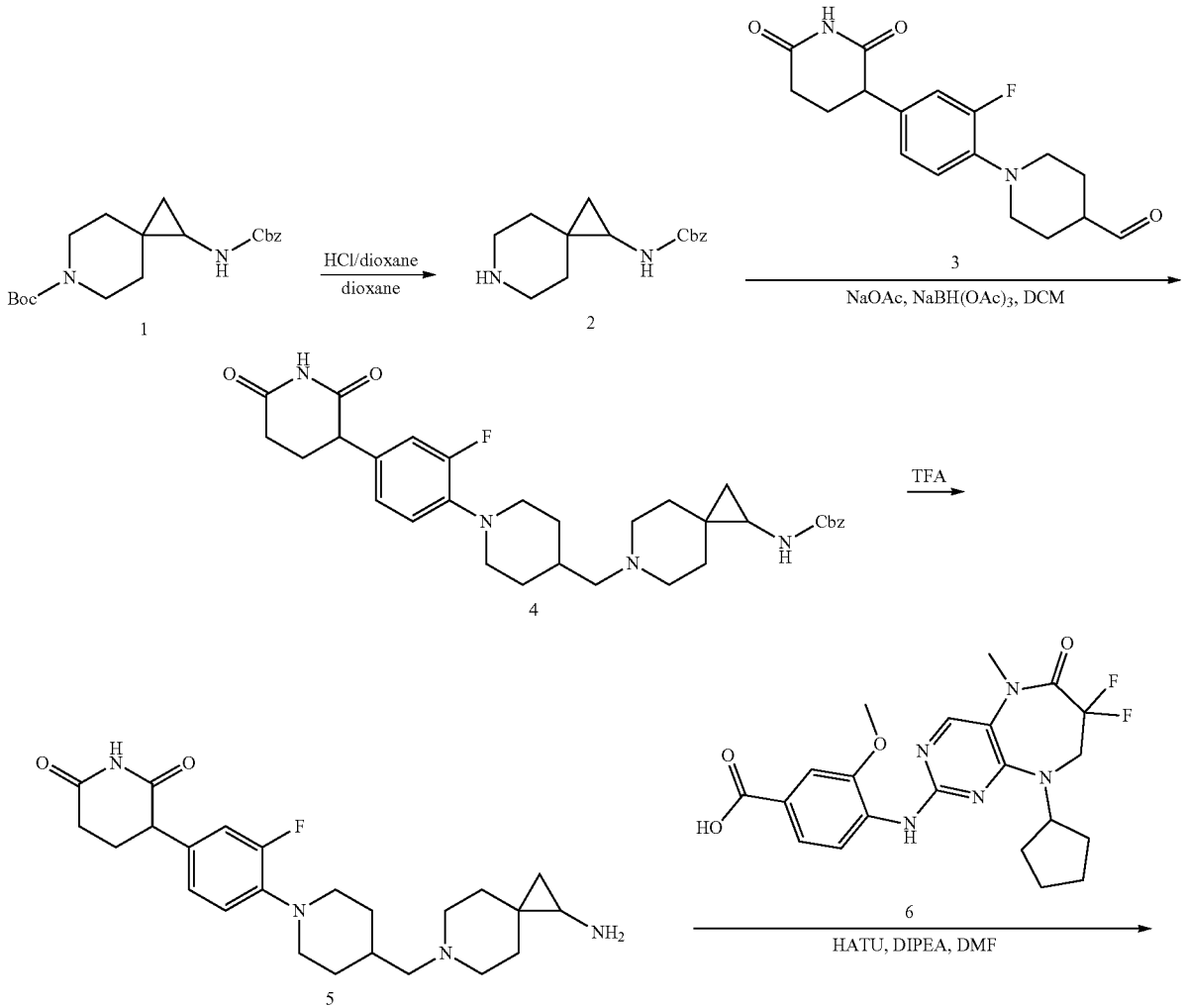

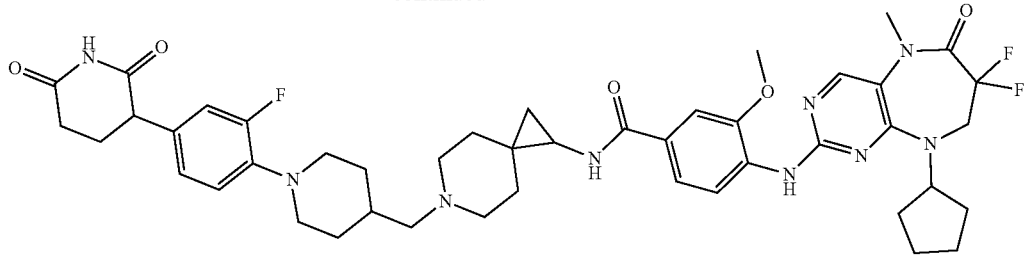

Compound 23

Step 1. Synthesis of benzyl (6-azaspiro[2.5]octan-1-yl)carbamate (2)

To a solution of tert-butyl 1-(((benzyloxy)carbonyl)amino)-6-azaspiro[2.5]octane-6-carboxylate (200 mg, 554.87 μmol) in dioxane (1 mL) was added HCl/dioxane (4 M, 1 mL). The mixture was stirred at 20° C. for 1 hr. LC-MS showed tert-butyl 1-(((benzyloxy)carbonyl)amino)-6-azaspiro[2.5]octane-6-carboxylate was consumed completely and one peak (89%) with desired mass was detected. The reaction mixture was concentrated under reduced pressure to remove solvent to give benzyl (6-azaspiro[2.5]octan-1-yl)carbamate (164 mg, 552.58 μmol, 99.59% yield, HCl) as a yellow solid. MS (M+H)$^+$=261.1

Step 2. Synthesis of benzyl (6-((1-(4-(2,6-dioxopiperidin-3-yl)-2-fluorophenyl)piperidin-4-yl)methyl)-6-azaspiro[2.5]octan-1-yl)carbamate (4)

To a solution of benzyl (6-azaspiro[2.5]octan-1-yl)carbamate (164 mg, 552.58 μmol, HCl) and 1-(4-(2,6-dioxopiperidin-3-yl)-2-fluorophenyl)piperidine-4-carbaldehyde (175.91 mg, 552.58 μmol) in DCM (3 mL) was added NaOAc (90.66 mg, 1.11 mmol). The mixture was stirred at 20° C. for 1 hour, then NaBH(OAc)$_3$ (585.57 mg, 2.76 mmol) was added, the mixture was stirred for another 16 hours. LC-MS showed 1-(4-(2,6-dioxopiperidin-3-yl)-2-fluorophenyl)piperidine-4-carbaldehyde was consumed completely and one peak (34%) with desired mass was detected. The reaction mixture was quenched with water (20 mL) at 25° C., and then extracted with EtOAc (50 mL×2). The combined organic layers were washed with brine (30 mL), dried over Na$_2$SO$_4$, filtered and concentrated under reduced pressure to give a residue. The residue was purified by flash silica gel chromatography (ISCO; 12 g SepaFlash Silica Flash Column, Eluent of 0~100% EtOAc/Petroleum ether gradient @ 50 mL/min) to give benzyl (6-((1-(4-(2,6-dioxopiperidin-3-yl)-2-fluorophenyl)piperidin-4-yl)methyl)-6-azaspiro[2.5]octan-1-yl)carbamate (125 mg, 199.94 μmol, 36.18% yield, 90% purity) as a white solid. MS (M+H)$^+$=563.3

Step 3. Synthesis of 3-(4-(4-((1-amino-6-azaspiro[2.5]octan-6-yl)methyl)piperidin-1-yl)-3-fluorophenyl)piperidine-2,6-dione (5)

A solution of benzyl (6-((1-(4-(2,6-dioxopiperidin-3-yl)-2-fluorophenyl)piperidin-4-yl)methyl)-6-azaspiro[2.5]octan-1-yl)carbamate (105 mg, 186.61 μmol) in TFA (3 mL) was stirred at 60° C. for 5 hr. LC-MS showed benzyl (6-((1-(4-(2,6-dioxopiperidin-3-yl)-2-fluorophenyl)piperidin-4-yl)methyl)-6-azaspiro[2.5]octan-1-yl)carbamate was consumed completely and one peak (60%) with desired mass was detected. The reaction mixture was concentrated under reduced pressure to remove solvent to give 3-(4-(4-((1-amino-6-azaspiro[2.5]octan-6-yl)methyl)piperidin-1-yl)-3-fluorophenyl)piperidine-2,6-dione (100 mg, crude, TFA) as yellow solid, it was used into the next step without further purification. MS (M+H)$^+$=429.2

Step 4. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(6-((1-(4-(2,6-dioxopiperidin-3-yl)-2-fluorophenyl)piperidin-4-yl)methyl)-6-azaspiro[2.5]octan-1-yl)-3-methoxybenzamide (Compound 23)

A mixture of 3-(4-(4-((1-amino-6-azaspiro[2.5]octan-6-yl)methyl)piperidin-1-yl)-3-fluorophenyl)piperidine-2,6-dione (100 mg, 184.31 μmol, TFA), 4-((9-cyclopentyl-7,7-difluoro-5-methyl-6-oxo-6,7,8,9-tetrahydro-5H-pyrimido[4,5-b][1,4]diazepin-2-yl)amino)-3-methoxybenzoic acid (82.47 mg, 184.31 μmol), DIPEA (119.10 mg, 921.55 μmol, 160.52 μL), HATU (105.12 mg, 276.46 μmol) in DMF (3 mL) was stirred at 20° C. for 16 h. LC-MS showed 3-(4-(4-((1-amino-6-azaspiro[2.5]octan-6-yl)methyl)piperidin-1-yl)-3-fluorophenyl)piperidine-2,6-dione was consumed completely and one peak (63%) with desired mass was detected. The reaction mixture was quenched with aq. sat. NaHCO$_3$ (20 mL) at 0° C., and then extracted with EtOAc (40 mL×2). The combined organic layers were washed with brine (30 mL), dried over Na$_2$SO$_4$, filtered and concentrated under reduced pressure to give a residue. The residue was purified by prep-HPLC (column: Phenomenex Synergi Polar-RP 100*25 mm*4 μm; mobile phase: [water (TFA)—ACN]; B %: 33%-53%, 7 min) and re-purified by prep-HPLC (column: Waters Xbridge 150*25 mm*5 μm; mobile phase: [water (NH$_4$HCO$_3$)—ACN]; B %: 47%-77%, 8 min) followed by lyophilization to give 4-((9-cyclopentyl-7,7-difluoro-5-methyl-6-oxo-6,7,8,9-tetrahydro-5H-pyrimido[4,5-b][1,4]diazepin-2-yl)amino)-N-(6-((1-(4-(2,6-dioxopiperidin-3-yl)-2-fluorophenyl)piperidin-4-yl)methyl)-6-azaspiro[2.5]octan-1-yl)-3-methoxybenzamide (18.2 mg, 20.79 μmol, 11.28% yield, 98% purity) as a white solid. MS (M+H)$^+$=858.3

$^1$H NMR (400 MHz, DMSO-d$_6$) δ=10.80 (s, 1H), 8.29-8.22 (m, 2H), 8.18 (d, J=4.3 Hz, 1H), 7.98 (s, 1H), 7.53-7.43 (m, 2H), 7.03-6.90 (m, 3H), 4.77-4.73 (m, 1H), 4.04 (t, J=13.9 Hz, 2H), 3.93 (s, 3H), 3.80-3.76 (m, 1H), 3.30-3.28 (m, 6H), 2.73-2.58 (m, 5H), 2.45-2.43 (m, 2H), 2.37-2.36 (m, 1H), 2.30-2.25 (m, 1H), 2.17-2.14 (m, 2H), 2.02-1.90 (m, 3H), 1.83-1.68 (m, 4H), 1.65-1.54 (m, 5H), 1.50-1.33 (m, 4H), 1.29-1.19 (m, 2H), 0.74-0.63 (m, 2H).

Example 24. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-((6-(((1-(4-(2,6-dioxopiperidin-3-yl)-2-fluorophenyl)piperidin-4-yl)methyl)-6-azaspiro[2.5]octan-1-yl)methyl)-3-methoxybenzamide (Compound 24)
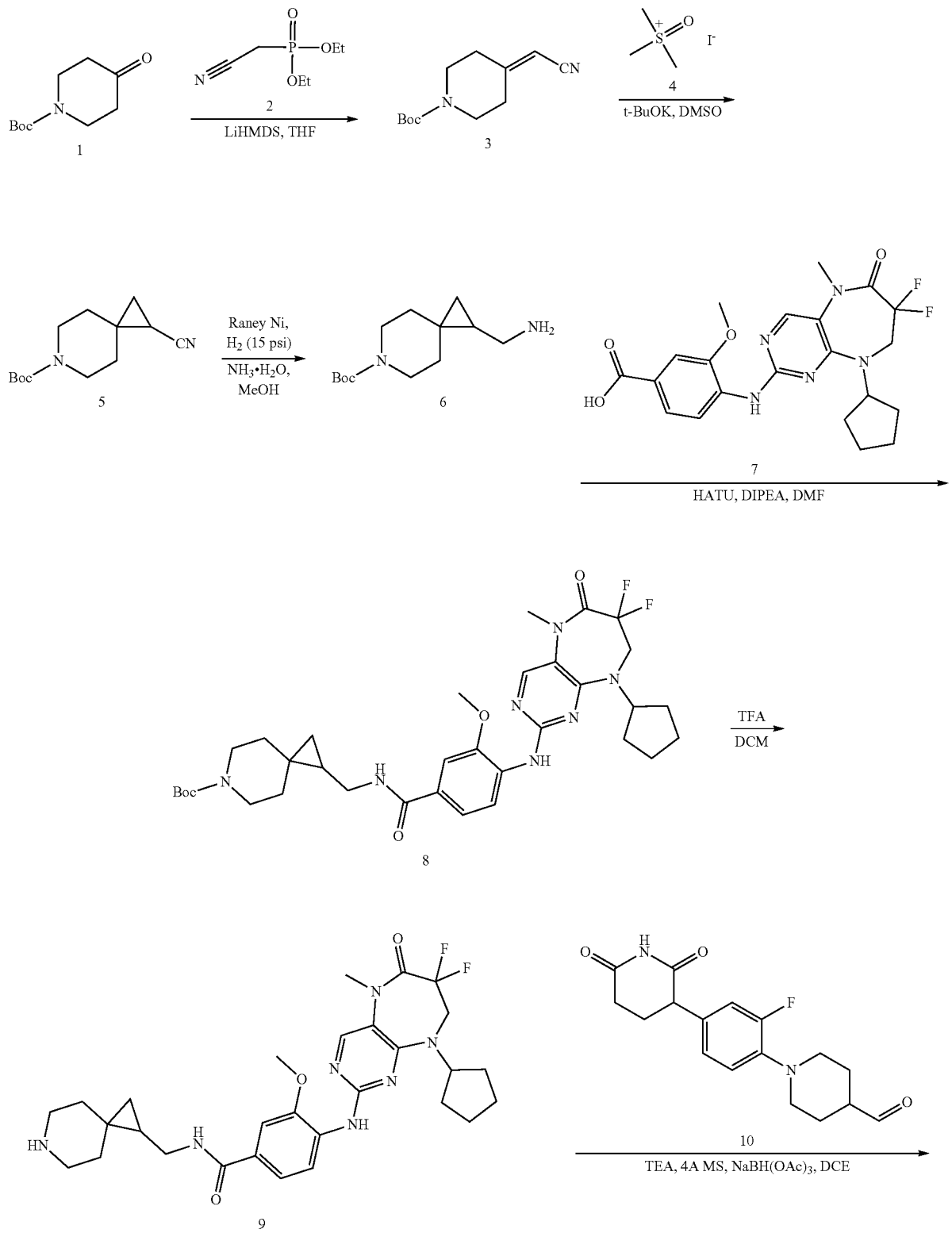

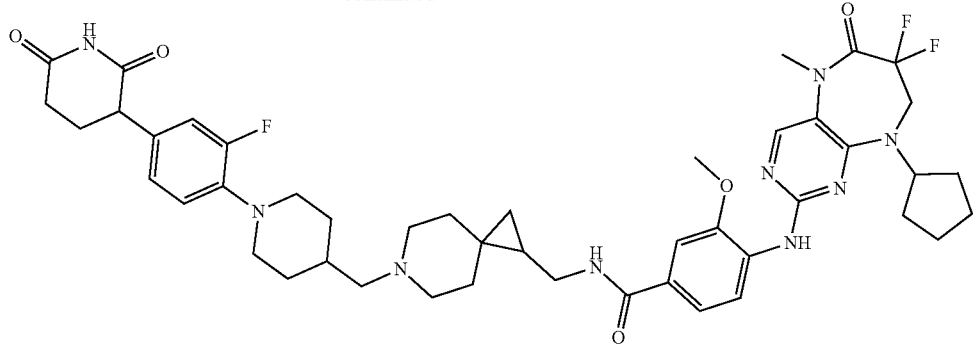

Compound 24

Step 1. Synthesis of tert-butyl 4-(cyanomethylene)piperidine-O-carboxylate (3)

To a solution of diethyl (cyanomethyl)phosphonate (933.49 mg, 5.27 mmol, 848.63 µL) in THF (15 mL) was added LiHMDS (1 M, 5.52 mL) dropwise at −70° C. under N$_2$. Then tert-butyl 4-oxopiperidine-1-carboxylate (1 g, 5.02 mmol) was added to the mixture at −70° C. after 0.5 h. The mixture was stirred at −70° C. for 1 h under N$_2$ LCMS showed ~85% of desired mass. The reaction mixture was quenched with saturated ammonium chloride solution (50 mL) and extracted with EtOAc (50 mL×3). The combined organic layers were washed with saturated brine (50 m), dried over anhydrous sodium sulfate, filtered and concentrated under reduced pressure to give a residue. The residue was purified by flash silica gel chromatography (ISCO; 40 g SepaFlash Silica Flash Column, Eluent of 0~25% petroleum ether:EtOAc gradient @ 80 mL/min) to give tert-butyl 4-(cyanomethylene)piperidine-1-carboxylate (0.8 g, 3.60 mmol, 71.71% yield) as a white solid.

MS (M−t−Bu+H)$^+$=167.1

Step 2. Synthesis of tert-butyl 1-cyano-6-azaspiro[2.5]octane-6-carboxylate (5)

To a solution of t-BuOK (222.12 mg, 1.98 mmol) in DMSO (4 mL) was added trimethylsulfoxonium iodide (435.62 mg, 1.98 mmol) slowly at 20° C. Then a solution of tert-butyl 4-(cyanomethylene)piperidine-1-carboxylate (0.4 g, 1.80 mmol) in DMSO (4 mL) was added to the mixture at 0° C. after 1.5 h. The mixture was stirred at 50° C. for 16 h under N$_2$. LCMS showed tert-butyl 4-(cyanomethylene) piperidine-1-carboxylate was consumed completely. The reaction mixture was quenched with saturated ammonium chloride solution (50 mL) and extracted with EtOAc (50 mL×3). The combined organic layers were washed with brine (50 mL), dried over anhydrous sodium sulfate, filtered and concentrated under reduced pressure to give tert-butyl 1-cyano-6-azaspiro[2.5]octane-6-carboxylate (0.56 g, crude) as yellow oil. MS (M+H)$^+$=237.3

Step 3. Synthesis of tert-butyl 1-(aminomethyl)-6-azaspiro[2.5]octane-6-carboxylate (6)

To a solution of tert-butyl 1-cyano-6-azaspiro[2.5]octane-6-carboxylate (0.56 g, 2.37 mmol) in MeOH (20 mL) and NH$_3$·H$_2$O (2 mL) was added Raney-Ni (101.52 mg, 1.18 mmol) under N$_2$. The mixture was stirred at 25° C. for 12 h under H$_2$ (15 PSI). LCMS showed ~67% of desired mass. The mixture was filtered to remove the catalyst. The filtrate was concentrated under reduced pressure to give a residue. The residue was diluted with water (60 mL) and extracted with EtOAc (50 mL×3). The combined organic layers were washed with brine (50 mL), dried over anhydrous sodium sulfate, filtered and concentrated under reduced pressure to give tert-butyl 1-(aminomethyl)-6-azaspiro[2.5]octane-6-carboxylate (0.4 g, crude) as yellow oil. MS (M-t-Bu+H)$^+$=185.1

Step 4. Synthesis of tert-butyl 1-((4-((9-cyclopentyl-7,7-difluoro-5-methyl-6-oxo-6,7,8,9-tetrahydro-5H-pyrimido[4,5-b][1,4]diazepin-2-yl)amino)-3-methoxybenzamido)methyl)-6-azaspiro[2.5]octane-6-carboxylate (8)

To a solution of 4-((9-cyclopentyl-7,7-difluoro-5-methyl-6-oxo-6,7,8,9-tetrahydro-5H-pyrimido[4,5-b][1,4]diazepin-2-yl)amino)-3-methoxybenzoic acid (595.73 mg, 1.33 mmol) in DMF (5 mL) were added HATU (949.23 mg, 2.50 mmol) and DIEA (430.20 mg, 3.33 mmol, 579.78 µL). Then tert-butyl 1-(aminomethyl)-6-azaspiro[2.5]octane-6-carboxylate (0.4 g, 1.66 mmol) was added to the mixture after 0.5 h. The mixture was stirred at 25° C. for 2 h. LCMS showed ~36% of desired mass. The reaction mixture was diluted with water (50 mL) and extracted with EtOAc (50 mL×3). The combined organic layers were washed with brine (50 mL), dried over anhydrous sodium sulfate, filtered and concentrated under reduced pressure to give a residue. The residue was purified by flash silica gel chromatography (ISCO; 20 g SepaFlash Silica Flash Column, Eluent of 0~70% petroleum ether:EtOAc gradient @ 80 mL/min) to afford tert-butyl 1-((4-((9-cyclopentyl-7,7-difluoro-5-methyl-6-oxo-6,7,8,9-tetrahydro-5H-pyrimido[4,5-b][1,4]diazepin-2-yl)amino)-3-methoxybenzamido)methyl)-6-azaspiro[2.5]octane-6-carboxylate (0.83 g, 1.14 mmol, 68.73% yield, 92.3% purity) as yellow oil. MS (M+H)$^+$=670.3

Step 5. Synthesis of N-((6-azaspiro[2.5]octan-1-yl)methyl)-4-((9-cyclopentyl-7,7-difluoro-5-methyl-6-oxo-6,7,8,9-tetrahydro-5H-pyrimido[4,5-b][1,4]diazepin-2-yl)amino)-3-methoxybenzamide (9)

To a solution of tert-butyl 1-((4-((9-cyclopentyl-7,7-difluoro-5-methyl-6-oxo-6,7,8,9-tetrahydro-5H-pyrimido[4,5-b][1,4]diazepin-2-yl)amino)-3-methoxybenzamido)methyl)-6-azaspiro[2.5]octane-6-carboxylate (0.7 g, 1.05 mmol) in DCM (15 mL) was added TFA (4.62 g, 40.52 mmol, 3 mL) at 0° C. The mixture was stirred at 25° C. for 1 h. LCMS showed ~84% of desired mass. The mixture was concentrated under reduced pressure to give N-((6-azaspiro[2.5]octan-1-yl)methyl)-4-((9-cyclopentyl-7,7-difluoro-5-methyl-6-oxo-6,7,8,9-tetrahydro-5H-pyrimido[4,5-b][1,4]diazepin-2-yl)amino)-3-methoxybenzamide (1 g, crude, TFA) as yellow oil.

MS (M+H)$^+$=570.1

Step 6. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-((6-(((1-(4-(2,6-dioxopiperidin-3-yl)-2-fluorophenyl)piperidin-4-yl)methyl)-6-azaspiro[2.5]octan-1-yl)methyl)-3-methoxybenzamide (Compound 24)

To a solution of 1-(4-(2,6-dioxopiperidin-3-yl)-2-fluorophenyl)piperidine-4-carbaldehyde (140 mg, 439.78 µmol), and N-((6-azaspiro[2.5]octan-1-yl)methyl)-4-((9-cyclopentyl-7,7-difluoro-5-methyl-6-oxo-6,7,8,9-tetrahydro-5H-pyrimido[4,5-b][1,4]diazepin-2-yl)amino)-3-methoxybenzamide (250.52 mg, crude, TFA) in DCE (5 mL) were added TEA (267.00 mg, 2.64 mmol, 367.27 µL) and 4A MS (50 mg), the mixture was stirred at 20° C. for 0.5 h. Then NaBH(OAc)$_3$ (279.62 mg, 1.32 mmol) was added, the resulting mixture was stirred at 20° C. for 15 h. LCMS showed a peak (25%) with desired mass. The reaction mixture was quenched by addition NaHCO$_3$ (10 mL), extracted with EtOAc (15 mL×3). The combined organic layers were washed with brine (30 mL×2), dried over Na$_2$SO$_4$, filtered. The filtrate was concentrated in vacuum to afford a residue. The residue was purified by prep-TLC (SiO$_2$, DCM:MeOH=10:1) and re-purified by reversed-phase HPLC (column: Waters Xbridge 150*25 mm*5 µm; mobile phase: [water (NH$_4$HCO$_3$)—ACN]; B %: 45%-75%, 8 min). The eluent was lyophilized to afford a residue. The residue was re-purified by prep-TLC (SiO$_2$, DCM:MeOH=10:1) to afford 4-((9-cyclopentyl-7,7-difluoro-5-methyl-6-oxo-6,7,8,9-tetrahydro-5H-pyrimido[4,5-b][1,4]diazepin-2-yl)amino)-N-((6-(((1-(4-(2,6-dioxopiperidin-3-yl)-2-fluorophenyl)piperidin-4-yl)methyl)-6-azaspiro[2.5]octan-1-yl)methyl)-3-methoxybenzamide (29.5 mg, 31.80 µmol, 8.47% yield, 94% purity) as a white solid.

MS (M+H)$^+$=872.5

$^1$H NMR (400 MHz, DMSO-d$_6$) δ=10.80 (s, 1H), 8.47-8.38 (m, 1H), 8.31-8.24 (m, 2H), 7.97 (s, 1H), 7.55-7.46 (m, 2H), 7.04-6.89 (m, 3H), 4.83-4.70 (m, 1H), 4.04 (t, J=14.0 Hz, 2H), 3.94 (s, 3H), 3.83-3.75 (m, 1H), 3.47-3.35 (m, 2H), 3.30-3.15 (m, 5H), 2.65-2.55 (m, 4H), 2.48-2.37 (m, 3H), 2.32-2.26 (m, 1H), 2.25-2.09 (m, 3H), 2.03-1.91 (m, 3H), 1.83-1.68 (m, 4H), 1.68-1.51 (m, 6H), 1.51-1.33 (m, 2H), 1.29-1.18 (m, 3H), 1.06-0.89 (m, 1H), 0.50-0.40 (m, 1H), 0.25-0.15 (m, 1H).

Example 25. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(7-((1-(4-(2,6-dioxopiperidin-3-yl)-2-methylphenyl)piperidin-4-yl)methyl)-7-azaspiro[3.5]nonan-2-yl)-3-methoxybenzamide (Compound 25)

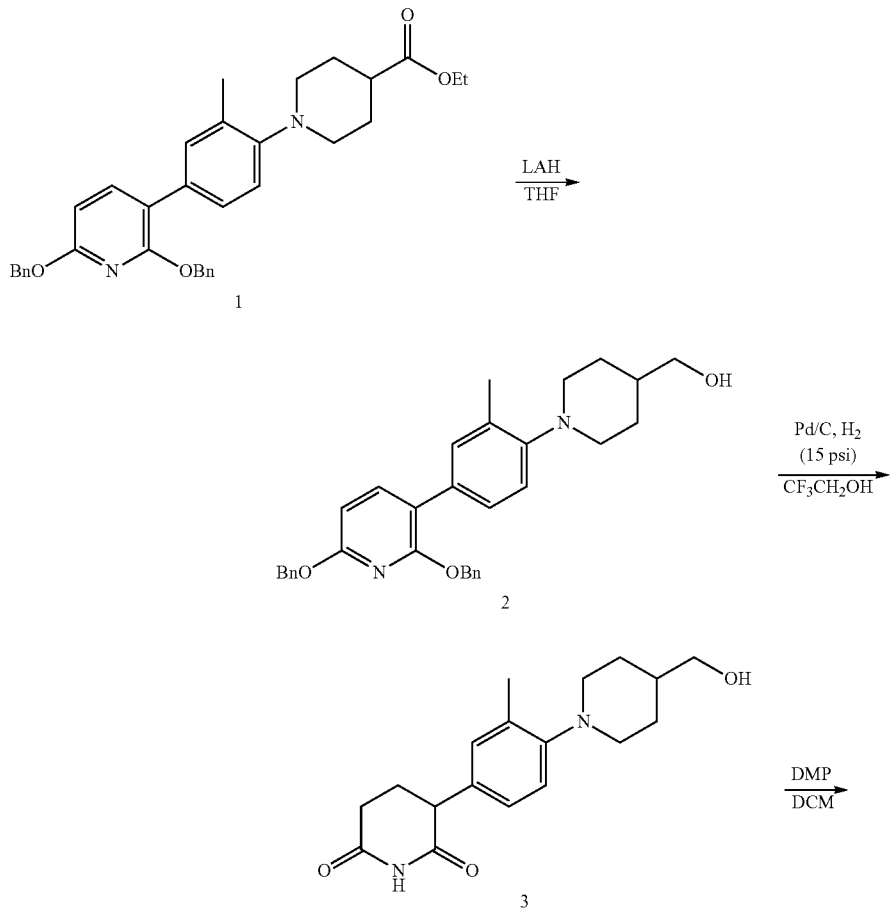

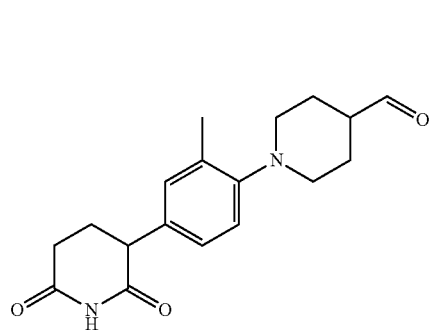

4

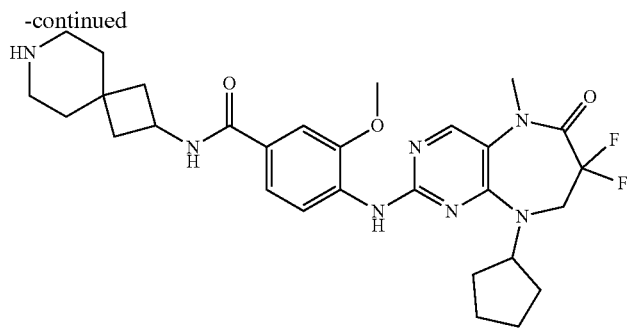

5

NaBH₃CN, NaOAc, AcOH, MeOH

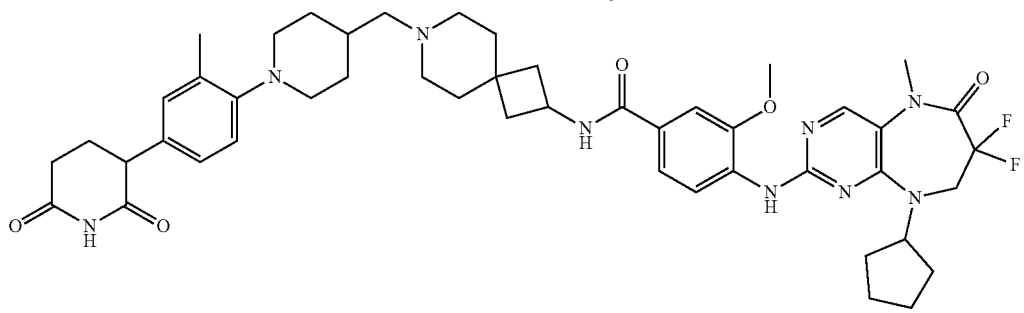

Compound 25

Step 1. Synthesis of (1-(4-(2,6-bis(benzyloxy)pyridin-3-yl)-2-methylphenyl)piperidin-4-yl)methanol (2)

To a solution of LiAlH₄ (25.46 mg, 670.82 μmol) in THF (3 mL) was added ethyl 1-(4-(2,6-bis(benzyloxy)pyridin-3-yl)-2-methylphenyl)piperidine-4-carboxylate (0.3 g, 559.01 μmol) in THF (2 mL) dropwise at 0° C. under N₂ atmosphere. Then the mixture was warmed to 25° C. and stirred for 2 h. LCMS showed the starting material was consumed completely and a main peak with desired mass. The reaction was quenched by EtOAc (5 mL) dropwise at 0° C. under N₂ atmosphere. The mixture was diluted with THF (20 mL) filtered through a celite pad and the filtrate was concentrated, to afford (1-(4-(2,6-bis(benzyloxy)pyridin-3-yl)-2-methylphenyl)piperidin-4-yl)methanol (0.3 g, crude) as white solid, which was used for the next step directly. MS $(M+H)^+=495.2$

Step 2. Synthesis of 3-(4-(4-(hydroxymethyl)piperidin-1-yl)-3-methylphenyl)piperidine-2,6-dione (3)

To a solution of (1-(4-(2,6-bis(benzyloxy)pyridin-3-yl)-2-methylphenyl)piperidin-4-yl)methanol (0.3 g, crude) in CF₃CH₂OH (10 mL) was added Pd/C (0.1 g, 10% purity) at 25° C. The mixture was stirred at 25° C. under H₂ (1.23 mg, 606.52 μmol) (15Psi) for 24 hr. LCMS showed the starting material was consumed completely and a main peak with desired mass. The reaction mixture was filtered through a celite pad and the filtrate was concentrated to give 3-(4-(4-(hydroxymethyl)piperidin-1-yl)-3-methylphenyl)piperidine-2,6-dione (150 mg, crude) as black brown solid, which was used for the next step directly. MS $(M+H)^+=317.1$

Step 3. Synthesis of 1-(4-(2,6-dioxopiperidin-3-yl)-2-methylphenyl)piperidine-4-carbaldehyde (4)

A mixture of 3-(4-(4-(hydroxymethyl)piperidin-1-yl)-3-methylphenyl)piperidine-2,6-dione (150 mg, 474.09 μmol) and DMP (301.62 mg, 711.14 μmol, 220.16 μL) in DCM (3 mL) was stirred at 25° C. for 2 hr. LCMS showed the starting material was consumed completely. The reaction mixture was filtered through a celite pad and the filtrate was concentrated, to afford 1-(4-(2,6-dioxopiperidin-3-yl)-2-methylphenyl)piperidine-4-carbaldehyde (150 mg, crude) as black brown solid, which was used for the next step directly. MS $(M+H)^+=315.1$

Step 4. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(7-((1-(4-(2,6-dioxopiperidin-3-yl)-2-methylphenyl)piperidin-4-yl)methyl)-7-azaspiro[3.5]nonan-2-yl)-3-methoxybenzamide (Compound 25)

A mixture of 1-(4-(2,6-dioxopiperidin-3-yl)-2-methylphenyl)piperidine-4-carbaldehyde (150 mg, crude) and NaOAc (17.59 mg, 214.48 μmol) in MeOH (2 mL) was stirred at 25° C. for 20 min. To above mixture was added 4-((9-cyclopentyl-7,7-difluoro-5-methyl-6-oxo-6,7,8,9-tetrahydro-5H-pyrimido[4,5-b][1,4]diazepin-2-yl)amino)-3-methoxy-N-(7-azaspiro[3.5]nonan-2-yl)benzamide (130 mg, 214.48 μmol, HCl) and AcOH (12.88 mg, 214.48 μmol, 12.27 μL) at 25° C. The resulting mixture was stirred at 25° C. for 30 min. To reaction mixture was added NaBH₃CN (40.43 mg, 643.45 μmol) at 25° C., the mixture was stirred at 25° C. for 1 h. LCMS showed the starting material was consumed completely and a peak (28%) with desired mass. The reaction solution was concentrated, dissolved with EtOAc (30 mL), washed with saturated NaHCO₃ (10 mL), dried over Na₂SO₄, filtered and concentrated under reduced pressure to give a residue. The residue was purified by flash silica gel chromatography (4 g SepaFlash Silica Flash Column, Eluent of 0~100% EtOAc/Petroleum ether gradient @ 100 mL/min; Eluent of 0~50% Methanol/EtOAc @ 100 mL/min) to give crude product. The crude product was purified by prep-HPLC (column: Waters □bridge 150×25 mm×5 um; mobile phase: [water (NH₄HCO₃)—ACN]; B %: 57%-87%, 8 min) and lyophilized to afford 4-((9-cyclopentyl-7,7-difluoro-5-methyl-6-oxo-6,7,8,9-tetrahydro-5H-pyrimido[4,5-b][1,4]diazepin-2-yl)amino)-N-(7-((1-(4-(2,6-dioxopiperidin-3-yl)-2-methylphenyl)piperidin-4-yl)methyl)-7-azaspiro[3.5]nonan-2-yl)-3-methoxybenzamide (25.3 mg, 27.40 μmol, 12.77% yield, 94% purity) as white solid. MS (M+H)⁺=868.3

¹H NMR (400 MHz, DMSO-d₆) δ=10.78 (s, 1H), 8.43 (d, J=7.4 Hz, 1H), 8.30-8.23 (m, 2H), 7.96 (s, 1H), 7.52-7.45 (m, 2H), 7.02-6.89 (m, 3H), 4.84-4.69 (m, 1H), 4.48-4.30 (m, 1H), 4.14-4.00 (m, 2H), 3.94 (s, 3H), 3.73 (dd, J=4.9, 11.1 Hz, 1H), 3.30 (s, 3H), 3.02 (d, J=11.8 Hz, 2H), 2.65-2.60 (m, 2H), 2.36-2.23 (m, 4H), 2.20 (s, 3H), 2.19-2.08 (m, 5H), 2.03-1.90 (m, 3H), 1.86-1.50 (m, 16H), 1.41-1.09 (m, 3H).

Example 26. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(7-((1-(4-(2,6-dioxopiperidin-3-yl)-2-fluorophenyl)-4-methylpiperidin-4-yl)methyl)-7-azaspiro[3.5]nonan-2-yl)-3-methoxybenzamide (Compound 26)

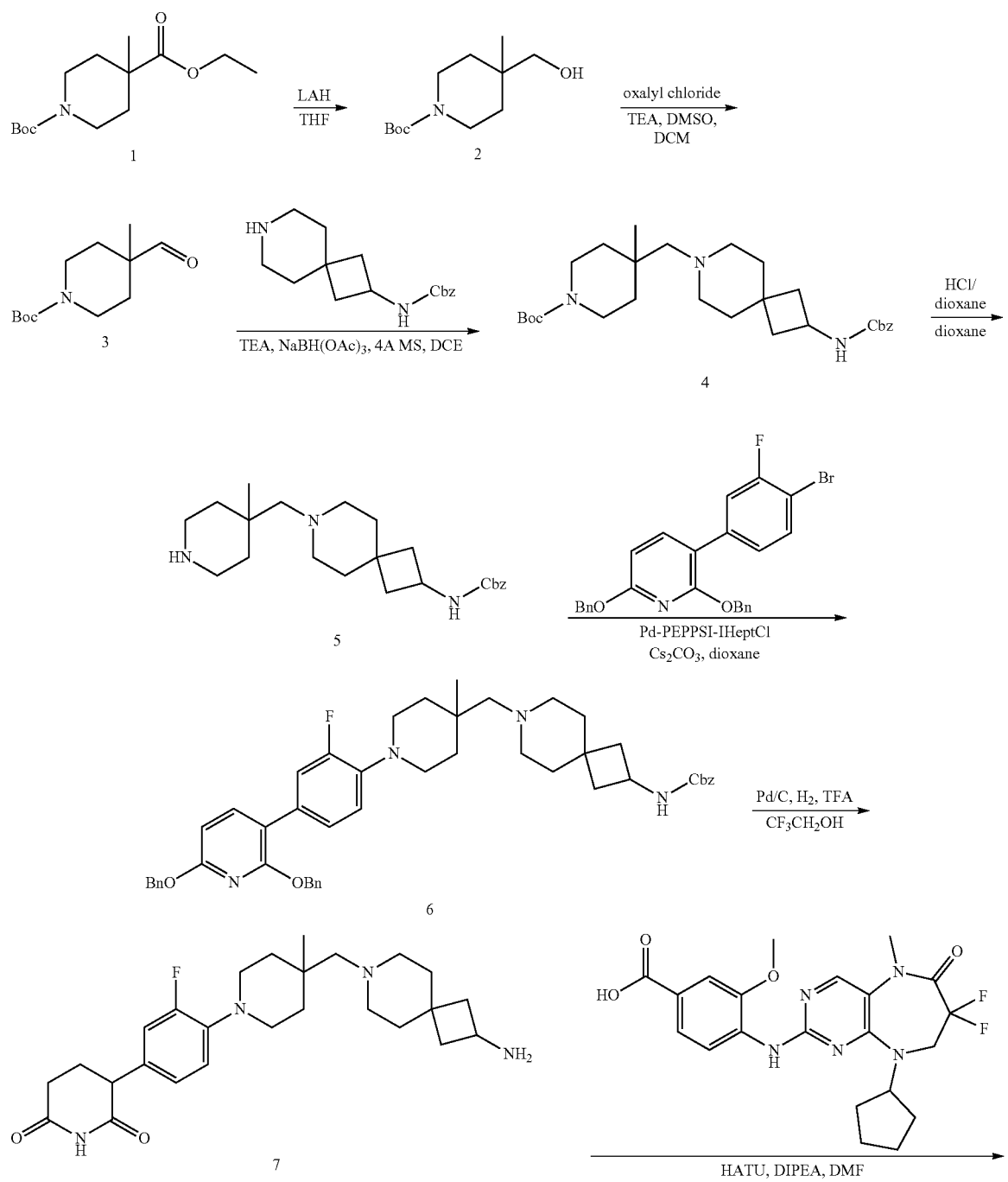

-continued

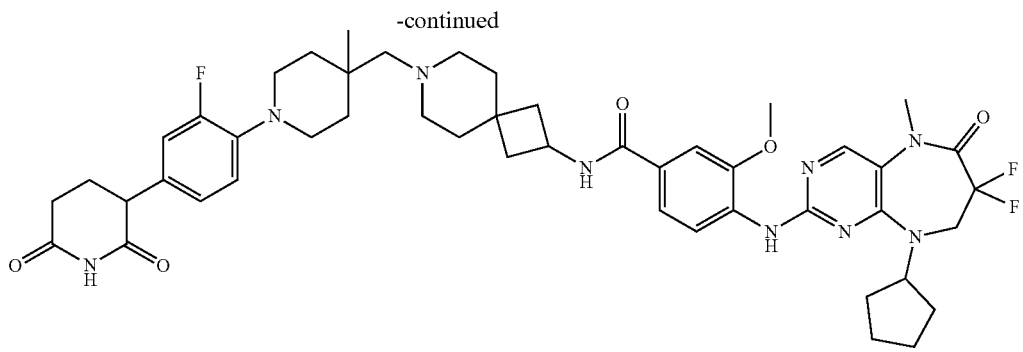

Compound 26

Step 1. Synthesis of tert-butyl 4-(hydroxymethyl)-4-methylpiperidine-1-carboxylate (2)

To a solution of 1-(tert-butyl) 4-ethyl 4-methylpiperidine-1,4-dicarboxylate (5 g, 18.43 mmol) in THF (20 mL) was added LiAlH$_4$ (839.23 mg, 22.11 mmol) at 0° C. under N$_2$, the mixture was stirred at 0° C. for 0.5 h. TLC (Petroleum ether:EtOAc=5:1) showed the starting material consumed up. The reaction mixture was quenched with H$_2$O (0.8 mL), aqueous of NaOH (15%, 0.8 mL), H$_2$O (2.4 mL), then filtered. The filtrate was dried over Na$_2$SO$_4$, concentrated under vacuum to afford tert-butyl 4-(hydroxymethyl)-4-methylpiperidine-1-carboxylate (4.1 g, crude) as yellow oil. MS (M+H)$^+$=230.3

Step 2. Synthesis of tert-butyl 4-formyl-4-methylpiperidine-1-carboxylate (3)

To a solution of DMSO (4.43 g, 56.69 mmol, 4.43 mL) in DCM (10 mL) was added oxalyl chloride (1.08 g, 8.50 mmol, 744.36 µL) at −70° C. and stirred for 10 min, then the solution of tert-butyl 4-(hydroxymethyl)-4-methylpiperidine-1-carboxylate (1.3 g, 5.67 mmol) in DCM (5 mL) was added at −65° C. over 20 min, TEA (2.87 g, 28.35 mmol, 3.95 mL) was added dropwise at −65° C., then the mixture was warmed to 20° C. and stirred for 0.5 h. TLC (Petroleum ether:EtOAc=1:1) showed the starting material consumed up. The mixture was diluted with water (3 mL), extracted with EtOAc (5 mL×3). The combined organic layer was dried over Na$_2$SO$_4$, filtered and concentrated under vacuum to afford tert-butyl 4-formyl-4-methylpiperidine-1-carboxylate (1.2 g, crude) as yellow oil. MS (M+H)$^+$=228.3

Step 3. Synthesis of tert-butyl 4-((2-(((benzyloxy)carbonyl)amino)-7-azaspiro[3.5]nonan-7-yl)methyl)-4-methylpiperidine-1-carboxylate (4)

To a solution of benzyl (7-azaspiro[3.5]nonan-2-yl)carbamate (984.56 mg, 3.17 mmol, HCl salt) and tert-butyl 4-formyl-4-methylpiperidine-1-carboxylate (1.2 g, 5.28 mmol) in DCE (20 mL) were added TEA (5.34 g, 52.79 mmol, 7.35 mL) and 4A MS (10 mg), the mixture was stirred at 20° C. for 2 h, then NaBH(OAc)$_3$ (1.12 g, 5.28 mmol) was added, the mixture was stirred at 20° C. for 14 h. LCMS showed the desired mass, the mixture was diluted with water (15 mL), extracted with EtOAc (15 mL×3). The combined organic layer was dried over Na$_2$SO$_4$, filtered and concentrated under vacuum. The crude product was purified by flash silica gel chromatography (Biotage, 4 g SepaFlash Silica Flash Column, Eluent of 4-90% EtOAc/Petroleum ether gradient @ 40 mL/min) to afford tert-butyl 4-((2-(((benzyloxy)carbonyl)amino)-7-azaspiro[3.5]nonan-7-yl)methyl)-4-methylpiperidine-1-carboxylate (1.05 g, 1.88 mmol, 35.63% yield, 87% purity) as yellow oil. MS (M+H)$^+$=486.3

Step 4. Synthesis of benzyl (7-((4-methylpiperidin-4-yl)methyl)-7-azaspiro[3.5]nonan-2-yl)carbamate (5)

To a solution of tert-butyl 4-((2-(((benzyloxy)carbonyl)amino)-7-azaspiro[3.5]nonan-7-yl)methyl)-4-methylpiperidine-1-carboxylate (1.05 g, 2.16 mmol) in dioxane (10 mL) was added HCl/dioxane (4 M, 10 mL), the mixture was stirred at 20° C. for 1 hr. TLC (Petroleum ether:EtOAc) showed desired product and the starting material consumed. The mixture was concentrated under vacuum to afford benzyl (7-((4-methylpiperidin-4-yl)methyl)-7-azaspiro[3.5]nonan-2-yl)carbamate (1 g, crude, HCl salt) as yellow oil. MS (M+H)$^+$=386.6

Step 5. Synthesis of benzyl (7-((1-(4-(2,6-bis(benzyloxy)pyridin-3-yl)-2-fluorophenyl)-4-methylpiperidin-4-yl)methyl)-7-azaspiro[3.5]nonan-2-yl)carbamate (6)

To a solution of benzyl (7-((4-methylpiperidin-4-yl)methyl)-7-azaspiro[3.5]nonan-2-yl)carbamate (1 g, crude, HCl salt) and 2,6-bis(benzyloxy)-3-(4-bromo-3-fluorophenyl)pyridine (1.10 g, 2.37 mmol) in dioxane (30 mL) were added Cs$_2$CO$_3$ (1.54 g, 4.74 mmol) and Pd-PEPPSI-IHeptCl (115.26 mg, 118.48 µmol) under N$_2$ atmosphere, the mixture was stirred at 100° C. for 16 hr under N$_2$ atmosphere. LCMS showed desired mass, the mixture was diluted with water (30 mL), extracted with EtOAc (15 mL×3). The organic layer was dried over sodium sulfate, filtered and concentrated under vacuum. The crude product was purified by flash silica gel chromatography (Biotage, 4 g SepaFlash Silica Flash Column, Eluent of 4-98% EtOAc/Petroleum ether gradient @ 35 mL/min) to afford benzyl (7-((1-(4-(2,6-bis(benzyloxy)pyridin-3-yl)-2-fluorophenyl)-4-methylpiperidin-4-yl)methyl)-7-azaspiro[3.5]nonan-2-yl)carbamate (260 mg, 324.60 µmol, 13.70% yield, 96% purity) as yellow oil. MS (M+H)$^+$=769.3

Step 6. Synthesis of 3-(4-(4-((2-amino-7-azaspiro [3.5]nonan-7-yl)methyl)-4-methylpiperidin-1-yl)-3-fluorophenyl)piperidine-2,6-dione (7)

To a solution of benzyl (7-((1-(4-(2,6-bis(benzyloxy)pyridin-3-yl)-2-fluorophenyl)-4-methylpiperidin-4-yl)methyl)-7-azaspiro[3.5]nonan-2-yl)carbamate (260 mg, 338.12 µmol) in CF$_3$CH$_2$OH (10 mL) were added TFA (3.86 mg, 33.81 µmol, 2.50 µL) and Pd/C (200 mg, 10% purity) under N$_2$ atmosphere. The mixture was degassed and purged with H$_2$ for 3 times, the reaction mixture was stirred at 20° C. for 16 h under 15 psi of H$_2$. LCMS showed desired mass, the mixture was filtered, the filtrate was concentrated under vacuum to afford 3-(4-(4-((2-amino-7-azaspiro[3.5]nonan-7-yl)methyl)-4-methylpiperidin-1-yl)-3-fluorophenyl)piperidine-2,6-dione (180 mg, crude) as brown oil. MS (M+H)$^+$=457.2

Step 7. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(7-((1-(4-(2,6-dioxopiperidin-3-yl)-2-fluorophenyl)-4-methylpiperidin-4-yl)methyl)-7-azaspiro[3.5]nonan-2-yl)-3-methoxybenzamide (Compound 26)

To a solution of 4-((9-cyclopentyl-7,7-difluoro-5-methyl-6-oxo-6,7,8,9-tetrahydro-5H-pyrimido[4,5-b][1,4]diazepin-2-yl)amino)-3-methoxybenzoic acid (200 mg, 446.99 µmol) in DMF (6 mL) were added HATU (254.94 mg, 670.49 µmol) and DIPEA (173.31 mg, 1.34 mmol, 233.57 µL), then 3-(4-(4-((2-amino-7-azaspiro[3.5]nonan-7-yl)methyl)-4-methylpiperidin-1-yl)-3-fluorophenyl)piperidine-2,6-dione (163.28 mg, 357.59 µmol) was added, the mixture was stirred at 20° C. for 16 hr. LCMS showed the desired mass, the mixture was diluted with water (3 mL), extracted with EtOAc (5 mL×3). The organic layer was dried over sodium sulfate, filtered and concentrated under vacuum. The crude product was purified by flash silica gel chromatography (Biotage, 4 g SepaFlash Silica Flash Column, Eluent of 4-20% MeOH/EtOAc gradient @ 30 mL/min) and re-purified by Prep-HPLC (column: Waters □bridge BEH C18 150*25 mm*5 um; mobile phase: [water (NH$_4$HCO$_3$)—ACN]; B %: 65%-95%, 10 min) and the eluent was freeze dried to afford 4-((9-cyclopentyl-7,7-difluoro-5-methyl-6-oxo-6,7,8,9-tetrahydro-5H-pyrimido[4,5-b][1,4]diazepin-2-yl)amino)-N-(7-((1-(4-(2,6-dioxopiperidin-3-yl)-2-fluorophenyl)-4-methylpiperidin-4-yl)methyl)-7-azaspiro[3.5] nonan-2-yl)-3-methoxybenzamide (5.5 mg, 6.05 µmol, 1.35% yield, 97.5% purity) as a white powder. MS (M+H)$^+$=886.3

$^1$H NMR (400 MHz, DMSO-d$_6$) δ=10.81 (s, 1H), 8.43 (d, J=7.3 Hz, 1H), 8.32-8.23 (m, 2H), 7.97 (s, 1H), 7.52-7.45 (m, 2H), 7.05-6.90 (m, 3H), 4.84-4.71 (m, 1H), 4.47-4.32 (m, 1H), 4.05 (t, J=13.8 Hz, 2H), 3.95 (s, 3H), 3.80 (dd, J=4.7, 11.7 Hz, 1H), 3.33 (s, 3H), 3.12-3.01 (m, 2H), 2.92-2.83 (m, 2H), 2.41-2.36 (m, 2H), 2.18-2.12 (m, 4H), 2.10-1.89 (m, 4H), 1.81 (dd, J=9.1, 10.5 Hz, 2H), 1.75-1.68 (m, 2H), 1.66-1.52 (m, 11H), 1.42-1.20 (m, 4H), 0.93 (s, 3H), 0.89-0.85 (m, 1H).

Example 27. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(7-((1-(4-(2,6-dioxopiperidin-3-yl)-2-fluorophenyl)-3-methylpiperidin-4-yl)methyl)-7-azaspiro[3.5]nonan-2-yl)-3-methoxybenzamide (Compound 27)

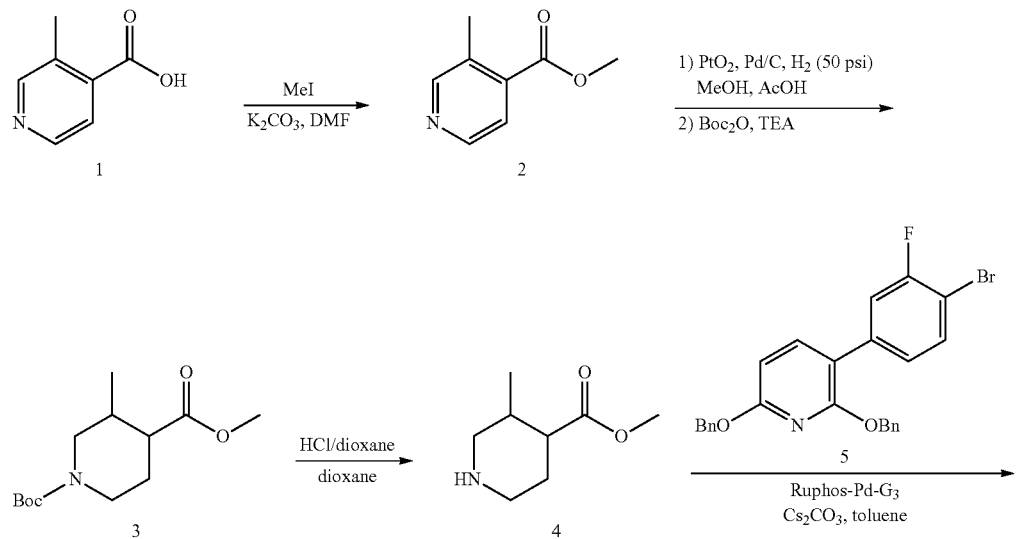

-continued
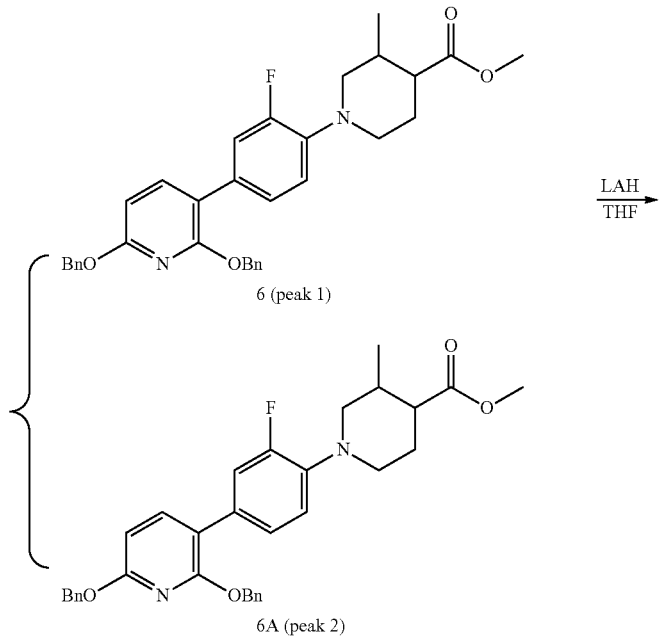
6 (peak 1)
6A (peak 2)
LAH / THF →
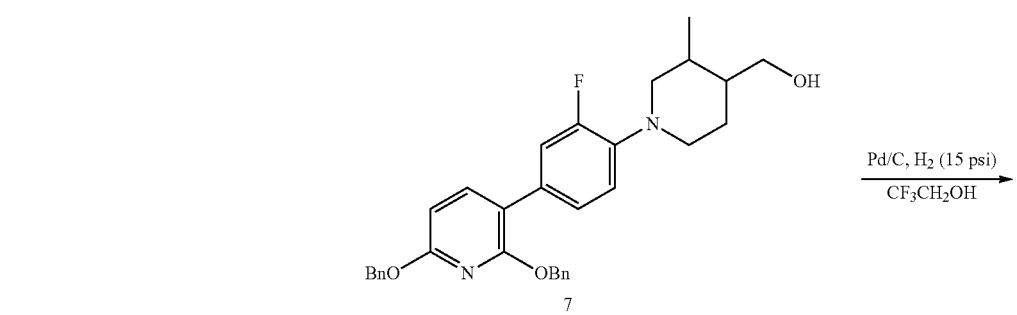
7
Pd/C, H₂ (15 psi) / CF₃CH₂OH →
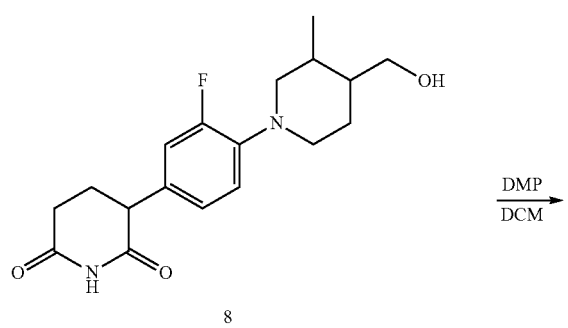
8
DMP / DCM →
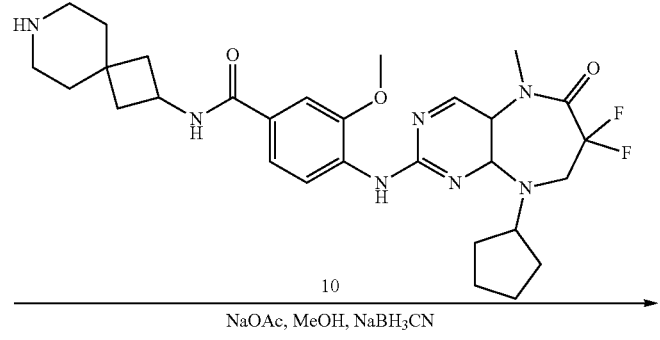
9
10
NaOAc, MeOH, NaBH₃CN →

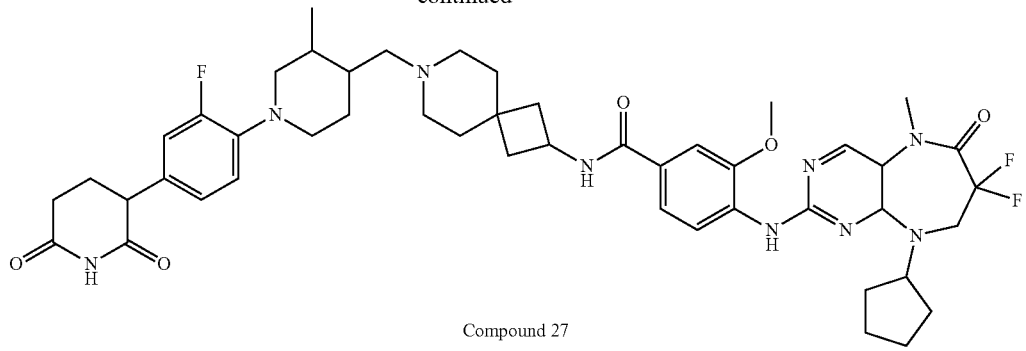

Compound 27

Step 1. Synthesis of methyl 3-methylisonicotinate (2)

To a solution of 3-methylisonicotinic acid (5 g, 36.46 mmol) in DMF (30 mL) were added $K_2CO_3$ (6.05 g, 43.75 mmol) and iodomethane (5.18 g, 36.46 mmol, 2.27 mL), the mixture was stirred at 15° C. for 3 hours. LCMS showed the starting material was consumed completely and a major peak (96%) with desired mass. The mixture was quenched by addition of $H_2O$ (5 mL) at 0° C., then diluted with $H_2O$ (200 mL) and extracted with EtOAc (150 mL×3). The combined organic layers were washed with saturated $CaCl_2$) solution (300 mL×5), dried over $Na_2SO_4$, filtered and concentrated in vacuum to afford methyl 3-methylisonicotinate (2.42 g) as a red oil, which was used directly. MS $(M+H)^+$=152.2

Step 2. Synthesis of 1-(tert-butyl) 4-methyl 3-methylpiperidine-1,4-dicarboxylate (3)

To a solution of methyl 3-methylisonicotinate (7.4 g, 48.95 mmol) in MeOH (70 mL) were added $PtO_2$ (1.00 g, 4.41 mmol), Pd/C (1 g, 48.95 mmol, 10% purity) and AcOH (293.98 mg, 4.90 mmol, 279.98 μL) under $N_2$ atmosphere at 15° C. The suspension was degassed under vacuum and purged with $H_2$ for several times. The mixture was stirred at 50° C. for 32 hours under $H_2$ (50 psi). TLC ($SiO_2$, Petroleum ether:EtOAc=5:1) showed the starting material remained and a new spot with lager polarity was detected, $Boc_2O$ (16.03 g, 73.43 mmol, 16.87 mL) and TEA (9.91 g, 97.91 mmol, 13.63 mL) were added and the resulting mixture was stirred at 15° C. for 16 hours. TLC ($SiO_2$, Petroleum ether:EtOAc=5:1) indicated a new spot with lower polarity was detected. The mixture was filtered and the filter cake was washed with EtOAc (300 mL). The filtrate was concentrated in vacuum. The residue was purified by flash silica gel chromatography (20 g SepaFlash Silica Flash Column, Eluent of 4-6% EtOAc/Petroleum ether gradient @ 200 mL/min) to afford 1-(tert-butyl) 4-methyl 3-methylpiperidine-1,4-dicarboxylate (10.5 g, 40.80 mmol, 83.35% yield) as a colorless oil. MS $(M+H)^+$=258.3

Step 3. Synthesis of methyl 3-methylpiperidine-4-carboxylate (4)

To a solution of 1-(tert-butyl) 4-methyl 3-methylpiperidine-1,4-dicarboxylate (3 g, 11.66 mmol) in dioxane (6 mL) was added HCl/dioxane (4 M, 30 mL), the mixture was stirred at 15° C. for 4 hours. LCMS showed the starting material was consumed completely and desired mass. The mixture was concentrated in vacuum to afford methyl 3-methylpiperidine-4-carboxylate (2.85 g, HCl salt) as an off-white solid, which was used directly. MS $(M+H)^+$=157.8

Step 4. Synthesis of methyl 1-(4-(2,6-bis(benzyloxy)pyridin-3-yl)-2-fluorophenyl)-3-methylpiperidine-4-carboxylate (6 and 6A)

To a solution of methyl 3-methylpiperidine-4-carboxylate (2 g, 10.33 mmol, HCl salt) and 2,6-dibenzyloxy-3-(4-bromo-3-fluoro-phenyl) pyridine (5.1 g, 10.98 mmol) in toluene (80 mL) were added Ruphos-Pd-G3 (863.70 mg, 1.03 mmol) and $Cs_2CO_3$ (10.09 g, 30.98 mmol) under $N_2$ atmosphere, the suspension was stirred at 100° C. for 16 hours under $N_2$ atmosphere. LCMS showed 2,6-bis(benzyloxy)-3-(4-bromo-3-fluorophenyl)pyridine was consumed completely and a peak (30%) with desired mass. The mixture was concentrated in vacuum and purified by flash silica gel chromatography (80 g SepaFlash Silica Flash Column, Eluent of 5-15% EtOAc/Petroleum ether gradient @ 200 mL/min) and re-purified by prep-HPLC (column: Phenomenex Luna C18 200*40 mm*10 μm; mobile phase: [water (TFA)—ACN]; B %: 80%-100%, 10 min) to afford A (peak 1), B (peak 2) and 360 mg mixture of A and B, which was re-purified by prep-HPLC (column: Welch Ultimate C18 150*25 mm*5 μm; mobile phase: [water (TFA)—ACN]; B %: 80%-100%, 10 min) to afford C (peak 1) and D (peak 2). A and C was combined and concentrated in vacuum to afford methyl 1-(4-(2,6-bis(benzyloxy)pyridin-3-yl)-2-fluorophenyl)-3-methylpiperidine-4-carboxylate (350 mg, 647.40 μmol, 6.27% yield) as a brown oil; B and D was combined and concentrated in vacuum to afford methyl 1-(4-(2,6-bis(benzyloxy)pyridin-3-yl)-2-fluorophenyl)-3-methylpiperidine-4-carboxylate (690 mg, 1.28 mmol, 12.36% yield) as a brown oil. MS $(M+H)^+$=541.3

Step 5. Synthesis of (1-(4-(2,6-bis(benzyloxy)pyridin-3-yl)-2-fluorophenyl)-3-methylpiperidin-4-yl) methanol (7)

To a solution of LAH (50 mg, 1.32 mmol) in THF (3 mL) was added dropwise a mixture of methyl 1-(4-(2,6-bis(benzyloxy)pyridin-3-yl)-2-fluorophenyl)-3-methylpiperidine-4-carboxylate (350 mg, 647.40 μmol) in THF (7 mL) at 0° C., the mixture was stirred at 20° C. for 4 hours under $N_2$ atmosphere. LCMS showed the starting material was consumed completely and a major peak (95%) with desired mass. The mixture was diluted with THF (20 mL), then quenched by addition of $H_2O$ (0.1 mL) at 0° C., then 15% NaOH solution (0.1 mL) and $H_2O$ (0.3 mL) were added and the suspension was dried over Na$_2$SO$_4$, filtered and concentrated in vacuum to afford (1-(4-(2,6-bis(benzyloxy)pyridin-3-yl)-2-fluorophenyl)-3-methylpiperidin-4-yl)methanol (330 mg) as a yellow oil. MS (M+H)$^+$=513.5

Step 6. Synthesis of 3-(3-fluoro-4-(4-(hydroxymethyl)-3-methylpiperidin-1-yl)phenyl)piperidine-2,6-dione (8)

A mixture of (1-(4-(2,6-bis(benzyloxy)pyridin-3-yl)-2-fluorophenyl)-3-methylpiperidin-4-yl)methanol (330 mg, 643.76 μmol) and Pd/C (50 mg, 10% purity) in CF$_3$CH$_2$OH (10 mL) was degassed and purged with H$_2$ for 3 times, the resulting mixture was stirred at 20° C. for 12 h under H$_2$ (15 Psi) atmosphere. LCMS showed a peak (50%) with desired mass. The mixture was filtered through a pad of celite. The filter cake was washed with CF$_3$CH$_2$OH (20 mL), The filtrate was concentrated in vacuum to afford 3-(3-fluoro-4-(4-(hydroxymethyl)-3-methylpiperidin-1-yl)phenyl)piperidine-2,6-dione (200 mg, crude) as a brown oil. MS (M+H)$^+$=335.1

Step 7. Synthesis of 1-(4-(2,6-dioxopiperidin-3-yl)-2-fluorophenyl)-3-methylpiperidine-4-carbaldehyde (9)

To a solution of 3-(3-fluoro-4-(4-(hydroxymethyl)-3-methylpiperidin-1-yl)phenyl)piperidine-2,6-dione (100 mg, 299.06 μmol) in DCM (1 mL) was added DMP (152.21 mg, 358.87 μmol, 111.10 μL), the mixture was stirred at 20° C. for 1 h. TLC indicated the starting material was consumed completely, and one major new spot was detected. The mixture was filtered. The filtrate was concentrated in vacuum to afford 1-(4-(2,6-dioxopiperidin-3-yl)-2-fluorophenyl)-3-methylpiperidine-4-carbaldehyde (99 g, crude) as a brown oil. MS (M+H)$^+$=333.1

Step 8. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(7-((1-(4-(2,6-dioxopiperidin-3-yl)-2-fluorophenyl)-3-methylpiperidin-4-yl)methyl)-7-azaspiro[3.5]nonan-2-yl)-3-methoxybenzamide (Compound 27)

To a solution of 4-((9-cyclopentyl-7,7-difluoro-5-methyl-6-oxo-6,7,8,9-tetrahydro-5H-pyrimido[4,5-b][1,4]diazepin-2-yl)amino)-3-methoxy-N-(7-azaspiro[3.5]nonan-2-yl)benzamide (164.12 mg, 270.78 μmol, HCl salt), 1-(4-(2,6-dioxopiperidin-3-yl)-2-fluorophenyl)-3-methylpiperidine-4-carbaldehyde (90 mg, 270.78 μmol) in MeOH (2 mL) was added NaOAc (44.43 mg, 541.57 μmol), the mixture was stirred at 20° C. for 0.5 h, NaBH$_3$CN (51.05 mg, 812.35 μmol) was added, the mixture was stirred at 20° C. for 12 h. LCMS showed a peak (11%) with desired mass. The reaction mixture was quenched by addition of NaHCO$_3$ (sat, aq. 5 mL), and extracted with EtOAc (10 mL×3). The combined organic layers were washed with brine (20 mL×3), dried over Na$_2$SO$_4$, filtered. The filtrate was concentrated in vacuum. The residue was purified by prep-TLC (SiO$_2$, DCM:MeOH=10:1) and re-purified by reversed-phase HPLC (column: Waters Xbridge 150*25 mm*5 μm; mobile phase: [water (NH$_4$HCO$_3$)—ACN]; B %: 50%-80%, 8 min). The eluent was lyophilized to afford 4-((9-cyclopentyl-7,7-difluoro-5-methyl-6-oxo-6,7,8,9-tetrahydro-5H-pyrimido[4,5-b][1,4]diazepin-2-yl)amino)-N-(7-((1-(4-(2,6-dioxopiperidin-3-yl)-2-fluorophenyl)-3-methylpiperidin-4-yl)methyl)-7-azaspiro[3.5]nonan-2-yl)-3-methoxybenzamide (7.1 mg, 7.29 μmol, 2.69% yield, 91% purity) as a white solid. MS (M+H)$^+$=886.7

$^1$H NMR (400 MHz, DMSO-d$_6$) δ=10.81 (s, 1H), 8.42 (d, J=7.1 Hz, 1H), 8.31-8.23 (m, 2H), 7.96 (s, 1H), 7.52-7.44 (m, 2H), 7.04-6.90 (m, 3H), 4.84-4.69 (m, 1H), 4.45-4.35 (m, 1H), 4.05 (t, J=14.2 Hz, 2H), 3.94 (s, 3H), 3.82-3.75 (m, 1H), 3.30-3.29 (m, 4H), 3.26-3.19 (m, 1H), 2.66-2.54 (m, 2H), 2.45-2.37 (m, 2H), 2.32-2.27 (m, 2H), 2.25-2.05 (m, 6H), 2.03-1.90 (m, 4H), 1.85-1.77 (m, 2H), 1.76-1.41 (m, 12H), 1.30-1.19 (m, 2H), 0.92 (d, J=6.5 Hz, 3H).

Example 28. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(4-(3-(2,4-dioxotetrahydropyrimidin-1(2H)-yl)-4-methoxyphenoxy)butanoyl)piperidin-4-yl)-2-fluoro-5-methoxybenzamide (Compound 28)

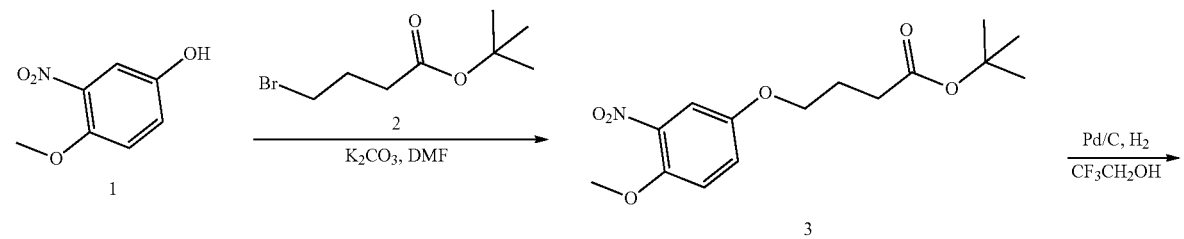

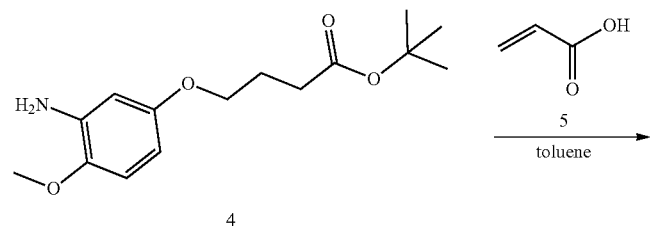

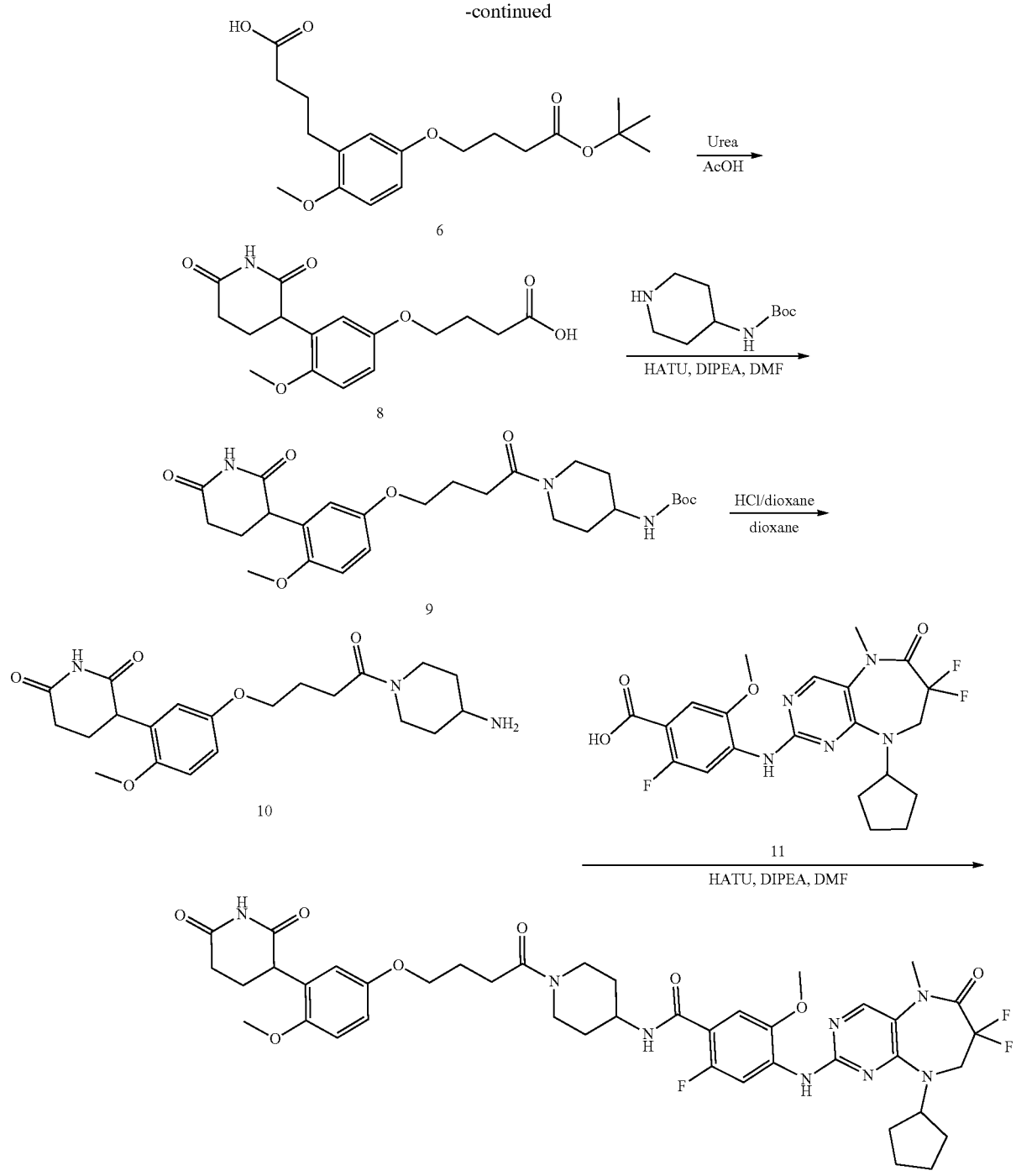

Compound 28

Step 1. Synthesis of tert-butyl 4-(4-methoxy-3-nitrophenoxy)butanoate (3)

To a solution of 4-methoxy-3-nitro-phenol (2 g, 11.82 mmol) in DMF (20 mL) were added K₂CO₃ (4.90 g, 35.47 mmol) and tert-butyl 4-bromobutanoate (3.43 g, 15.37 mmol) at 20° C. and the resulting mixture was stirred at 60° C. for 16 h. TLC (SiO₂, Petroleum ether:EtOAc=10:1) indicated 4-methoxy-3-nitro-phenol was consumed completely and one new spot was detected. The reaction mixture was combined with other scale (0.5 g scale) work-up. The reaction mixture was diluted with H₂O (20 mL) and extracted with EtOAc (20 mL×3). The organic layer was washed with brine (20 mL×3), dried over Na₂SO₄, filtered and concentrated. The residue was purified by flash silica gel chromatography (40 g SepaFlash Silica Flash Column, Eluent of 0~8% EtOAc/Petroleum ether gradient @ 100 mL/min) to afford tert-butyl 4-(4-methoxy-3-nitrophenoxy) butanoate (4.6 g, 11.56 mmol, 97.79% yield) as a yellow oil. MS (M+H)⁺=312.3

Step 2. Synthesis of tert-butyl 4-(3-amino-4-methoxyphenoxy)butanoate (4)

To a solution of tert-butyl 4-(4-methoxy-3-nitrophenoxy)butanoate (4.5 g, 14.45 mmol) in CF$_3$CH$_2$OH (50 mL) was added Pd/C (0.5 g, 1.45 mmol, 10% purity) under N$_2$ atmosphere. The suspension was degassed and purged with H$_2$ for 3 times. The mixture was stirred under H$_2$ (15 Psi) at 20° C. for 16 h. LCMS showed 28% of tert-butyl 4-(4-methoxy-3-nitrophenoxy)butanoate remained and 67% peak with desired mass was detected and the reaction mixture was stirred under H$_2$ (15 Psi) at 20° C. for another 16 h. LCMS showed tert-butyl 4-(4-methoxy-3-nitrophenoxy)butanoate was consumed completely and 98% peak with desired mass was detected. The reaction mixture was diluted with CF$_3$CH$_2$OH (150 mL) and filtered. The filtrate was concentrated in vacuum to afford tert-butyl 4-(3-amino-4-methoxyphenoxy)butanoate (3.7 g, 13.15 mmol, 90.98% yield) as a yellow oil. MS (M−56+H)$^+$=226.5

Step 3. Synthesis of 3-((5-(4-(tert-butoxy)-4-oxobutoxy)-2-methoxyphenyl)amino)propanoic acid (6)

To a solution of tert-butyl 4-(3-amino-4-methoxyphenoxy)butanoate (3.7 g, 13.15 mmol) in toluene (40 mL) was added acrylic acid (1.90 g, 26.30 mmol, 1.81 mL) at 20° C. and the resulting mixture was stirred at 120° C. for 4 h. LCMS showed 9% of tert-butyl 4-(3-amino-4-methoxyphenoxy)butanoate remained and 82% peak with desired mass was detected and the reaction mixture was stirred at 120° C. for another 8 h. LCMS showed tert-butyl 4-(3-amino-4-methoxyphenoxy)butanoate was consumed completely and 88% peak with desired mass was detected. The reaction mixture was concentrated in vacuum to afford 3-((5-(4-(tert-butoxy)-4-oxobutoxy)-2-methoxyphenyl)amino)propanoic acid (4.7 g, crude) as a yellow oil. MS (M+H)$^+$=354.4

Step 4. Synthesis of 4-(3-(2,4-dioxotetrahydropyrimidin-1(2H)-yl)-4-methoxyphenoxy)butanoic acid (8)

To a solution of 3-((5-(4-(tert-butoxy)-4-oxobutoxy)-2-methoxyphenyl)amino)propanoic acid (4.7 g, 13.30 mmol) in AcOH (50 mL) was added urea (3.99 g, 66.50 mmol, 3.57 mL) at 20° C. and the resulting mixture was stirred at 120° C. for 12 h. LCMS showed 3-((5-(4-(tert-butoxy)-4-oxobutoxy)-2-methoxyphenyl)amino)propanoic acid was consumed completely and 74% peak with desired mass was detected. The reaction mixture was concentrated in vacuum. The crude product was purified by reversed-phase HPLC (0.1% HCl, method: Column 330 g Flash Column Welch Ultimate XB_C18 20-40 μm; 120 A; Solvent for sample dissolution about 6.00 grams of sample dissolved in mL of DMF; Flow rate 100 mL/min; Mobile phase MeCN/H$_2$O; Gradient B % 5-40% 20 min; 40-100% 20 min; Instrument TELEDYNE ISCO CombiFlashRf150) and the eluent was lyophilized to afford 4-(3-(2,4-dioxotetrahydropyrimidin-1(2H)-yl)-4-methoxyphenoxy)butanoic acid (1.8 g, 5.58 mmol, 41.99% yield) as an off-white solid. MS (M+H)$^+$=323.3

Step 5. Synthesis of tert-butyl (1-(4-(3-(2,4-dioxotetrahydropyrimidin-1(2H)-yl)-4-methoxyphenoxy)butanoyl)piperidin-4-yl)carbamate (9)

To a solution of 4-(3-(2,4-dioxotetrahydropyrimidin-1(2H)-yl)-4-methoxyphenoxy)butanoic acid (0.6 g, 1.86 mmol) in DMF (6 mL) were added HATU (778.60 mg, 2.05 mmol) and DIPEA (721.78 mg, 5.58 mmol, 972.74 μL). The reaction mixture was stirred at 20° C. for 10 min and a solution of tert-butyl N-(4-piperidyl) carbamate (447.39 mg, 2.23 mmol) in DMF (6 mL) was added and the resulting mixture was stirred at 20° C. for 1 h. LCMS showed all starting material was consumed completely and 81% peak with desired mass was detected. The reaction mixture was diluted with H$_2$O (20 mL) and extracted with EtOAc (20 mL×3). The organic layer was washed with brine (20 mL×3), dried over Na$_2$SO$_4$, filtered and concentrated. The crude product was triturated with EtOAc (6 mL) at 20° C. for 0.5 h and filtered. The filter cake was dried in vacuum to afford tert-butyl (1-(4-(3-(2,4-dioxotetrahydropyrimidin-1(2H)-yl)-4-methoxyphenoxy)butanoyl)piperidin-4-yl)carbamate (453 mg, 852.90 μmol, 45.82% yield, 95% purity) as a white solid. MS (M−100+H)$^+$=405.3

Step 6. Synthesis of 1-(5-(4-(4-aminopiperidin-1-yl)-4-oxobutoxy)-2-methoxyphenyl)dihydropyrimidine-2,4(1H,3H)-dione (10)

To a solution of tert-butyl (1-(4-(3-(2,4-dioxotetrahydropyrimidin-1(2H)-yl)-4-methoxyphenoxy)butanoyl)piperidin-4-yl)carbamate (450 mg, 891.84 μmol) in dioxane (5 mL) was added HCl/dioxane (4 M, 15 mL) at 20° C. and the resulting mixture was stirred at 20° C. for 1 h. LCMS showed starting material was consumed completely and 95% peak with desired mass was detected. The reaction mixture was concentrated in vacuum to afford 1-(5-(4-(4-aminopiperidin-1-yl)-4-oxobutoxy)-2-methoxyphenyl)dihydropyrimidine-2,4(1H,3H)-dione (396 mg, crude, HCl salt) as an off-white solid. MS (M+H)$^+$=405.3

Step 7. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(4-(3-(2,4-dioxotetrahydropyrimidin-1(2H)-yl)-4-methoxyphenoxy)butanoyl)piperidin-4-yl)-2-fluoro-5-methoxybenzamide (Compound 28)

To a solution of 4-((9-cyclopentyl-7,7-difluoro-5-methyl-6-oxo-6,7,8,9-tetrahydro-5H-pyrimido[4,5-b][1,4]diazepin-2-yl)amino)-2-fluoro-5-methoxybenzoic acid (80 mg, 171.89 μmol) in DMF (4 mL) were added HATU (71.89 mg, 189.07 μmol) and DIPEA (44.43 mg, 343.77 μmol, 59.88 μL). The reaction mixture was stirred at 20° C. for 10 min and a solution of 1-(5-(4-(4-aminopiperidin-1-yl)-4-oxobutoxy)-2-methoxyphenyl)dihydropyrimidine-2,4(1H,3H)-dione (83.37 mg, 189.07 μmol, HCl salt) in DMF (4 mL) with DIPEA (44.43 mg, 343.77 μmol, 59.88 μL) was added and the resulting mixture was stirred at 20° C. for 1 h. LCMS showed starting material was consumed completely and 93% peak with desired mass was detected. The reaction mixture was diluted with H$_2$O (15 mL) and extracted with EtOAc (15 mL×3). The organic layer was washed with brine (15 mL×3), dried over Na$_2$SO$_4$, filtered and concentrated. The residue was purified by prep-HPLC (column: Unisil 3-100 C18 μLtra 150*50 mm*3 μm; mobile phase: [water (FA)-ACN]; B %: 32%-62%, 10 min) and the eluent was lyophilized to afford 4-((9-cyclopentyl-7,7-difluoro-5-methyl-6-oxo-6,7,8,9-tetrahydro-5H-pyrimido[4,5-b][1,4]diazepin-2-yl)amino)-N-(1-(4-(3-(2,4-dioxotetrahydropyrimidin-1(2H)-yl)-4-methoxyphenoxy)butanoyl)piperidin-4-yl)-2-fluoro-5-methoxybenzamide (61.8 mg, 71.10 μmol, 41.36% yield, 98% purity) as a white solid.

MS (M+H)$^+$=852.0

$^1$H NMR (400 MHz, DMSO-d$_6$) δ=10.28 (s, 1H), 8.27 (s, 1H), 8.16 (d, J=12.1 Hz, 1H), 8.04 (s, 1H), 7.89 (br d, J=7.2 Hz, 1H), 7.03-6.98 (m, 1H), 6.96 (d, J=6.1 Hz, 1H), 6.89-

6.84 (m, 2H), 4.83-4.72 (m, 1H), 4.32 (br d, J=12.2 Hz, 1H), 4.05 (br t, J=13.9 Hz, 2H), 3.92-3.80 (m, 6H), 3.73 (s, 3H), 3.60-3.50 (m, 3H), 3.32 (s, 3H), 3.19-3.07 (m, 1H), 3.03-2.91 (m, 1H), 2.65 (t, J=6.6 Hz, 2H), 2.22 (br t, J=7.3 Hz, 2H), 1.98-1.86 (m, 4H), 1.85-1.78 (m, 1H), 1.76-1.65 (m, 3H), 1.65-1.51 (m, 4H), 1.40-1.22 (m, 2H)
Example 29. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(4-(4-(2,4-dioxotetrahydropyrimidin-1(2H)-yl)-3-methoxyphenoxy)butanoyl)piperidin-4-yl)-2-fluoro-5-methoxybenzamide (Compound 29)
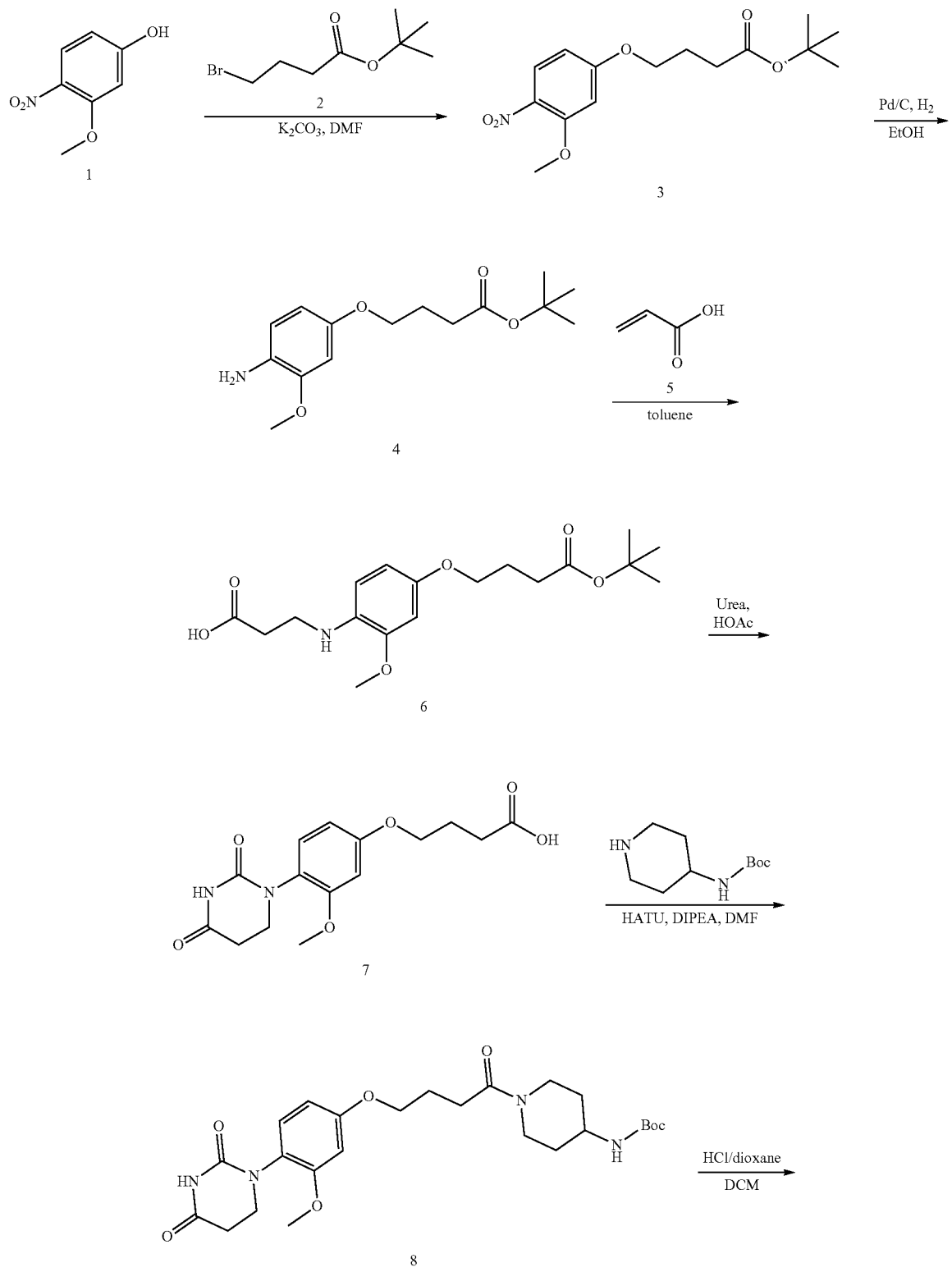

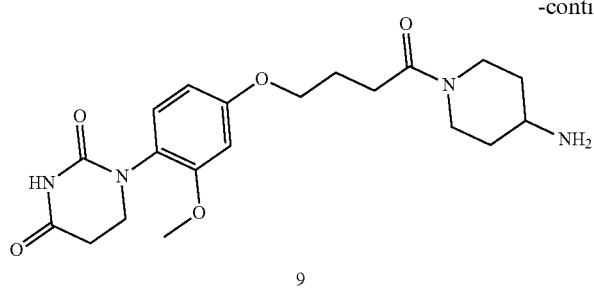

9

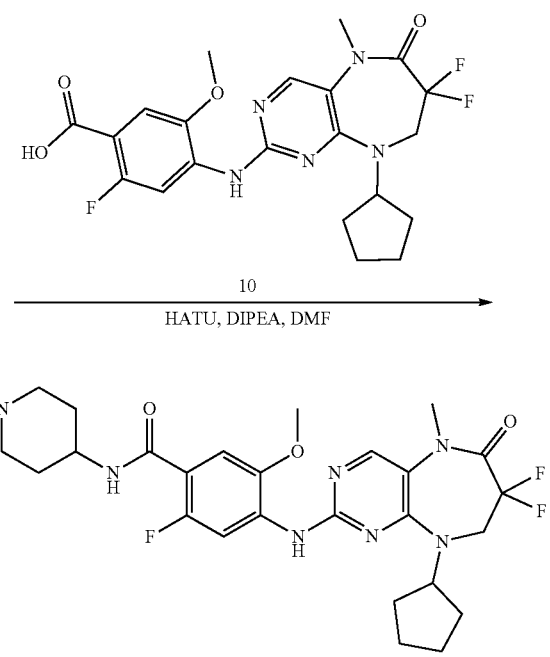

10

→ HATU, DIPEA, DMF

Compound 29

Step 1. Synthesis of tert-butyl 4-(3-methoxy-4-nitrophenoxy)butanoate (3)

To a solution of 3-methoxy-4-nitrophenol (2 g, 11.82 mmol) in DMF (25 mL) was added $K_2CO_3$ (4.90 g, 35.47 mmol) and tert-butyl 4-bromobutanoate (3.96 g, 17.74 mmol). The mixture was stirred at 90° C. for 3 h. LC-MS showed 3-methoxy-4-nitrophenol was consumed completely and one main peak with desired mass. The reaction mixture was diluted with water 300 mL and extracted with EtOAc (70 mL×3). The combined organic layers were washed with brine 70 mL, dried over anhydrous sodium sulfate, filtered and concentrated under reduced pressure to give a residue. The crude product was purified by reversed-phase HPLC (0.1% $NH_3·H_2O$) and the eluent was lyophilized to afford tert-butyl 4-(3-methoxy-4-nitrophenoxy)butanoate (3.5 g, 11.13 mmol, 94.12% yield, 99% purity) as colorless oil. MS (M+H−56)+=256.2.

Step 2. Synthesis of tert-butyl 4-(4-amino-3-methoxyphenoxy)butanoate (4)

To a solution of tert-butyl 4-(3-methoxy-4-nitrophenoxy)butanoate (500 mg, 1.61 mmol) in EtOH (8 mL) was added Pd/C (10%, 50 mg) under $N_2$ atmosphere. The suspension was degassed and purged with $H_2$ for 3 times. The mixture was stirred under $H_2$ (15 Psi) at 25° C. for 2 h. LC-MS showed tert-butyl 4-(3-methoxy-4-nitrophenoxy)butanoate was consumed completely and one main peak with desired mass. The reaction mixture was filtered and filter cake was washed with EtOAc (50 mL), the filtrate was concentrated in vacuo to afford tert-butyl 4-(4-amino-3-methoxyphenoxy)butanoate (450 mg, 1.60 mmol, 99.59% yield) as black brown oil, which was used directly for next step. MS (M+H−56)+=226.2

Step 3. Synthesis of 3-((4-(4-(tert-butoxy)-4-oxobutoxy)-2-methoxyphenyl)amino)propanoic acid (6)

A mixture of tert-butyl 4-(4-amino-3-methoxyphenoxy)butanoate (450 mg, 1.60 mmol), acrylic acid (230.52 mg, 3.20 mmol, 219.54 µL) in toluene (5 mL) was stirred at 110° C. for 16 h. The reaction mixture was concentrated under reduced pressure to remove solvent to afford 3-((4-(4-(tert-butoxy)-4-oxobutoxy)-2-methoxyphenyl)amino)propanoic acid (530 mg, crude) as black brown oil, which was used directly for next step. MS (M+H)+=354.4

Step 4. Synthesis of 4-(4-(2,4-dioxotetrahydropyrimidin-1(2H)-yl)-3-methoxyphenoxy)butanoic acid (7)

A mixture of 3-((4-(4-(tert-butoxy)-4-oxobutoxy)-2-methoxyphenyl)amino)propanoic acid (530 mg, 1.50 mmol) and urea (450.32 mg, 7.50 mmol, 402.07 µL) in AcOH (6 mL) was stirred at 120° C. for 16 h. LC-MS showed 3-((4-(4-(tert-butoxy)-4-oxobutoxy)-2-methoxyphenyl) amino)propanoic acid was consumed completely and the desired mass. The reaction mixture was diluted with water 100 mL and extracted with EtOAc (30 mL×3). The combined organic layers were washed with brine 30 mL, dried over anhydrous sodium sulfate, filtered and concentrated under reduced pressure to give a residue. The crude product was purified by reversed-phase HPLC (0.1% FA condition: Instrument: Agela HP1000; Column: Welch µLtimate XB_$C_{18}$ 150×400 mm 20/40 µm; eluent A: water, eluent B: acetonitrile; gradient: 0-40 min 0-65% B; flow 50 mL/min; temperature: room temperature; Detector: UV 220/254 nm) and the eluent was lyophilized to afford 4-(4-(2,4-dioxotetrahydropyrimidin-1(2H)-yl)-3-methoxyphenoxy)butanoic acid (350 mg, 912.16 µmol, 60.82% yield, 84% purity) as a white solid. MS (M+H)+=323.2

Step 5. Synthesis of tert-butyl (1-(4-(4-(2,4-dioxotetrahydropyrimidin-1(2H)-yl)-3-methoxyphenoxy)butanoyl)piperidin-4-yl)carbamate (8)

To a solution of 4-(4-(2,4-dioxotetrahydropyrimidin-1 (2H)-yl)-3-methoxyphenoxy)butanoic acid (300 mg, 930.77

µmol) and tert-butyl piperidin-4-ylcarbamate (186.41 mg, 930.77 µmol) in DMF (1.5 mL) was added HATU (530.86 mg, 1.40 mmol) and DIPEA (360.89 mg, 2.79 mmol, 486.37 µL). The mixture was stirred at 25° C. for 1.5 h. LC-MS showed the starting material was consumed completely and the desired mass. The reaction mixture was diluted with water 100 mL and extracted with EtOAc (30 mL×3). The combined organic layers were washed with brine 30 mL, dried over anhydrous sodium sulfate, filtered and concentrated under reduced pressure to give a residue. The residue was purified by column chromatography (SiO$_2$, MeOH/EtOAc=0-10%) to afford tert-butyl (1-(4-(4-(2,4-dioxotetrahydropyrimidin-1(2H)-yl)-3-methoxyphenoxy)butanoyl)piperidin-4-yl)carbamate (380 mg, 722.99 µmol, 77.68% yield, 96% purity) as a light yellow solid. MS (M+H–100)*=405.3

Step 6. Synthesis of 1-(4-(4-(4-aminopiperidin-1-yl)-4-oxobutoxy)-2-methoxyphenyl) dihydropyrimidine-2,4(1H,3H)-dione (9)

A mixture of tert-butyl (1-(4-(4-(2,4-dioxotetrahydropyrimidin-1(2H)-yl)-3-methoxyphenoxy) butanoyl)piperidin-4-yl)carbamate (100 mg, 198.19 µmol) and HCl/dioxane (4 M, 1.5 mL) in DCM (1.5 mL) was stirred at 25° C. for 0.5 h. LC-MS showed one main peak with desired mass was detected. The reaction mixture was concentrated under reduced pressure to remove solvent to afford 1-(4-(4-(4-aminopiperidin-1-yl)-4-oxobutoxy)-2-methoxyphenyl)dihydropyrimidine-2,4(1H,3H)-dione (300 mg, crude, HCl salt) as a light yellow solid, which was used directly for next step. MS (M+H)$^+$=404.9

Step 7. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(4-(4-(2,4-dioxotetrahydropyrimidin-1(2H)-yl)-3-methoxyphenoxy)butanoyl)piperidin-4-yl)-2-fluoro-5-methoxybenzamide (Compound 29)

To a solution of 1-(4-(4-(4-aminopiperidin-1-yl)-4-oxobutoxy)-2-methoxyphenyl)dihydropyrimidine-2,4(1H, 3H)-dione (100 mg, 226.80 µmol, HCl salt) and 4-((9-cyclopentyl-7,7-difluoro-5-methyl-6-oxo-6,7,8,9-tetrahydro-5H-pyrimido[4,5-b][1,4]diazepin-2-yl)amino)-2-fluoro-5-methoxybenzoic acid (105.56 mg, 226.80 µmol) in DMF (3 mL) was added HATU (129.35 mg, 340.20 µmol) and DIPEA (87.94 mg, 680.40 µmol, 118.51 µL). The mixture was stirred at 25° C. for 2 h. LC-MS showed 1-(4-(4-(4-aminopiperidin-1-yl)-4-oxobutoxy)-2-methoxyphenyl)dihydropyrimidine-2,4(1H,3H)-dione was consumed completely and the desired mass. The reaction mixture was diluted with water 50 mL and extracted with EtOAc (20 mL×3). The combined organic layers were washed with brine 20 mL, dried over anhydrous sodium sulfate, filtered and concentrated under reduced pressure to give a residue. The residue was purified by column chromatography (SiO$_2$, MeOH/EtOAc=0-10%). Then the residue was purified by prep-HPLC (neutral condition: column: Waters Xbridge BEH C18 150×25 mm×5 µm; mobile phase: [water (NH$_4$HCO$_3$)—ACN]; B %: 38%-68%, min) and the eluent was lyophilized to afford 4-((9-cyclopentyl-7,7-difluoro-5-methyl-6-oxo-6,7,8,9-tetrahydro-5H-pyrimido[4,5-b][1,4]diazepin-2-yl)amino)-N-(1-(4-(4-(2,4-dioxotetrahydropyrimidin-1(2H)-yl)-3-methoxyphenoxy)butanoyl)piperidin-4-yl)-2-fluoro-5-methoxybenzamide (37.9 mg, 43.16 µmol, 19.03% yield, 97% purity) as a white solid. MS (M+H)$^+$= 852.5

$^1$H NMR (400 MHz, DMSO-d$_6$) δ=10.23 (s, 1H), 8.34-8.20 (m, 2H), 8.05 (s, 1H), 8.01-7.94 (m, 1H), 7.20 (d, J=6.7 Hz, 1H), 7.13 (d, J=8.6 Hz, 1H), 6.66 (d, J=2.4 Hz, 1H), 6.53 (dd, J=2.6, 8.6 Hz, 1H), 4.89-4.77 (m, 1H), 4.36-4.32 (m, 1H), 4.12-4.01 (m, 5H), 3.95 (s, 3H), 3.94-3.80 (m, 1H), 3.78 (s, 3H), 3.57-3.52 (m, 2H), 3.34 (s, 3H), 3.23-3.16 (m, 1H), 2.80-2.73 (m, 1H), 2.68-2.63 (m, 2H), 2.49-2.45 (m, 2H), 2.01-1.93 (m, 4H), 1.92-1.80 (m, 2H), 1.79-1.74 (m, 2H), 1.68-1.57 (m, 4H), 1.55-1.40 (m, 2H).

Example 30. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(3-(4-(4-(2,4-dioxotetrahydropyrimidin-1(2H)-yl)-3-methoxyphenyl)piperazin-1-yl)propanoyl)piperidin-4-yl)-3-methoxybenzamide (Compound 30)

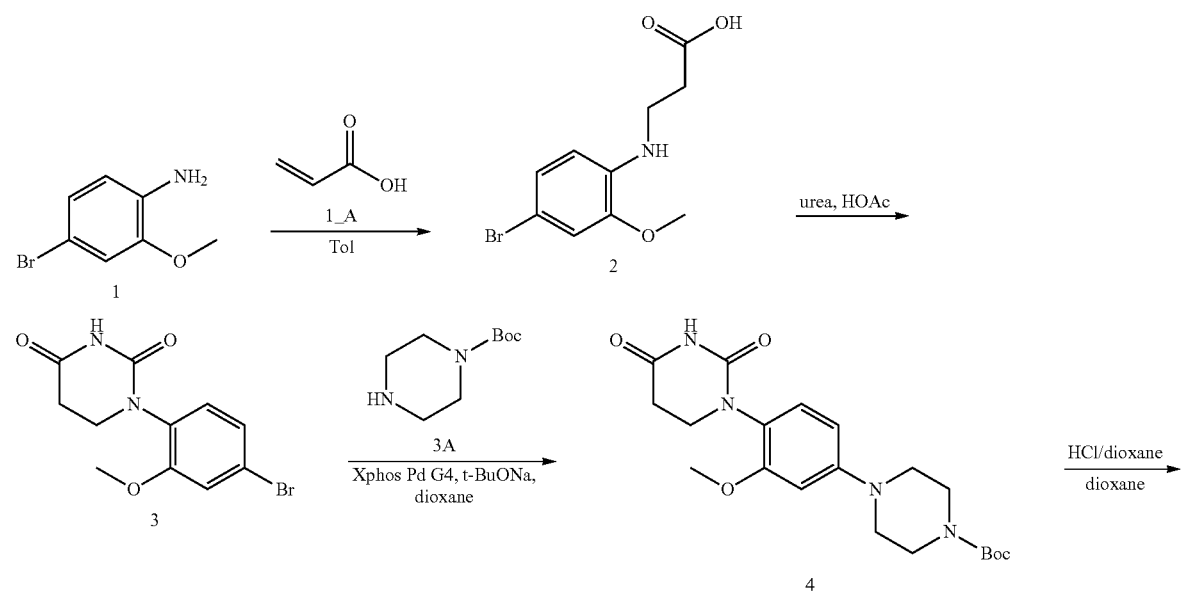

-continued

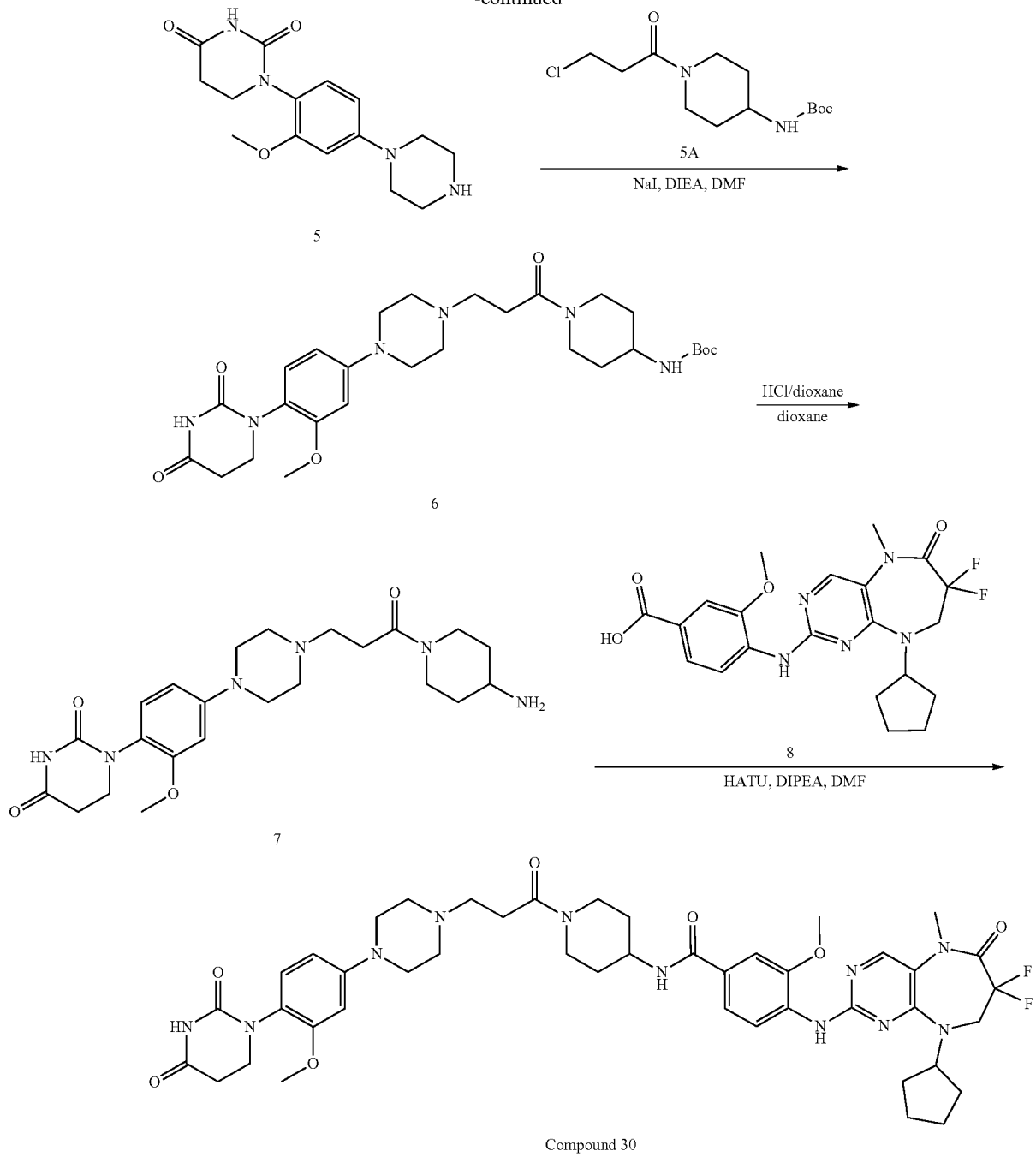

Compound 30

Step 1. Synthesis of 3-((4-bromo-2-methoxyphenyl)amino)propanoic acid (2)

A mixture of 4-bromo-2-methoxyaniline (2 g, 9.90 mmol) and acrylic acid (1.07 g, 14.85 mmol, 1.02 mL) in Tol (30 mL) was stirred at 100° C. for 16 hr. LCMS showed a main peak with desired mass. The mixture was concentrated under vacuum to obtain 3-((4-bromo-2-methoxyphenyl)amino) propanoic acid (2.71 g, 6.82 mmol, 68.92% yield, 69% purity) as brown powder. MS (M+H)$^+$=273.9

Step 2. Synthesis of 1-(4-bromo-2-methoxyphenyl) dihydropyrimidine-2,4(1H,3H)-dione (3)

To a solution of 3-((4-bromo-2-methoxyphenyl)amino) propanoic acid (2.71 g, 9.89 mmol) in AcOH (15 mL) was added urea (2.97 g, 49.43 mmol, 2.65 mL), the mixture was stirred at 120° C. for 16 hr. LCMS showed a peak (64%) with desired mass. The mixture was diluted with water 50 mL, extracted with EtOAc (20 mL×3). The organic layer was dried over Na$_2$SO$_4$, filtered and concentrated under vacuum. The crude product was purified by flash silica gel chromatography (Biotage, 4 g SepaFlash Silica Flash Column, Eluent of 4-100% EtOAc/Petroleum ether gradient @

35 mL/min) to afford 1-(4-bromo-2-methoxyphenyl)dihydropyrimidine-2,4(1H,3H)-dione (2.1 g, 7.02 mmol, 71.01% yield) as gray powder. MS (M+H)$^+$=300.9

$^1$H NMR (400 MHz, DMSO-d$_6$) δ=10.36 (s, 1H), 7.31 (s, 1H), 7.25-7.15 (m, 2H), 3.83 (s, 3H), 3.56 (t, J=6.5 Hz, 2H), 2.67 (t, J=6.4 Hz, 2H).

Step 3. Synthesis of tert-butyl 4-(4-(2,4-dioxotetrahydropyrimidin-1(2H)-yl)-3-methoxyphenyl)piperazine-1-carboxylate (4)

To a solution of 1-(4-bromo-2-methoxyphenyl)dihydropyrimidine-2,4(1H,3H)-dione (1 g, 3.34 mmol) in dioxane (10 mL) were added t-BuONa (2 M, 5.01 mL) and Xphos Pd G4 (287.67 mg, 334.31 μmol), then tert-butyl piperazine-1-carboxylate (933.99 mg, 5.01 mmol) was added, the mixture was stirred at 90° C. for 16 h. LCMS showed a peak (54%) with desired mass. The mixture was diluted with brine (10 mL), extracted with EtOAc (5 mL×3). The organic layer was dried over Na$_2$SO$_4$, filtered and concentrated under vacuum. The crude product was purified by flash silica gel chromatography (Biotage, 4 g SepaFlash Silica Flash Column, Eluent of 4-60% EtOAc/Petroleum ether gradient @ 20 mL/min) to afford tert-butyl 4-(4-(2,4-dioxotetrahydropyrimidin-1(2H)-yl)-3-methoxyphenyl)piperazine-1-carboxylate (830 mg, 1.81 mmol, 54.02% yield, 88% purity) as brown powder. MS (M+H)$^+$=405.0

Step 4. Synthesis of 1-(2-methoxy-4-(piperazin-1-yl)phenyl)dihydropyrimidine-2,4(1H,3H)-dione (5)

To a solution of tert-butyl 4-(4-(2,4-dioxotetrahydropyrimidin-1(2H)-yl)-3-methoxyphenyl)piperazine-1-carboxylate (300 mg, 741.73 μmol) in dioxane (6 mL) was added HCl/dioxane (4 M, 1.85 mL), the mixture was stirred at 25° C. for 2 hr. LCMS showed a peak with desired mass. The mixture was concentrated under vacuum to afford 1-(2-methoxy-4-(piperazin-1-yl)phenyl)dihydropyrimidine-2,4(1H,3H)-dione (252 mg, 739.43 μmol, 99.69% yield, HCl salt) as yellow oil, which was used directly. MS (M+H)$^+$=305.0

Step 5. Synthesis of tert-butyl (1-(3-(4-(4-(2,4-dioxotetrahydropyrimidin-1(2H)-yl)-3-methoxyphenyl)piperazin-1-yl)propanoyl)piperidin-4-yl)carbamate (6)

To a solution of 1-(2-methoxy-4-(piperazin-1-yl)phenyl)dihydropyrimidine-2,4(1H,3H)-dione (446.59 mg, 1.31 mmol, 1.66 μL, HCl salt) and tert-butyl (1-(3-chloropropanoyl)piperidin-4-yl)carbamate (457.25 mg, 1.57 mmol,) in DMF (20 mL) were added DIEA (677.44 mg, 5.24 mmol, 912.99 μL) and NaI (39.28 mg, 262.08 μmol) and the resulting mixture was stirred at 70° C. for 16 hr. LCMS showed desired mass. The mixture was diluted with brine (10 mL), extracted with EtOAc (5 mL×3). The combined organic layer was dried over Na$_2$SO$_4$, filtered and concentrated under vacuum. The crude product was purified by flash silica gel chromatography (Biotage, 4 g SepaFlash Silica Flash Column, Eluent of 4-60% MeOH/Petroleum ether gradient @ 30 mL/min) to afford tert-butyl (1-(3-(4-(4-(2,4-dioxotetrahydropyrimidin-1(2H)-yl)-3-methoxyphenyl)piperazin-1-yl)propanoyl)piperidin-4-yl)carbamate (370 mg, 602.68 μmol, 45.99% yield, 91% purity) as yellow oil. MS (M+H)$^+$=559.1

Step 6. Synthesis of 1-(4-(4-(3-(4-aminopiperidin-1-yl)-3-oxopropyl)piperazin-1-yl)-2-methoxyphenyl)dihydropyrimidine-2,4(1H,3H)-dione (7)

To a solution of tert-butyl (1-(3-(4-(4-(2,4-dioxotetrahydropyrimidin-1(2H)-yl)-3-methoxyphenyl)piperazin-1-yl)propanoyl)piperidin-4-yl)carbamate (370 mg, 662.29 μmol) in dioxane (1 mL) was added HCl/dioxane (4 M, 7.40 mL), the mixture was stirred at 25° C. for 2 hr. LCMS showed desired mass. The mixture was concentrated under vacuum to afford 1-(4-(4-(3-(4-aminopiperidin-1-yl)-3-oxopropyl)piperazin-1-yl)-2-methoxyphenyl)dihydropyrimidine-2,4(1H,3H)-dione (350 mg, 636.35 μmol, 96.08% yield, 90% purity, HCl salt) as a yellow solid, which was used directly. MS (M+H)$^+$=459.0

Step 7. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(3-(4-(4-(2,4-dioxotetrahydropyrimidin-1(2H)-yl)-3-methoxyphenyl)piperazin-1-yl)propanoyl)piperidin-4-yl)-3-methoxybenzamide (Compound 30)

To a solution of 4-((9-cyclopentyl-7,7-difluoro-5-methyl-6-oxo-6,7,8,9-tetrahydro-5H-pyrimido[4,5-b][1,4]diazepin-2-yl)amino)-3-methoxybenzoic acid (100 mg, 223.50 μmol) in DMF (2 mL) were added HATU (127.47 mg, 335.24 μmol) and DIEA (86.66 mg, 670.49 μmol, 116.79 μL), after stirring for 0.5 h, then 1-(4-(4-(3-(4-aminopiperidin-1-yl)-3-oxopropyl)piperazin-1-yl)-2-methoxyphenyl) dihydropyrimidine-2,4(1H,3H)-dione (110.63 mg, 223.50 μmol, HCl salt) was added and the resulting mixture was stirred at 25° C. for 16 h. LCMS showed a peak (50%) with desired mass. The mixture was diluted with water (5 mL), extracted with EtOAc (5 mL×3). The combined organic layer was dried over Na$_2$SO$_4$, filtered and concentrated under vacuum. The residue was purified by flash silica gel chromatography (Biotage, 4 g SepaFlash Silica Flash Column, Eluent of 4-100% EtOAc/Petroleum ether gradient @ 20 mL/min) followed by Prep-HPLC (column: Waters Xbridge 150*25 mm*5 μm; mobile phase: [water (NH$_4$HCO$_3$)—ACN]; B %: 35%-65%, 9 min) and the eluent was freeze dried to afford 4-((9-cyclopentyl-7,7-difluoro-5-methyl-6-oxo-6,7,8,9-tetrahydro-5H-pyrimido[4,5-b][1,4]diazepin-2-yl)amino)-N-(1-(3-(4-(4-(2,4-dioxotetrahydropyrimidin-1(2H)-yl)-3-methoxyphenyl)piperazin-1-yl)propanoyl)piperidin-4-yl)-3-methoxybenzamide (31.2 mg, 34.40 μmol, 15.39% yield, 97.9% purity) as white powder.

MS (M+H)$^+$=888.0

$^1$H NMR (400 MHz, DMSO-d$_6$) δ=10.20 (s, 1H), 8.33-8.25 (m, 2H), 8.16 (br d, J=7.7 Hz, 1H), 7.97 (s, 1H), 7.53-7.46 (m, 2H), 7.03 (d, J=8.6 Hz, 1H), 6.61 (d, J=2.2 Hz, 1H), 6.49 (dd, J=2.3, 8.6 Hz, 1H), 4.85-4.71 (m, 1H), 4.40 (d, J=12.6 Hz, 1H), 4.15-3.88 (m, 7H), 3.78 (s, 3H), 3.51 (t, J=6.5 Hz, 2H), 3.35 (s, 3H), 3.27-3.05 (m, 5H), 2.74-2.55 (m, 11H), 2.02-1.33 (m, 12H).

Example 31. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(3-(4-(3-(2,4-dioxotetrahydropyrimidin-1(2H)-yl)-4-methoxyphenyl)piperazin-1-yl)propanoyl)piperidin-4-yl)-3-methoxybenzamide (Compound 31)
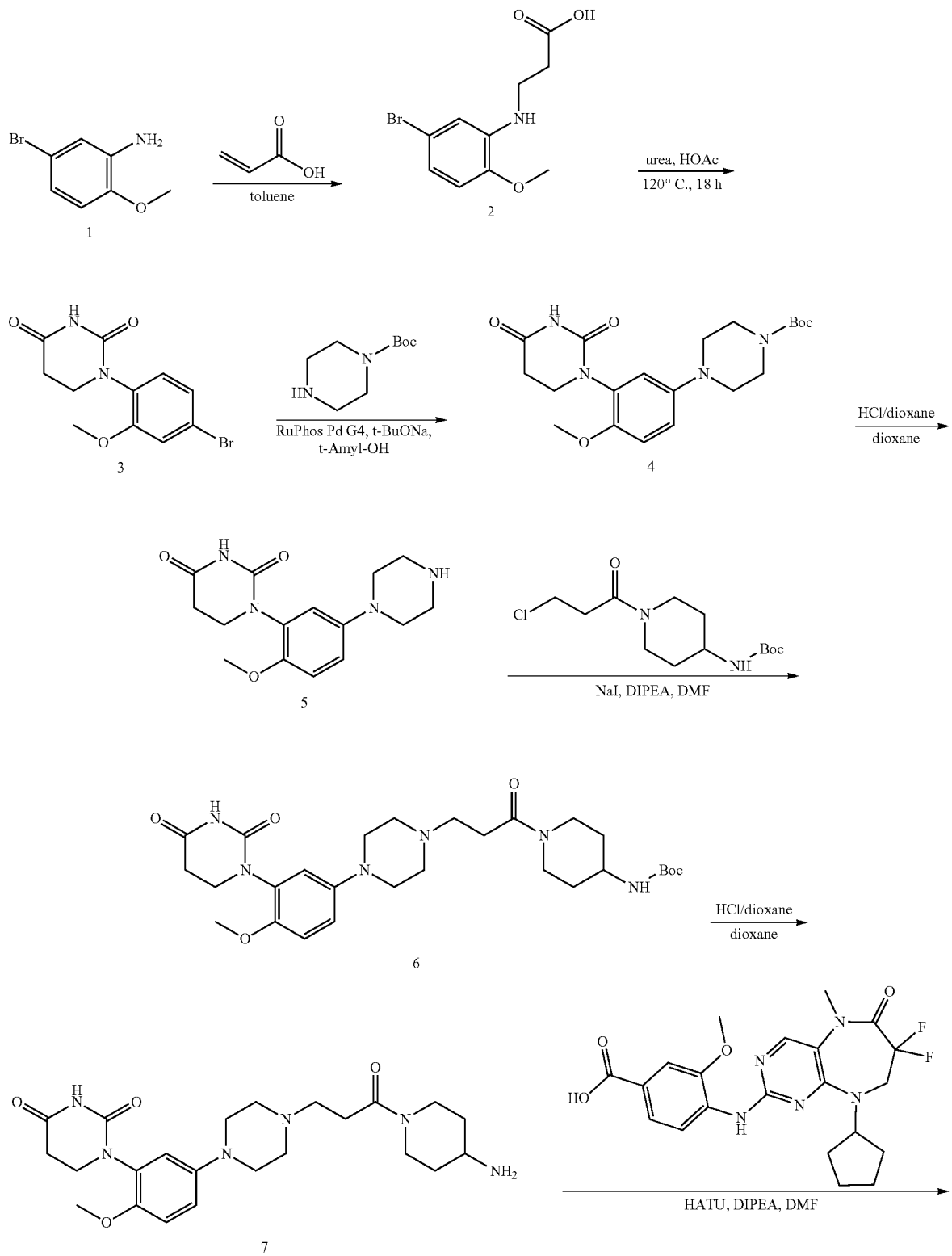

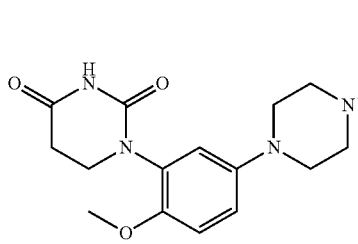
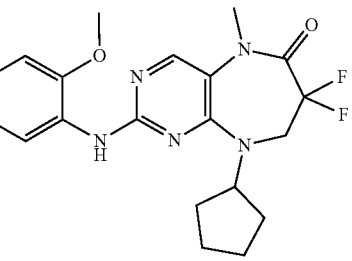

-continued

Compound 31

Step 1. Synthesis of 3-((5-bromo-2-methoxyphenyl)amino)propanoic acid (2)

A solution of 5-bromo-2-methoxy-aniline (4 g, 19.80 mmol) and acrylic acid (2.14 g, 29.70 mmol) in toluene (50 mL) was stirred at 100° C. for 3 hrs. LCMS showed the desired mass. The reaction solution was concentrated to afford 3-((5-bromo-2-methoxyphenyl)amino)propanoic acid (5.4 g, crude) as black brown solid. The crude product was used for the next step directly. MS (M−H)$^{+}$=271.9

Step 2. Synthesis of 1-(5-bromo-2-methoxyphenyl) dihydropyrimidine-2,4(1H,3H)-dione (3)

A solution of 3-((5-bromo-2-methoxyphenyl)amino)propanoic acid (5.4 g, 19.70 mmol) in AcOH (50 mL) was stirred at 120° C. for 10 min. Then urea (5.92 g, 98.50 mmol) was added and the resulting mixture was stirred at 120° C. for 18 hrs. LCMS showed the starting material was consumed completely and the desired mass. The reaction mixture was poured into ice water (100 mL) and extracted with EtOAc (50 mL×4). The combined organic layers were washed with brine (50 mL), dried over Na$_2$SO$_4$ and concentrated to afford the crude product, which was purified by flash silica gel chromatography (40 g silica gel column, EtOAc/petroleum ether=5-100%, 100 mL/min) to afford 1-(5-bromo-2-methoxyphenyl)dihydropyrimidine-2,4(1H,3H)-dione (3.5 g, 11.23 mmol, 57.02% yield, 96% purity) as a gray solid. MS (M+H)$^{+}$=301.3

Step 3. Synthesis of tert-butyl 4-(3-(2,4-dioxotetrahydropyrimidin-1(2H)-yl)-4-methoxyphenyl) piperazine-1-carboxylate (4)

To a mixture of 1-(5-bromo-2-methoxyphenyl)dihydropyrimidine-2,4(1H,3H)-dione (600 mg, 2.01 mmol), tert-butyl piperazine-1-carboxylate (448.32 mg, 2.41 mmol) and t-BuONa (2 M, 2.01 mL) in 2-methyl-2-butanol (10 mL) was added RuPhos Pd G4 (85.29 mg, 100.29 μmol) at 25° C. The resulting mixture was purged and degassed with N$_2$ for 3 times, heated to 90° C. and stirred for 14 hrs (note: two batches). LCMS showed the starting material was consumed completely and the desired mass. The two batches of the reaction mixture were combined and filtered. The filtrate was concentrated to afford the crude product, which was purified by flash (10 g silica gel column, EtOAc/petroleum ether=10-50%, 60 mL/min) to afford tert-butyl 4-(3-(2,4-dioxotetrahydropyrimidin-1(2H)-yl)-4-methoxyphenyl)piperazine-1-carboxylate (160 mg, 300.65 μmol, 7.49% yield, 76% purity) as a yellow solid. MS (M+H)$^{+}$=405.2

Step 4. Synthesis of 1-(2-methoxy-5-(piperazin-1-yl)phenyl)dihydropyrimidine-2,4(1H,3H)-dione (5)

A solution of tert-butyl 4-(3-(2,4-dioxotetrahydropyrimidin-1(2H)-yl)-4-methoxyphenyl) piperazine-1-carboxylate (160 mg, 395.59 μmol) and HCl/dioxane (4 M, 3 mL) in dioxane (1 mL) was stirred at 25° C. for 1 h. LCMS showed the starting material was consumed completely and the desired mass. The reaction mixture was concentrated to afford 1-(2-methoxy-5-(piperazin-1-yl)phenyl)dihydropyrimidine-2,4(1H,3H)-dione (130 mg, crude, HCl) as a yellow solid. The crude product was used for the next step directly. MS (M+H)$^{+}$=305.0

Step 5. Synthesis of tert-butyl (1-(3-(4-(3-(2,4-dioxotetrahydropyrimidin-1(2H)-yl)-4-methoxyphenyl)piperazin-1-yl)propanoyl)piperidin-4-yl)carbamate (6)

To a solution of 1-(2-methoxy-5-(piperazin-1-yl)phenyl) dihydropyrimidine-2,4(1H,3H)-dione (130 mg, 381.45 μmol, HCl) and tert-butyl N-[1-(3-chloropropanoyl)-4-piperidyl]carbamate (133.10 mg, 457.74 μmol) in DMF (3 mL) were added DIPEA (147.90 mg, 1.14 mmol) and NaI (5.72 mg, 38.15 μmol) at 25° C. The resulting mixture was stirred at 70° C. for 12 hrs. LCMS showed the starting material was consumed completely and the desired mass. The reaction mixture was poured into brine (30 mL) and extracted with EtOAc (10 mL×4). The combined organic layers were washed with brine (10 mL×2), dried over Na$_2$SO$_4$ and concentrated to afford the crude product, which was purified by flash silica gel chromatography (4 g silica gel column, EtOAc/petroleum ether=20-100% and then methanol/ethyl aceate=10%, 40 mL/min) to afford tert-butyl (1-(3-(4-(3-(2,4-dioxotetrahydropyrimidin-1(2H)-yl)-4-methoxyphenyl)piperazin-1-yl)propanoyl)piperidin-4-yl)carbamate (50 mg, 89.50 μmol, 23.46% yield) as a yellow solid.
MS (M+H)$^{+}$=559.3

Step 6. Synthesis of 1-(5-(4-(3-(4-aminopiperidin-1-yl)-3-oxopropyl)piperazin-1-yl)-2-methoxyphenyl) dihydropyrimidine-2,4(1H,3H)-dione (7)

A solution of tert-butyl (1-(3-(4-(3-(2,4-dioxotetrahydropyrimidin-1(2H)-yl)-4-methoxyphenyl)piperazin-1-yl)propanoyl)piperidin-4-yl)carbamate (50 mg, 89.50 μmol) and HCl/dioxane (4 M, 2 mL) in dioxane (2 mL) was stirred at 25° C. for 1 h. LCMS showed trace of the starting material remained and the desired mass. The reaction mixture was stirred at 25° C. for another 1 h. The reaction mixture was concentrated to afford 1-(5-(4-(3-(4-aminopiperidin-1-yl)-3-oxopropyl)piperazin-1-yl)-2-methoxyphenyl)dihydropyrimidine-2,4(1H,3H)-dione (45 mg, crude, HCl) as a brown solid. The crude product was used for the next step directly. MS (M+H)⁺=459.3

Step 7. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(3-(4-(3-(2,4-dioxotetrahydropyrimidin-1(2H)-yl)-4-methoxyphenyl)piperazin-1-yl)propanoyl)piperidin-4-yl)-3-methoxybenzamide (Compound 31)

To a mixture of 4-((9-cyclopentyl-7,7-difluoro-5-methyl-6-oxo-6,7,8,9-tetrahydro-5H-pyrimido[4,5-b][1,4]diazepin-2-yl)amino)-3-methoxybenzoic acid (39.77 mg, 88.89 μmol), DIPEA (52.22 mg, 404.03 μmol) and HATU (39.94 mg, 105.05 μmol) in DMF (2 mL) was added 1-(5-(4-(3-(4-aminopiperidin-1-yl)-3-oxopropyl)piperazin-1-yl)-2-methoxyphenyl)dihydropyrimidine-2,4(1H,3H)-dione (40 mg, 80.81 μmol, HCl) at 25° C. The resulting mixture was stirred at 25° C. for 1 h. LCMS showed the reaction was complete. The reaction mixture was poured into brine (30 mL) and extracted with EtOAc (10 mL×4). The combined organic layers were washed with brine (10 mL×2), dried over Na₂SO₄ and concentrated to give the crude product. The crude product was purified by flash silica gel chromatography (4 g silica gel column, EtOAc/petroleum ether=20-100% and then methanol/EtOAc=10-30%, 40 mL/min) to afford the product (50 mg). The crude product was further purified by prep-HPLC (column: Waters Xbridge 150*25 mm*5 μm; mobile phase: [water (NH₄HCO₃)—ACN]; B %: 36%-66%, 10 min) and lyophilized to afford 4-((9-cyclopentyl-7,7-difluoro-5-methyl-6-oxo-6,7,8,9-tetrahydro-5H-pyrimido[4,5-b][1,4]diazepin-2-yl)amino)-N-(1-(3-(4-(3-(2,4-dioxotetrahydropyrimidin-1(2H)-yl)-4-methoxyphenyl)piperazin-1-yl)propanoyl)piperidin-4-yl)-3-methoxybenzamide (10.8 mg, 11.34 μmol, 14.03% yield, 93.2% purity) as white solid. MS (M+H)⁺=888.6

¹H NMR (400 MHz, DMSO-d₆) δ=10.24 (s, 1H), 8.27-8.25 (m, 2H), 8.14 (d, J=8.0 Hz, 1H), 7.95 (s, 1H), 7.48-7.46 (m, 2H), 6.95 (d, J=8.0 Hz, 1H), 6.87-6.84 (m, 2H), 4.79-4.70 (m, 1H), 4.41-4.35 (m, 1H), 4.06-3.99 (m, 4H), 3.92 (s, 3H), 3.70 (s, 3H), 3.54 (t, J=8.0 Hz, 2H), 3.31 (s, 3H), 3.13-3.08 (m, 1H), 3.04-2.99 (m, 4H), 2.68-2.62 (m, 3H), 2.59-2.53 (m, 8H), 1.97-1.83 (m, 4H), 1.73-1.66 (m, 2H), 1.61-1.53 (m, 4H), 1.48-1.37 (m, 2H).

Example 32. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(3-(4-(4-(2,4-dioxotetrahydropyrimidin-1(2H)-yl)phenyl)piperazin-1-yl)propanoyl)piperidin-4-yl)-3-methoxybenzamide (Compound 32)

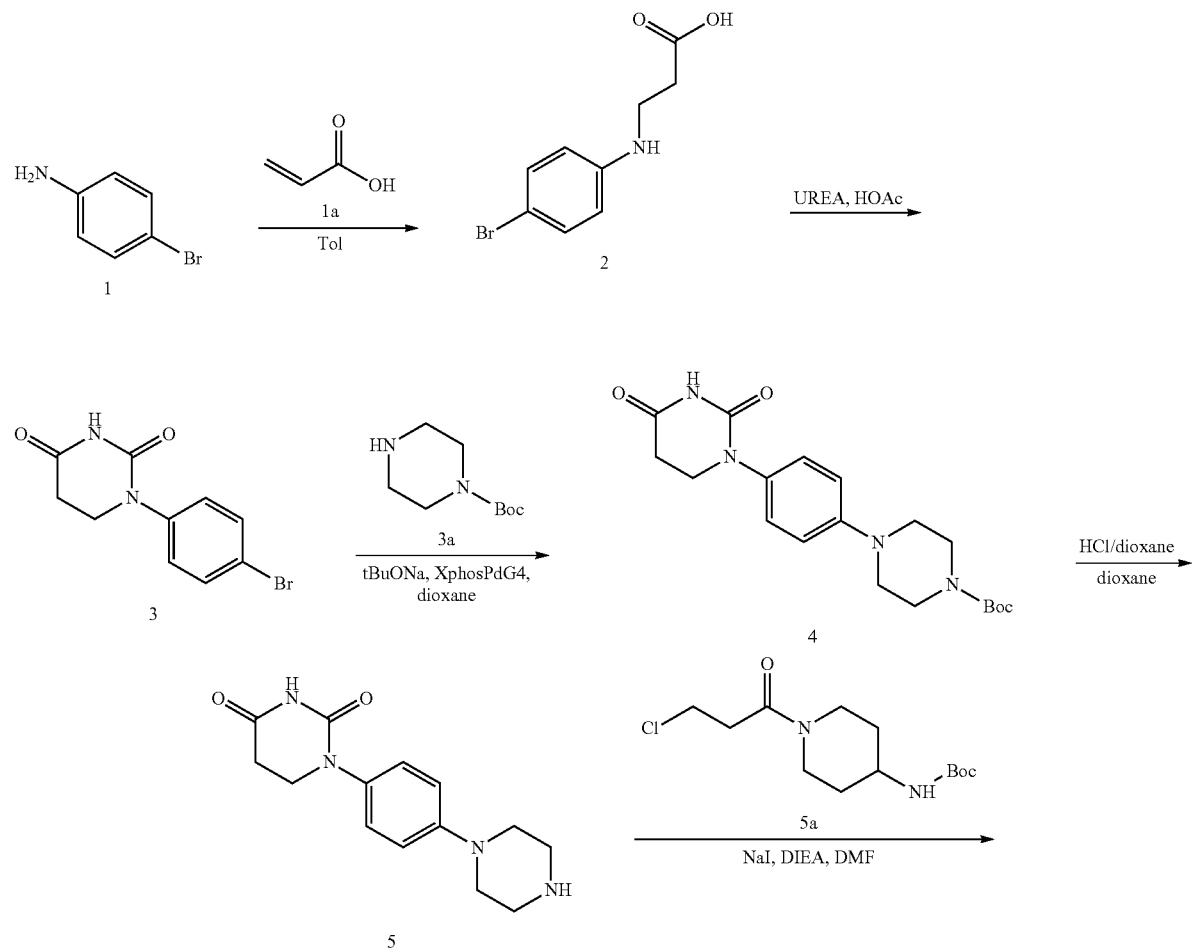

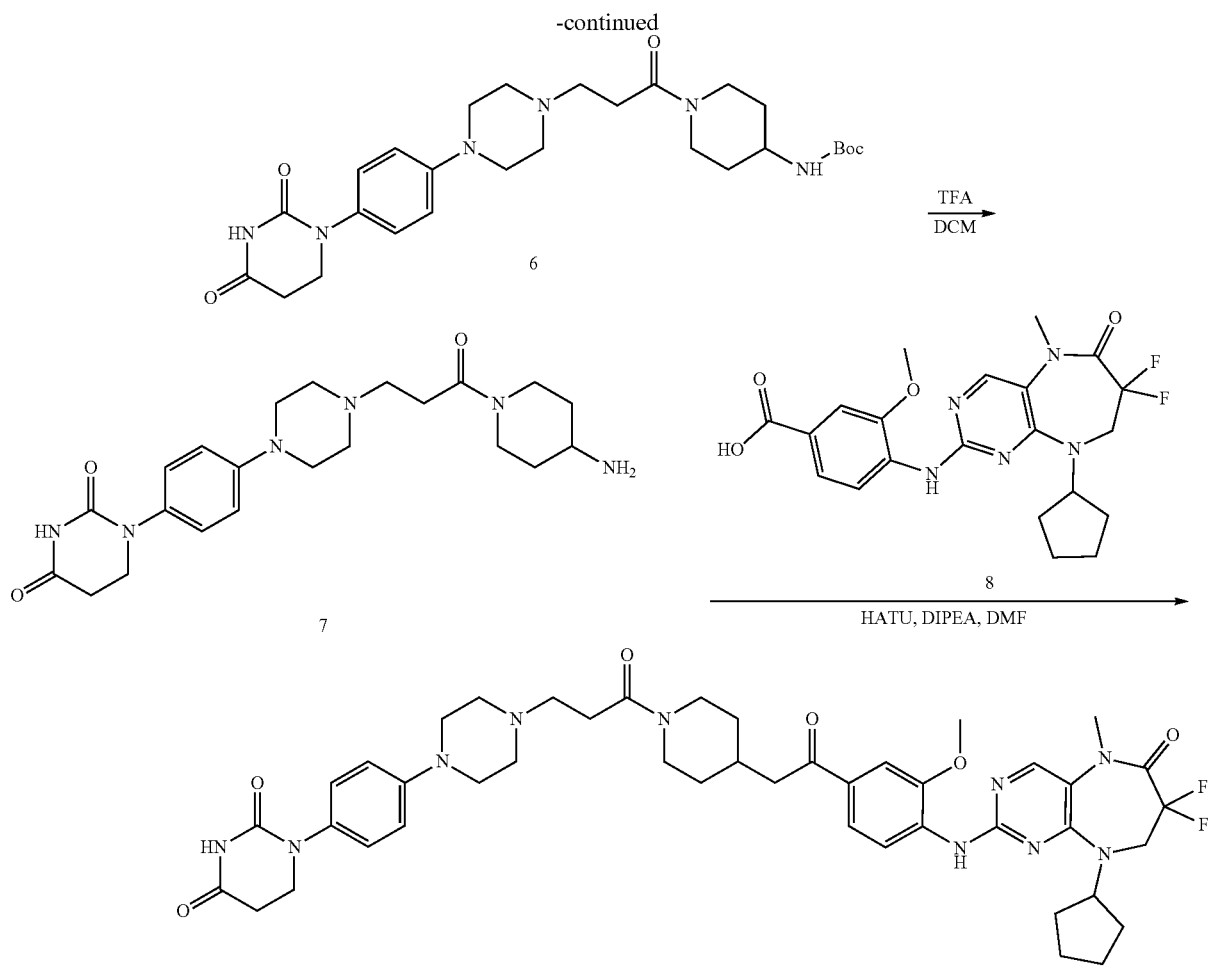

Compound 32

Step 1. Synthesis of 3-((4-bromophenyl)amino)propanoic acid (2)

A mixture of 4-bromoaniline (2 g, 11.63 mmol) and acrylic acid (1.26 g, 17.44 mmol, 1.20 mL) in toluene (30 mL) was stirred at 100° C. for 12 hr. LCMS showed the starting material was consumed completely, and a peak (60%) with desired mass. The reaction mixture was concentrated under reduced pressure. The crude product was dissolved in Petroleum ether:EtOAc=10:1 (20 mL) and stirred for 20 min, filtered. The filter cake was collected and dried to afford 3-((4-bromophenyl)amino)propanoic acid (3 g, crude) as brown solid. MS (M+H)$^+$=244.0

Step 2. Synthesis of 1-(4-bromophenyl)dihydropyrimidine-2,4(1H,3H)-dione (3)

To a solution of 3-((4-bromophenyl)amino)propanoic acid (3 g, 5.35 mmol) in AcOH (20 mL) was added UREA (3.22 g, 53.55 mmol, 2.87 mL), the mixture was stirred at 120° C. for 12 hr. LCMS showed the starting material was consumed completely and a main peak with desired mass. The reaction mixture was concentrated under reduced pressure. The crude product was dissolved in EtOAc (20 mL) and stirred for 20 min, filtered. The filter cake was collected and dried to afford 1-(4-bromophenyl)dihydropyrimidine-2,4(1H,3H)-dione (1.6 g, crude) as a gray solid, MS (M+H)$^+$= 269

Step 3. Synthesis of tert-butyl 4-(4-(2,4-dioxotetrahydropyrimidin-1(2H)-yl)phenyl)piperazine-1-carboxylate (4)

To a solution of 1-(4-bromophenyl)dihydropyrimidine-2,4(1H,3H)-dione (1.3 g, 4.83 mmol) in dioxane (100 mL) were added tBuONa (2 M, 7.25 mL) and tert-butyl piperazine-1-carboxylate (1.08 g, 4.83 mmol), then XphosPdG$_4$ (415.70 mg, 483.10 μmol) was added at 25° C. The mixture was stirred under N$_2$ at 90° C. for 12 h. LCMS showed the 1-(4-bromophenyl)dihydropyrimidine-2,4(1H,3H)-dione was consumed completely and a peak (53%) with desired mass. The mixture was diluted with EtOAc (50 mL) and H$_2$O (100 mL), filtered. The filtrate was extracted with EtOAc (40 mL×3). The combined organic layers were dried over Na$_2$SO$_4$. filtered. The filtrate was concentrated. The crude product was triturated with Petroleum ether: EtOAc=1:1 (60 mL) and stirred for 0.5 h. Then the mixture was filtered. The filter cake was collected and dried to afford tert-butyl 4-(4-(2,4-dioxotetrahydropyrimidin-1(2H)-yl) phenyl)piperazine-1-carboxylate (1.5 g, crude) as gray solid. MS (M+H)$^+$=375.1

Step 4. Synthesis of 1-(4-(piperazin-1-yl)phenyl) dihydropyrimidine-2,4(1H,3H)-dione (5)

To a solution of tert-butyl 4-(4-(2,4-dioxotetrahydropyrimidin-1(2H)-yl)phenyl)piperazine-1-carboxylate (0.5 g, 1.34 mmol) in dioxane (2 mL) was added HCl/dioxane (4 M, 15 mL) at 25° C. The resulting mixture was stirred at 25° C. for 0.5 hr. LCMS showed the starting material was consumed completely and a main peak with desired mass. The mixture solution was concentrated under reduced pressure, to afford 1-(4-(piperazin-1-yl)phenyl)dihydropyrimidine-2,4(1H,3H)-dione (420 mg, crude, HCl salt) as brown oil. MS (M+H)$^+$=275.1

Step 5. Synthesis of tert-butyl (1-(3-(4-(4-(2,4-dioxotetrahydropyrimidin-1(2H)-yl)phenyl)piperazin-1-yl)propanoyl)piperidin-4-yl)carbamate (6)

To a solution of tert-butyl (1-(3-chloropropanoyl)piperidin-4-yl)carbamate (785.96 mg, 2.70 mmol) and 1-(4-(piperazin-1-yl)phenyl)dihydropyrimidine-2,4(1H,3H)-dione (420 mg, 1.35 mmol, HCl salt) in DMF (3 mL) were added NaI (20.26 mg, 135.14 μmol) and DIPEA (523.98 mg, 4.05 mmol, 706.18 μL) at 25° C., the mixture was stirred at 80° C. for 16 hr. LCMS showed the 1-(4-(piperazin-1-yl)phenyl) dihydropyrimidine-2,4(1H,3H)-dione was consumed completely, and a peak (30%) with desired mass. The mixture was diluted with DCM (30 mL) and concentrated. The residue was purified by flash silica gel chromatography (4 g SepaFlash Silica Flash Column, Eluent of 0~100% EtOAc/Petroleum ether gradient @ 70 mL/min; Eluent of 0~50% Methanol/EtOAc @ 70 mL/min), to afford tert-butyl (1-(3-(4-(4-(2,4-dioxotetrahydropyrimidin-1(2H)-yl)phenyl)piperazin-1-yl)propanoyl)piperidin-4-yl)carbamate (0.5 g, crude) as brown solid.
MS (M+H)$^+$=529.3

Step 6. Synthesis of 1-(4-(4-(3-(4-aminopiperidin-1-yl)-3-oxopropyl)piperazin-1-yl)phenyl)dihydropyrimidine-2,4(1H,3H)-dione (7)

To a solution of tert-butyl (1-(3-(4-(4-(2,4-dioxotetrahydropyrimidin-1(2H)-yl)phenyl)piperazin-1-yl)propanoyl)piperidin-4-yl)carbamate (180 mg, 340.50 μmol) in DCM (5 mL) was added TFA (1.54 g, 13.51 mmol, 1 mL) at 25° C. The resulting mixture was stirred at 25° C. for 0.5 hr. LCMS showed the starting material was consumed completely and a main peak with desired mass. The reaction mixture was concentrated under reduced pressure to afford 1-(4-(4-(3-(4-aminopiperidin-1-yl)-3-oxopropyl)piperazin-1-yl)phenyl) dihydropyrimidine-2,4(1H,3H)-dione (180 mg, crude, TFA salt) as brown oil. MS (M+H)$^+$=429.2

Step 7. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(3-(4-(4-(2,4-dioxotetrahydropyrimidin-1(2H)-yl)phenyl)piperazin-1-yl)propanoyl)piperidin-4-yl)-3-methoxybenzamide (Compound 32)

To a solution of 4-((9-cyclopentyl-7,7-difluoro-5-methyl-6-oxo-6,7,8,9-tetrahydro-5H-pyrimido[4,5-b][1,4]diazepin-2-yl)amino)-3-methoxybenzoic acid (70 mg, 156.45 μmol) in DMF (2 mL) were added HATU (89.23 mg, 234.68 μmol) and DIPEA (60.66 mg, 469.35 μmol, 81.75 μL), after stirring for 10 min, then 1-(4-(4-(3-(4-aminopiperidin-1-yl)-3-oxopropyl)piperazin-1-yl)phenyl)dihydropyrimidine-2,4(1H, 3H)-dione (118.83 mg, 219.03 μmol, TFA salt) was added and the resulting mixture was stirred at 25° C. for 2 h. LCMS showed a peak (48%) with desired mass. The reaction mixture was concentrated under reduced pressure. The residue was purified by flash silica gel chromatography (4 g SepaFlash Silica Flash Column, Eluent of 0~100% EtOAc/Petroleum ether gradient @ 60 mL/min; Eluent of 0~50% Methanol/EtOAc @ 60 mL/min) and re-purified by prep-TLC (Dichloromethane:Methanol=10:1; Rf=0.5) and prep-HPLC (column: Waters Xbridge 150×25 mm×5 μm; mobile phase: [water (NH$_4$HCO$_3$)—ACN]; B %: 26%-59%, 8 min), the eluent was lyophilized to afford 4-((9-cyclopentyl-7,7-difluoro-5-methyl-6-oxo-6,7,8,9-tetrahydro-5H-pyrimido[4,5-b][1,4]diazepin-2-yl)amino)-N-(1-(3-(4-(4-(2,4-dioxotetrahydropyrimidin-1(2H)-yl)phenyl)piperazin-1-yl) propanoyl)piperidin-4-yl)-3-methoxybenzamide (23.6 mg, 26.96 μmol, 17.23% yield, 98% purity) as white solid.
MS (M+H)$^+$=858.5
$^1$H NMR (400 MHz, DMSO-d$_6$) δ=10.25 (s, 1H), 8.30-8.24 (m, 2H), 8.15 (d, J=7.8 Hz, 1H), 7.96 (s, 1H), 7.53-7.44 (m, 2H), 7.14 (d, J=9.0 Hz, 2H), 6.93 (d, J=9.1 Hz, 2H), 4.83-4.70 (m, 1H), 4.39 (br d, J=12.5 Hz, 1H), 4.04 (br t, J=14.0 Hz, 3H), 3.93 (s, 4H), 3.69 (t, J=6.7 Hz, 2H), 3.32-3.28 (m, 3H), 3.19-3.06 (m, 5H), 2.72-2.64 (m, 3H), 2.63-2.53 (m, 8H), 1.98-1.78 (m, 4H), 1.73-1.36 (m, 8H).

Example 33. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(7-((1-(4-(2,4-dioxotetrahydropyrimidin-1(2H)-yl)phenyl) piperidin-4-yl)methyl)-7-azaspiro[3.5]nonan-2-yl)-3-methoxybenzamide (Compound 33)

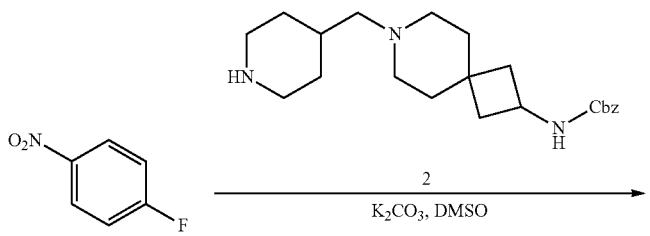

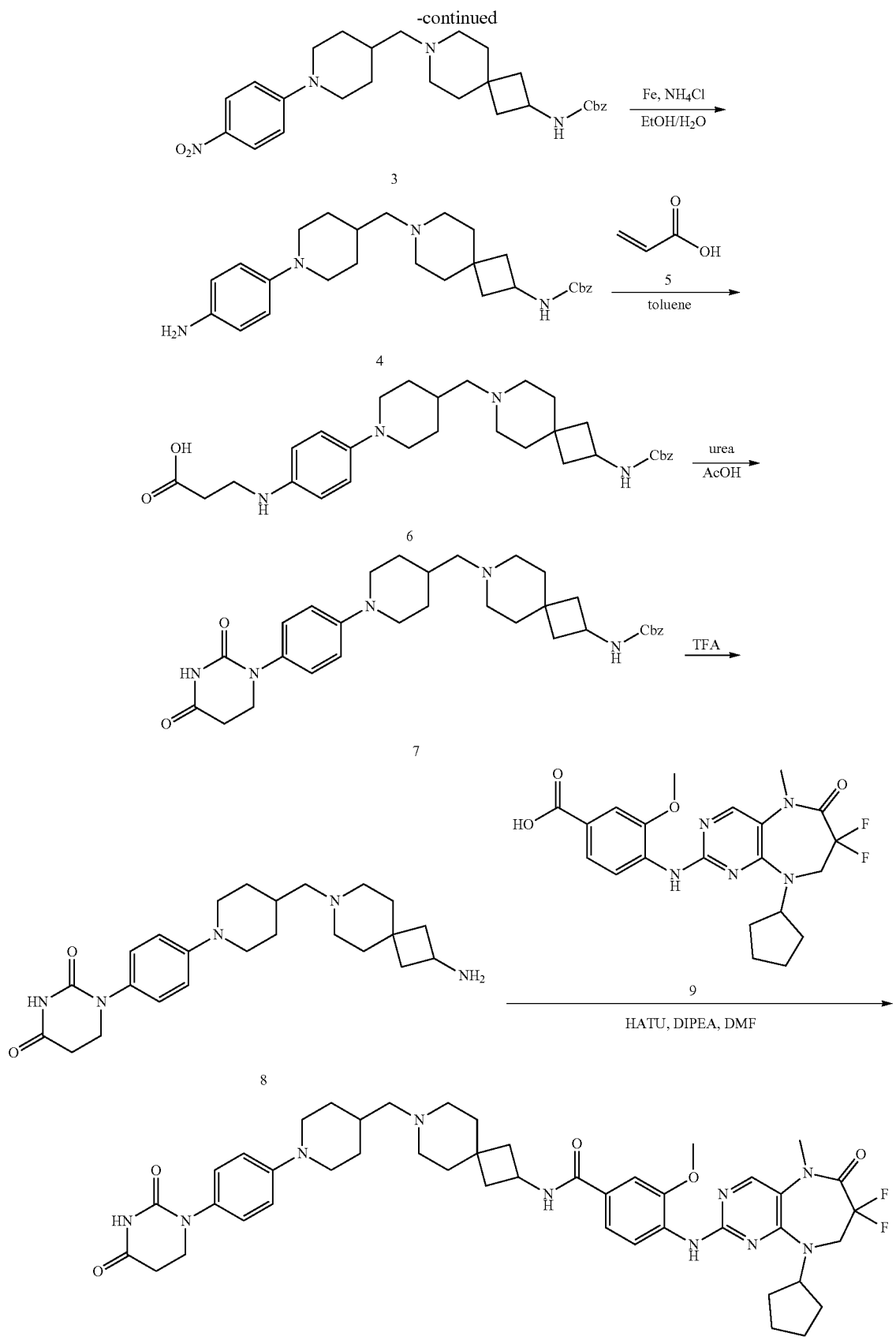
Compound 33

Step 1. Synthesis of benzyl (7-((1-(4-nitrophenyl) piperidin-4-yl)methyl)-7-azaspiro[3.5]nonan-2-yl) carbamate (3)

To a solution of 1-fluoro-4-nitro-benzene (0.2 g, 1.42 mmol, 150.38 µL) in DMSO (4 mL) were added $K_2CO_3$ (587.70 mg, 4.25 mmol) and benzyl (7-(piperidin-4-ylmethyl)-7-azaspiro[3.5]nonan-2-yl)carbamate (636.11 mg, 1.56 mmol, HCl salt) at 20° C. and the resulting mixture was stirred at 40° C. for 1 h. LCMS showed benzyl (7-(piperidin-4-ylmethyl)-7-azaspiro[3.5]nonan-2-yl)carbamate was consumed completely and a peak (50%) with desired mass. The reaction mixture was diluted with $H_2O$ (15 mL) and extracted with EtOAc (15 mL×3). The organic layer was washed with brine (15 mL×3), dried over $Na_2SO_4$, filtered and concentrated. The residue was purified by flash silica gel chromatography (10 g SepaFlash Silica Flash Column, Eluent of 0~100% EtOAc/Petroleum ether gradient @ 100 mL/min) to afford benzyl (7-((1-(4-nitrophenyl)piperidin-4-yl)methyl)-7-azaspiro[3.5]nonan-2-yl)carbamate (431 mg, 874.93 µmol, 61.73% yield) as a yellow solid. MS $(M+H)^+=493.3$

Step 2. Synthesis of benzyl (7-((1-(4-aminophenyl) piperidin-4-yl)methyl)-7-azaspiro[3.5]nonan-2-yl) carbamate (4)

To a solution of benzyl (7-((1-(4-nitrophenyl)piperidin-4-yl)methyl)-7-azaspiro[3.5]nonan-2-yl)carbamate (431 mg, 874.93 µmol) in EtOH (10 mL) and $H_2O$ (2 mL) were added Fe (244.30 mg, 4.37 mmol) and $NH_4Cl$ (234.01 mg, 4.37 mmol) at 20° C. and the resulting mixture was stirred at 80° C. for 6 h. LCMS showed starting material was consumed completely and a main peak (91%) with desired mass. The reaction mixture was adjusted the pH=10 by using saturated $NaHCO_3$ (15 mL), then extracted with EtOAc (15 mL×3). The combined organic layer was dried over $Na_2SO_4$, filtered and concentrated to afford benzyl (7-((1-(4-aminophenyl)piperidin-4-yl)methyl)-7-azaspiro[3.5]nonan-2-yl)carbamate (485 mg, crude) as a purple oil. MS $(M+H)^+=463.4$

Step 3. Synthesis of 3-((4-(4-((2-(((benzyloxy)carbonyl)amino)-7-azaspiro[3.5]nonan-7-yl)methyl) piperidin-1-yl)phenyl)amino)propanoic acid (6)

To a solution of benzyl (7-((1-(4-aminophenyl)piperidin-4-yl)methyl)-7-azaspiro[3.5]nonan-2-yl)carbamate (485 mg, 1.05 mmol) in toluene (6 mL) was added acrylic acid (75.55 mg, 1.05 mmol, 71.95 µL) at 20° C. and the resulting mixture was stirred at 100° C. for 15 h. LCMS showed starting material remained and a peak with desired mass. Additional acrylic acid (37.77 mg, 524.18 µmol, 35.98 µL) was added at 20° C. and the reaction mixture was stirred at 100° C. for another 12 h. LCMS showed a little starting material remained and a peak (43%) with desired mass. The reaction mixture was concentrated in vacuum to afford 3-((4-(4-((2-(((benzyloxy)carbonyl)amino)-7-azaspiro[3.5] nonan-7-yl)methyl)piperidin-1-yl)phenyl)amino)propanoic acid (560 mg, crude) as a black brown solid. MS $(M+H)^+=535.3$

Step 4. Synthesis of benzyl (7-((1-(4-(2,4-dioxotetrahydropyrimidin-1(2H)-yl)phenyl)piperidin-4-yl) methyl)-7-azaspiro[3.5]nonan-2-yl)carbamate (7)

To a solution of 3-((4-(4-((2-(((benzyloxy)carbonyl) amino)-7-azaspiro[3.5]nonan-7-yl)methyl)piperidin-1-yl) phenyl)amino)propanoic acid (560 mg, 1.05 mmol) in AcOH (10 mL) was added urea (628.98 mg, 10.47 mmol, 561.59 µL) at 20° C. and the resulting mixture was stirred at 120° C. for 12 h. LCMS showed starting material was consumed completely and a peak (37%) with desired mass. The reaction mixture was diluted with $H_2O$ (20 mL) and extracted with EtOAc (20 mL×3). LCMS showed desired product was in aqueous phase. The aqueous phase was concentrated in vacuum. The crude product was purified by flash silica gel chromatography (10 g SepaFlash Silica Flash Column, Eluent of 0~100% EtOAc/Petroleum ether to 0~10% Dichloromethane/Methanol gradient @ 100 mL/min) to afford benzyl (7-((1-(4-(2,4-dioxotetrahydropyrimidin-1(2H)-yl)phenyl)piperidin-4-yl)methyl)-7-azaspiro [3.5]nonan-2-yl)carbamate (156 mg, 262.00 µmol, 25.02% yield, 94% purity) as a yellow solid. MS $(M+H)^+=560.3$

Step 5. Synthesis of 1-(4-(4-((2-amino-7-azaspiro [3.5]nonan-7-yl)methyl)piperidin-1-yl)phenyl)dihydropyrimidine-2,4(1H,3H)-dione (8)

A mixture of benzyl (7-((1-(4-(2,4-dioxotetrahydropyrimidin-1(2H)-yl)phenyl)piperidin-4-yl)methyl)-7-azaspiro [3.5]nonan-2-yl)carbamate (56 mg, 100.05 µmol) in TFA (2 mL) at 20° C. and the resulting mixture was stirred at 40° C. for 4 h. LCMS showed a little starting material remained and a peak with desired mass. The reaction mixture was concentrated in vacuum to afford 1-(4-(4-((2-amino-7-azaspiro [3.5]nonan-7-yl)methyl)piperidin-1-yl)phenyl)dihydropyrimidine-2,4(1H,3H)-dione (54 mg, crude, TFA salt) as a yellow oil. MS $(M+H)^+=426.4$

Step 6. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(7-((1-(4-(2,4-dioxotetrahydropyrimidin-1(2H)-yl)phenyl)piperidin-4-yl) methyl)-7-azaspiro[3.5]nonan-2-yl)-3-methoxybenzamide (Compound 33)

To a solution of 4-((9-cyclopentyl-7,7-difluoro-5-methyl-6-oxo-6,7,8,9-tetrahydro-5H-pyrimido[4,5-b][1,4]diazepin-2-yl)amino)-3-methoxybenzoic acid (40 mg, 89.40 µmol) in DMF (1 mL) were added HATU (37.39 mg, 98.34 µmol) and DIPEA (23.11 mg, 178.80 µmol, 31.14 µL). The mixture was stirred at 20° C. for 10 min and a solution of 1-(4-(4-((2-amino-7-azaspiro[3.5]nonan-7-yl)methyl)piperidin-1-yl) phenyl)dihydropyrimidine-2,4(1H,3H)-dione (53.06 mg, 98.34 µmol, TFA salt) in DMF (1 mL) with DIPEA (69.32 mg, 536.39 µmol, 93.43 µL) was added and the resulting mixture was stirred at 20° C. for 1 h. LCMS showed all starting material was consumed completely and a peak (33%) with desired mass. The reaction mixture was combined with another batch (60 mg scale) for work-up. The combined reaction mixture was diluted with $H_2O$ (12 mL) and extracted with EtOAc (12 mL×3). The combined organic layer was washed with brine (12 mL×3), dried over $Na_2SO_4$, filtered and concentrated in vacuum. The residue was purified by prep-TLC ($SiO_2$, Dichloromethane: Methanol=8:1) and re-purified by prep-HPLC (column: Phenomenex Synergi Polar-RP 100*25 mm*4 µm; mobile phase: [water (TFA)—ACN]; B %: 25%-45%, 7 min), the eluent was lyophilized to afford pure product B and impure product C. The impure product C was re-purified by prep-HPLC (column: Phenomenex Synergi Polar-RP 100*25 mm*4 µm; mobile phase: [water (TFA)—ACN]; B %: 26%-46%, 7 min), the eluent was lyophilized afford product D. The product B and product D was combined to lyophilize to afford 4-((9-cyclopentyl-7,7-difluoro-5-methyl-6-oxo-6,7,8,9-tetrahydro-5H-pyrimido[4,5-b][1,4]diazepin-2-yl)amino)-N-(7-((1-(4-(2,4-dioxotetrahydropyrimidin-1(2H)-yl)phenyl)piperidin-4-yl)methyl)-7-azaspiro[3.5]nonan-2-yl)-3-methoxybenzamide (16.9 mg, 15.14 µmol, 16.93% yield, 97% purity, 2TFA) as a white solid. MS (M+H)⁺=855.2

¹H NMR (400 MHz, CD₃CN) δ=9.34-9.23 (m, 1H), 8.22-8.10 (m, 2H), 7.98 (s, 1H), 7.48-7.40 (m, 2H), 7.29-7.20 (m, 3H), 7.11 (d, J=8.9 Hz, 2H), 4.95-4.83 (m, 1H), 4.57-4.44 (m, 1H), 4.01 (t, J=12.8 Hz, 2H), 3.95 (s, 3H), 3.75 (t, J=6.7 Hz, 2H), 3.70 (br d, J=12.0 Hz, 2H), 3.52-3.39 (m, 2H), 3.32 (s, 3H), 3.00-2.94 (m, 2H), 2.90 (dt, J=1.8, 12.2 Hz, 3H), 2.73-2.70 (m, 2H), 2.49-2.45 (m, 1H), 2.31-2.24 (m, 1H), 2.14-1.95 (m, 8H), 1.91-1.70 (m, 6H), 1.65-1.46 (m, 6H).

Example 34. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(7-((1-(3-(2,4-dioxotetrahydropyrimidin-1(2H)-yl)phenyl)piperidin-4-yl)methyl)-7-azaspiro[3.5]nonan-2-yl)-3-methoxybenzamide (Compound 34)

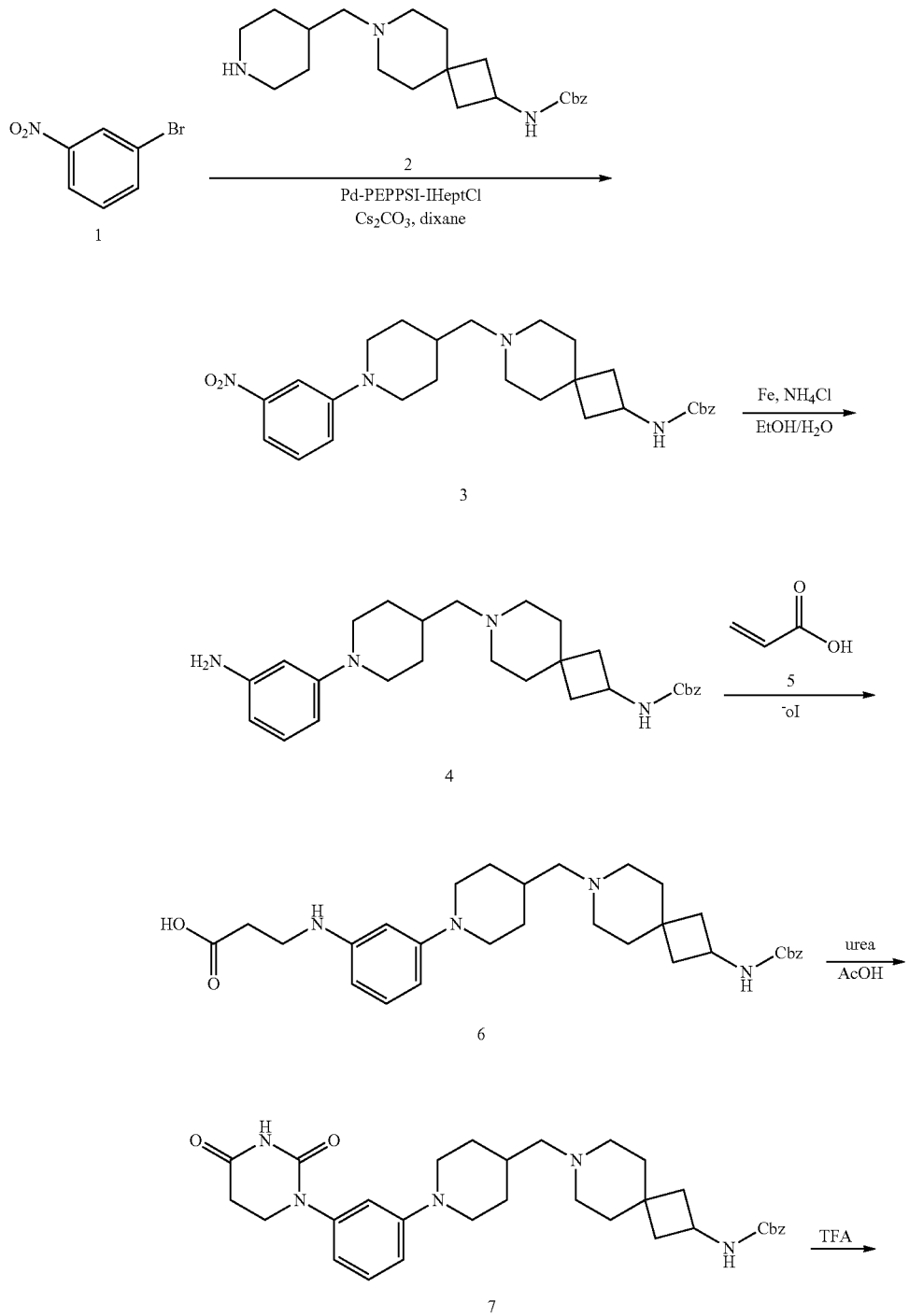

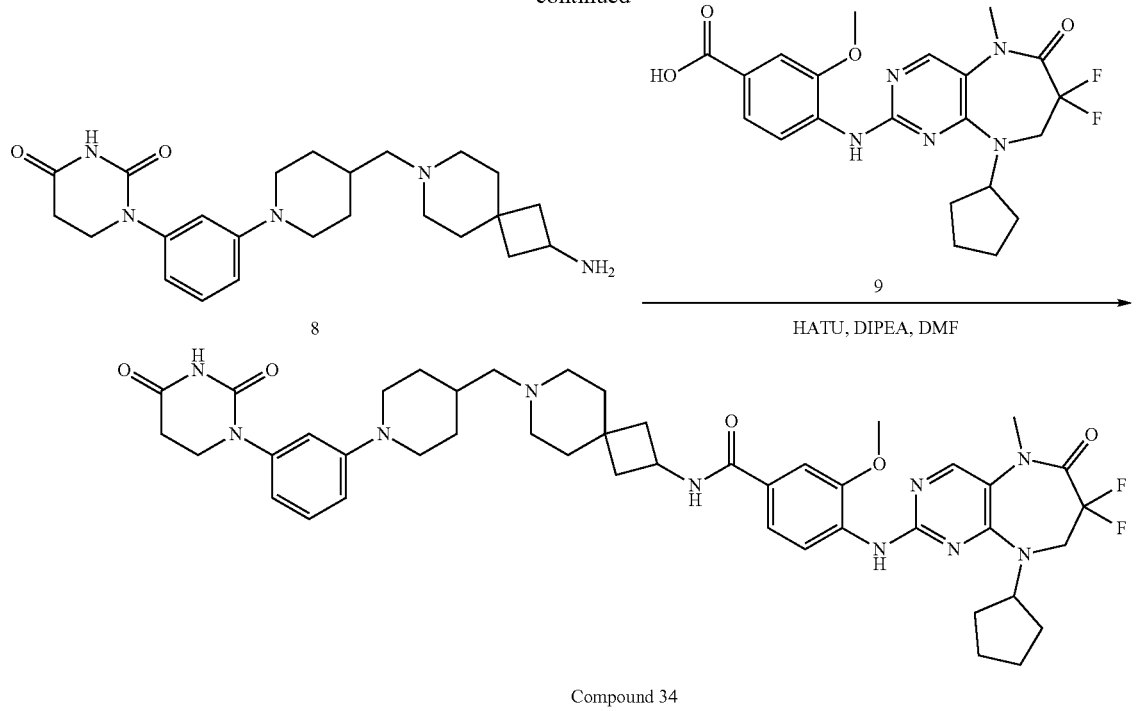

Compound 34

Step 1. Synthesis of benzyl (7-((1-(3-nitrophenyl)piperidin-4-yl)methyl)-7-azaspiro[3.5]nonan-2-yl)carbamate (3)

To a solution of 1-bromo-3-nitrobenzene (500 mg, 2.48 mmol) and benzyl (7-(piperidin-4-ylmethyl)-7-azaspiro[3.5]nonan-2-yl)carbamate (1.11 g, 2.72 mmol, HCl salt) in dioxane (10 mL) were added $Cs_2CO_3$ (2.42 g, 7.43 mmol) and Pd-PEPPSI-IHeptCl (24.08 mg, 24.75 μmol) at 20° C. under $N_2$ atmosphere and the resulting mixture was stirred at 100° C. for 12 h. LCMS showed starting material was consumed completely and a peak with desired mass. The reaction mixture was concentrated in vacuum. The residue was purified by flash silica gel chromatography (10 g SepaFlash Silica Flash Column, Eluent of 0~60% EtOAc/Petroleum ether gradient @ 100 mL/min) to afford benzyl (7-((1-(3-nitrophenyl)piperidin-4-yl)methyl)-7-azaspiro[3.5]nonan-2-yl)carbamate (1 g, 2.03 mmol, 82.01% yield) as a yellow oil. MS $(M+H)^+=493.2$

Step 2. Synthesis of benzyl (7-((1-(3-aminophenyl)piperidin-4-yl)methyl)-7-azaspiro[3.5]nonan-2-yl)carbamate (4)

To a solution of benzyl (7-((1-(3-nitrophenyl)piperidin-4-yl)methyl)-7-azaspiro[3.5]nonan-2-yl)carbamate (1 g, 2.03 mmol) in EtOH (20 mL) and $H_2O$ (4 mL) were added Fe (566.83 mg, 10.15 mmol) and $NH_4Cl$ (542.94 mg, 10.15 mmol) at 20° C. and the resulting mixture was stirred at 80° C. for 6 h. LCMS showed starting material was consumed completely and a peak (77%) with desired mass. The reaction mixture was adjusted the pH=10 by using saturated $NaHCO_3$ (15 mL), then extracted with EtOAc (15 mL×3). The combined organic layer was dried over $Na_2SO_4$, filtered and concentrated to afford benzyl (7-((1-(3-aminophenyl)piperidin-4-yl)methyl)-7-azaspiro[3.5]nonan-2-yl)carbamate (862 mg, crude) as a yellow oil. MS $(M+H)^+=463.4$

Step 3. Synthesis of 3-((3-(4-((2-(((benzyloxy)carbonyl)amino)-7-azaspiro[3.5]nonan-7-yl)methyl)piperidin-1-yl)phenyl)amino)propanoic acid (6)

To a solution of benzyl (7-((1-(3-aminophenyl)piperidin-4-yl)methyl)-7-azaspiro[3.5]nonan-2-yl)carbamate (862 mg, 1.86 mmol) in toluene (10 mL) was added acrylic acid (134.27 mg, 1.86 mmol, 127.88 μL) at 20° C. and the resulting mixture was stirred at 100° C. for 18 h. LCMS showed starting material was consumed completely and a peak (33%) with desired mass. The reaction mixture was concentrated in vacuum to afford 3-((3-(4-((2-(((benzyloxy)carbonyl)amino)-7-azaspiro[3.5]nonan-7-yl)methyl)piperidin-1-yl)phenyl)amino)propanoic acid (997 mg, crude) as a yellow oil. MS $(M+H)^+=535.4$

Step 4. Synthesis of benzyl (7-((1-(3-(2,4-dioxotetrahydropyrimidin-1(2H)-yl)phenyl)piperidin-4-yl)methyl)-7-azaspiro[3.5]nonan-2-yl)carbamate (7)

To a solution of 3-((3-(4-((2-(((benzyloxy)carbonyl)amino)-7-azaspiro[3.5]nonan-7-yl)methyl)piperidin-1-yl)phenyl)amino)propanoic acid (997 mg, 1.86 mmol) in AcOH (10 mL) was added urea (1.12 g, 18.65 mmol, 999.83 μL) at 20° C. and the resulting mixture was stirred at 120° C. for 12 h. LCMS showed starting material was consumed completely and a peak (21%) with desired mass. The reaction mixture was concentrated in vacuum. The residue was purified by flash silica gel chromatography (20 g SepaFlash Silica Flash Column, Eluent of 0~100% EtOAc/Petroleum ether to 0~10% Dichloromethane: Methanol gradient @ 100 mL/min) followed by prep-TLC ($SiO_2$, Dichloromethane: Methanol=10:1) to afford benzyl (7-((1-(3-(2,4-dioxotetrahydropyrimidin-1(2H)-yl)phenyl)piperidin-4-yl)methyl)-7-azaspiro[3.5]nonan-2-yl)carbamate (325 mg, 557.44 μmol, 29.90% yield, 96% purity) as a yellow solid. MS $(M+H)^+=560.3$ Step 5. Synthesis of 1-(3-(4-((2-amino-7-azaspiro[3.5]nonan-7-yl)methyl)piperidin-1-yl)phenyl)dihydropyrimidine-2,4(1H,3H)-dione (8)

A mixture of benzyl (7-((1-(3-(2,4-dioxotetrahydropyrimidin-1(2H)-yl)phenyl)piperidin-4-yl)methyl)-7-azaspiro[3.5]nonan-2-yl)carbamate (100 mg, 178.67 μmol) in TFA (4 mL) was stirred at 40° C. for 18 h. LCMS showed starting material was consumed completely and a peak with desired mass. The reaction mixture was concentrated in vacuum to afford 1-(3-(4-((2-amino-7-azaspiro[3.5]nonan-7-yl)methyl)piperidin-1-yl)phenyl)dihydropyrimidine-2,4(1H,3H)-dione (98 mg, crude, TFA salt) as a yellow oil. MS (M+H)$^+$=426.4

Step 6. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(7-((1-(3-(2,4-dioxotetrahydropyrimidin-1(2H)-yl)phenyl)piperidin-4-yl)methyl)-7-azaspiro[3.5]nonan-2-yl)-3-methoxybenzamide (Compound 34)

To a solution of 4-((9-cyclopentyl-7,7-difluoro-5-methyl-6-oxo-6,7,8,9-tetrahydro-5H-pyrimido[4,5-b][1,4]diazepin-2-yl)amino)-3-methoxybenzoic acid (60 mg, 134.10 μmol) in DMF (1 mL) were added HATU (56.09 mg, 147.51 μmol) and DIPEA (51.99 mg, 402.29 μmol, 70.07 μL). The mixture was stirred at 20° C. for 10 min and a solution of 1-(3-(4-((2-amino-7-azaspiro[3.5]nonan-7-yl)methyl)piperidin-1-yl)phenyl)dihydropyrimidine-2,4(1H,3H)-dione (94.07 mg, 174.33 μmol, TFA salt) in DMF (1 mL) with DIPEA (51.99 mg, 402.29 μmol, 70.07 μL) was added and the resulting mixture stirred at 20° C. for 1 h. LCMS showed starting material was consumed completely and a peak (64%) with desired mass. The reaction mixture was diluted with H$_2$O (12 mL) and extracted with EtOAc (12 mL×3). The organic layer was dried over Na$_2$SO$_4$, filtered and concentrated. The residue was purified by prep-HPLC (column: Phenomenex Synergi Polar-RP 100*25 mm*4 μm; mobile phase: [water (TFA)—ACN]; B %: 24%-44%, 7 min) and re-purified by prep-HPLC (column: Waters Xbridge 150*25 mm*5 μm; mobile phase: [water (NH$_4$HCO$_3$)—ACN]; B %: 52%-82%, 8 min) and the eluent was lyophilized to afford 4-((9-cyclopentyl-7,7-difluoro-5-methyl-6-oxo-6,7,8,9-tetrahydro-5H-pyrimido[4,5-b][1,4]diazepin-2-yl)amino)-N-(7-((1-(3-(2,4-dioxotetrahydropyrimidin-1(2H)-yl)phenyl)piperidin-4-yl)methyl)-7-azaspiro[3.5]nonan-2-yl)-3-methoxybenzamide (13 mg, 14.75 μmol, 11.00% yield, 97% purity) as a white solid. MS (M+H)$^+$=855.2

$^1$H NMR (400 MHz, DMSO-d$_6$) δ=10.29 (s, 1H), 8.43 (br d, J=7.3 Hz, 1H), 8.31-8.24 (m, 2H), 7.96 (s, 1H), 7.51-7.45 (m, 2H), 7.18 (t, J=8.1 Hz, 1H), 6.86 (s, 1H), 6.80 (br d, J=8.3 Hz, 1H), 6.67 (d, J=7.9 Hz, 1H), 4.76 (quin, J=8.0 Hz, 1H), 4.45-4.33 (m, 1H), 4.04 (br t, J=14.1 Hz, 2H), 3.94 (s, 3H), 3.74 (t, J=6.7 Hz, 2H), 3.66 (br d, J=12.1 Hz, 2H), 3.51-3.32 (m, 5H), 2.71-2.63 (m, 4H), 2.31-2.22 (m, 2H), 2.18-2.09 (m, 4H), 1.98-1.89 (m, 2H), 1.85-1.66 (m, 7H), 1.64-1.53 (m, 8H), 1.24-1.12 (m, 2H).

Example 35. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(4-((6-(2,6-dioxopiperidin-3-yl)pyridin-2-yl)oxy)butanoyl)piperidin-4-yl)-3-methoxybenzamide (Compound 35)

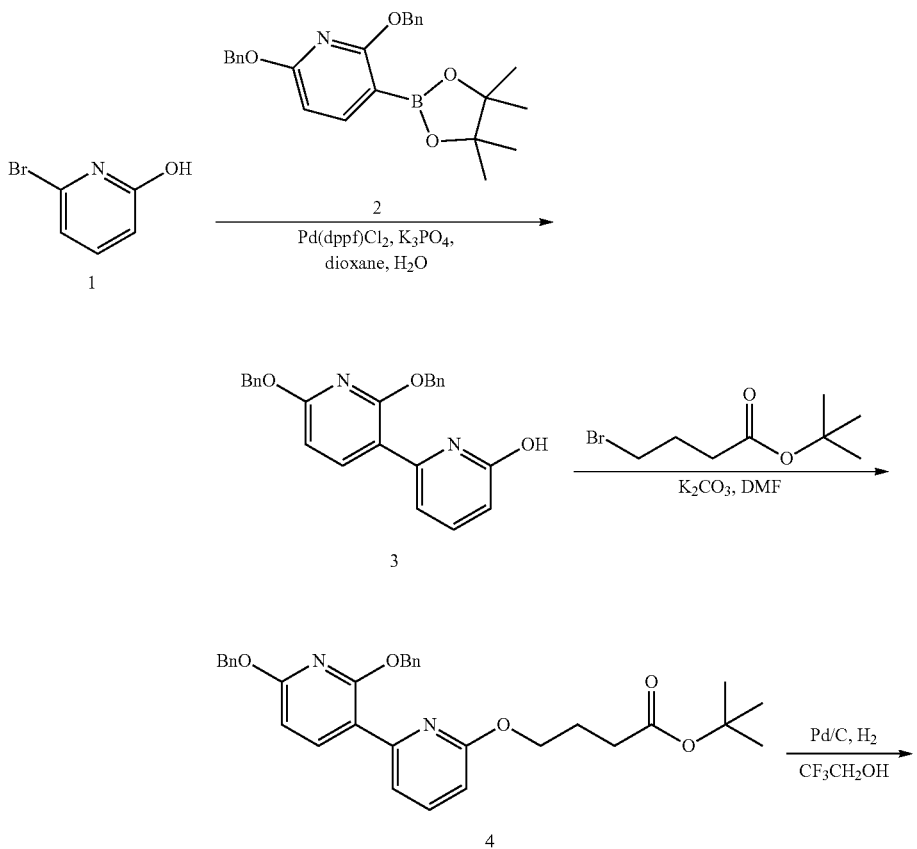

-continued

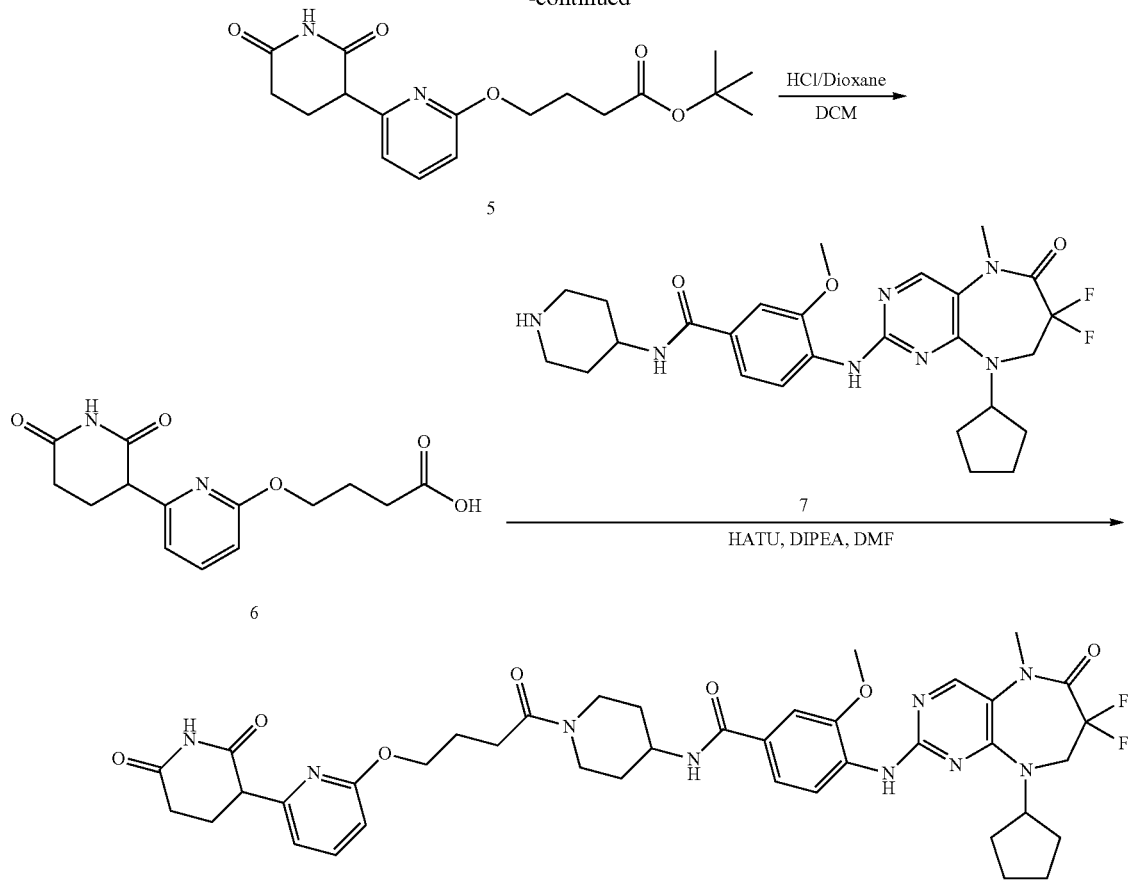

Compound 35

Step 1. Synthesis of 2',6'-bis(benzyloxy)-[2,3'-bipyridin]-6-ol (3)

To a solution of 6-bromopyridin-2-ol (400 mg, 2.30 mmol) and 2,6-bis(benzyloxy)-3-(4,4,5,5-tetramethyl-1,3,2-dioxaborolan-2-yl)pyridine (959.35 mg, 2.30 mmol) in dioxane (8 mL) and $H_2O$ (0.8 mL) were added Pd(dppf)Cl$_2$ (168.21 mg, 229.89 μmol) and $K_3PO_4$ (1.46 g, 6.90 mmol). The mixture was stirred at 90° C. for 2 h under $N_2$ atmosphere. LCMS showed a peak (40%) with desired mass. The reaction mixture was concentrated under reduced pressure. The residue was purified by column chromatography (SiO$_2$, Petroleum ether/EtOAc=3/4 to 0/1) to afford 2',6'-bis(benzyloxy)-[2,3'-bipyridin]-6-ol (420 mg, 852.18 μmol, 37.07% yield, 78% purity) as a white solid. MS (M+H)$^+$=385.3

Step 2. Synthesis of tert-butyl 4-((2',6'-bis(benzyloxy)-[2,3'-bipyridin]-6-yl)oxy)butanoate (4)

To a solution of 2',6'-bis(benzyloxy)-[2,3'-bipyridin]-6-ol (390 mg, 1.01 mmol) in DMF (8 mL) were added $K_2CO_3$ (420.63 mg, 3.04 mmol) and tert-butyl 4-bromobutanoate (226.34 mg, 1.01 mmol). The mixture was stirred at 70° C. for 5 h. LCMS showed 2',6'-bis(benzyloxy)-[2,3'-bipyridin]-6-ol was consumed completely and one main peak with desired mass. The reaction mixture was diluted with water (100 mL) and extracted with EtOAc (30 mL×3). The combined organic layers were washed with brine (30 mL), dried over anhydrous sodium sulfate, filtered and concentrated under reduced pressure. The residue was purified by column chromatography (SiO$_2$, Petroleum ether/EtOAc=1/0 to 100/3) to afford tert-butyl 4-((2',6'-bis(benzyloxy)-[2,3'-bipyridin]-6-yl)oxy)butanoate (420 mg, 765.64 μmol, 75.47% yield, 96% purity) as a white solid.
MS (M+H)$^+$=527.9

Step 3. Synthesis of tert-butyl 4-((6-(2,6-dioxopiperidin-3-yl)pyridin-2-yl)oxy)butanoate (5)

To a solution of tert-butyl 4-((2',6'-bis(benzyloxy)-[2,3'-bipyridin]-6-yl)oxy)butanoate (370 mg, 702.59 μmol) in $CF_3CH_2OH$ (20 mL) was added Pd/C (10%, 50 mg) under $N_2$ atmosphere. The suspension was degassed and purged with $H_2$ for 3 times. The mixture was stirred at 25° C. for 4 h under $H_2$ (15 Psi). LCMS showed tert-butyl 4-((2',6'-bis(benzyloxy)-[2,3'-bipyridin]-6-yl)oxy)butanoate was consumed completely, and a peak (74%) with desired mass. The reaction mixture was filtered and filter cake was washed with EtOAc (100 mL), the filtrate was concentrated in vacuo to afford tert-butyl 4-((6-(2,6-dioxopiperidin-3-yl)pyridin-2-yl)oxy)butanoate (260 mg, crude) as colorless oil. MS (M+H)$^+$=349.2

Step 4. Synthesis of 4-((6-(2,6-dioxopiperidin-3-yl)pyridin-2-yl)oxy)butanoic acid (6)

A mixture of tert-butyl 4-((6-(2,6-dioxopiperidin-3-yl)pyridin-2-yl)oxy)butanoate (230 mg, 660.17 μmol) in HCl/ dioxane (4 M, 2 mL) and DCM (2 mL) was stirred at 25° C. for 0.5 h. LCMS showed tert-butyl 4-((6-(2,6-dioxopiperidin-3-yl)pyridin-2-yl)oxy)butanoate was consumed completely and one main peak with desired mass. The reaction mixture was concentrated under reduced pressure to afford 4-((6-(2,6-dioxopiperidin-3-yl)pyridin-2-yl)oxy)butanoic acid (190 mg, crude) as a white solid. MS (M+H)$^+$=292.8

Step 5. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(4-((6-(2,6-dioxopiperidin-3-yl)pyridin-2-yl)oxy)butanoyl)piperidin-4-yl)-3-methoxybenzamide (Compound 35)

To a solution of 4-((6-(2,6-dioxopiperidin-3-yl)pyridin-2-yl)oxy)butanoic acid (80 mg, 273.70 μmol) and 4-((9-cyclopentyl-7,7-difluoro-5-methyl-6-oxo-6,7,8,9-tetrahydro-5H-pyrimido[4,5-b][1,4]diazepin-2-yl)amino)-3-methoxy-N-(piperidin-4-yl)benzamide (144.95 mg, 273.70 μmol) in DMF (3 mL) were added HATU (156.11 mg, 410.56 μmol) and DIPEA (106.12 mg, 821.11 μmol, 143.02 μL). The mixture was stirred at 25° C. for 2 h. LCMS showed 4-((6-(2,6-dioxopiperidin-3-yl)pyridin-2-yl)oxy)butanoic acid was consumed completely, a peak (73%) with desired mass. The reaction mixture was diluted with water (50 mL) and extracted with EtOAc (20 mL×3). The combined organic layers were washed with brine (20 mL), dried over anhydrous sodium sulfate, filtered and concentrated under reduced pressure. The residue was purified by column chromatography (SiO$_2$, MeOH/EtOAc=0/1 to 1/10) followed by prep-HPLC (neutral condition: column: Waters Xbridge 150×25 mm×5 μm; mobile phase: [water (NH$_4$HCO$_3$)—ACN]; B %: 40%-70%, 8 min) and the eluent was lyophilized to afford 4-((9-cyclopentyl-7,7-difluoro-5-methyl-6-oxo-6,7,8,9-tetrahydro-5H-pyrimido[4,5-b][1,4]diazepin-2-yl)amino)-N-(1-(4-((6-(2,6-dioxopiperidin-3-yl)pyridin-2-yl)oxy)butanoyl)piperidin-4-yl)-3-methoxybenzamide (56.1 mg, 65.60 μmol, 23.97% yield, 94% purity) as a white solid. MS (M+H)$^+$=804.0

$^1$H NMR (400 MHz, DMSO-d$_6$) δ=10.87 (s, 1H), 8.32-8.24 (m, 2H), 8.18-8.07 (m, 1H), 7.98 (s, 1H), 7.68 (dd, J=7.4, 8.3 Hz, 1H), 7.53-7.45 (m, 2H), 6.94 (d, J=7.1 Hz, 1H), 6.73 (d, J=8.3 Hz, 1H), 4.83-4.72 (m, 1H), 4.48-37 (m, 1H), 4.27-4.17 (m, 2H), 4.10-4.02 (m, 3H), 3.97-3.86 (m, 5H), 3.33 (s, 3H), 3.17-3.06 (m, 1H), 2.74-2.56 (m, 3H), 2.49-2.40 (m, 2H), 2.30-2.20 (m, 1H), 2.18-2.10 (m, 1H), 1.99-1.78 (m, 6H), 1.77-1.69 (m, 2H), 1.66-1.55 (m, 4H), 1.51-1.35 (m, 2H).

Example 36. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(3-(4-(6-(2,6-dioxopiperidin-3-yl)pyridin-2-yl)piperazin-1-yl)propanoyl)piperidin-4-yl)-3-methoxybenzamide (Compound 36)

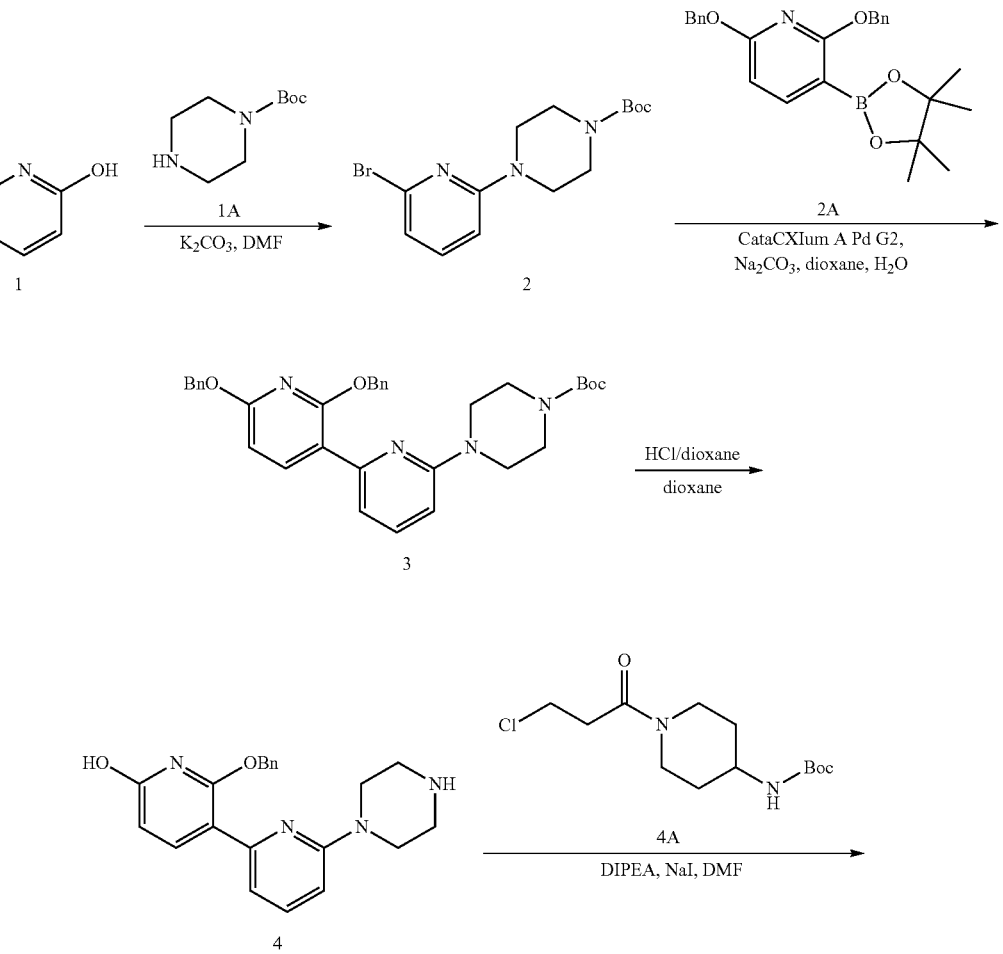

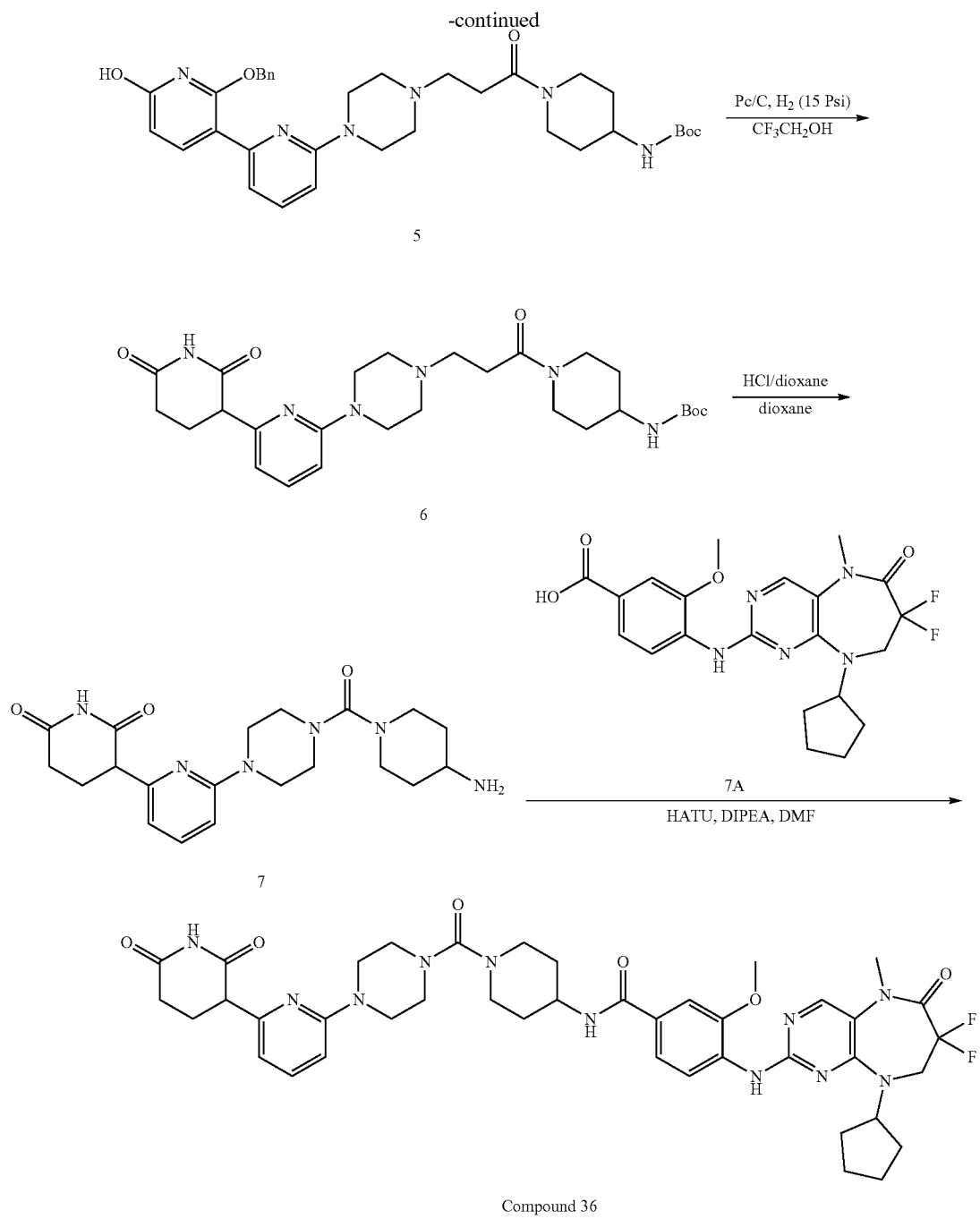

Compound 36

Step 1. Synthesis of tert-butyl 4-(6-bromopyridin-2-yl)piperazine-1-carboxylate (2)

To a solution of 2,6-dibromopyridine (3 g, 12.66 mmol) in DMF (20 mL) were added $K_2CO_3$ (3.50 g, 25.33 mmol) and tert-butyl piperazine-1-carboxylate (2.36 g, 12.66 mmol). The mixture was stirred at 80° C. for 16 hrs. LCMS showed a peak with desired mass. The reaction mixture was diluted with water (100 mL) and extracted with EtOAc (100 mL×3). The combined organic layers were washed with brine (50 mL×4), dried over $Na_2SO_4$, filtered and concentrated under reduced pressure. The residue was purified by flash silica gel chromatography (40 g silica gel column, EtOAc/petroleum ether=10-20%, 60 mL/min) to afford tert-butyl 4-(6-bromopyridin-2-yl)piperazine-1-carboxylate (3 g, 8.77 mmol, 69.22% yield, 100% purity) as a white solid. MS $(M+H)^+=342.1$

Step 2. Synthesis of tert-butyl 4-(2',6'-bis(benzyloxy)-[2,3'-bipyridin]-6-yl)piperazine-1-carboxylate (3)

A mixture of 2,6-bis(benzyloxy)-3-(4,4,5,5-tetramethyl-1,3,2-dioxaborolan-2-yl)pyridine (1.5 g, 3.59 mmol), tert-butyl 4-(6-bromopyridin-2-yl)piperazine-1-carboxylate (1.23 g, 3.59 mmol), CataCXium A Pd G2 (120.02 mg, 179.50 μmol), and $Na_2CO_3$ (761.01 mg, 7.18 mmol) in dioxane (20 mL) and H₂O (5 mL) was degassed and purged with N₂ for 3 times, then the mixture was stirred at 60° C. for 16 hrs under N₂ atmosphere. LCMS showed a peak with desired mass. The reaction mixture was diluted with water (100 mL) and extracted with EtOAc (100 mL×3). The combined organic layers were washed with brine (50 mL×4), dried over Na₂SO₄, filtered and concentrated under reduced pressure. The residue was purified by flash silica gel chromatography (40 g silica gel column, EtOAc/petroleum ether=0-10%, 60 mL/min) and re-purified by prep-HPLC (column: Waters Xbridge C18 150×50 mm×10 μm; mobile phase: [water (NH₄HCO₃)—ACN]; B %: 68%-98%, 11 min) and the eluent was lyophilized to afford tert-butyl 4-(2',6'-bis(benzyloxy)-[2,3'-bipyridin]-6-yl)piperazine-1-carboxylate (0.5 g, 624.25 μmol, 17.39% yield, 69% purity) as a white solid. MS (M+H)⁺=553.5

Step 3. Synthesis of 2'-(benzyloxy)-6-(piperazin-1-yl)-[2,3'-bipyridin]-6'-ol (4)

To a solution of tert-butyl 4-(2',6'-bis(benzyloxy)-[2,3'-bipyridin]-6-yl)piperazine-1-carboxylate (0.5 g, 904.71 μmol) in dioxane (10 mL) was added HCl/dioxane (4 M, 226.18 μL). The mixture was stirred at 25° C. for 2 hrs. LCMS showed a peak with desired mass. The reaction solution was concentrated to afford 2'-(benzyloxy)-6-(piperazin-1-yl)-[2,3'-bipyridin]-6'-ol (400 mg, crude, HCl) as a yellow solid. MS (M+H)⁺=363.3

Step 4. Synthesis of tert-butyl (1-(3-(4-(2'-(benzyloxy)-6'-hydroxy-[2,3'-bipyridin]-6-yl)piperazin-1-yl)propanoyl)piperidin-4-yl)carbamate (5)

To a solution of 2'-(benzyloxy)-6-(piperazin-1-yl)-[2,3'-bipyridin]-6'-ol (200 mg, 501.40 μmol, HCl salt) and tert-butyl (1-(3-chloropropanoyl)piperidin-4-yl)carbamate (437.40 mg, 1.50 mmol) in DMF (4 mL) were added NaI (7.52 mg, 50.14 μmol) and DIPEA (259.20 mg, 2.01 mmol, 349.33 μL). The mixture was stirred at 80° C. for 16 hrs. LCMS showed a peak with desired mass. The reaction mixture was diluted with water (50 mL) and extracted with EtOAc (10 mL×2). The combined organic layers were washed with brine (20 mL×3), dried over Na₂SO₄, filtered and concentrated under reduced pressure. The residue was purified by flash silica gel chromatography (10 g silica gel column, EtOAc/petroleum ether=0-10%, 20 mL/min) to afford tert-butyl (1-(3-(4-(2'-(benzyloxy)-6'-hydroxy-[2,3'-bipyridin]-6-yl)piperazin-1-yl)propanoyl)piperidin-4-yl)carbamate (230 mg, 372.92 μmol, 74.38% yield) as a yellow oil. MS (M+H)⁺=617.5

Step 5. Synthesis of tert-butyl (1-(3-(4-(6-(2,6-dioxopiperidin-3-yl)pyridin-2-yl)piperazin-1-yl)propanoyl)piperidin-4-yl)carbamate (6)

To a solution of tert-butyl (1-(3-(4-(2'-(benzyloxy)-6'-hydroxy-[2,3'-bipyridin]-6-yl)piperazin-1-yl)propanoyl)piperidin-4-yl)carbamate (200 mg, 324.28 μmol) in 2,2,2-trifluoroethanol (30 mL) was added Pd/C (149.74 mg, 10% purity) under N₂ atmosphere. The mixture was degassed and purged with H₂ for 3 times, then the resulting mixture was stirred at 25° C. for 16 hrs under H₂ (15 psi) atmosphere. LCMS showed a peak with desired mass. The reaction mixture was filtered and the filtrate was concentrated under reduced pressure. The residue was purified by prep-HPLC (column: Waters Xbridge 150×25 mm×5 μm; mobile phase: [water (NH₄HCO₃)—ACN]; B %: 23%-53%, 8 min) and the eluent was lyophilized to afford tert-butyl (1-(3-(4-(6-(2,6-dioxopiperidin-3-yl)pyridin-2-yl)piperazin-1-yl)propanoyl)piperidin-4-yl)carbamate (60 mg, 110.09 μmol, 33.95% yield, 97% purity) as a yellow solid. MS (M+H)⁺=529.4

¹H NMR (400 MHz, CDCl₃) δ=8.03 (br s, 1H), 7.53-7.45 (m, 1H), 6.66-6.52 (m, 2H), 4.60-4.43 (m, 2H), 3.92-3.79 (m, 2H), 3.75-3.47 (m, 5H), 3.20-3.08 (m, 1H), 300-2.53 (m, 11H), 2.40-2.25 (m, 2H), 2.10-1.90 (m, 3H), 1.45 (s, 9H), 1.40-1.23 (m, 3H).

Step 6. Synthesis of 3-(6-(4-(3-(4-aminopiperidin-1-yl)-3-oxopropyl)piperazin-1-yl)pyridin-2-yl)piperidine-2,6-dione (7)

To a solution of tert-butyl (1-(3-(4-(6-(2,6-dioxopiperidin-3-yl)pyridin-2-yl)piperazin-1-yl)propanoyl)piperidin-4-yl)carbamate (60 mg, 113.50 μmol) in dioxane (5 mL) was added HCl/dioxane (4 M, 15.00 mL). The mixture was stirred at 25° C. for 1 hrs. LCMS showed a peak with desired mass. The reaction mixture was concentrated under reduced pressure to afford 3-(6-(4-(3-(4-aminopiperidin-1-yl)-3-oxopropyl)piperazin-1-yl)pyridin-2-yl)piperidine-2,6-dione (60 mg, crude, HCl salt) as a yellow solid. MS (M+H)⁺=429.3

Step 7. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(3-(4-(6-(2,6-dioxopiperidin-3-yl)pyridin-2-yl)piperazin-1-yl)propanoyl)piperidin-4-yl)-3-methoxybenzamide (Compound 36)

To a solution of 4-((9-cyclopentyl-7,7-difluoro-5-methyl-6-oxo-6,7,8,9-tetrahydro-5H-pyrimido[4,5-b][1,4]diazepin-2-yl)amino)-3-methoxybenzoic acid (52.21 mg, 116.68 μmol) in DMF (1 mL) were added HATU (53.24 mg, 140.01 μmol) and DIPEA (30.16 mg, 233.36 μmol, 40.65 μL), the mixture was stirred at 25° C. for 10 min, then a solution of 3-(6-(4-(3-(4-aminopiperidin-1-yl)-3-oxopropyl)piperazin-1-yl)pyridin-2-yl)piperidine-2,6-dione (50 mg, 116.68 μmol, HCl salt) and DIPEA (45.24 mg, 350.04 μmol, 60.97 μL) in DMF (0.2 mL) was added dropwise at 25° C. and the resulting mixture was stirred at 25° C. for 1 hrs. LCMS showed a peak with desired mass. The reaction mixture was diluted with water (20 mL) and extracted with EtOAc (10 mL×2). The combined organic layers were washed with brine (5 mL×3), dried over Na₂SO₄, filtered and concentrated under reduced pressure. The residue was purified by prep-HPLC (column: Waters Xbridge 150×25 mm×5 μm; mobile phase: [water (NH₄HCO₃)—ACN]; B %: 33%-63%, 9 min) and the eluent was lyophilized to afford 4-((9-cyclopentyl-7,7-difluoro-5-methyl-6-oxo-6,7,8,9-tetrahydro-5H-pyrimido[4,5-b][1,4]diazepin-2-yl)amino)-N-(1-(3-(4-(6-(2,6-dioxopiperidin-3-yl)pyridin-2-yl)piperazin-1-yl)propanoyl)piperidin-4-yl)-3-methoxybenzamide (30.5 mg, 34.48 μmol, 29.55% yield, 97% purity) as a yellow solid. MS (M+H)⁺=858.5

¹H NMR (400 MHz, DMSO-d₆) δ=10.79 (s, 1H), 8.31-8.23 (m, 2H), 8.15 (d, J=7.70 Hz, 1H), 7.96 (s, 1H), 7.57-7.43 (m, 3H), 6.72 (d, J=8.56 Hz, 1H), 6.60 (d, J=7.21 Hz, 1H), 4.83-4.70 (m, 1H), 4.46-4.34 (m, 1H), 4.13-4.00 (m, 3H), 4.00-3.89 (m, 4H), 3.81 (t, J=6.36 Hz, 1H), 3.50-3.38 (m, 4H), 3.28 (br d, J=3.55 Hz, 3H), 3.18-3.07 (m, 1H), 2.72-2.52 (m, 10H), 2.48-2.46 (m, 1H), 2.19-2.08 (m, 2H), 1.99-1.79 (m, 4H), 1.75-1.33 (m, 8H).

Example 37. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(3-(4-(2-(2,6-dioxopiperidin-3-yl)pyridin-4-yl)piperazin-1-yl)propanoyl)piperidin-4-yl)-3-methoxybenzamide (Compound 37)
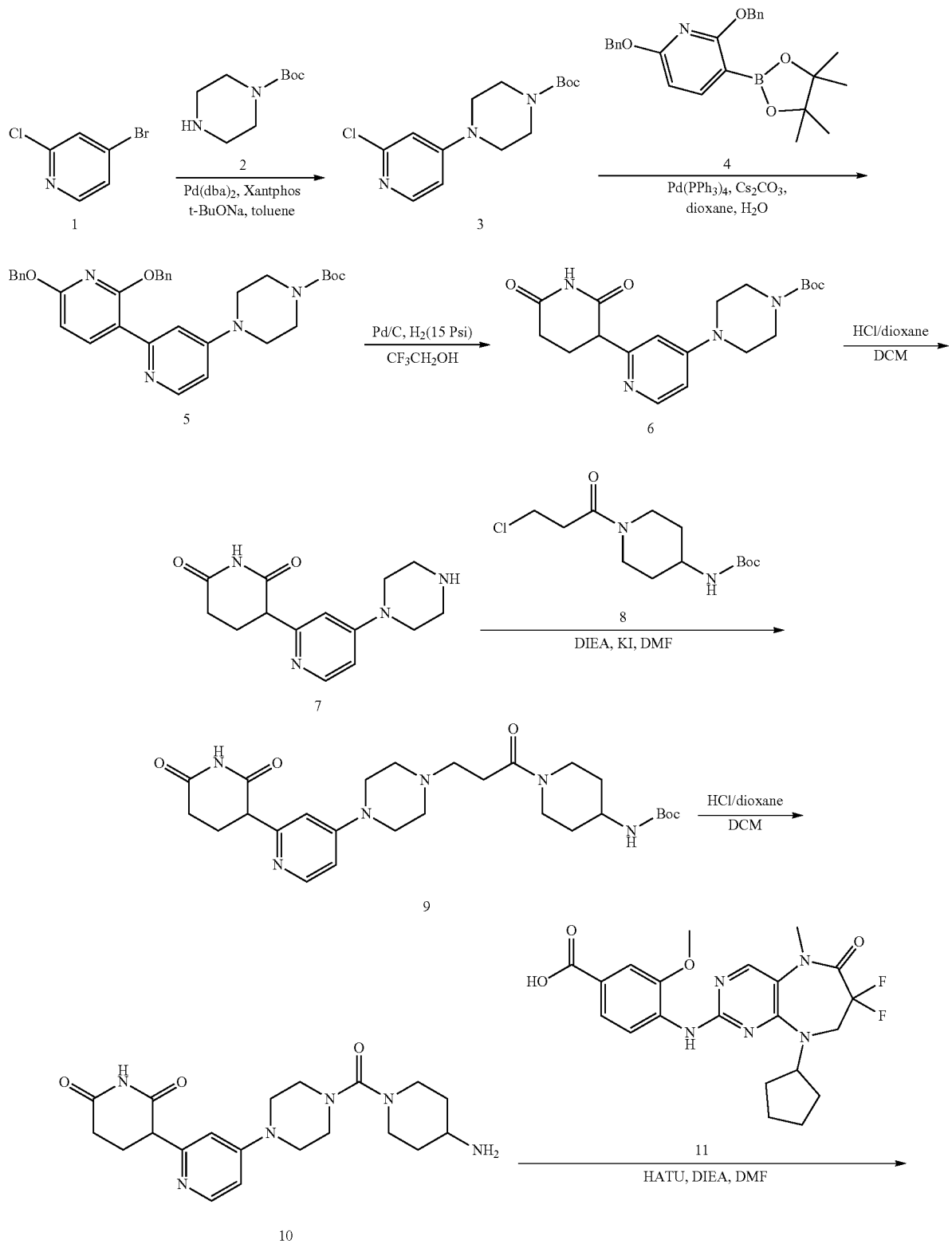

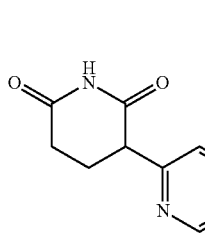
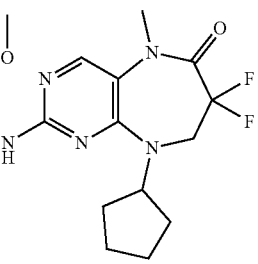

Compound 37

Step 1. Synthesis of tert-butyl 4-(2-chloropyridin-4-yl)piperazine-1-carboxylate (3)

To a solution of 4-bromo-2-chloropyridine (1 g, 5.20 mmol) and tert-butyl piperazine-1-carboxylate (967.83 mg, 5.20 mmol) in toluene (10 mL) was added Pd(dba)$_2$ (298.80 mg, 519.64 μmol), Xantphos (601.35 mg, 1.04 mmol) and t-BuONa (1.50 g, 15.59 mmol) under N$_2$ atmosphere. The mixture was stirred at 90° C. for 5 h under N$_2$ atmosphere. LCMS showed a peak (16%) with desired mass. The reaction mixture was concentrated under reduced pressure. The residue was purified by column chromatography (SiO$_2$, Petroleum ether/EtOAc=3/1 to 2/1) followed by reversed-phase HPLC (0.1% FA condition: Column: 120 g Flash Column Welch Ultimate XB_C$_{18}$ 20-40 μm; Flow rate:85 mL/min; Mobile phase: MeCN/H$_2$O; Gradient B %: 5-40% 10 min; 40-100% 30 min, Instrument: TELEDYNE ISCO CombiFlashRf150) and the eluent was lyophilized to afford tert-butyl 4-(2-chloropyridin-4-yl)piperazine-1-carboxylate (650 mg, 1.96 mmol, 37.81% yield, 90% purity) as a white solid. MS (M+H)$^+$=298.2

Step 2. Synthesis of tert-butyl 4-(2',6'-bis(benzyloxy)-[2,3'-bipyridin]-4-yl)piperazine-1-carboxylate (5)

To a solution of tert-butyl 4-(2-chloropyridin-4-yl)piperazine-1-carboxylate (600 mg, 2.01 mmol) and 2,6-bis(benzyloxy)-3-(4,4,5,5-tetramethyl-1,3,2-dioxaborolan-2-yl)pyridine (840.83 mg, 2.01 mmol) in dioxane (10 mL) and H$_2$O (1 mL) was added Pd(PPh$_3$)$_4$ (232.84 mg, 201.49 μmol) and Cs$_2$CO$_3$ (1.97 g, 6.04 mmol) under N$_2$ atmosphere. The mixture was stirred under microwave at 125° C. for 1 h. LCMS showed 14% of tert-butyl 4-(2-chloropyridin-4-yl)piperazine-1-carboxylate remained, and a peak (60%) with desired mass. The reaction mixture was concentrated under reduced pressure. The residue was purified by column chromatography (SiO$_2$, Petroleum ether/EtOAc=4/1 to 3/1) to afford tert-butyl 4-(2',6'-bis(benzyloxy)-[2,3'-bipyridin]-4-yl)piperazine-1-carboxylate (450 mg, 781.67 μmol, 38.79% yield, 96% purity) as a white solid.
MS (M+H)$^+$=553.3

Step 3. Synthesis of tert-butyl 4-(2-(2,6-dioxopiperidin-3-yl)pyridin-4-yl)piperazine-1-carboxylate (6)

To a solution of tert-butyl 4-(2',6'-bis(benzyloxy)-[2,3'-bipyridin]-4-yl)piperazine-1-carboxylate (450 mg, 814.24 μmol) in CF$_3$CH$_2$OH (10 mL) was added Pd/C (10%, 50 mg) under N$_2$ atmosphere. The suspension was degassed and purged with H$_2$ for 3 times. The mixture was stirred at 25° C. for 4 h under H$_2$ (15 Psi). LCMS showed the starting material was consumed completely, and a peak (74%) with desired mass. The reaction mixture was filtered and filter cake was washed with EtOAc (100 mL), the filtrate was concentrated in vacuo. The residue was purified by column chromatography (SiO$_2$, Petroleum ether/EtOAc=4/5 to 0/1) to afford tert-butyl 4-(2-(2,6-dioxopiperidin-3-yl)pyridin-4-yl)piperazine-1-carboxylate (170 mg, 431.32 μmol, 52.97% yield, 95% purity) as a light green solid. MS (M+H)$^+$=375.3

Step 4. Synthesis of 3-(4-(piperazin-1-yl)pyridin-2-yl)piperidine-2,6-dione (7)

A mixture of tert-butyl 4-(2-(2,6-dioxopiperidin-3-yl)pyridin-4-yl)piperazine-1-carboxylate (140 mg, 373.90 μmol), HCl/dioxane (4 M, 1 mL) in DCM (1 mL) was stirred at 25° C. for 0.5 h. LCMS showed the starting material was consumed completely and one main peak with desired mass. The reaction mixture was concentrated under reduced pressure to afford 3-(4-(piperazin-1-yl)pyridin-2-yl)piperidine-2,6-dione (140 mg, crude, HCl salt) as a white solid. MS (M+H)$^+$=275.2

Step 5. Synthesis of tert-butyl (1-(3-(4-(2-(2,6-dioxopiperidin-3-yl)pyridin-4-yl)piperazin-1-yl)propanoyl)piperidin-4-yl)carbamate (9)

To a solution of 3-(4-(piperazin-1-yl)pyridin-2-yl)piperidine-2,6-dione (140 mg, 450.48 μmol, HCl salt) and tert-butyl (1-(3-chloropropanoyl)piperidin-4-yl)carbamate (130.99 mg, 450.48 μmol) in DMF (4 mL) were added KI (74.78 mg, 450.48 μmol) and DIPEA (174.66 mg, 1.35 mmol, 235.40 μL). The mixture was stirred at 80° C. for 3 h. LCMS showed 3-(4-(piperazin-1-yl)pyridin-2-yl)piperidine-2,6-dione was consumed completely, and a peak (59%) with desired mass. The reaction mixture was diluted with water (50 mL) and extracted with EtOAc (20 mL×3). The combined organic layers were washed with brine (20 mL, dried over anhydrous sodium sulfate, filtered and concentrated under reduced pressure. The residue was purified by column chromatography (SiO$_2$, MeOH/EtOAc=0/1 to 1/10) to afford tert-butyl (1-(3-(4-(2-(2,6-dioxopiperidin-3-yl)pyridin-4-yl)piperazin-1-yl)propanoyl)piperidin-4-yl)carbamate (50 mg, 91.74 μmol, 20.37% yield, 97% purity) as a light yellow solid. MS (M+H)$^+$=529.3

Step 6. Synthesis of 3-(4-(4-(3-(4-aminopiperidin-1-yl)-3-oxopropyl)piperazin-1-yl)pyridine-2-yl)piperidine-2,6-dione (10)

A mixture of tert-butyl (1-(3-(4-(2-(2,6-dioxopiperidin-3-yl)pyridin-4-yl)piperazin-1-yl)propanoyl)piperidin-4-yl)

carbamate (50 mg, 94.58 µmol) in HCl/dioxane (4 M, 0.5 mL) and DCM (0.5 mL) was stirred at 25° C. for 0.5 h. LCMS showed the starting material was consumed completely, and a peak (46%) with desired mass. The reaction mixture was concentrated under reduced pressure to afford 3-(4-(4-(3-(4-aminopiperidin-1-yl)-3-oxopropyl)piperazin-1-yl)pyridine-2-yl)piperidine-2,6-dione (50 mg, crude, HCl salt) as a yellow solid. MS (M+H)$^+$=429.4

Step 7. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(3-(4-(2-(2,6-dioxopiperidin-3-yl)pyridin-4-yl)piperazin-1-yl)propanoyl)piperidin-4-yl)-3-methoxybenzamide (Compound 37)

To a solution of 3-(4-(4-(3-(4-aminopiperidin-1-yl)-3-oxopropyl)piperazin-1-yl)pyridine-2-yl)piperidine-2,6-dione (50 mg, 107.53 µmol, HCl salt) and 4-((9-cyclopentyl-7,7-difluoro-5-methyl-6-oxo-6,7,8,9-tetrahydro-5H-pyrimido[4,5-b][1,4]diazepin-2-yl)amino)-3-methoxybenzoic acid (48.11 mg, 107.53 µmol) in DMF (1.5 mL) were added HATU (61.33 mg, 161.29 µmol) and DIPEA (41.69 mg, 322.59 µmol, 56.19 µL). The mixture was stirred at 25° C. for 2 h. LCMS showed a peak (42%) with desired mass. The reaction mixture was diluted with water (50 mL) and extracted with EtOAc (20 mL×3). The combined organic layers were washed with brine (20 mL), dried over anhydrous sodium sulfate, filtered and concentrated under reduced pressure. The residue was purified by prep-HPLC (neutral condition: column: Waters Xbridge 150×25 mm×5 µm; mobile phase: [water (NH$_4$HCO$_3$)—ACN]; B %: 28%-58%, 8 min) and the eluent was lyophilized to afford 4-((9-cyclopentyl-7,7-difluoro-5-methyl-6-oxo-6,7,8,9-tetrahydro-5H-pyrimido[4,5-b][1,4]diazepin-2-yl)amino)-N-(1-(3-(4-(2-(2,6-dioxopiperidin-3-yl)pyridin-4-yl)piperazin-1-yl)propanoyl)piperidin-4-yl)-3-methoxybenzamide (12.6 mg, 22.27 µmol, 20.71% yield, 96% purity) as a white solid. MS (M+H)$^+$=858.1

$^1$H NMR (400 MHz, DMSO-d$_6$) δ=10.77 (s, 1H), 8.30-8.26 (m, 2H), 8.16 (br d, J=7.8 Hz, 1H), 8.07 (d, J=6.0 Hz, 1H), 7.98 (s, 1H), 7.51-7.48 (m, 2H), 6.82 (d, J=2.3 Hz, 1H), 6.74 (dd, J=2.4, 6.0 Hz, 1H), 4.81-4.75 (m, 1H), 4.43-4.36 (m, 1H), 4.11-3.97 (m, 4H), 3.94 (s, 3H), 3.85-3.80 (m, 1H), 3.33 (br s, 3H), 3.31 (br s, 4H), 3.17-3.12 (m, 1H), 2.68-2.54 (m, 9H), 2.23-2.10 (m, 2H), 1.99-1.79 (m, 5H), 1.75-1.68 (m, 2H), 1.66-1.55 (m, 5H), 1.51-1.36 (m, 2H).

Example 38. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(4-(7-(5-(2,6-dioxopiperidin-3-yl)pyrimidin-2-yl)-2,7-diazaspiro[3.5]nonan-2-yl)piperidin-1-yl)-3-methoxybenzamide (Compound 38)

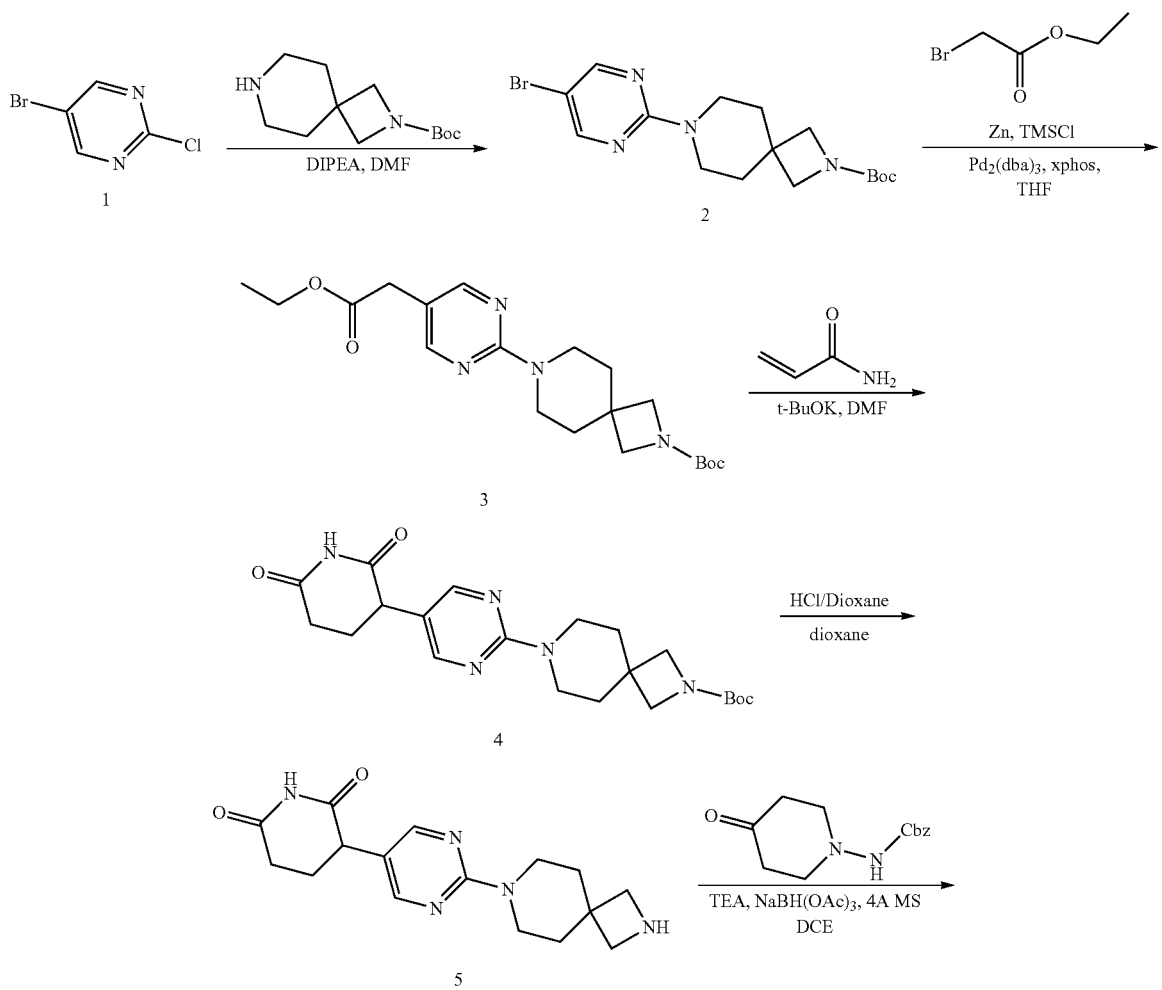

-continued

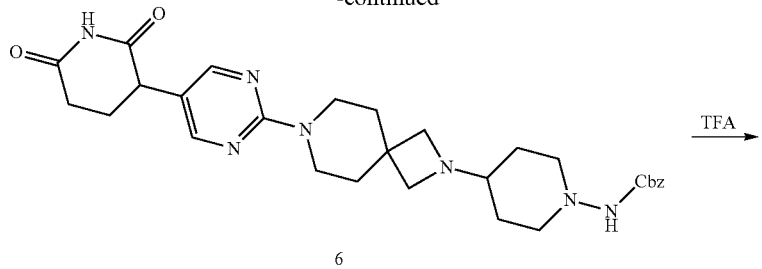

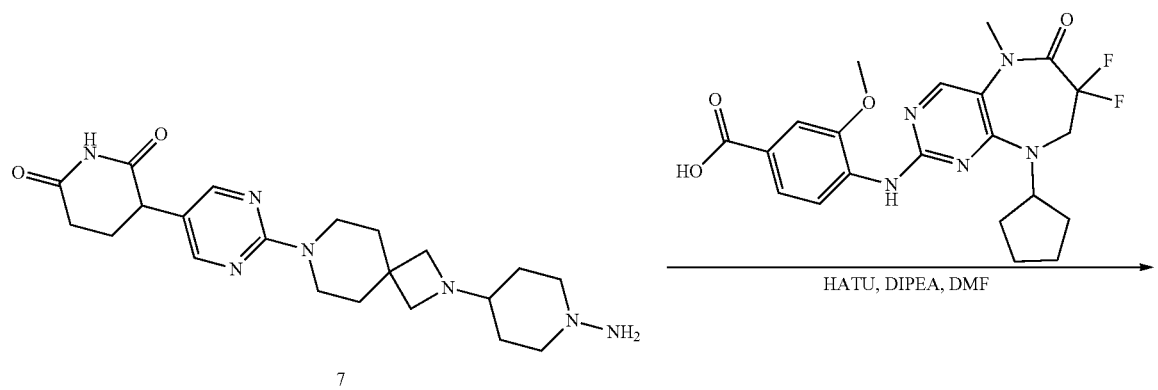

Compound 38

Step 1. Synthesis of tert-butyl 7-(5-bromopyrimidin-2-yl)-2,7-diazaspiro[3.5]nonane-2-carboxylate (2)

To a solution of 5-bromo-2-chloropyrimidine (5 g, 25.85 mmol) and tert-butyl 2,7-diazaspiro[3.5]nonane-2-carboxylate (6.44 g, 28.43 mmol) in DMF (25 mL) was added DIPEA (6.68 g, 51.70 mmol, 9.00 mL), the mixture was stirred at 100° C. for 16 hr. LCMS showed a major peak with desired mass. The mixture was filtered, the filtrate was diluted with water (50 mL), extracted with EtOAc (30 mL×3). The organic layer was washed with brine (50 mL×3), dried over $Na_2SO_4$, filtered and concentrated under vacuum to afford tert-butyl 7-(5-bromopyrimidin-2-yl)-2,7-diazaspiro[3.5]nonane-2-carboxylate (10 g, crude) as a brown powder. MS $(M+H)^+=383.0$

Step 2. Synthesis of tert-butyl 7-(5-(2-ethoxy-2-oxoethyl)pyrimidin-2-yl)-2,7-diazaspiro[3.5]nonane-2-carboxylate (3)

A solution of Zn (4.78 g, 73.05 mmol) and TMSCl (396.83 mg, 3.65 mmol, 463.59 µL) in THF (20 mL) was heated to 40° C. and stirred for 10 min, then ethyl 2-bromoacetate (6.10 g, 36.53 mmol, 4.04 mL) was added dropwise at 20° C. over 20 min, the mixture was cooled to 20° C., then a solution of tert-butyl 7-(5-bromopyrimidin-2-yl)-2,7-diazaspiro[3.5]nonane-2-carboxylate (7 g, 18.26 mmol) in THF (60 mL) was added, followed by $Pd_2(dba)_3$ (2.51 g, 2.74 mmol) and XPhos (2.61 g, 5.48 mmol) under $N_2$ atmosphere, the mixture was stirred at 60° C. for 16 h. LCMS showed a major peak with desired mass. The mixture was cooled to 20° C., diluted with EtOAc (50 mL), then quenched with saturated aqueous NH₄Cl (10 mL). The organic layer was washed with brine (10 mL×3), dried over Na₂SO₄, filtered and concentrated under vacuum, the crude product was purified by flash silica gel chromatography (Biotage, 25 g SepaFlash Silica Flash Column, Eluent of 4-35% EtOAc/Petroleum ether gradient @ 40 mL/min) to afford tert-butyl 7-(5-(2-ethoxy-2-oxoethyl)pyrimidin-2-yl)-2,7-diazaspiro[3.5]nonane-2-carboxylate (5.4 g, 12.58 mmol, 68.91% yield, 91% purity) as brown oil. MS (M+H)⁺= 391.2

Step 3. Synthesis of tert-butyl 7-(5-(2,6-dioxopiperidin-3-yl)pyrimidin-2-yl)-2,7-diazaspiro[3.5]nonane-2-carboxylate (4)

To a solution of tert-butyl 7-(5-(2-ethoxy-2-oxoethyl)pyrimidin-2-yl)-2,7-diazaspiro[3.5]nonane-2-carboxylate (1 g, 2.56 mmol) in DMF (10 mL) were added t-BuOK (287.37 mg, 2.56 mmol) and prop-2-enamide (182.03 mg, 2.56 mmol, 176.73 µL), the mixture was stirred at 0° C. for 2 h. LCMS showed a main peak with desired mass, the mixture was diluted with water (10 mL), extracted with EtOAc (15 mL×3). The organic layer was dried over Na₂SO₄, filtered and concentrated under vacuum. The crude product was purified by flash silica gel chromatography (Biotage, 4 g SepaFlash Silica Flash Column, Eluent of 4-98% EtOAc/Petroleum ether gradient @ 20 mL/min) to afford tert-butyl 7-(5-(2,6-dioxopiperidin-3-yl)pyrimidin-2-yl)-2,7-diazaspiro[3.5]nonane-2-carboxylate (1 g, 2.41 mmol, 93.98% yield, 100% purity) as a yellow powder. MS (M+H)⁺=416.2

Step 4. Synthesis of 3-(2-(2,7-diazaspiro[3.5]nonan-7-yl)pyrimidin-5-yl)piperidine-2,6-dione (5)

To a solution of tert-butyl 7-(5-(2,6-dioxopiperidin-3-yl)pyrimidin-2-yl)-2,7-diazaspiro[3.5]nonane-2-carboxylate (0.5 g, 1.20 mmol) in dioxane (10 mL) was added HCl/dioxane (4 M, 300.85 µL), the mixture was stirred at 20° C. for 1 hr. LCMS showed the desired mass, the mixture was concentrated under vacuum to afford 3-(2-(2,7-diazaspiro[3.5]nonan-7-yl)pyrimidin-5-yl)piperidine-2,6-dione (480 mg, crude, HCl) as a brown solid. MS (M+H)⁺=316.1

Step 5. Synthesis of benzyl (4-(7-(5-(2,6-dioxopiperidin-3-yl)pyrimidin-2-yl)-2,7-diazaspiro[3.5]nonan-2-yl)piperidin-1-yl)carbamate (6)

To a solution of 3-(2-(2,7-diazaspiro[3.5]nonan-7-yl)pyrimidin-5-yl)piperidine-2,6-dione (200 mg, crude, HCl salt) in DCE (8 mL) was added benzyl (4-oxopiperidin-1-yl)carbamate (173.20 mg, 697.59 µmol), 4A MS (10 mg, 634.18 µmol) and TEA (641.72 mg, 6.34 mmol, 882.69 µL), the mixture was stirred at 20° C. for 1 h, then NaBH(OAc)₃ (201.61 mg, 951.27 µmol) was added, the mixture was stirred at 20° C. for 15 h. LCMS showed major peak with desired mass. The mixture was diluted with water (3 mL), extracted with EtOAc (5 mL×3), the organic layer was dried over Na₂SO₄, filtered and concentrated under vacuum. The crude product was purified by flash silica gel chromatography (Biotage, 4 g SepaFlash Silica Flash Column, Eluent of 4-50% Methanol/EtOAc gradient @ 20 mL/min) to afford benzyl (4-(7-(5-(2,6-dioxopiperidin-3-yl)pyrimidin-2-yl)-2,7-diazaspiro[3.5]nonan-2-yl)piperidin-1-yl)carbamate (190 mg, 322.65 µmol, 50.88% yield, 93% purity) as white powder. MS (M+H)⁺=548.3

Step 6. Synthesis of 3-(2-(2-(1-aminopiperidin-4-yl)-2,7-diazaspiro[3.5]nonan-7-yl)pyrimidin-5-yl)piperidine-2,6-dione (7)

A solution of benzyl (4-(7-(5-(2,6-dioxopiperidin-3-yl)pyrimidin-2-yl)-2,7-diazaspiro[3.5]nonan-2-yl)piperidin-1-yl)carbamate (190 mg, 346.94 µmol) in TFA (1.5 mL) stirred at 60° C. for 5 hr. LCMS showed desired mass, the mixture was concentrated under vacuum to afford 3-(2-(2-(1-aminopiperidin-4-yl)-2,7-diazaspiro[3.5]nonan-7-yl)pyrimidin-5-yl)piperidine-2,6-dione (200 mg, crude, TFA) as brown oil. MS (M+H)⁺=414.3

Step 7. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(4-(7-(5-(2,6-dioxopiperidin-3-yl)pyrimidin-2-yl)-2,7-diazaspiro[3.5]nonan-2-yl)piperidin-1-yl)-3-methoxybenzamide (Compound 38)

To a solution of 4-((9-cyclopentyl-7,7-difluoro-5-methyl-6-oxo-6,7,8,9-tetrahydro-5H-pyrimido[4,5-b][1,4]diazepin-2-yl)amino)-3-methoxybenzoic acid (140 mg, 312.90 µmol) in DMF (2 mL) were added HATU (178.46 mg, 469.34 µmol) and DIPEA (121.32 mg, 938.69 µmol, 163.50 µL), followed by 3-(2-(2-(1-aminopiperidin-4-yl)-2,7-diazaspiro[3.5]nonan-7-yl)pyrimidin-5-yl)piperidine-2,6-dione (200 mg, crude, TFA), the mixture was stirred at 20° C. for 16 hr. LCMS showed main peak with desired mass, the mixture was diluted with water (3 mL), extracted with EtOAc (5 mL×3), the organic layer was dried over Na₂SO₄, filtered and concentrated under vacuum. The crude product was purified by Prep-HPLC (column: Phenomenex Synergi Polar-RP 100*25 mm*4 µm; mobile phase: [water (TFA)—ACN]; B %: 29%-49%, 7 min) and Prep-HPLC (column: Waters Xbridge C18 150*50 mm*10 µm; mobile phase: [water (NH₄HCO₃)—ACN]; B %: 26%-56%, 10 min), the eluent was lyophilized to afford 4-((9-cyclopentyl-7,7-difluoro-5-methyl-6-oxo-6,7,8,9-tetrahydro-5H-pyrimido[4,5-b][1,4]diazepin-2-yl)amino)-N-(4-(7-(5-(2,6-dioxopiperidin-3-yl)pyrimidin-2-yl)-2,7-diazaspiro[3.5]nonan-2-yl)piperidin-1-yl)-3-methoxybenzamide (37.5 mg, 43.20 µmol, 13.81% yield, 97.1% purity) as white powder.

MS (M+H)⁺=843.5

¹H NMR (400 MHz, DMSO-d₆) δ=10.88 (s, 1H), 9.35 (s, 1H), 8.29-8.24 (m, 2H), 8.23-8.18 (m, 2H), 7.97 (s, 1H), 7.49-7.37 (m, 2H), 4.83-4.69 (m, 1H), 4.05 (t, J=14.0 Hz, 2H), 3.93 (s, 3H), 3.77-3.66 (m, 5H), 3.33 (s, 3H), 3.07-2.91 (m, 6H), 2.79 (t, J=8.7 Hz, 2H), 2.71-2.56 (m, 2H), 2.28-2.09 (m, 2H), 2.02-1.91 (m, 3H), 1.74-1.56 (m, 12H), 1.38-1.25 (m, 2H).

Example 39. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(7-((1-(6-(2,6-dioxopiperidin-3-yl)pyridin-3-yl)piperidin-4-yl)methyl)-7-azaspiro[3.5]nonan-2-yl)-3-methoxybenzamide (Compound 39)
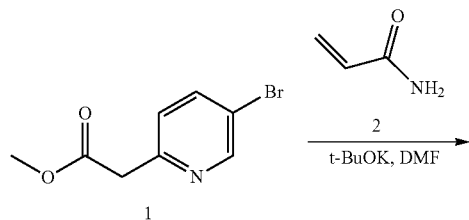
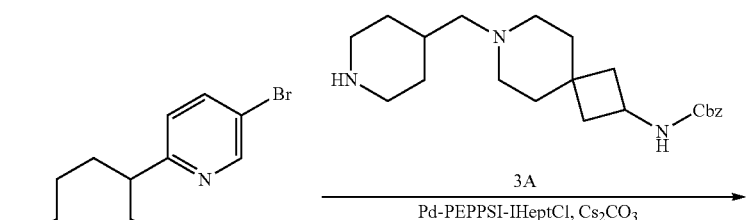
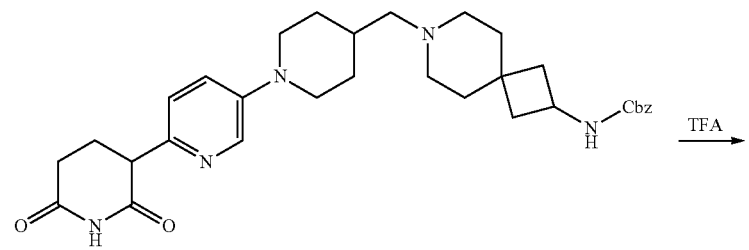
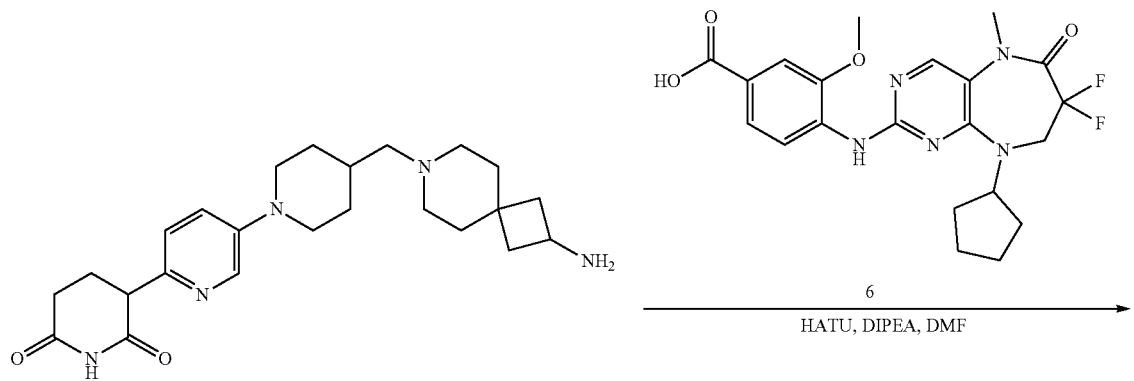

-continued

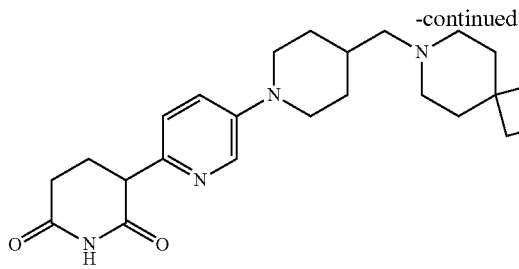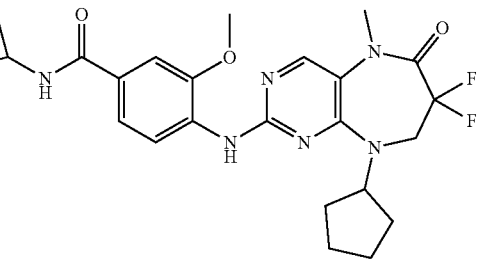

Compound 39

Step 1. Synthesis of 3-(5-bromopyridin-2-yl)piperidine-2,6-dione (3)

To a solution of methyl 2-(5-bromopyridin-2-yl)acetate (1 g, 4.35 mmol) in DMF (10 mL) were added prop-2-enamide (308.96 mg, 4.35 mmol, 299.96 μL) and t-BuOK (2 M, 2.17 mL) at 0° C. and the mixture was stirred at 0° C. for 2 h. LCMS showed a peak (55%) with desired mass. The mixture was poured into water (50 mL) and extracted with EtOAc (50 mL×3), the combined organic layer was washed with brine (100 mL), dried over $Na_2SO_4$, filtered and concentrated. The residue was purified by flash silica gel chromatography (20 g SepaFlash Silica Flash Column, Eluent of 0~20% EtOAc/Petroleum ether gradient @ 80 mL/min) to afford 3-(5-bromopyridin-2-yl)piperidine-2,6-dione (0.5 g, 1.86 mmol, 42.75% yield, 100% purity) as a white solid. MS $(M+H)^+=269.1$

Step 2. Synthesis of benzyl (7-((1-(6-(2,6-dioxopiperidin-3-yl)pyridin-3-yl)piperidin-4-yl)methyl)-7-azaspiro[3.5]nonan-2-yl)carbamate (4)

Two batches in parallel: To the solution of 3-(5-bromopyridin-2-yl)piperidine-2,6-dione (100 mg, 371.62 μmol) and benzyl (7-(piperidin-4-ylmethyl)-7-azaspiro[3.5]nonan-2-yl)carbamate (165.16 mg, 404.83 μmol, HCl) in dioxane (10 mL) were added Pd-PEPPSI-IHeptCl (36.15 mg, 37.16 μmol) and $Cs_2CO_3$ (605.40 mg, 1.86 mmol) and the resulting mixture was stirred at 100° C. for 12 h under $N_2$. LCMS showed a main peak with desired mass. The mixture was poured into water (50 mL) and extracted with EtOAc (50 mL×3), the combined organic layer was washed with brine (100 mL), dried over $Na_2SO_4$, filtered and concentrated. The residue was purified by prep-TLC (EtOAc/Methanol=10/1) to afford benzyl (7-((1-(6-(2,6-dioxopiperidin-3-yl)pyridin-3-yl)piperidin-4-yl)methyl)-7-azaspiro[3.5]nonan-2-yl)carbamate (250 mg, 281.40 μmol, 37.86% yield, 63% purity) as yellow oil. MS $(M+H)^+=560.4$

Step 3. Synthesis of 3-(5-(4-((2-amino-7-azaspiro[3.5]nonan-7-yl)methyl)piperidin-1-yl)pyridin-2-yl)piperidine-2,6-dione (5)

A mixture of benzyl (7-((1-(6-(2,6-dioxopiperidin-3-yl)pyridin-3-yl)piperidin-4-yl)methyl)-7-azaspiro[3.5]nonan-2-yl)carbamate (0.2 g, 357.34 μmol) in TFA (2 mL) was stirred at 20° C. for 14 h. LCMS showed a main peak with desired mass. The mixture was concentrated to afford 3-(5-(4-((2-amino-7-azaspiro[3.5]nonan-7-yl)methyl)piperidin-1-yl)pyridin-2-yl)piperidine-2,6-dione (190 mg, 352.12 μmol, 98.54% yield, TFA) as red oil. MS $(M+H)^+=426.2$

Step 4. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(7-((1-(6-(2,6-dioxopiperidin-3-yl)pyridin-3-yl)piperidin-4-yl)methyl)-7-azaspiro[3.5]nonan-2-yl)-3-methoxybenzamide (Compound 39)

To the solution of 4-((9-cyclopentyl-7,7-difluoro-5-methyl-6-oxo-6,7,8,9-tetrahydro-5H-pyrimido [4,5-b][1,4]diazepin-2-yl)amino)-3-methoxybenzoic acid (157.55 mg, 352.12 μmol) in DMF (5 mL) were added HATU (160.66 mg, 422.54 μmol) and DIPEA (182.04 mg, 1.41 mmol, 245.33 μL) and the mixture was stirred at 20° C. for 1 h. 3-(5-(4-((2-amino-7-azaspiro[3.5]nonan-7-yl) methyl)piperidin-1-yl)pyridin-2-yl)piperidine-2,6-dione (190 mg, 352.12 μmol, TFA) was added and the resulting mixture was stirred at 20° C. for 1 h. LCMS showed a main peak with desired mass. The mixture was poured into water (20 mL) and extracted with EtOAc (20 mL×3), the combined organic layer was washed with (50 mL), dried over $Na_2SO_4$, filtered and concentrated. The residue was purified by prep-HPLC (column: Waters Xbridge C18 150*50 mm*10 μm; mobile phase: [water ($NH_4HCO_3$)—ACN]; B %: 38%-68%, 10 min) and re-purified by prep-HPLC (column: Phenomenex luna C18 150*25 mm*10 μm; mobile phase: [water (FA)—ACN]; B %: 14%-44%, 11 min) and the eluent was lyophilized to afford 65 mg of crude product. The crude product was triturated with DMF (2 mL) and filtered, the filter cake was lyophilized to afford 4-((9-cyclopentyl-7,7-difluoro-5-methyl-6-oxo-6,7,8,9-tetrahydro-5H-pyrimido[4,5-b][1,4]diazepin-2-yl)amino)-N-(7-((1-(6-(2,6-dioxopiperidin-3-yl)pyridin-3-yl)piperidin-4-yl)methyl)-7-azaspiro[3.5]nonan-2-yl)-3-methoxybenzamide (25.1 mg, 26.72 μmol, 7.59% yield, 91% purity) as a white solid.

MS $(M+H)^+=855.4$ $^1$H NMR (400 MHz, DMSO-$d_6$) δ=10.78 (s, 1H), 8.44 (d, J=7.1 Hz, 1H), 8.30-8.26 (m, 2H), 8.19 (d, J=2.6 Hz, 1H), 7.97 (s, 1H), 7.51-7.47 (m, 2H), 7.31 (dd, J=2.9, 8.7 Hz, 1H), 7.16 (d, J=8.6 Hz, 1H), 4.82-4.73 (m, 1H), 4.45-4.35 (m, 1H), 4.05 (t, J=14.2 Hz, 2H), 3.95 (s, 3H), 3.91-3.86 (m, 1H), 3.76-3.70 (m, 2H), 3.31 (s, 3H), 2.73-2.61 (m, 4H), 2.29-2.06 (m, 10H), 1.99-1.93 (m, 2H), 1.86-1.74 (m, 6H), 1.72-1.55 (m, 9H), 1.25-1.17 (m, 2H).

Example 40. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(3-(4-(1-(2,6-dioxopiperidin-3-yl)-1H-pyrazol-4-yl)piperazin-1-yl)propanoyl)piperidin-4-yl)-3-methoxybenzamide (Compound 40)
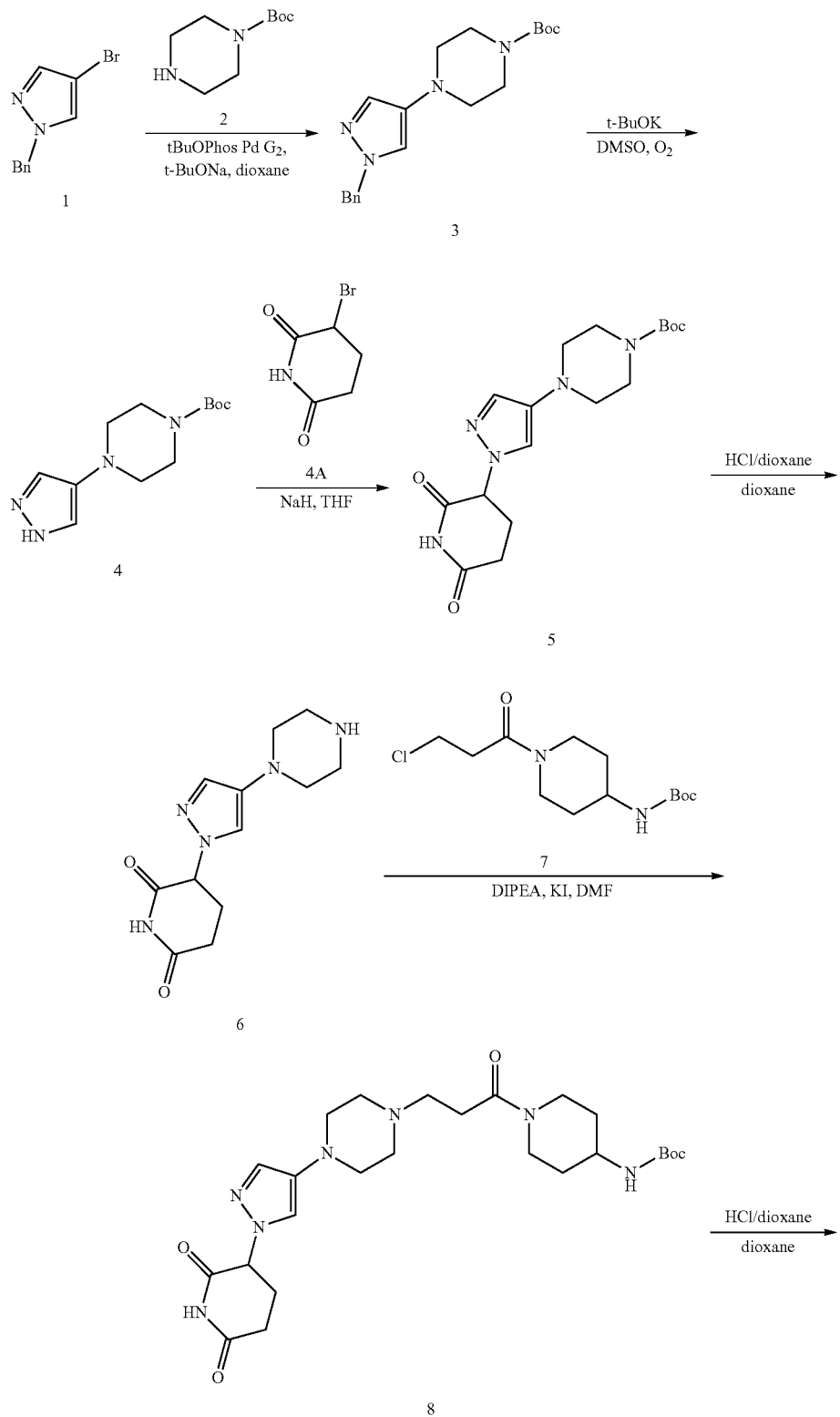

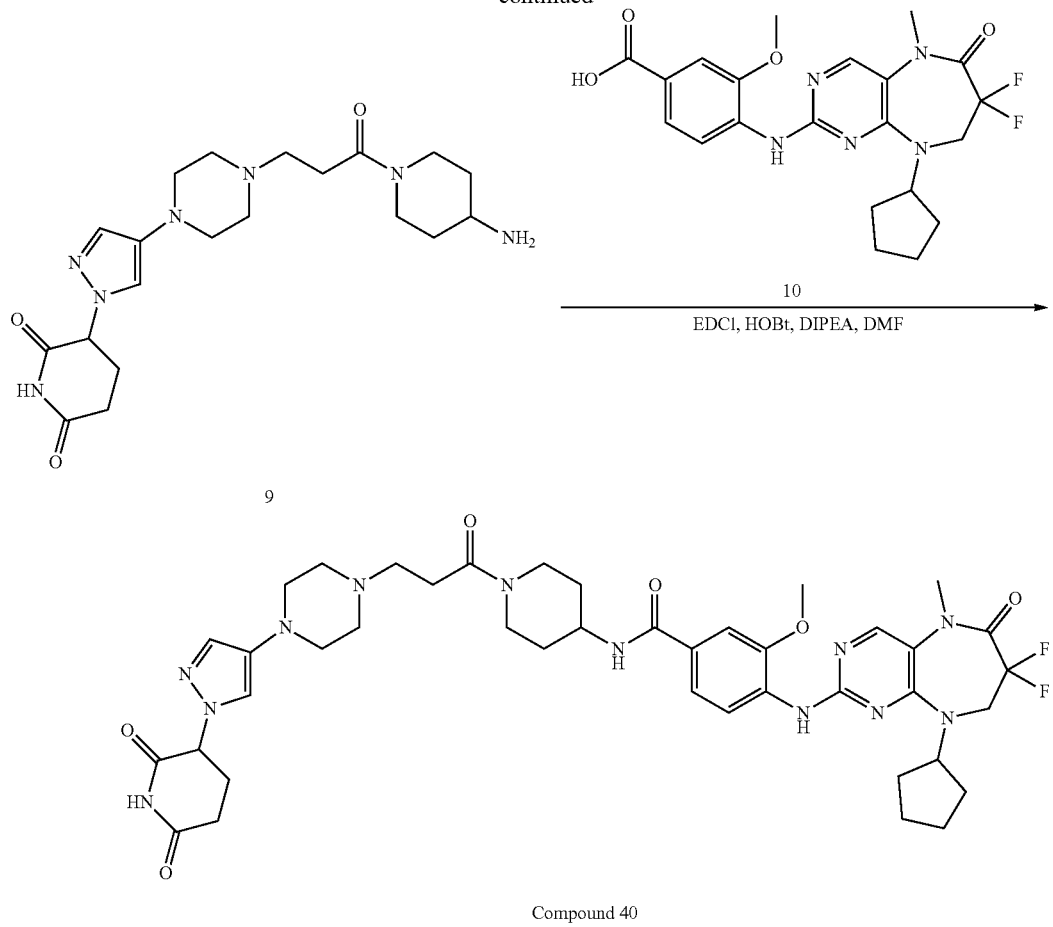

Compound 40

Step 1. Synthesis of tert-butyl 4-(1-benzyl-1H-pyrazol-4-yl)piperazine-1-carboxylate (3)

A mixture of 1-benzyl-4-bromo-1H-pyrazole (2 g, 8.44 mmol), tert-butyl piperazine-1-carboxylate (3.00 g, 13.47 mmol, HCl), tBuXPhos Pd G3 (600.00 mg, 755.31 µmol) and t-BuONa (2 M, 10.00 mL) in dioxane (40 mL) was degassed and purged with $N_2$ for 3 times, then the mixture was stirred at 100° C. or 16 hr under $N_2$ atmosphere. LCMS showed a peak (45%) with desired mass. The reaction mixture was filtered and the filtrate was concentrated under reduced pressure. The reaction mixture was diluted with $H_2O$ (40 mL), and extracted with EtOAc (80 mL×2). The combined organic layers were washed with brine (50 mL×3), dried over $Na_2SO_4$, filtered. The filtrate was concentrated under reduced pressure. The residue was purified by flash silica gel chromatography (Biotage; 40 g SepaFlash Silica Flash Column, Eluent of 0~20% EtOAc: Petroleum ether gradient, 60 mL/min) to afford tert-butyl 4-(1-benzyl-1H-pyrazol-4-yl)piperazine-1-carboxylate (1.9 g, 5.55 mmol, 65.78% yield) as a light yellow oil. MS (M+H)$^+$= 343.3

Step 2. Synthesis of tert-butyl 4-(1H-pyrazol-4-yl)piperazine-1-carboxylate (4)

To a solution of tert-butyl 4-(1-benzyl-1H-pyrazol-4-yl)piperazine-1-carboxylate (600 mg, 1.75 mmol) in DMSO (1.5 mL) was added t-BuOK (1 M, 24.00 mL), the mixture was stirred at 20° C. or 2 hr under O2 atmosphere (15 Psi). LCMS showed a peak (6%) with desired mass. The reaction mixture was diluted with NH$_4$Cl (25 mL) at 0° C. then extracted with EtOAc (30 mL×2). The combined organic layers were washed with brine (20 mL×3), dried over Na$_2$SO$_4$, filtered. The filtrate was concentrated under reduced pressure. The residue was combined another batch (500 mg scale) and purified by flash silica gel chromatography (Biotage; 40 g SepaFlash Silica Flash Column, Eluent of 0~10% Methanol:EtOAc gradient, 60 mL/min) to afford tert-butyl 4-(1H-pyrazol-4-yl)piperazine-1-carboxylate (440 mg, 1.74 mmol, 99.53% yield) as a light yellow solid.

MS (M+H)$^+$=253.1

Step 3. Synthesis of tert-butyl 4-(1-(2,6-dioxopiperidin-3-yl)-1H-pyrazol-4-yl)piperazine-1-carboxylate (5)

To a solution of tert-butyl 4-(1H-pyrazol-4-yl)piperazine-1-carboxylate (500 mg, 1.98 mmol) in THF (8 mL) was added NaH (160 mg, 4.00 mmol, 60% purity) at 0° C., the mixture was stirred at 0° C. for 0.5 hr, then a solution of 3-bromopiperidine-2,6-dione (420 mg, 2.19 mmol) in THF (6 mL) was added at 0° C. the resulting mixture was stirred at 25° C. for 2 hr. LCMS showed a main peak with the desired mass. The reaction mixture was diluted with NH$_4$Cl (sat. aq, 15 mL) at 0° C. and extracted with EtOAc (30 mL×2). The combined organic layers were washed with brine 60 mL (20 mL×3), dried over Na$_2$SO$_4$, filtered. The filtrate was concentrated under reduced pressure. The residue was purified by flash silica gel chromatography (Biotage; 20 g SepaFlash Silica Flash Column, Eluent of 0~10% Methanol: EtOAc gradient, 60 mL/min) to afford tert-butyl 4-(1-(2,6-dioxopiperidin-3-yl)-1H-pyrazol-4-yl)piperazine-1-carboxylate (710 mg, 1.95 mmol, 98.59% yield) as a gray solid. MS (M+H)$^+$=364.1

$^1$H NMR (400 MHz, DMSO-d$_6$) δ 10.99 (s, 1H), 7.36 (s, 1H), 7.26 (s, 1H), 5.24-5.15 (m, 1H), 3.47-3.37 (m, 4H), 2.84-2.78 (m, 4H), 2.78-2.71 (m, 1H), 2.66-2.57 (m, 1H), 2.47-2.42 (m, 1H), 2.19-2.11 (m, 1H), 1.45-1.37 (m, 9H)

Step 4. Synthesis of 3-(4-(piperazin-1-yl)-1H-pyrazol-1-yl)piperidine-2,6-dione (6)

To a solution of tert-butyl 4-(1-(2,6-dioxopiperidin-3-yl)-1H-pyrazol-4-yl)piperazine-1-carboxylate (500 mg, 1.38 mmol) in dioxane (10 mL) was added HCl/dioxane (4 M, 18.75 mL), the mixture was stirred at 20° C. hr. LCMS showed a main peak with the desired mass. The reaction mixture was concentrated under reduced pressure to afford 3-(4-(piperazin-1-yl)-1H-pyrazol-1-yl)piperidine-2,6-dione (410 mg, crude, HCl salt) as a light yellow solid. MS (M+H)$^+$=264.1

Step 5. Synthesis of tert-butyl (1-(3-(4-(1-(2,6-dioxopiperidin-3-yl)-1H-pyrazol-4-yl)piperazin-1-yl)propanoyl)piperidin-4-yl)carbamate (8)

To a solution of 3-(4-(piperazin-1-yl)-1H-pyrazol-1-yl)piperidine-2,6-dione (270 mg, 900.73 μmol, HCl) in DMF (8 mL) were added KI (94.86 mg, 571.46 μmol), tert-butyl (1-(3-chloropropanoyl)piperidin-4-yl)carbamate (400 mg, 1.38 mmol) and DIPEA (667.80 mg, 5.17 mmol, 900 μL) at 25° C. The mixture was stirred at 80° C. for 16 hr. LCMS showed a peak (41%) with desired mass. The reaction mixture was diluted with H$_2$O (10 mL), and extracted with EtOAc (40 mL×2). The combined organic layers were washed with brine (30 mL×3), dried over Na$_2$SO$_4$, filtered. The filtrate was concentrated under reduced pressure. The residue was purified by flash silica gel chromatography (Biotage; 20 g SepaFlash Silica Flash Column, Eluent of 5-25% Methanol: DCM gradient, 60 mL/min) to afford tert-butyl (1-(3-(4-(1-(2,6-dioxopiperidin-3-yl)-1H-pyrazol-4-yl)piperazin-1-yl)propanoyl)piperidin-4-yl)carbamate (200 mg, 386.38 μmol, 42.90% yield) as a light yellow solid. MS (M+H)$^+$=518.3

$^1$H NMR (400 MHz, DMSO-d$_6$) δ 11.00 (s, 1H), 7.31 (s, 1H), 7.24-7.18 (m, 1H), 6.93-6.78 (m, 1H), 5.25-5.13 (m, 1H), 4.27-4.19 (m, 1H), 3.88-3.79 (m, 1H), 3.48-3.41 (m, 1H), 3.37-3.26 (m, 4H), 3.09-3.01 (m, 1H), 2.88-2.80 (m, 4H), 2.79-2.72 (m, 1H), 2.68-2.54 (m, 5H), 2.20-2.11 (m, 1H), 1.78-1.66 (m, 2H), 1.38 (s, 9H), 1.30-1.15 (m, 4H).

Step 6. Synthesis of 3-(4-(4-(3-(4-aminopiperidin-1-yl)-3-oxopropyl)piperazin-1-yl)-1H-pyrazol-1-yl)piperidine-2,6-dione (9)

To a solution of tert-butyl (1-(3-(4-(1-(2,6-dioxopiperidin-3-yl)-1H-pyrazol-4-yl)piperazin-1-yl)propanoyl)piperidin-4-yl)carbamate (180 mg, 347.75 μmol) in dioxane (10 mL) was added HCl/dioxane (4 M, 10 mL), the mixture was stirred at 20° C. or 2 hr. LCMS showed a main peak with the desired mass. The reaction mixture was concentrated under reduced pressure to afford 3-(4-(4-(3-(4-aminopiperidin-1-yl)-3-oxopropyl)piperazin-1-yl)-1H-pyrazol-1-yl)piperidine-2,6-dione (120 mg, crude, HCl salt) as a light yellow solid. MS (M+H)$^+$=418.2

$^1$H NMR (400 MHz, DMSO-d$_6$) δ 11.23-11.09 (m, 1H), 11.03 (s, 1H), 8.43-8.29 (s, 3H), 7.47 (s, 1H), 7.33 (s, 1H), 5.30-5.17 (m, 1H), 4.41-4.32 (m, 1H), 4.02-3.90 (m, 1H), 3.63-3.58 (m, 1H), 3.47-3.40 (m, 2H), 3.36-3.25 (m, 3H), 3.20-3.09 (m, 3H), 3.04-2.93 (m, 4H), 2.81-2.60 (m, 3H), 2.23-2.14 (m, 1H), 2.00-1.91 (m, 2H), 1.54-1.37 (m, 2H), 1.32-1.25 (m, 2H)

Step 7. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(3-(4-(1-(2,6-dioxopiperidin-3-yl)-1H-pyrazol-4-yl)piperazin-1-yl)propanoyl)piperidin-4-yl)-3-methoxybenzamide (Compound 40)

To a solution of 4-((9-cyclopentyl-7,7-difluoro-5-methyl-6-oxo-6,7,8,9-tetrahydro-5H-pyrimido[4,5-b][1,4]diazepin-2-yl)amino)-3-methoxybenzoic acid (60 mg, 134.10 μmol) in DMF (3 mL) were added EDCI (60 mg, 312.99 μmol), HOBt (30 mg, 222.02 μmol), DIPEA (148.40 mg, 1.15 mmol, 200 μL) and 3-(4-(4-(3-(4-aminopiperidin-1-yl)-3-oxopropyl)piperazin-1-yl)-1H-pyrazol-1-yl)piperidine-2,6-dione (80 mg, 163.12 μmol, HCl salt) at 25° C. The mixture was stirred at 25° C. for 16 hr under N$_2$ atmosphere. LCMS showed a peak (85%) with desired mass. The mixture was filtered and the filtrate was purified by prep-HPLC (column: Phenomenex Synergi Polar-RP 100×25 mm×4 μm; mobile phase:[water (TFA)—ACN]; B %: 28%-48%, 7 min; Column Temp: 30° C. followed by prep-HPLC (column: Waters Xbridge 150×25 mm×5 μm; mobile phase:[water (NH$_4$HCO$_3$)—ACN]; B %: 29%-59%, 9 min; Column Temp: 30° C.), the eluent was lyophilized to afford 4-((9-cyclopentyl-7,7-difluoro-5-methyl-6-oxo-6,7,8,9-tetrahydro-5H-pyrimido[4,5-b][1,4]diazepin-2-yl)amino)-N-(1-(3-(4-(1-(2,6-dioxopiperidin-3-yl)-1H-pyrazol-4-yl)piperazin-1-yl)propanoyl)piperidin-4-yl)-3-methoxybenzamide (75.5 mg, 88.25 μmol, 65.81% yield, 99% purity) as a white solid. MS (M+H)$^+$=847.4

$^1$H NMR (400 MHz, DMSO-d$_6$) δ=11.00 (s, 1H), 8.35-8.24 (m, 2H), 8.19-8.08 (m, 1H), 7.97 (s, 1H), 7.52-7.44 (m, 2H), 7.32 (s, 1H), 7.23 (s, 1H), 5.24-5.14 (m, 1H), 4.83-4.71 (m, 1H), 4.46-4.35 (m, 1H), 4.10-3.96 (m, 4H), 3.94 (s, 3H), 3.30 (s, 3H), 3.17-3.09 (m, 1H), 2.90-2.83 (m, 4H), 2.78-2.56 (m, 10H), 2.22-2.14 (m, 1H), 2.00-1.78 (m, 5H), 1.77-1.69 (m, 2H), 1.68-1.53 (m, 5H), 1.52-1.38 (m, 2H).

Example 41. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(7-((1-(3-(2,6-dioxopiperidin-3-yl)phenyl)piperidin-4-yl)methyl)-7-azaspiro[3.5]nonan-2-yl)-3-methoxybenzamide (Compound 41)
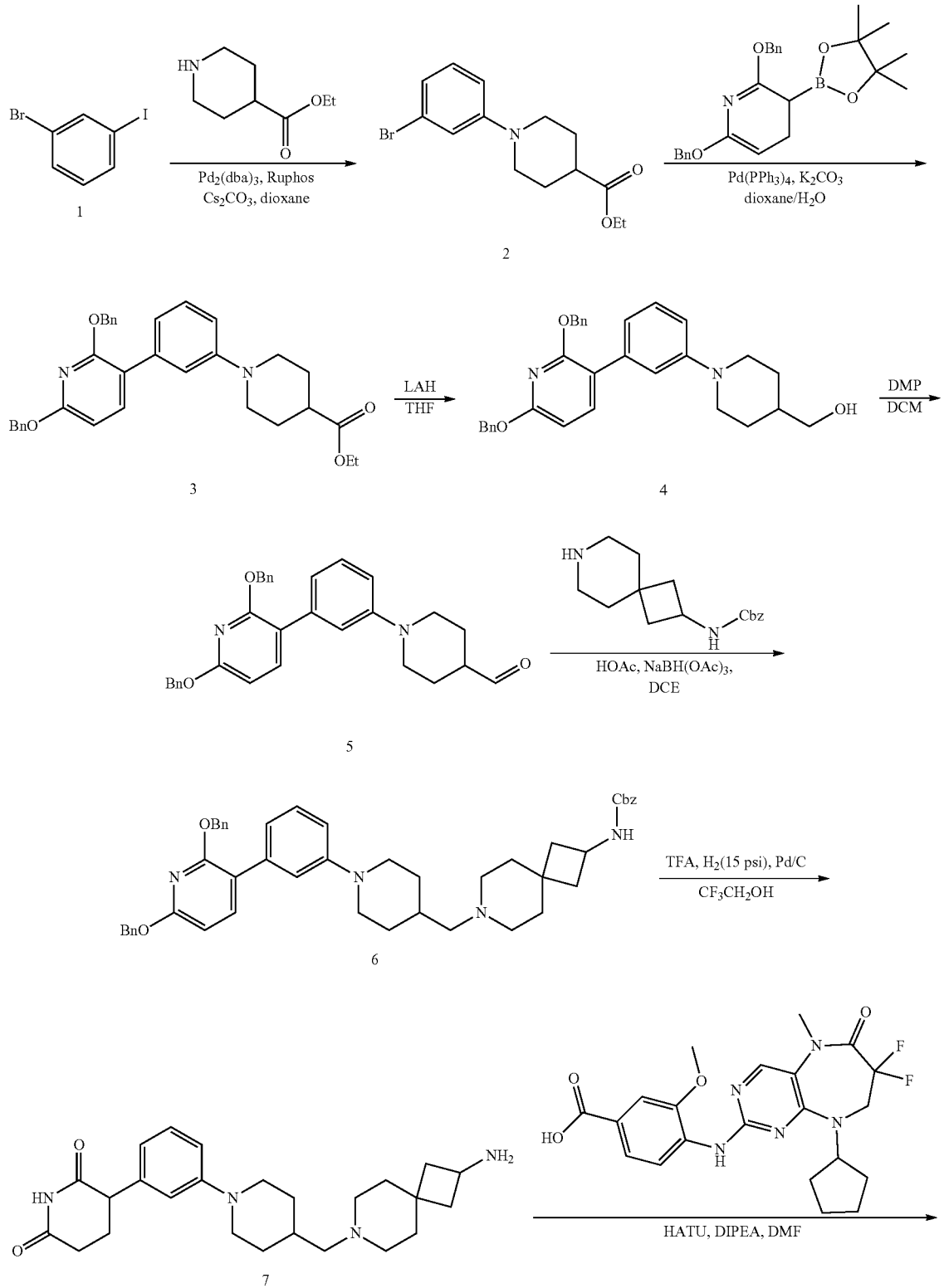

-continued

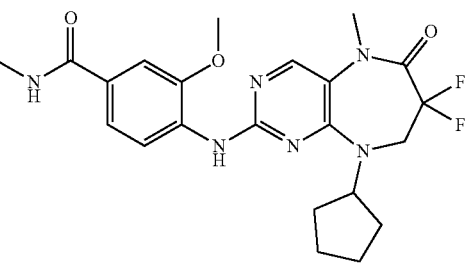

Compound 41

The compound 41 was synthesized by the method described in the scheme similar to the method described in the previous Examples.

MS (M+H)$^+$=854.0, $^1$H NMR (400 MHz, DMSO-d$_6$) δ=10.79 (s, 1H), 8.43 (d, J=7.3 Hz, 1H), 8.30-8.25 (m, 2H), 7.97 (s, 1H), 7.52-7.46 (m, 2H), 7.14 (t, J=7.9 Hz, 1H), 6.84-6.76 (m, 2H), 6.58 (d, J=7.2 Hz, 1H), 4.83-4.70 (m, 1H), 4.46-4.34 (m, 1H), 4.05 (br t, J=14.3 Hz, 2H), 3.94 (s, 3H), 3.76 (dd, J=4.7, 11.3 Hz, 1H), 3.66 (d, J=10.9 Hz, 2H), 3.38 (s, 3H), 2.69-2.61 (m, 4H), 2.38-2.28 (m, 3H), 2.21-2.10 (m, 5H), 2.06-1.87 (m, 4H), 1.85-1.69 (m, 6H), 1.67-1.51 (m, 9H), 1.24-1.11 (m, 2H).

Example 42. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(1-(1-(4-(2,6-dioxopiperidin-3-yl)-2-fluorophenyl)azetidin-3-yl)piperidin-4-yl)-3-methoxybenzamide (Compound 42)

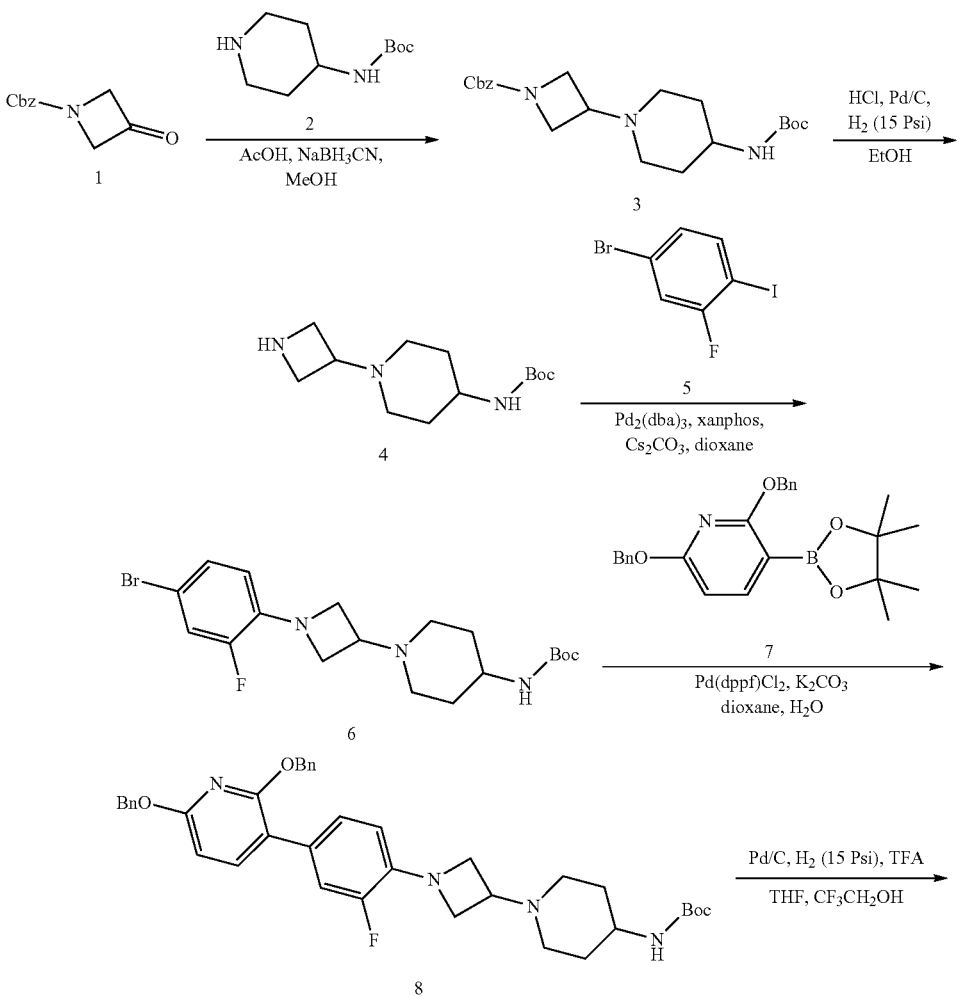

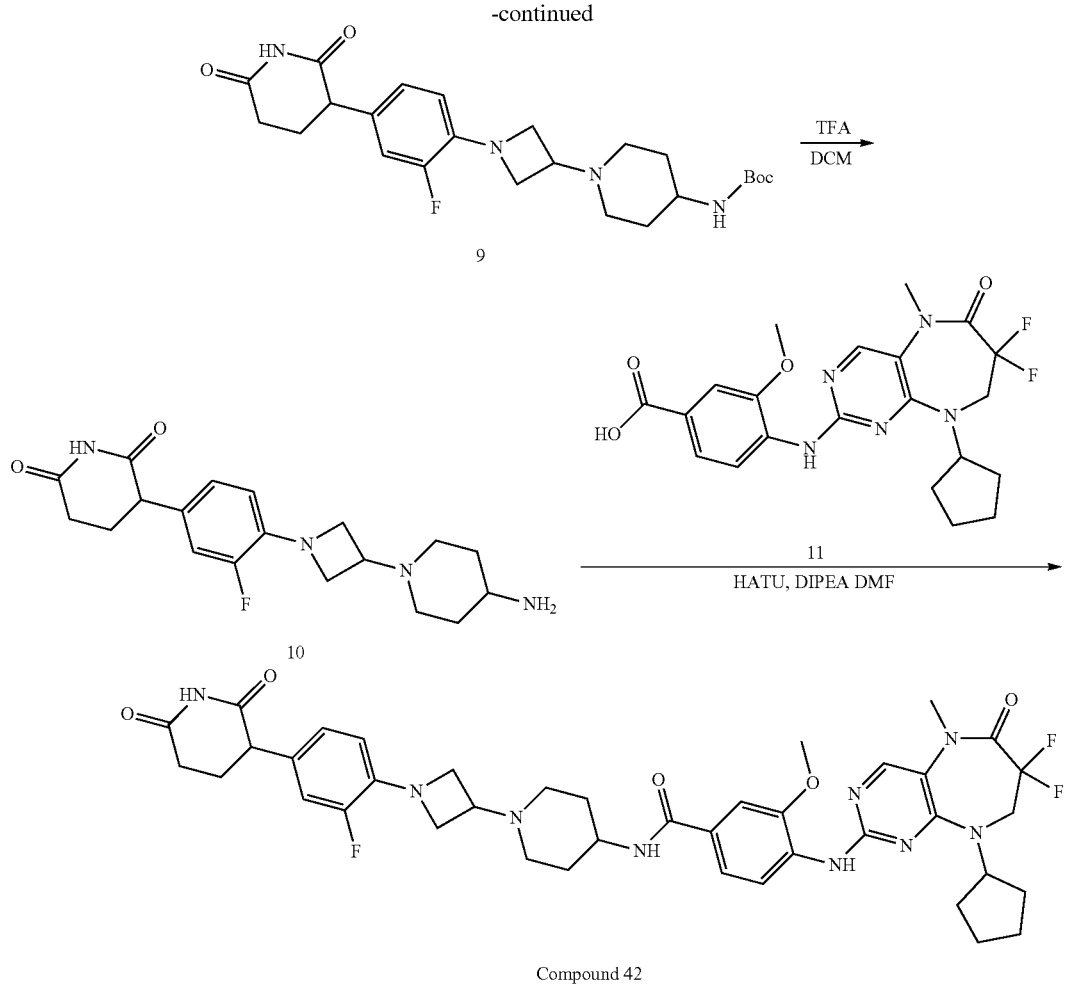

Compound 42

The compound 42 was synthesized by the method described in the scheme similar to the method described in the previous Examples.

MS (M+H)⁺=790.9, ¹H NMR (400 MHz, CDCl₃) δ=8.48 (d, J=8.4 Hz, 1H), 8.06 (s, 1H), 8.00-7.95 (m, 1H), 7.75 (s, 1H), 7.44-7.42 (m, 1H), 7.26-7.22 (m, 1H), 6.86-6.79 (m, 2H), 6.47 (t, J=8.9 Hz, 1H), 5.96 (br d, J=7.9 Hz, 1H), 4.87-4.77 (m, 1H), 4.15-4.03 (m, 3H), 3.99 (s, 3H), 3.94-3.80 (m, 4H), 3.68 (dd, J=4.9, 9.8 Hz, 1H), 3.41 (s, 3H), 3.37-3.30 (m, 1H), 2.93-2.85 (m, 2H), 2.78-2.58 (m, 2H), 2.30-2.05 (m, 8H), 1.84-1.68 (m, 8H).

Example 43. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(4-(1-(4-(2,6-dioxopiperidin-3-yl)-2-fluorophenyl)azetidin-3-yl)piperidin-1-yl)-3-methoxybenzamide (Compound 43)

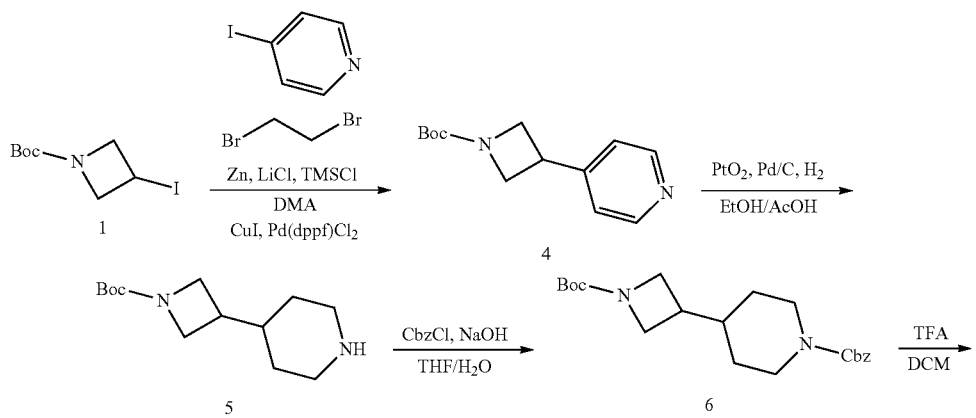

-continued
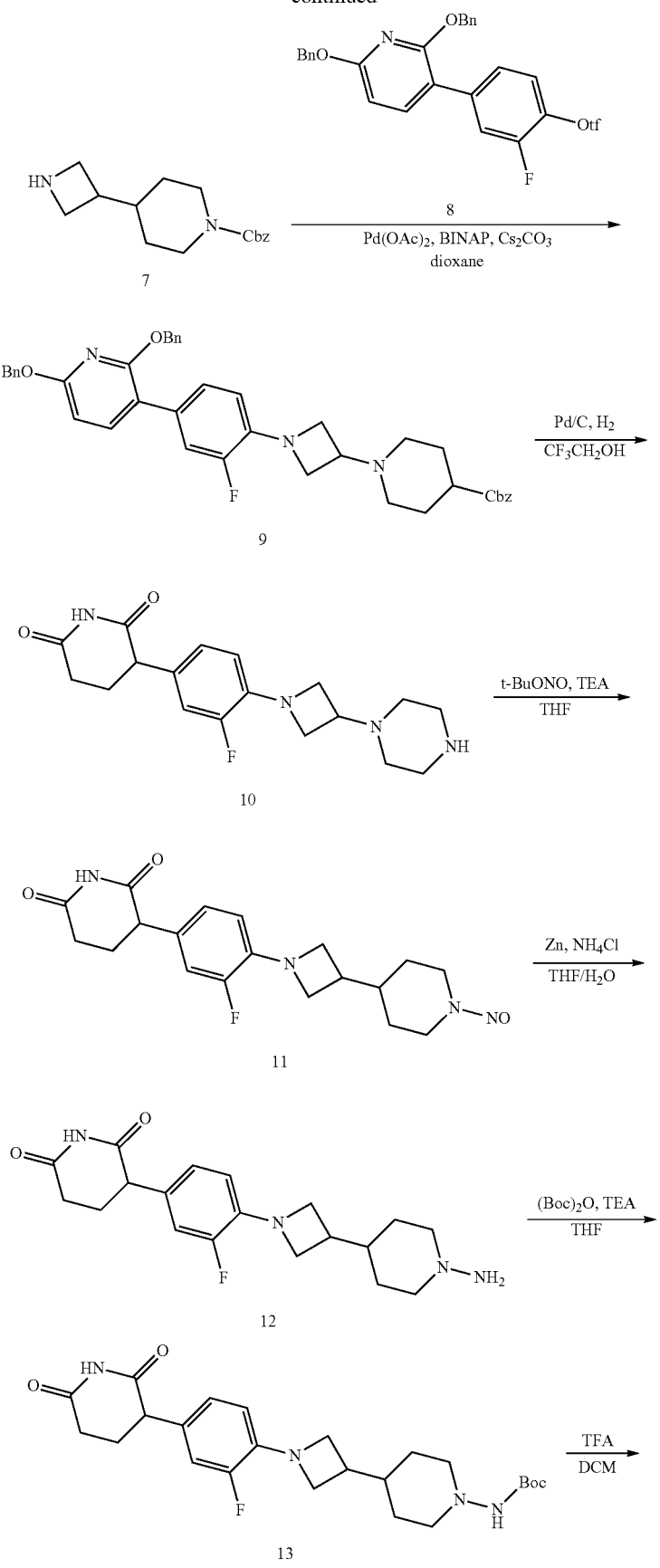

-continued

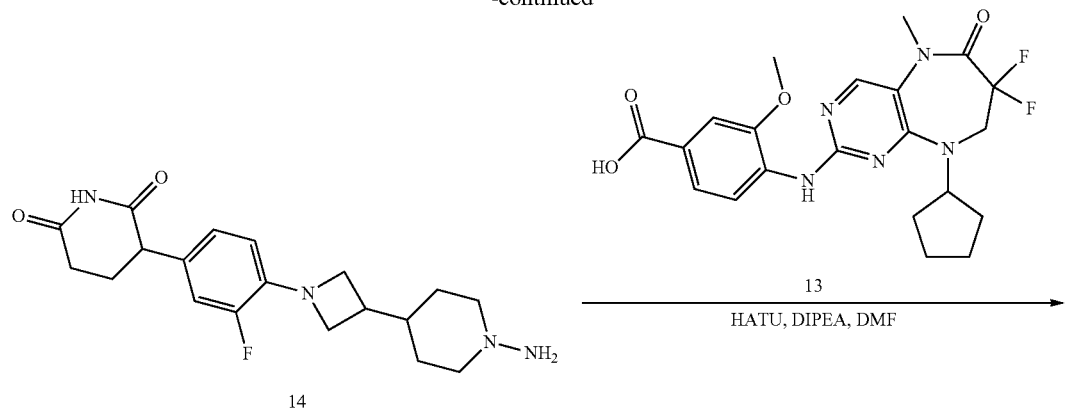

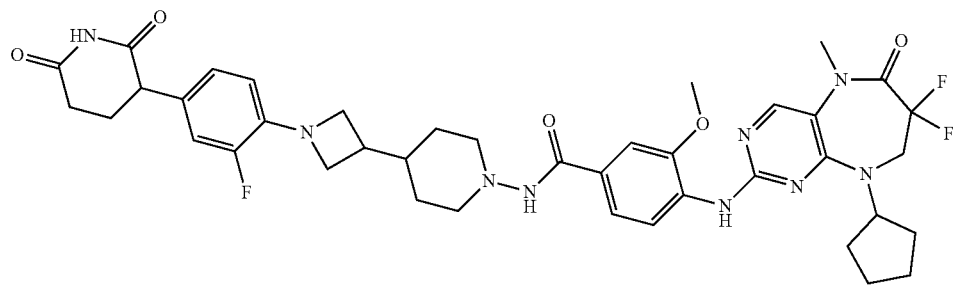

Compound 43

The compound 43 was synthesized by the method described in the scheme similar to the method described in the previous Examples.

MS (M+H)⁺=790.9, ¹H NMR (400 MHz, DMSO-d₆) δ=10.78 (s, 1H), 9.32 (s, 1H), 8.31-8.22 (m, 2H), 7.96 (s, 1H), 7.46-7.38 (m, 2H), 6.97-6.82 (m, 2H), 6.49 (t, J=9.0 Hz, 1H), 4.82-4.70 (m, 1H), 4.04 (br t, J=14.1 Hz, 2H), 3.97 (br t, J=6.7 Hz, 2H), 3.93 (s, 3H), 3.74 (dd, J=4.9, 11.5 Hz, 1H), 3.66-3.56 (m, 2H), 3.32 (br s, 3H), 3.02 (br d, J=10.3 Hz, 2H), 2.76 (br t, J=10.3 Hz, 2H), 2.67-2.59 (m, 1H), 2.49-2.42 (m, 2H), 2.23-2.10 (m, 1H), 2.03-1.87 (m, 3H), 1.70 (br d, J=9.4 Hz, 4H), 1.65-1.54 (m, 4H), 1.53-1.44 (m, 1H), 1.29-1.19 (m, 2H).

Example 44. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(4-(1-(4-(2,6-dioxopiperidin-3-yl)-2-fluorophenyl)azetidin-3-yl)piperidin-1-yl)-3-methoxybenzamide (Compound 44)

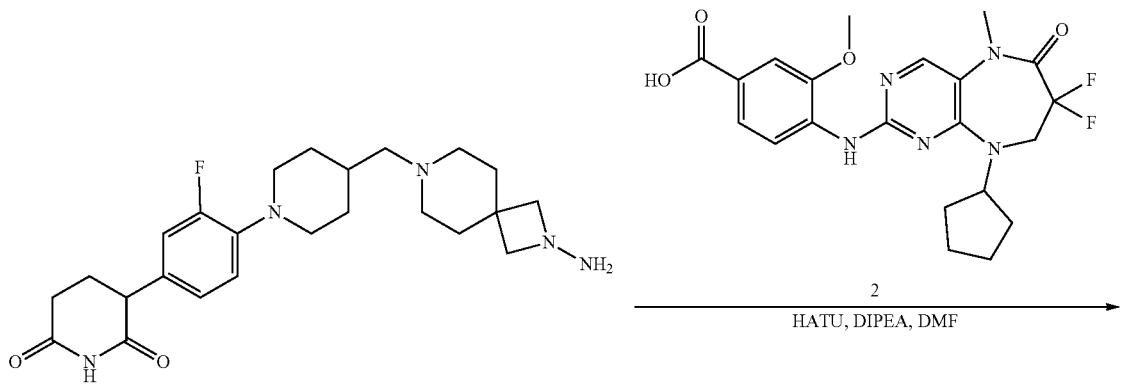

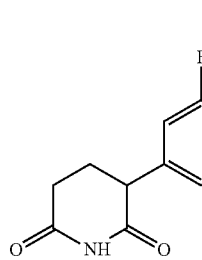
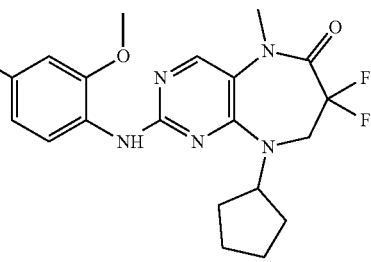

Compound 44

The compound 44 was synthesized by the method described in the scheme similar to the method described in the previous Examples.

MS (M+H)⁺=873.0, $^1$H NMR (400 MHz, DMSO-d$_6$) δ=10.81 (br s, 1H), 9.65-9.46 (m, 1H), 8.38-8.17 (m, 2H), 8.08-7.90 (m, 1H), 7.50-7.30 (m, 2H), 7.11-6.84 (m, 3H), 4.87-4.67 (m, 1H), 4.12-3.99 (m, 2H), 3.93 (br s, 3H), 3.84-3.74 (m, 1H), 3.68-3.51 (m, 4H), 3.33-3.32 (m, 5H), 2.70-2.60 (m, 3H), 2.36-2.07 (m, 5H), 2.05-1.43 (m, 18H), 1.42-1.03 (m, 3H).

Example 45. Synthesis of 4-((9-cyclopentyl-7,7-difluoro-5-methyl-6-oxo-6,7,8,9-tetrahydro-5H-pyrimido[4,5-b][1,4]diazepin-2-yl)amino)-N-(7-(2-(1-(4-(2,6-dioxopiperidin-3-yl)-2-fluorophenyl)piperidin-4-yl)ethyl)-7-azaspiro[3.5]nonan-2-yl)-3-methoxybenzamide (Compound 45)

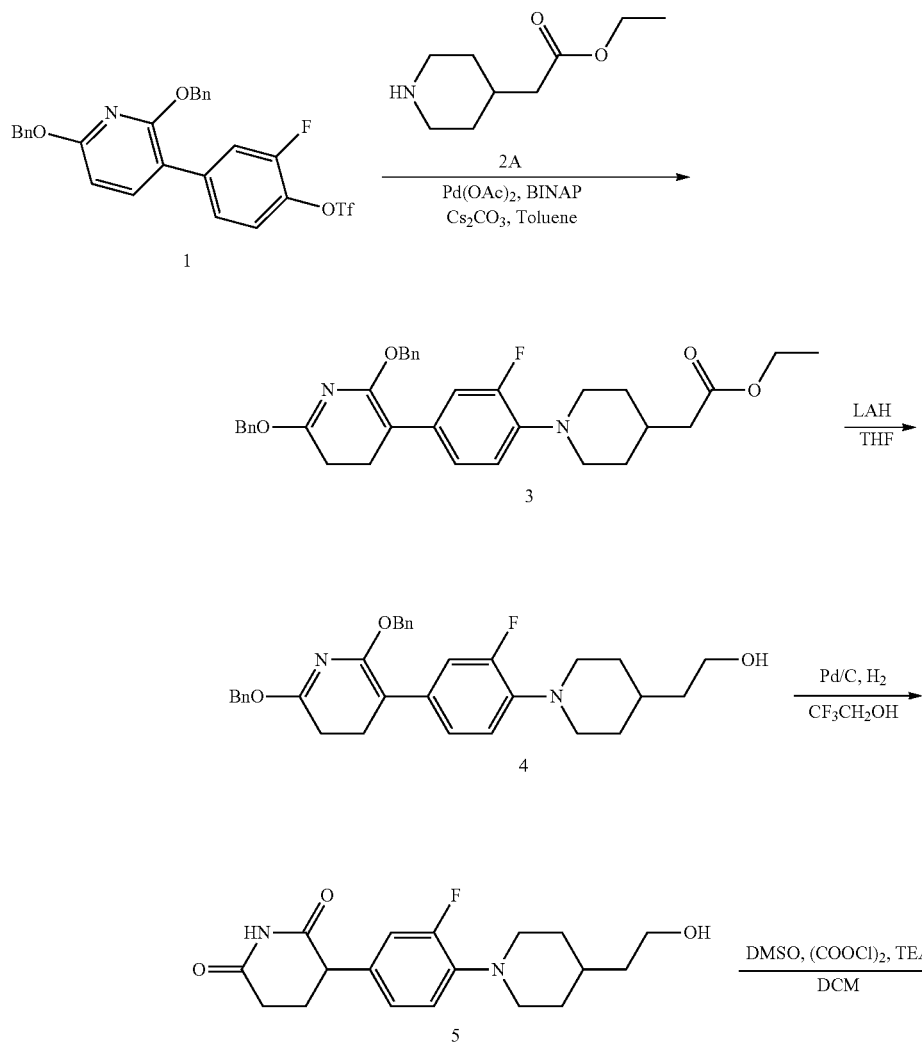

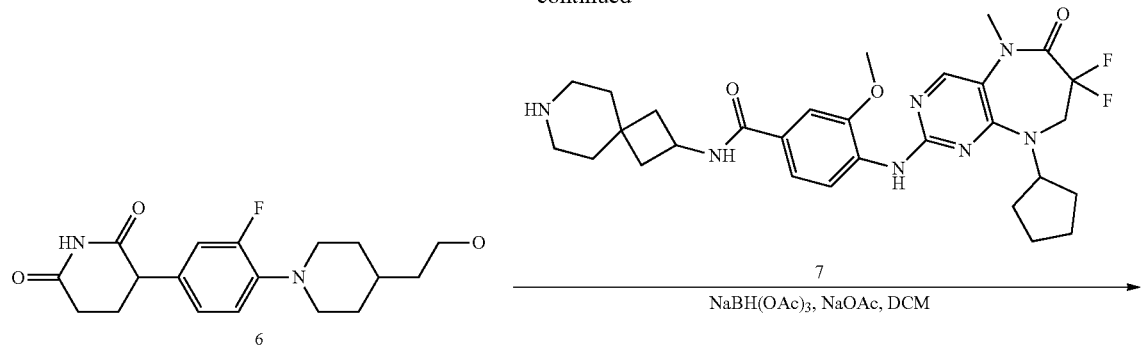

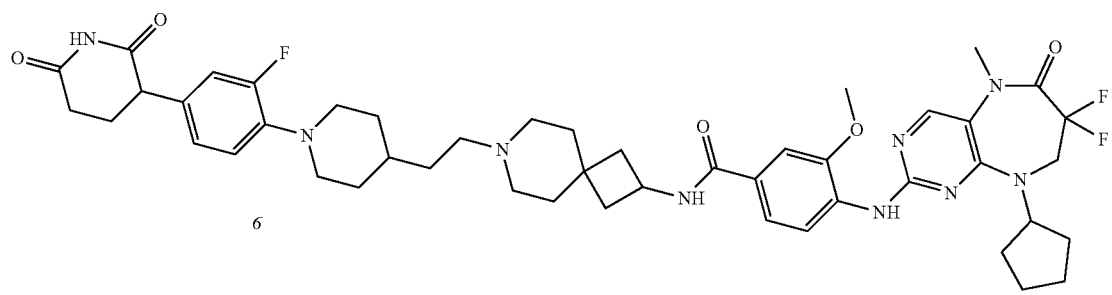

Compound 45

The compound 45 was synthesized by the method described in the scheme similar to the method described in the previous Examples.

MS (M+H)⁺=886.0, ¹H NMR (400 MHz, DMSO-d₆) δ=10.83-10.78 (m, 1H), 8.46-8.39 (m, 1H), 8.31-8.23 (m, 2H), 7.97 (s, 1H), 7.55-7.41 (m, 2H), 7.07-6.85 (m, 3H), 4.88-4.67 (m, 1H), 4.48-4.34 (m, 1H), 4.11-4.00 (m, 2H), 3.95 (s, 3H), 3.83-3.76 (m, 1H), 3.32-3.28 (m, 5H), 2.70-2.58 (m, 3H), 2.48-2.44 (m, 1H), 2.33-2.13 (m, 8H), 2.03-1.92 (m, 3H), 1.84-1.67 (m, 6H), 1.64-1.51 (m, 8H), 1.51-1.34 (m, 4H), 1.34-1.21 (m, 2H).

Example 46. Synthesis of –((9-cyclopentyl-7,7-difluoro-5-methyl-6-oxo-6,7,8,9-tetrahydro-5H-pyrimido[4,5-b][1,4]diazepin-2-yl)amino)-N-(7-(((3R,4S)-1-(4-(2,6-dioxopiperidin-3-yl)-2-fluorophenyl)-3-fluoropiperidin-4-yl)methyl)-7-azaspiro[3.5]nonan-2-yl)-3-methoxybenzamide (Compound 46)

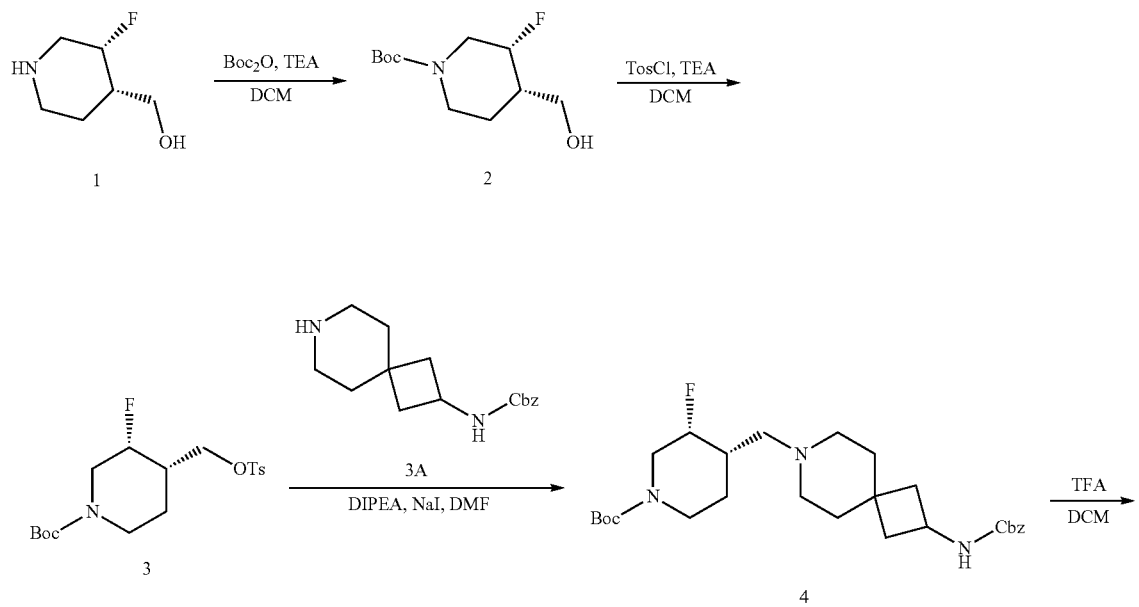

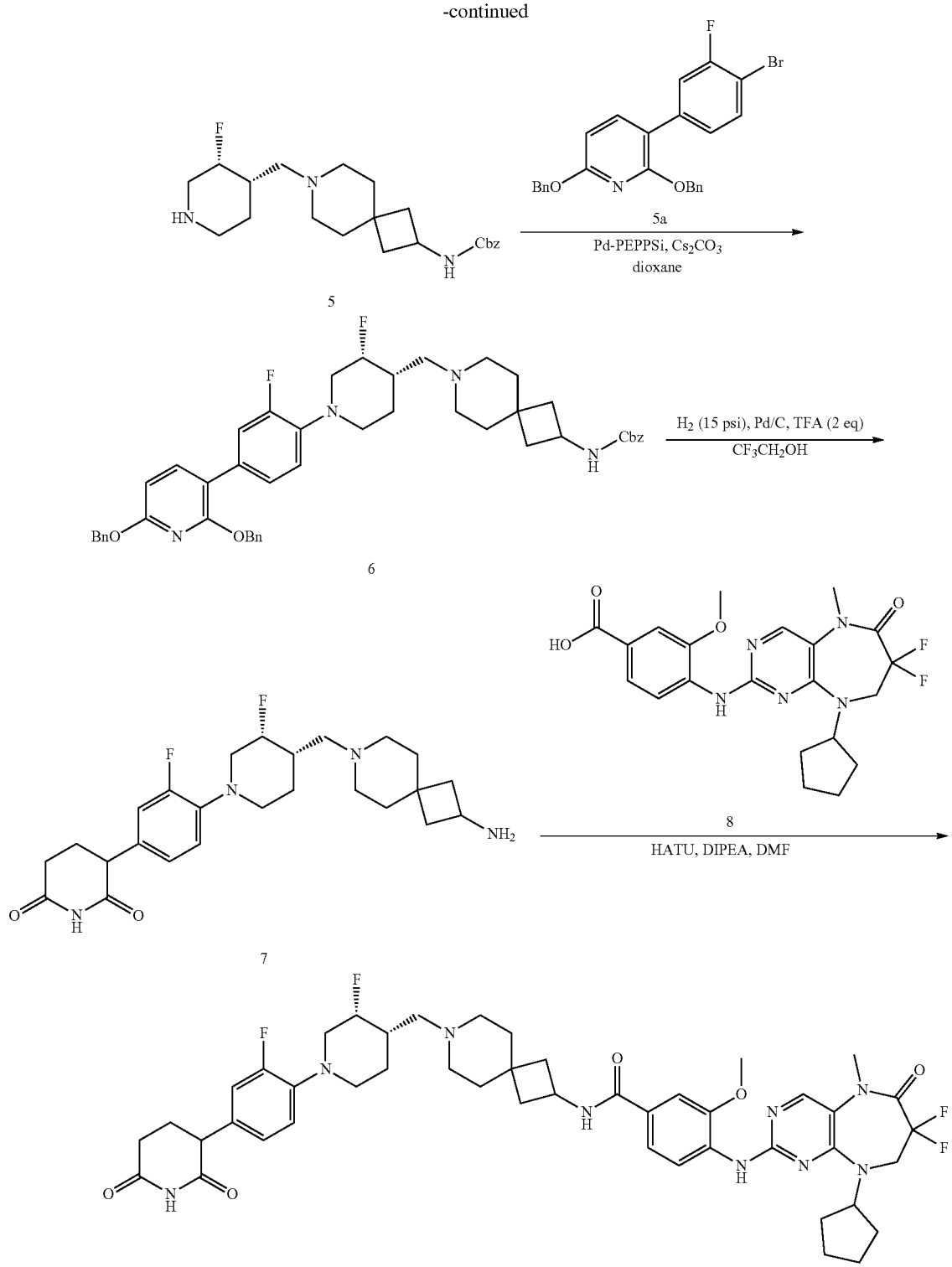
Compound 46
The compound 46 was synthesized by the method described in the scheme similar to the method described in the previous Examples.
MS (M+H)⁺=890.0, ¹H NMR (400 MHz, DMSO-d₆) δ=10.81 (s, 1H), 8.43 (d, J=7.5 Hz, 1H), 8.32-8.23 (m, 2H), 7.96 (s, 1H), 7.56-7.43 (m, 2H), 7.07-6.89 (m, 3H), 4.92-4.71 (m, 2H), 4.47-4.33 (m, 1H), 4.04 (br t, J=14.0 Hz, 2H), 3.94 (s, 3H), 3.79 (dd, J=4.8, 11.7 Hz, 1H), 3.67-3.54 (m, 1H), 3.39-3.34 (m, 1H), 3.33 (br s, 3H), 2.96-2.59 (m, 3H), 2.49-2.11 (m, 11H), 2.02-1.90 (m, 3H), 1.85-1.78 (m, 2H), 1.77-1.67 (m, 2H), 1.67-1.50 (m, 10H).

EXPERIMENTAL EXAMPLES

1. Western Blot Assay for PLK1

(1) Culture of HeLa Cell Line

The HeLa cell line was purchased from Korea Cell Line Bank (KCLB), Seoul, Korea. The passage in cell culture was maintained at P115 to P125.

For cell counting, cell counter (Thermo Fisher Scientific Inc., Catalog #AMQAX1000) and 0.4% trypan blue solution were used.

For cell culture, DMEM (Gibco, Cat. No. 1195-65; Lot. No. 2085318), FBS (Gibco, Cat. No. 16000-044; Lot. No. 2097593), Penicillin/Streptomycin (PS) (Gibco, Cat. No. 15140-122; Lot. No. 2058855), 100 mm$^2$ cell culture dish (SPL, Cat. No. 20100), 150 mm$^2$ cell culture dish (SPL, Cat. No. 20150), 12-well culture plate (SPL, Cat. No. 30012), PBS pH 7.4 (Gibco, Cat. No. 10010-023; Lot. No. 2085080), TrypLE™ Express (Gibco, Cat. No. 12605-010; Lot No. 2070638), Counting Chamber (Hematocytometer) (Hirschmann, Cat. No. 8100204), and 0.4% Trypan Blue Solution (DYNEBIO, Cat. No. CBT3710; Lot. No. 20190723) were used.

(2) Treatment of Compounds of the Present Invention $2 \times 10^5$ cells were seeded for each well of a 12-well plate (SPL), and the cells were cultured in the culture medium in a total volume of 2 mL.

The compounds of Examples were completely dissolved in DMSO and used in the experiment, and thymidine was completely dissolved in DW and used in the experiment. For thymidine block, the products were treated with 2 mM of thymidine (Sigma-Aldrich Cat. No. T9250-5G) and then incubated for 24 hours.

For release and chemical treatment, the medium was suctioned and washed 3 times with 1×PBS. Complete media was added, followed by incubation for 4 hours in a $CO_2$ incubator. Each compound was diluted three folds from the highest concentration of 3 μM to the lowest concentration and then incubated for 6 hours again.

(3) Western Blotting

For SDS-PAGE and Western blotting, 1×RIPA lysis buffer (Rockland, Cat. No. MB-030-0050; Lot no. 39751), 100☐ Protease Inhibitor Cocktail (Quartett, Cat. No. PPI1015; Lot no. PC050038424), Pierce™ BCA protein assay kit (ThermoScientific, Cat. No. 23225; Lot no. UC276876), albumin standard (ThermoScientific, Cat. No. 23209; Lot no. UB269561), 4-15% Mini-PROTEAN TGX stain-free gel (Bio-rad, Cat. No. 4568085; Lot no. L007041B), 100 Tris/Glycine/SDS buffer (Bio-rad, Cat. No. 1610732; Lot no. 10000044375B); 100 TBS (Bio-rad, Cat. No. 1706435; Lot no. 1000045140B), 10% Tween 20 (Cat. No. 1610781; Lot no. L004152B), Color protein standard broad range (NEB, Cat. No. P7719S; Lot no. 10040349), 40 Laemmli sample buffer (Bio-rad, Cat. No. 1610747; Lot no. L004133B), β-mercaptoethanol (Sigma-Aldrich, Cat. No. M3148; Lot no. 60-24-2), SuperBlock™ T20 (TBS) blocking buffer (ThermoScientific, Cat. No. 37536; Lot no. UC282578), 1 M sodium azide solution (Sigma-Aldrich, Cat. No. 08591-1 mL-F; Lot no. BCBV4989), α-Rabbit pAb to Ms IgG (abcam, Cat. No. ab97046; Lot no. GR3252115-1), α-Goat pAb to Rb IgG (CST, Cat. No. 7074S; Lot no. 28), α-GAPDH (abcam, Cat. No. ab8245; Lot no. GR3275542-2), α-PLK1 (CST, Cat. No. 208G4), α-BRD4 (CST, Cat. No. 13440S), ECL™ Prime western blotting reagents (GE Healthcare, Cat. No. RPN2232; Lot no. 17001655), Ponceau S solution (Sigma-Aldrich, Cat. No. P7170; Lot no. SLBV4112), Difco™ Skim milk (BD, Cat. No. 232100; Lot no. 8346795), and iBlot 2 NC Regular stacks (Invitrogen, Cat. No. IB23001; Lot no. 2NR110619-02) were used.

For cell harvesting, the cells were first separated from the plate using trypsin and then washed with the medium and PBS. Specifically, the medium was suctioned off and washed with 1 mL of PBS, and PBS was suctioned off. The cells were treated with 0.5 mL TrypLE™ Express at 37° C. minutes to separate the cells, and then 0.5 mL of complete medium was added to collect 1 mL of cell culture solution. Then, 1 mL of the cell collection solution was centrifuged at 8,000 rpm for 120 seconds, and the supernatant was removed. After washing with 0.2 mL of PBS, the PBS was removed.

For cell lysis, a lysis buffer was added and cell debris was removed to obtain a cell lysate. Specifically, the cells were treated with 70 μL of 1×RIPA buffer containing a protease inhibitor and incubated for 30 minutes on ice. Then, the cells were centrifuged at 4° C. 5,000 rpm for 10 minutes to obtain a cell lysate.

Then, a standard curve was obtained using the BCA assay, and the protein mass in the lysate was quantified by substituting the curve equation. The mixture was incubated at 37° C. 30 minutes using 20 μL of standard or sample solution, and 200 μL of BCA or Bradford solution, and measured at 562 nm absorbance. Samples were prepared by adding 4× sample buffer so that the quantity of protein added to each well was 15 pg.

Sodium dodecyl sulfate polyacrylamide gel electrophoresis (SDS-PAGE) was performed by setting a running time of 100 minutes at 120 V on a 4-15% Mini-PROTEAN TGX stain-free gel (15 well). Transferring was performed on iBlot 2 NC Mini stacks at PO mode of the dry blotting system. After staining using Ponceau S solution, blocking was performed for 1 hour with a blocking buffer (Thermo). After washing with 1×TBS containing 0.05% Tween 20, the product was reacted at 4° C. or 16 hours with anti-PLK1 (CST) antibody (1:500), anti-BRD4 (Cell signaling) antibody (1:1000) or anti-GAPDH (abcam) antibody (1:10,000) in IX TBS-T as a primary antibody. After washing three times for 10 minutes with 1×TBS containing 0.05% Tween20, the product was reacted at room temperature for 1 hour with anti-mouse antibody (abcam) (1:10000) or anti-rabbit antibody (CST) (1:5000) in 1×TBS-T as a secondary antibody. Then, after washing three times for 10 minutes with 1×TBS containing 0.05% Tween 20, the product was detected with an ECL working solution (1:1).

To analyze the results, an image analyzer (GE) was used to obtain final blot data. As a result, it was confirmed that all of the compounds of the present invention degraded PLK1 protein significantly.

2. Luciferase Assay for PLK1

(1) Preparation and Culture of HeLa LgBit (Plk1-HiBit KI) Cell Line

A HeLa cell line in which the LgBit vector was transfected and expressed stably was prepared. Then, after constructing gRNA and donor to express the HiBit amino acid sequence behind the C-terminal of the Plk1 gene, which was inherent in the cell, it was inserted into the cell together with a vector capable of expressing CRISPR/Cas9. Only the cells in which the insertion was completed and knock-in had progressed were selected, sub-cultured and used.

For cell culture, DMEM (Gibco, Cat. No. 11995-065; Lot. No. 2467189), FBS (Gibco, Cat. No. 16000-044; Lot. No. 2420173P), Penicillin/Streptomycin (PS)(Gibco, Cat. No. 15140-122; Lot. No. 2321114), 100 mm$^2$ cell culture dish (SPL, Cat. No. 20100), 150 mm$^2$ cell culture dish (SPL, Cat. No. 20150), 96-well culture plate (SPL, Cat. No. 30196), PBS pH 7.4 (Gibco, Cat. No. 10010-023; Lot. No. 2085080), TrypLE™ Express (Gibco, Cat. No. 12605-010; Lot. No. 2323417), Counting Chamber (Hematocytometer)(Marienfeld Superior, Cat. No. 0650010) and 0.4% Trypan Blue Solution (DYNEBIO, Cat. No. CBT3710; Lot. No. 20211201) were used.

(2) Treatment of Compounds of the Present Invention and Method of Luciferase Assay The compounds of Examples were completely dissolved in DMSO (Sigma-Aldrich Cat. No. D2438, Lot. No. RNBJ9566) and used in the experiment.

In the case of HeLa LgBit (Plk1-HiBit KI), the compounds were treated after being released after thymidine block, and the process was as follows. Thymidine (Sigma-Aldrich Cat. No. T9250-5G) was completely dissolved in DW and used in the experiment. For thymidine block, the products were treated with 2 mM of thymidine and then incubated for 24 hours. For release and chemical treatment, the medium was suctioned and washed with 1×PBS. TrypLE™ was added and incubated in 37° C. $CO_2$ incubator for 5 min. Cells neutralized by adding complete media were counted through a counter. For each well of a 96-well culture plate (SPL), $3.3 \times 10^4$ cells and a total medium volume of 150 μL were seeded and incubated in a $CO_2$ incubator.

Each cell line was incubated in a $CO_2$ incubator for 18 hours, and Endurazine was added to each well to make up 4% of the total volume. After adding the compound of the present invention in a 96-well white plate (SPL) to a concentration of 300 nM, the wavelength of the plate reader (BMG Labtech, CLARIOstar Plus) was set to 470-480 nM, and then the luminescence was tracked in real time. After 9 hours, the luminescence value was obtained and displayed as a bar graph through an Excel program.

The results are shown in Table 2 below and FIG. 1.

TABLE 2

| Examplary Compound | Activity |
| --- | --- |
| Compound 1 | ++ |
| Compound 2 | ++ |
| Compound 3 | ++ |
| Compound 4 | +++ |
| Compound 5 | ++ |
| Compound 6 | ++ |
| Compound 7 | +++ |
| Compound 8 | +++ |
| Compound 10 | +++ |
| Compound 11 | +++ |
| Compound 12 | +++ |
| Compound 13 | ++ |
| Compound 14 | ++ |
| Compound 15 | +++ |
| Compound 16 | +++ |
| Compound 17 | +++ |
| Compound 18 | ++ |
| Compound 19 | +++ |
| Compound 20 | +++ |
| Compound 21 | +++ |
| Compound 22 | +++ |
| Compound 23 | +++ |
| Compound 24 | +++ |
| Compound 25 | +++ |
| Compound 26 | ++ |
| Compound 27 | ++ |
| Compound 32 | ++ |
| Compound 33 | + |
| Compound 34 | ++ |
| Compound 35 | ++ |
| Compound 36 | ++ |
| Compound 37 | ++ |
| Compound 39 | ++ |
| Compound 41 | ++ |

TABLE 2-continued

| Examplary Compound | Activity |
| --- | --- |
| Compound 42 | +++ |
| Compound 43 | ++ |
| Compound 44 | ++ |
| Compound 45 | ++ |
| Compound 46 | +++ |

In Table 2, Activity represents the ratio of the luminescence value of each Exemplary Compound treatment group to DMSO treatment group (+++: <0.3, ++<0.6, +<0.7).

3. Cell Viability Assay for H526 Cell Line (1) Culture of NCI-H526 Cell Line

The NCI-H526 (hereafter H526) cell line was purchased from Korea Cell Line Bank (KCLB, Seoul, Korea). For cell culture, RPMI 1640 (Gibco, Cat. No. 22400-089; Lot. No. 2277021), FBS (Gibco, Cat. No. 16000-044; Lot. No. 2351176P), Penicillin/Streptomycin (PS)(Gibco, Cat. No. 15140-122; Lot. No. 2321114), 75T cell culture flask (SPL, Cat. No. 71075), 175T cell culture flask (SPL, Cat. No. 71175), 96-well cell culture plate (SPL, Cat. No. 30096), PBS pH 7.4 (Gibco, Cat. No. 10010-023; Lot. No. 2085080), TrypLE™ Express (Gibco, Cat. No. 12605-010; Lot. No. 2323417), Counting Chamber (Hematocytometer)(Marienfeld Superior, Cat. No. 0650010), and 0.4% Trypan Blue Solution (DYNEBIO, Cat. No. CBT3710; Lot. No. 20211201) were used.

(2) Treatment of Compounds of the Present Invention and Method of Cell Viability Assay The compounds of Examples were completely dissolved in DMSO (Sigma-Aldrich Cat. No. D2438, Lot. No. RNBJ9566) and used in the experiment.

$3 \times 10^4$ cells were seeded for each well of a 96-well plate (SPL), and the cells were cultured in total volume of 150 μL.

Each compound was diluted 3-folds from the highest concentration of 3000 nM to the lowest concentration of 0.46 nM. After treating the compound to each well to make the total volume of 200 μL, it was cultured in a $CO_2$ incubator (Thermo Fisher Science, Cat. No. 4111) for 5 days.

Then, after treating EZ-Cytox (DOGEN, Cat. NO. EZ-3000, Lot. No. DLS2109) 20 μL in each well, it was cultured in $CO_2$ incubator for 4 hours. The absorbance of the completely cultured sample was measured by setting the wavelength of a plate reader (BMG Labtech, CLARIOstar Plus) to 450 nM, and was measured after shaking for 3 minutes in a plate reader before measurement. The final measured value was arranged with Excel program, a graph was displayed through Prism-GraphPad program, and the $IC_{50}$ value was measured.

The results are shown in Table 3 below.

Cell Viability Assay for H526 cell line

TABLE 3

| Examplary Compound | Activity |
| --- | --- |
| Compound 1 | B |
| Compound 2 | B |
| Compound 3 | C |
| Compound 4 | B |
| Compound 5 | A |
| Compound 6 | A |
| Compound 7 | A |
| Compound 8 | A |
| Compound 10 | B |
| Compound 11 | A |

TABLE 3-continued

| Examplary Compound | Activity |
| --- | --- |
| Compound 12 | A |
| Compound 13 | B |
| Compound 14 | C |
| Compound 15 | A |
| Compound 16 | A |
| Compound 17 | D |
| Compound 18 | A |
| Compound 19 | A |
| Compound 20 | B |
| Compound 21 | B |
| Compound 22 | A |
| Compound 23 | A |
| Compound 24 | B |
| Compound 25 | A |
| Compound 26 | B |
| Compound 27 | A |
| Compound 32 | A |
| Compound 33 | A |
| Compound 34 | A |
| Compound 35 | B |
| Compound 36 | A |
| Compound 37 | B |
| Compound 39 | A |
| Compound 41 | A |
| Compound 42 | A |
| Compound 43 | B |
| Compound 44 | A |
| Compound 45 | A |

In Table 3, Activity represents $IC_{50}$ value of each Exemplary Compound treatment group to H526 cell line (A: <30 nM, B: <50 nM, C: <100 nM, D: <200 nM, E: <400 nM).

4. Cell Viability Assay for MRC-5 Cell Line (1) Culture of MRC-5 Cell Line

The MRC-5 cell line was purchased from Korea Cell Line Bank (KCLB), Seoul, Korea. Passage of cultured cells was maintained within P15.

For cell culture, MEM/EBSS (Hyclone, Cat. No. SH30024.01; Lot. No. AG29697698), FBS (Gibco, Cat. No. 16000-044; Lot. No. 2234018P), Penicillin/Streptomycin (PSXGibco, Cat. No. 15140-122; Lot. No. 2211099), 175T cell culture flask (SPL, Cat. No. 71175), 96-well cell culture plate (SPL, Cat. No. 30096), PBS pH 7.4 (Gibco, Cat. No. 10010-023; Lot. No. 2085080), TrypLE™ Express (Gibco, Cat. No. 12605-010; Lot. No. 2070638), Counting Chamber (Hematocytometer)(Hirschmann, Cat. No. 8100204), and 0.4% Trypan Blue Solution (DYNEBIO, Cat. No. CBT3710; Lot. No. 20190723) were used.

(2) Treatment of Compounds of the Present Invention

MRC-5 cell line cultured in 175T cell culture flask was isolated using TrypLE™ Express. $6\times10^3$ cells were seeded for each well of a 96-well plate (SPL), and the cells were cultured in total volume of 150 μL.

The compounds of Examples were completely dissolved in DMSO (Sigma-Aldrich, Cat. No. D2438-50ML, Lot. No. RNBK6387) and used in the experiment. Each compound was diluted 3-folds from the highest concentration of 10000 nM to the lowest concentration of 1.52 nM. Each well was mixed with a medium and treated, and the volume was set to 50 μL, so that the total volume of each well was 200 μL. Then, it was cultured in 37° C. $CO_2$ incubator (Thermo Fisher Science, Cat. No. 4111, Lot. No. 300512709) for 5 days.

The following compounds were used as comparative examples, and the cell viability assay was performed in the same manner as in the compounds of Examples.

Comparative Example 1. Exemplary compound described in Mu et al. *BBRC*, 2020, 521(4): 833 (Comparative compound 1)

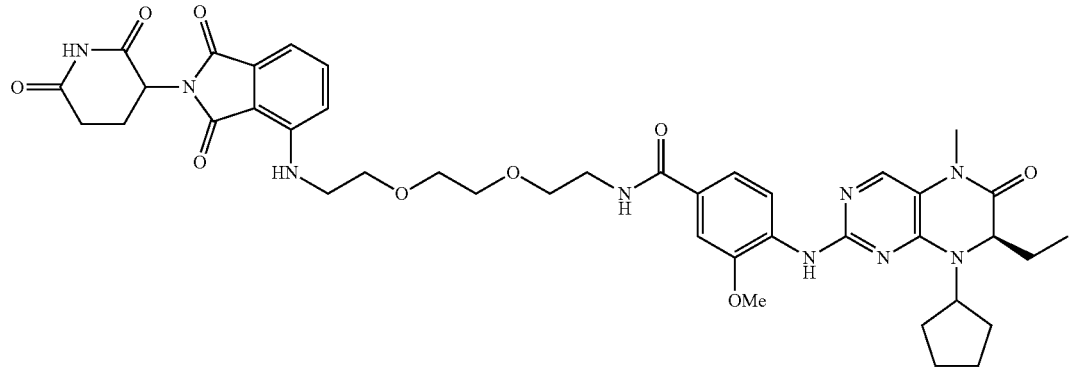 [SMILES: CC[C@@H]1C(=O)N(C)c2cnc(Nc3ccc(C(=O)NCCOCCOCCNc4cccc5c4C(=O)N(C4CCC(=O)NC4=O)C5=O)cc3OC)nc2N1C1CCCC1]

Comparative Example 2. BI2536 (Comparative compound 2)

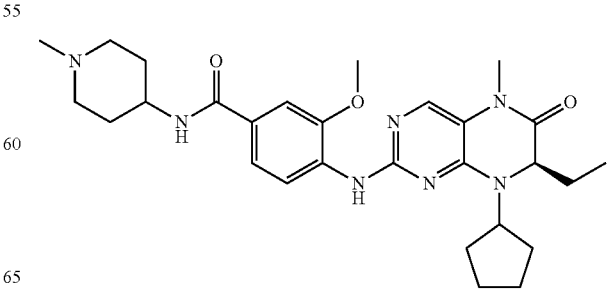

Comparative Example 3. Volasertib (Comparative compound 3)

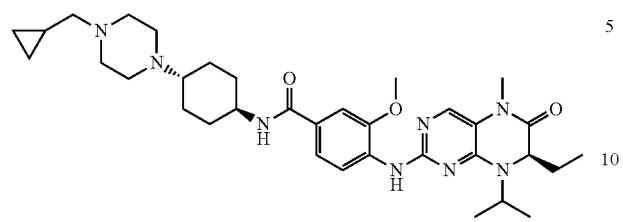

Comparative Example 4. TAK960 (Comparative compound 4)

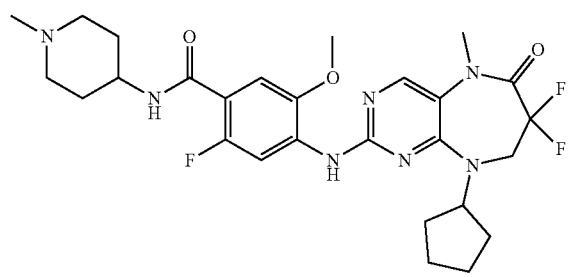 [SMILES: COc1cc(C(=O)NC2CCN(C)CC2)c(F)cc1Nc1ncc2c(n1)N(C1CCCC1)CC(F)(F)C(=O)N2C]

(3) Cytotoxicity Experiment

After treating EZ-Cytox (DOGEN, Cat. NO. EZ-3000, Lot. No. DLS2112) 20 μL in each well of completely cultured plate, it was cultured in 37° C. $CO_2$ incubator for 4 hours. The 96-well plate was placed in a plate reader (BMG Labtech, Clariostar Plus), mixed for 2 minutes, and absorbance was measured at 450 nM wavelength. The data were converted into graphs using the Prism (ver.9) program.

The results are shown in Table 4 and Table 5 below.

Cell Viability Assay for MRC-5 cell line

TABLE 4

| Exemplary Compound | Activity |
| --- | --- |
| Compound 1 | 25557 |
| Compound 2 | N.D. |
| Compound 3 | N.D. |
| Compound 4 | N.D. |
| Compound 5 | N.D. |
| Compound 6 | N.D. |

TABLE 4-continued

| Exemplary Compound | Activity |
| --- | --- |
| Compound 7 | N.D. |
| Compound 8 | N.D. |
| Compound 10 | N.D. |
| Compound 11 | N.D. |
| Compound 12 | 20028 |
| Compound 13 | N.D. |
| Compound 14 | N.D. |
| Compound 15 | N.D. |
| Compound 16 | 9119 |
| Compound 19 | N.D. |
| Compound 20 | N.D. |
| Compound 21 | N.D. |
| Compound 22 | N.D. |
| Compound 24 | N.D. |
| Compound 25 | N.D. |
| Compound 26 | 5590 |
| Compound 27 | N.D. |
| Compound 32 | N.D. |
| Compound 33 | N.D. |
| Compound 35 | N.D. |
| Compound 36 | N.D. |
| Compound 37 | N.D. |
| Compound 39 | N.D. |
| Compound 45 | 8675 |

In Table 4, Activity represents $IC_{50}$ value (nM) of each Exemplary Compound treatment group to MRC-5 cell line. N.D. (not determined) means that cytotoxicity did not appear until 10 M. As a result, it was confirmed that all of the compounds of the present invention specifically exhibited a high level of cytotoxicity in cancer cell lines rather than normal cell lines. Cell Viability Assay for MRC-5 cell line

TABLE 5

| Comparative Compound | Activity |
| --- | --- |
| Comparative Compound 1 | 106.6 |
| Comparative Compound 2 | 3085.4 |
| Comparative Compound 3 | 2939.3 |
| Comparative Compound 4 | 9152.5 |

In Table 5, Activity represents $IC_{50}$ value (nM) of each Comparative Compound treatment group to MRC-5 cell line. In particular, it was found that Comparative Compound 1, a known PROTAC compound, exhibited a high level of cytotoxicity in normal cell line, unlike the Exemplary Compounds of the present invention.

The invention claimed is:

1. A compound represented by the following Formula I:

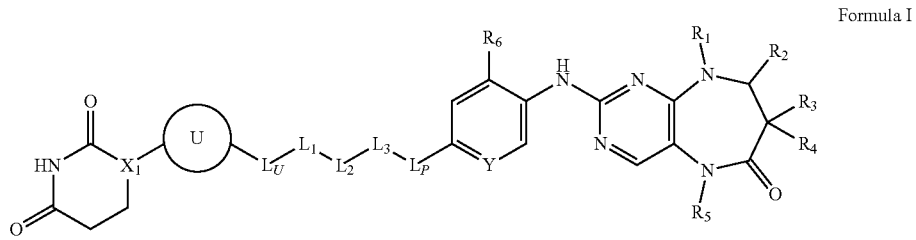

Formula I or a pharmaceutically acceptable salt or stereoisomer thereof,
wherein:
X₁ is CH or N;
ring U is phenylene or 5- or 6-membered heteroarylene, wherein the phenylene or 5- or 6-membered heteroarylene is optionally substituted with one or more independently selected $R_U$ substituents;
each $R_U$ is independently halo, $C_{1-4}$ alkyl, $C_{1-4}$ haloalkyl, $C_{1-4}$ aminoalkyl, $C_{1-4}$ hydroxyalkyl, or $OC_{1-4}$ alkyl;
$L_U$ is a bond, —(CH₂)$_x$—, —(CH₂)$_x$NH—, —(CH₂)$_x$O—, —C(O)—, or phenylene;
$L_1$ is a bond or heterocycloalkylene;
  wherein the heterocycloalkylene contains at least one nitrogen ring heteroatom; and
  wherein the heterocycloalkylene is optionally substituted with one or more substituents independently selected from halo, $C_{1-4}$ alkyl, $C_{1-4}$ haloalkyl, OH, $OC_{1-4}$ alkyl, or =O;
$L_2$ is a bond, —(CH₂)$_{y1}$—, —(CD₂)$_{y1}$-, —(CH₂)$_{y2}$—C(O)—(CH₂)$_{y3}$—, —(CH₂)$_{y2}$—NH—(CH₂)$_{y3}$—, —(CH₂)$_{y2}$—N(C$_{1-4}$ alkyl)-(CH₂)$_{y3}$—, or —(CH₂)$_{y1}$—(OC$_{1-4}$ alkylene)$_z$-OC$_{1-4}$ alkylene-;
$L_3$ is a bond, cycloalkylene, or heterocycloalkylene;
  wherein the heterocycloalkylene contains at least one nitrogen ring heteroatom; and
  wherein the cycloalkylene or heterocycloalkylene is optionally substituted with one or more substituents independently selected from halo, $C_{1-4}$ alkyl, or $C_{1-4}$ haloalkyl:
$L_P$ is —(CH₂)$_p$—NH—C(O)— or —(CH₂)$_p$—O—, wherein the —C(O)— or —O— of $L_P$ is bonded to the phenyl ring bearing $R_6$;
p is 0, 1, or 2;
x is 0, 1, 2, 3, or 4;
$y_1$ is 0, 1, 2, 3, 4, 5, or 6;
$y_2$ is 0, 1, 2, 3, 4, 5, or 6;
$y_3$ is 0, 1, 2, 3, 4, 5, or 6;
z is 0, 1, 2, 3, 4, 5, or 6;
Y is CR₇;
$R_6$ is halo, $C_{1-4}$ alkyl, or $OC_{1-4}$ alkyl;
$R_7$ is H or halo;
$R_1$ is 3- to 7-membered cycloalkyl;
$R_2$ is H or $C_{1-4}$ alkyl;
$R_3$ is H, halo, or $C_{1-4}$ alkyl;
$R_4$ is H, halo, or $C_{1-4}$ alkyl; and
$R_5$ is $C_{1-4}$ alkyl.

2. The compound according to claim 1, or a pharmaceutically acceptable salt or stereoisomer thereof, wherein:
ring U is phenylene, pyrazolylene, pyridinylene, or pyrimidinylene, wherein the phenylene, pyrazolylene, pyridinylene, or pyrimidinylene is optionally substituted with one or more independently selected $R_U$ substituents; and
each $R_U$ is independently halo, $C_{1-4}$ alkyl, $C_{1-4}$ haloalkyl, or $OC_{1-4}$ alkyl.

3. The compound according to claim 1, or a pharmaceutically acceptable salt or stereoisomer thereof, wherein:

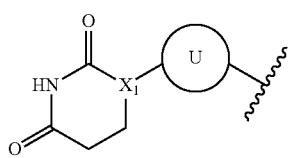

is:

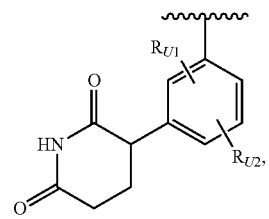

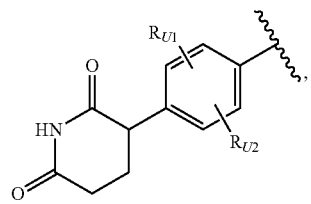

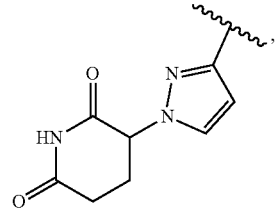 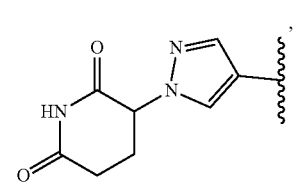

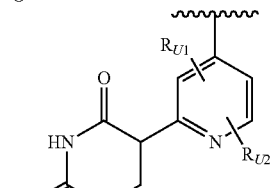 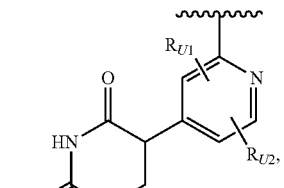

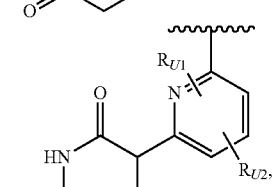 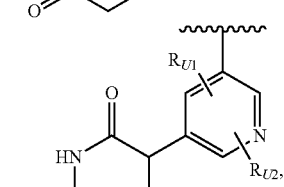

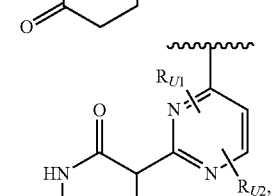 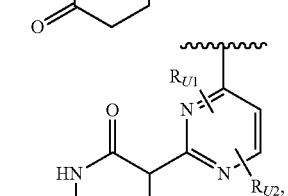

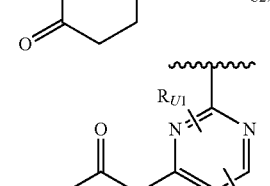 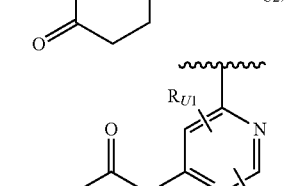

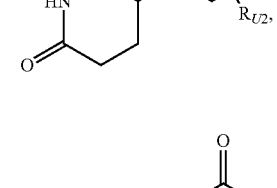 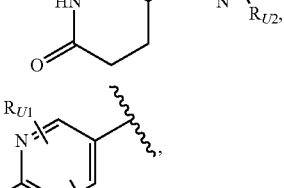

-continued
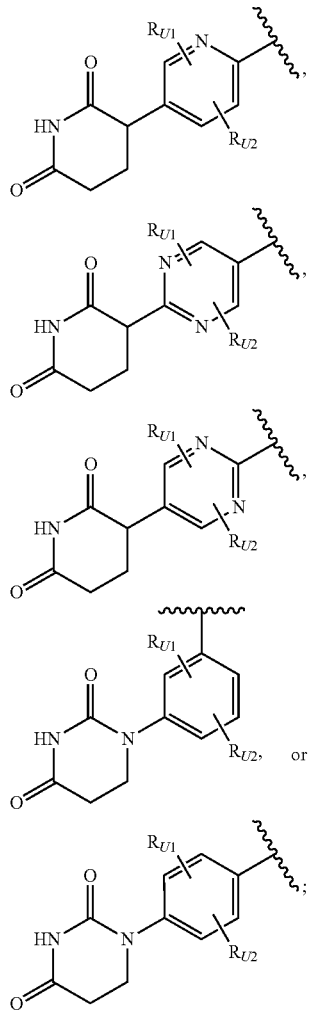
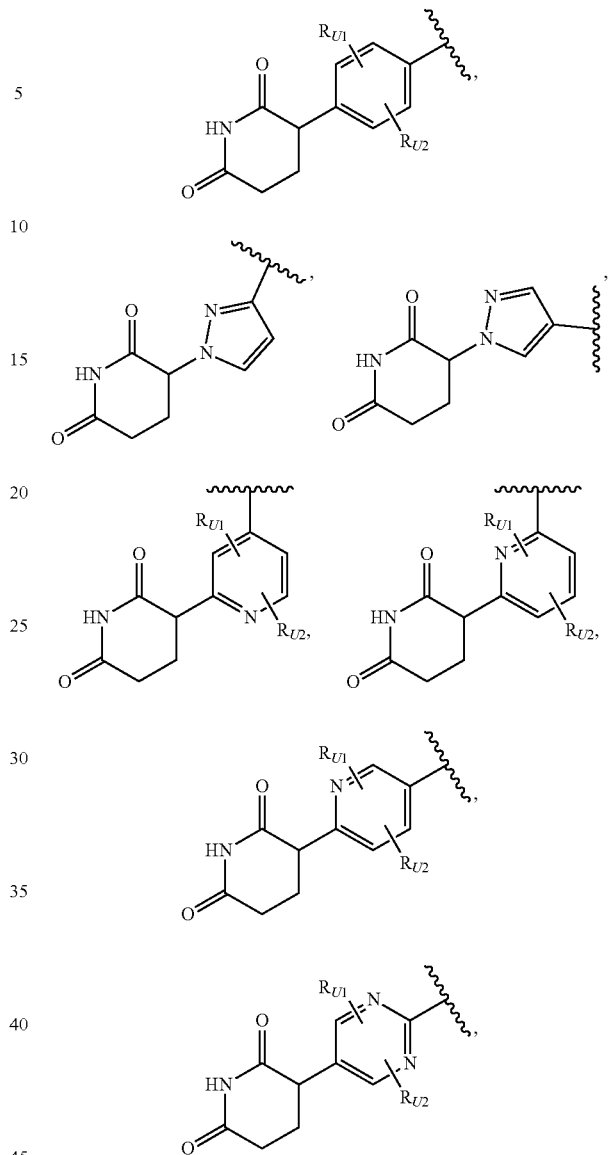
$R_{U1}$ is halo, $C_{1-4}$ alkyl, $C_{1-4}$ haloalkyl, or $OC_{1-4}$ alkyl; and
$R_{U2}$ is halo, $C_{1-4}$ alkyl, $C_{1-4}$ haloalkyl, or $OC_{1-4}$ alkyl.
4. The compound according to claim 3, or a pharmaceutically acceptable salt or stereoisomer thereof, wherein:
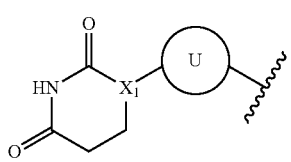
is:
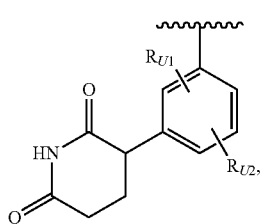
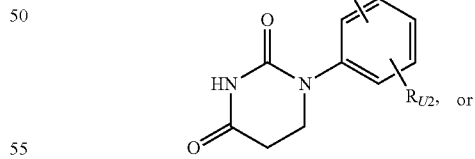
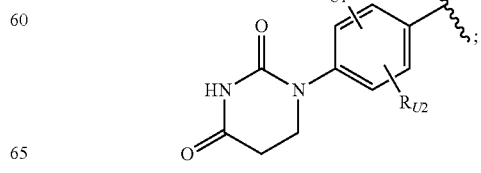

$R_{U1}$ is halo, $C_{1-4}$ alkyl, $C_{1-4}$ haloalkyl, or $OC_{1-4}$ alkyl; and
$R_{U2}$ is halo, $C_{1-4}$ alkyl, $C_{1-4}$ haloalkyl, or $OC_{1-4}$ alkyl.
5. The compound according to claim 1, or a pharmaceutically acceptable salt or stereoisomer thereof, wherein:
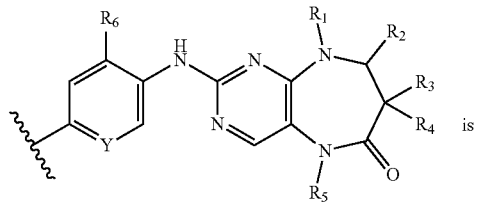
is
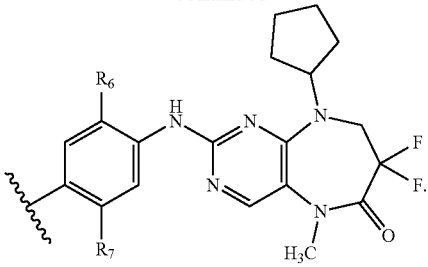
6. The compound according to claim 1, or a stereoisomer thereof, wherein the compound, or stereoisomer thereof, is selected from:
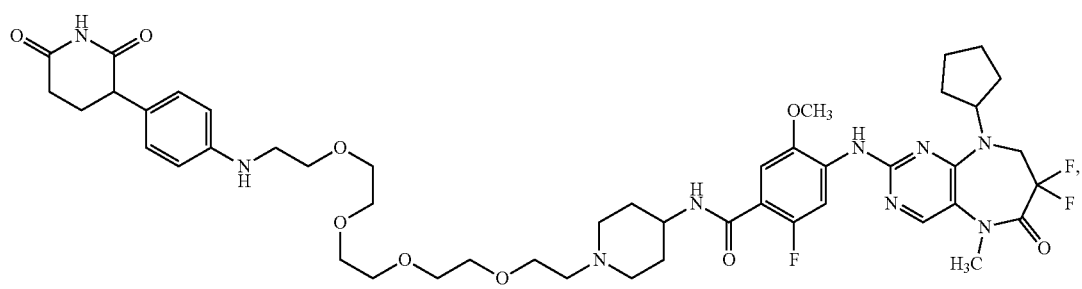
1
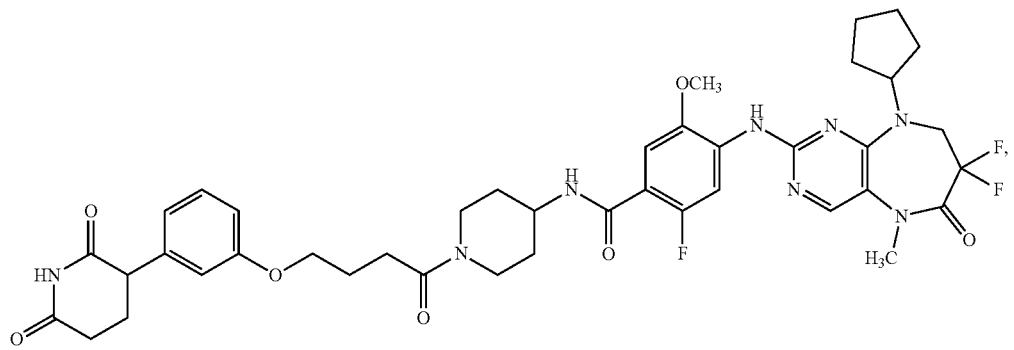
2
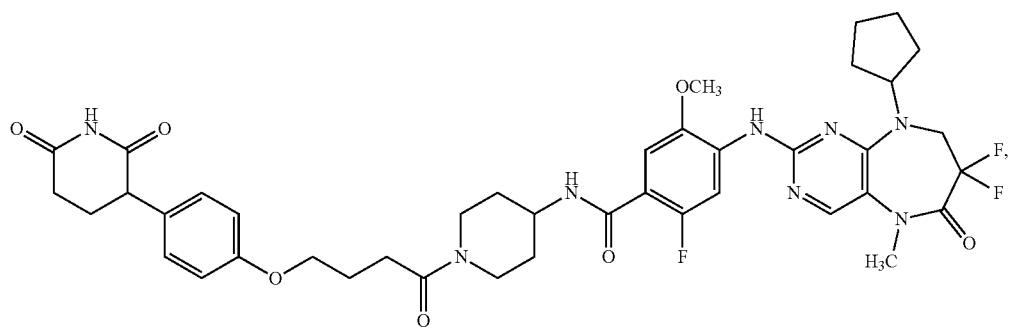
3

-continued
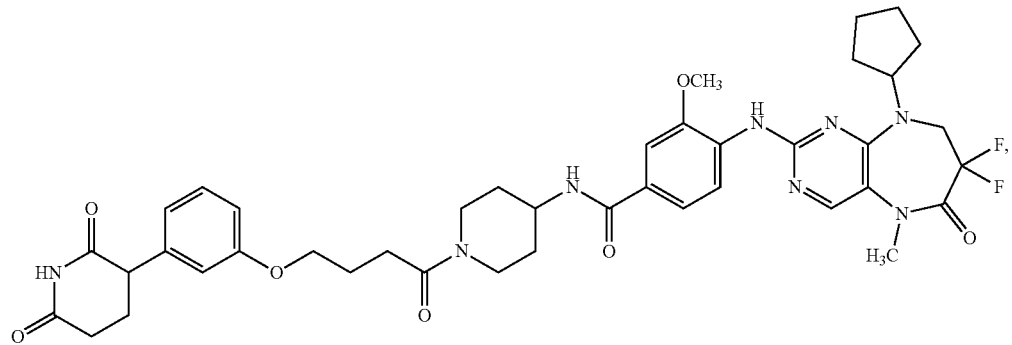
4
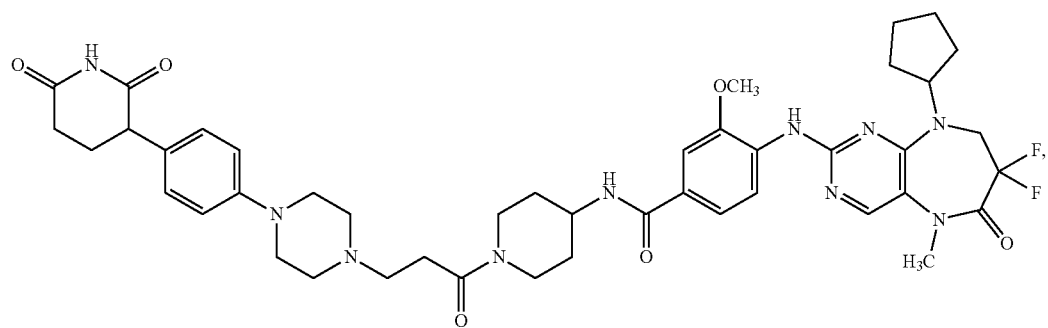
5
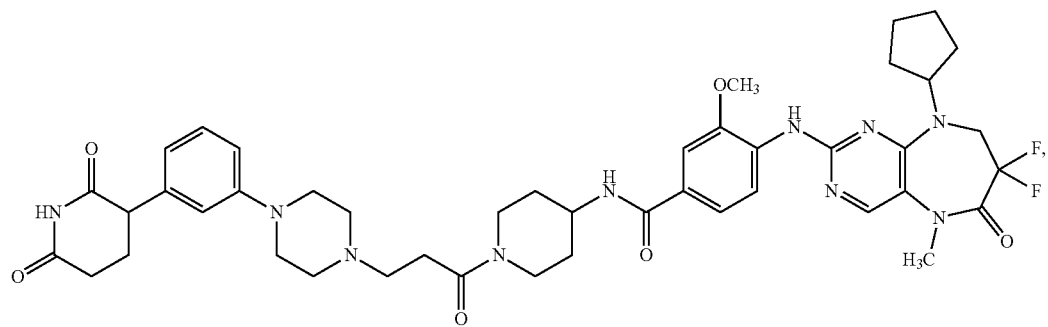
6
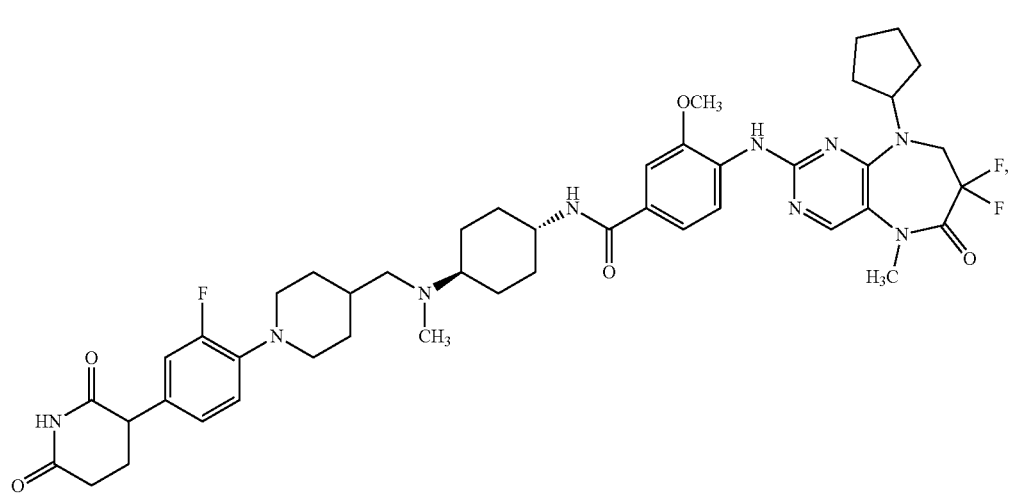
7

8
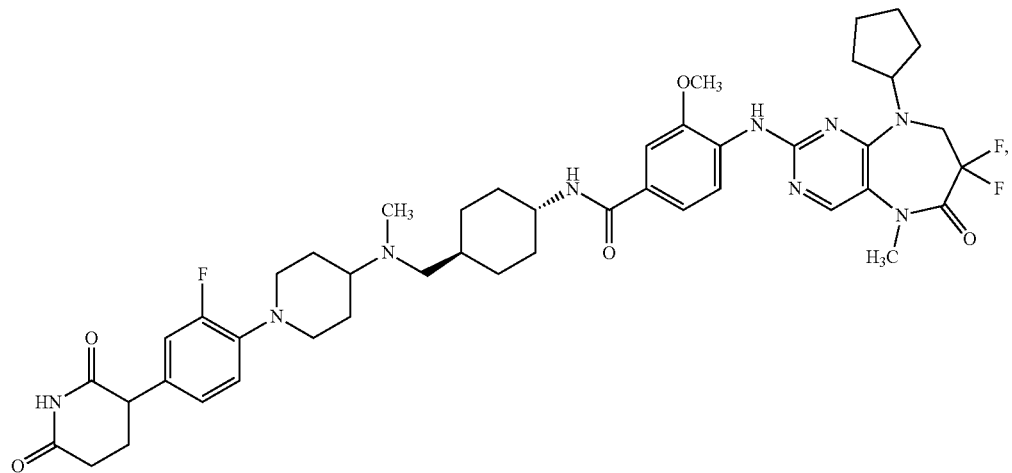
9
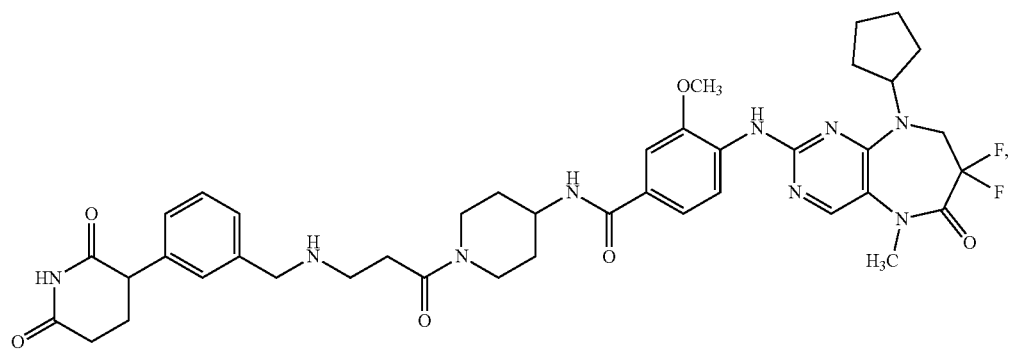
10
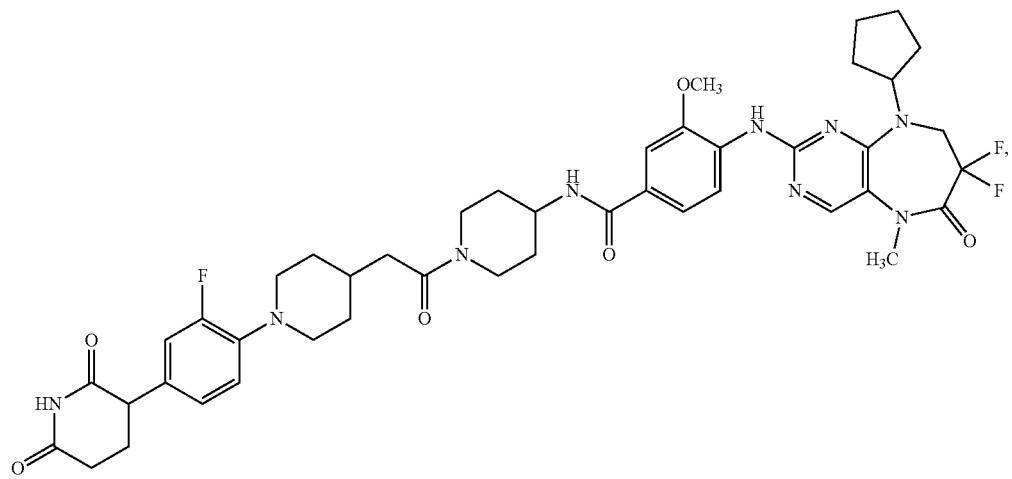
11
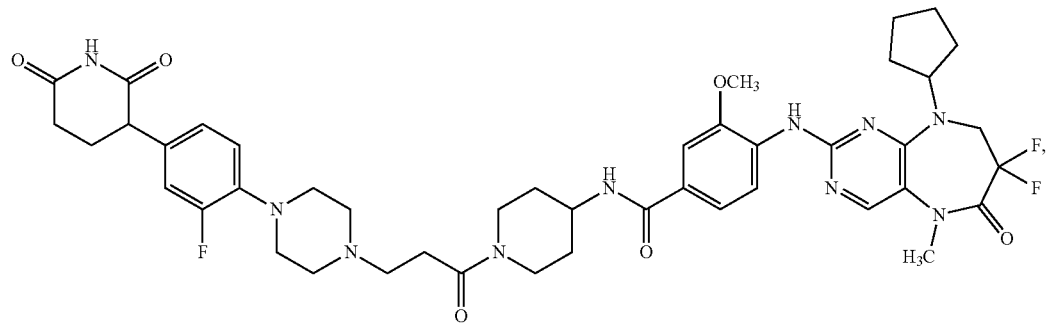

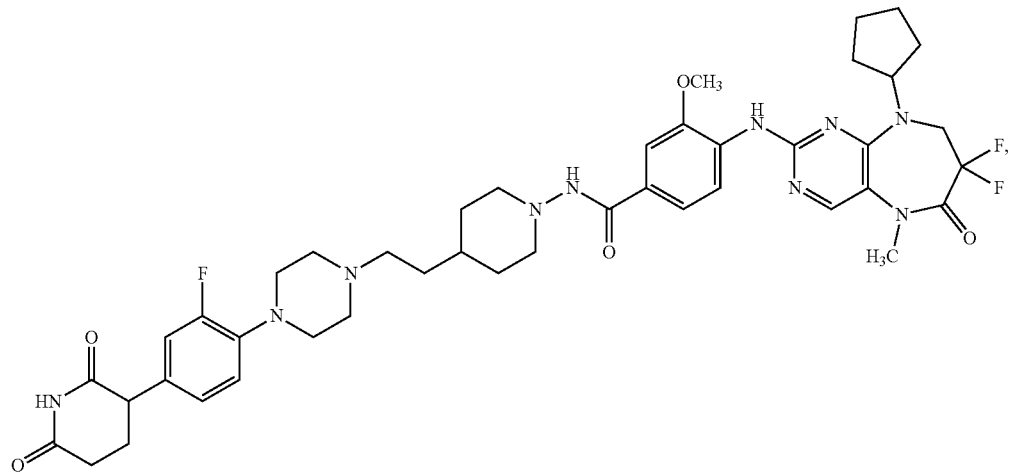
12
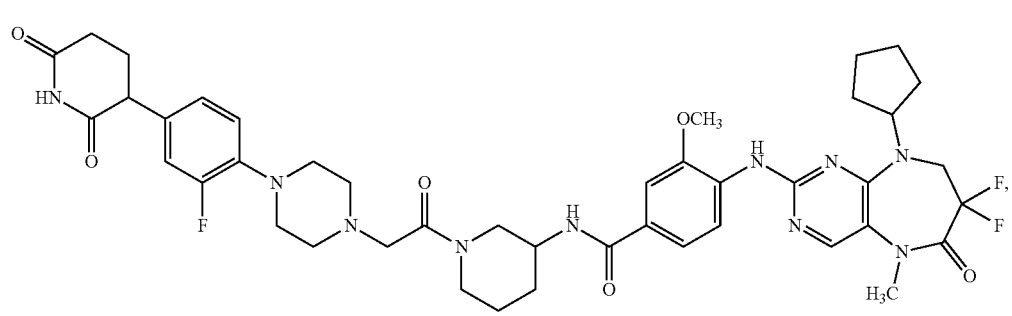
13
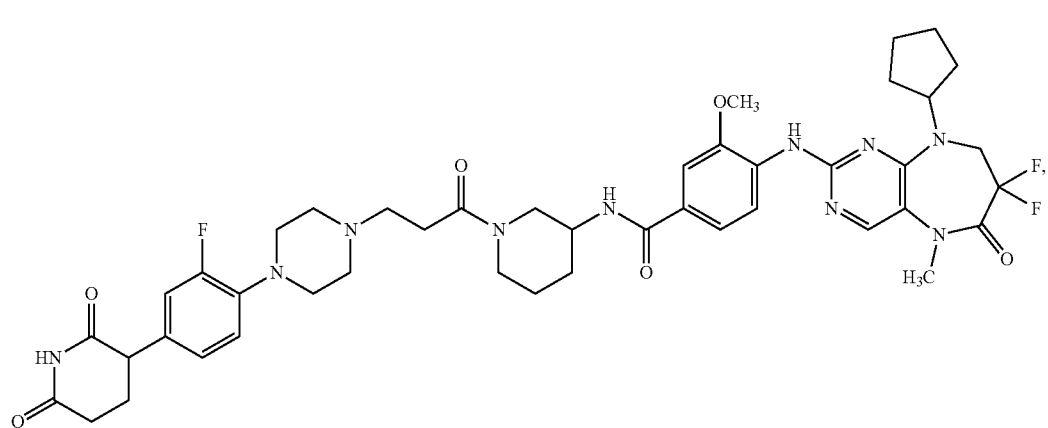
14
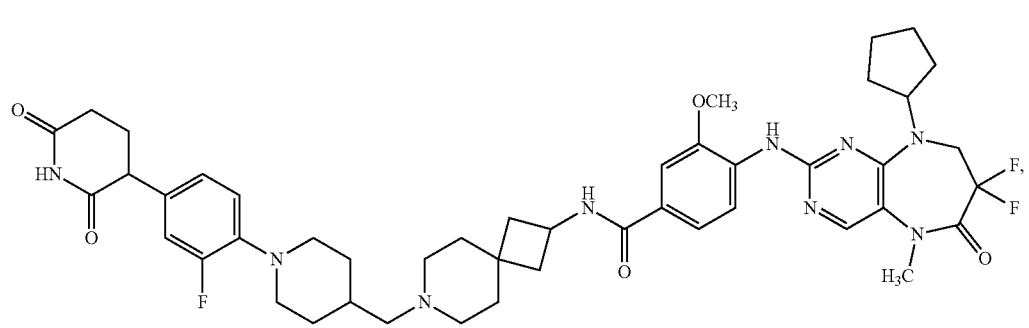
15

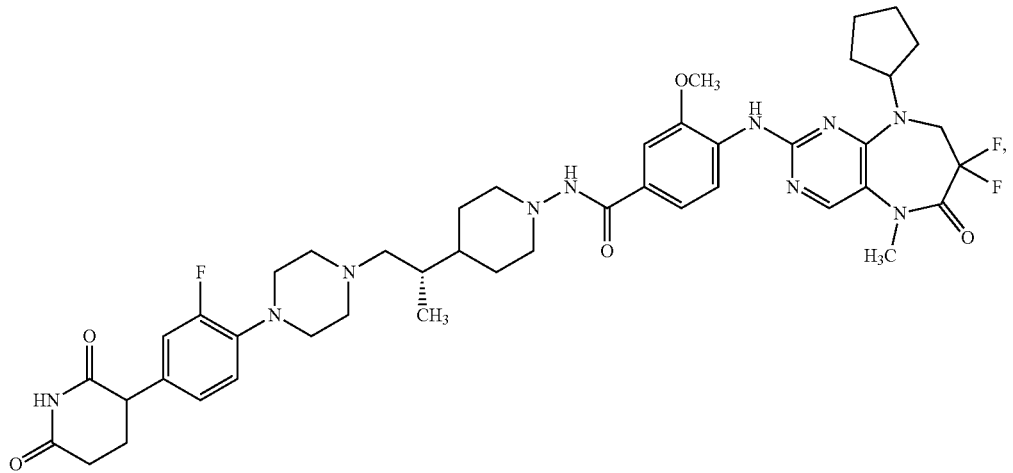
20
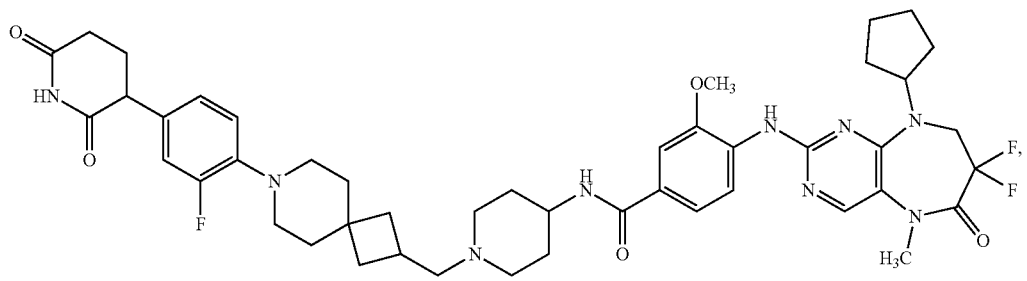
21
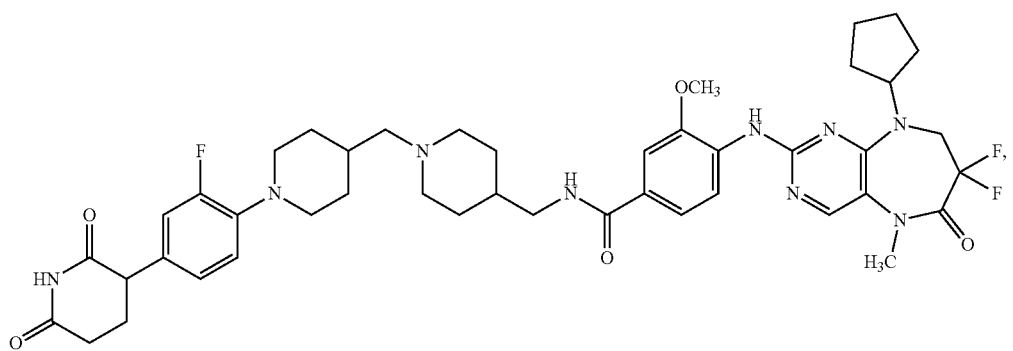
22
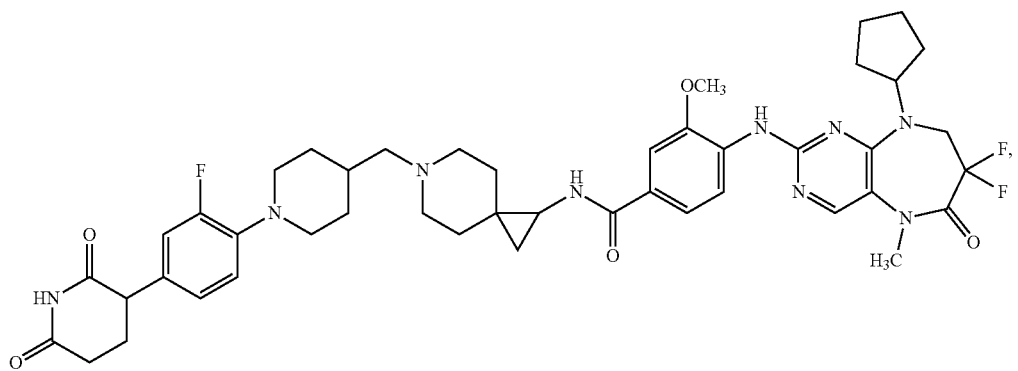
23

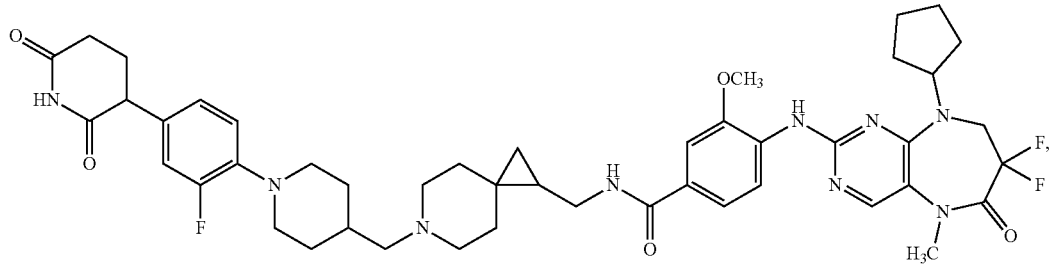
24
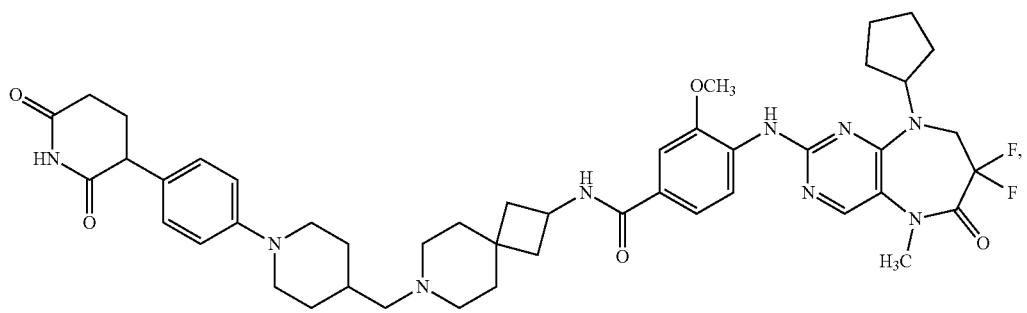
16
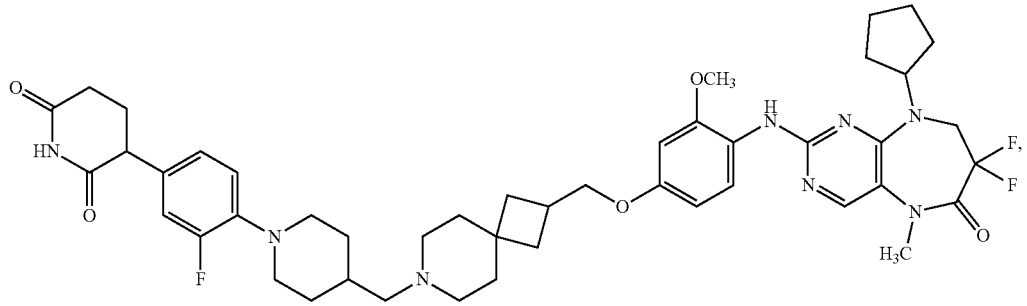
17
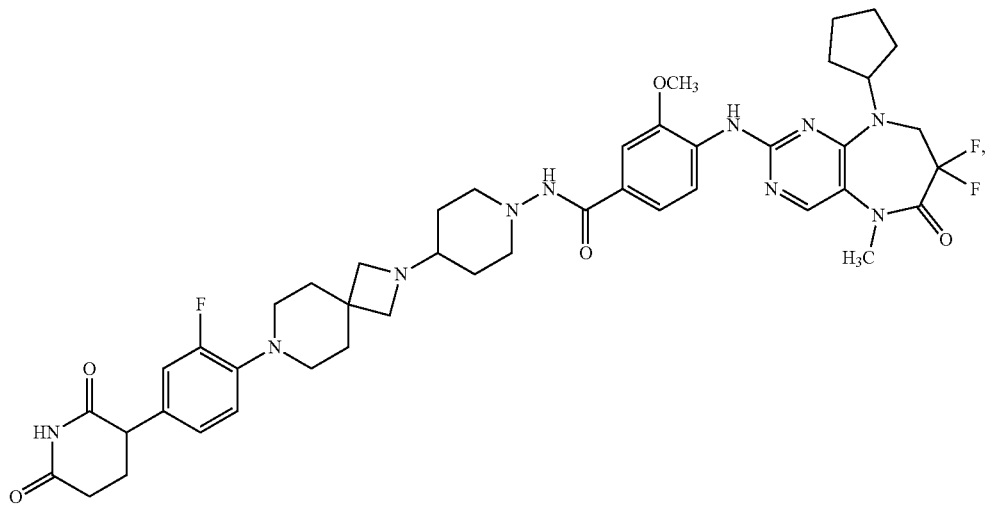
18

-continued
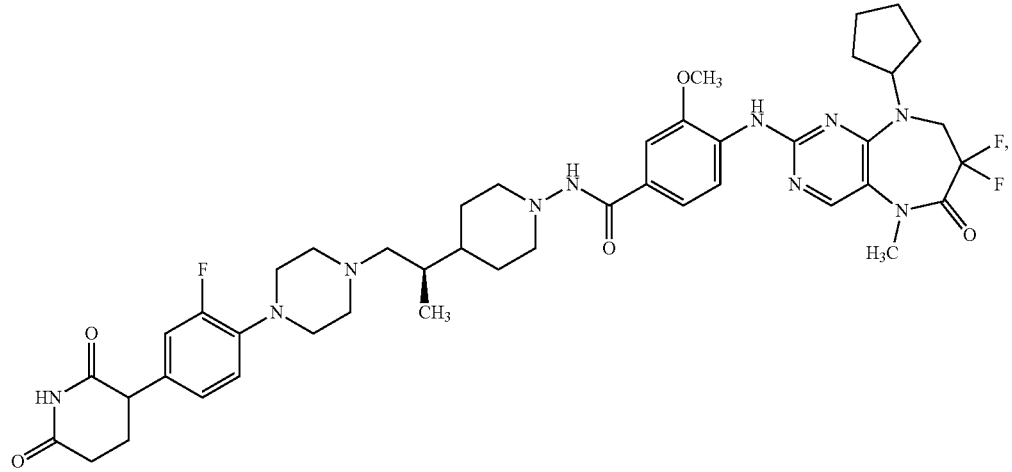
19
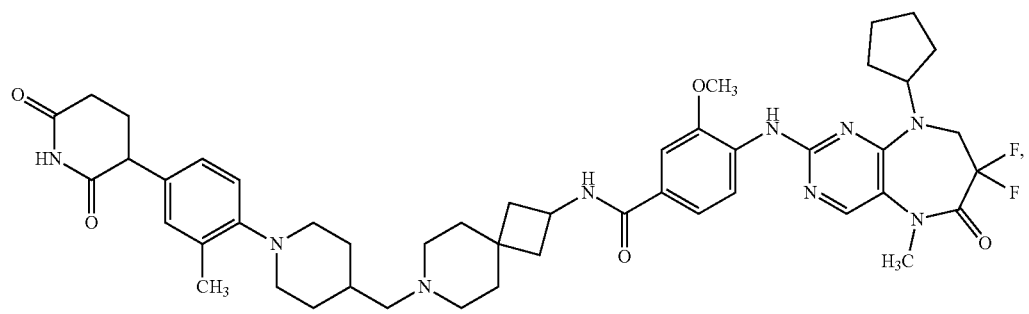
25
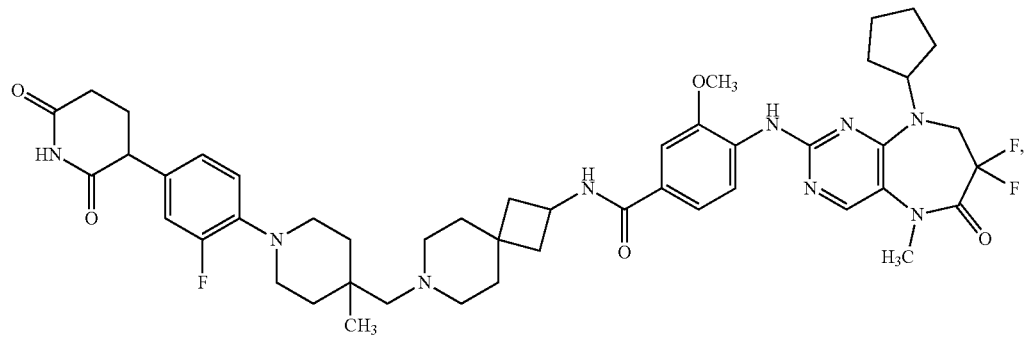
26
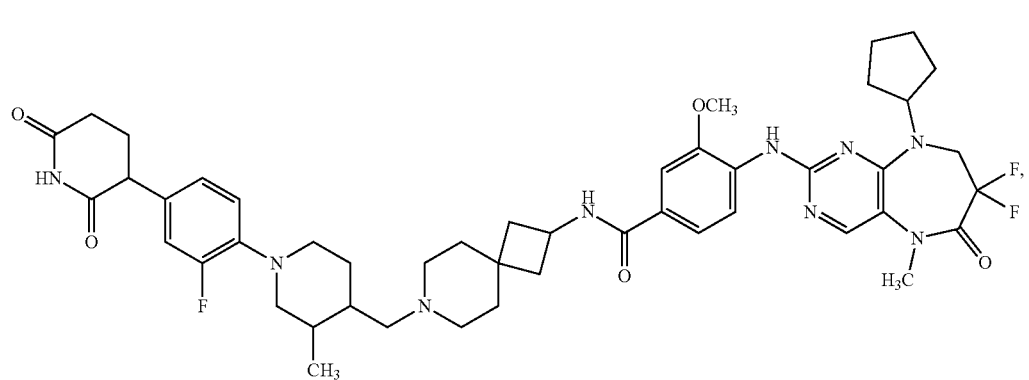
27

28
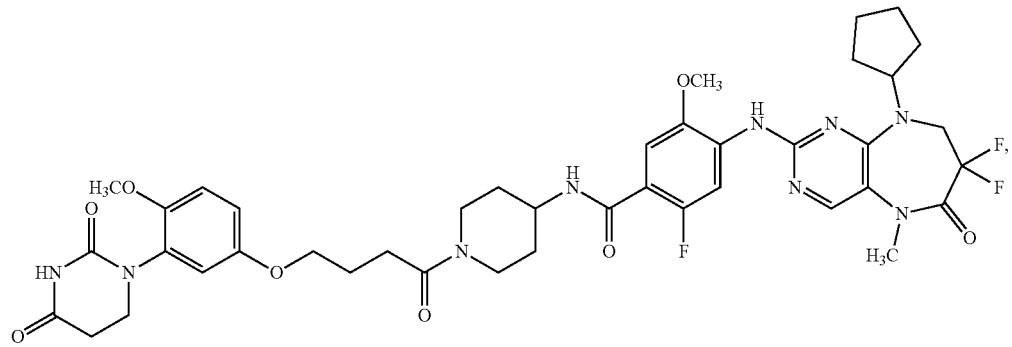
29
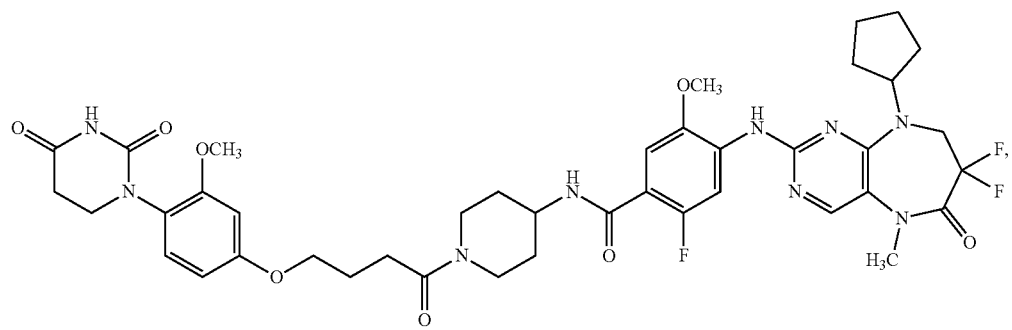
30
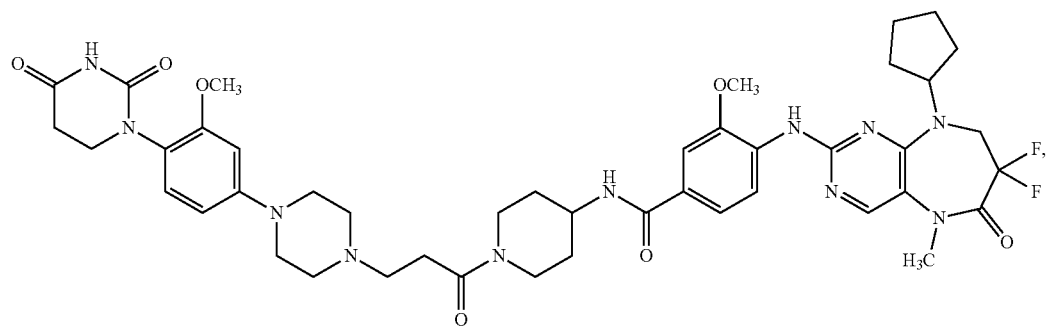
31
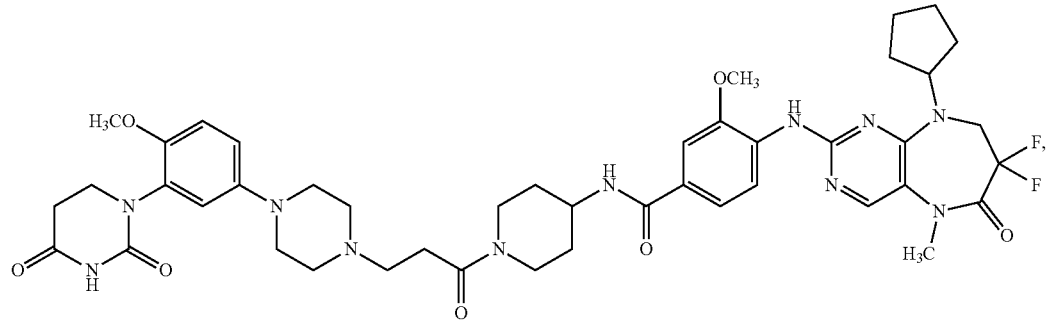
32
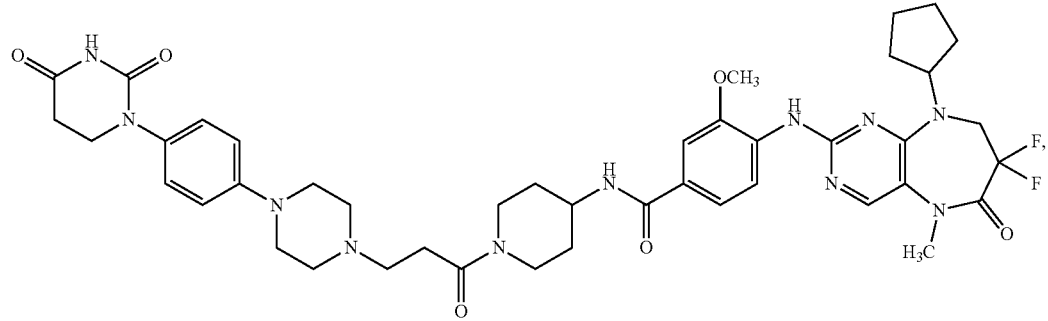

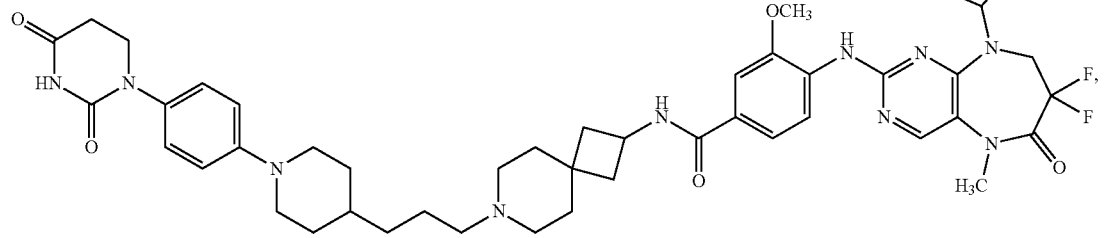
33
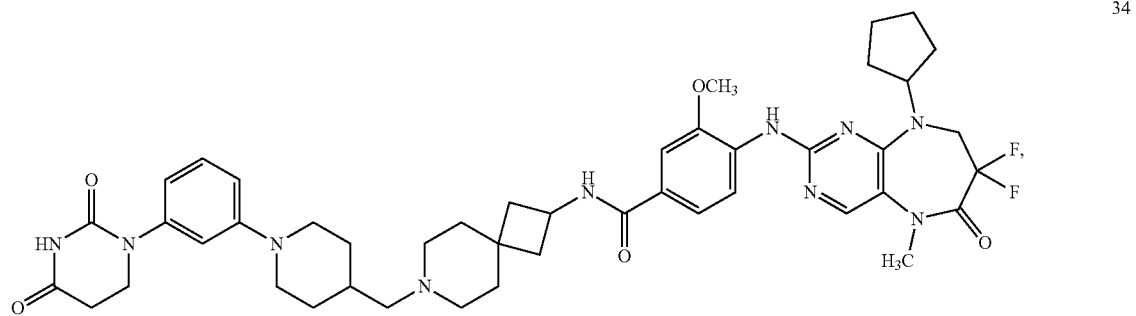
34
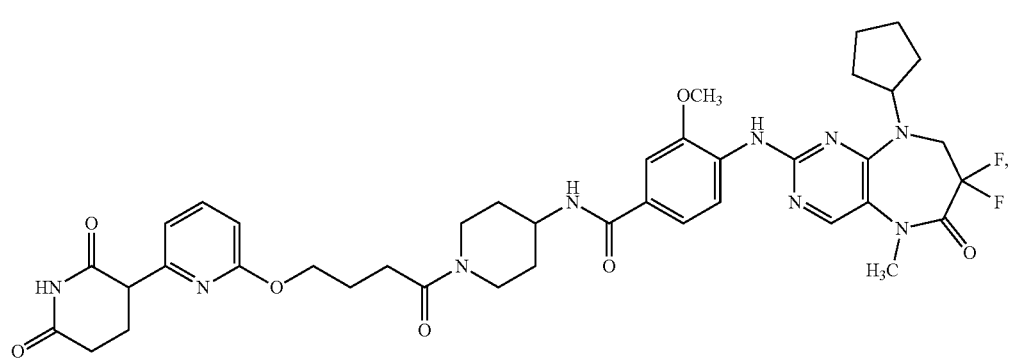
35
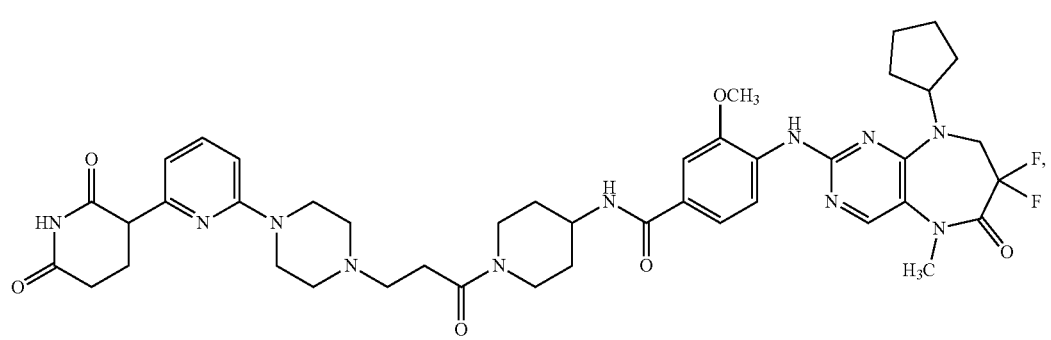
36
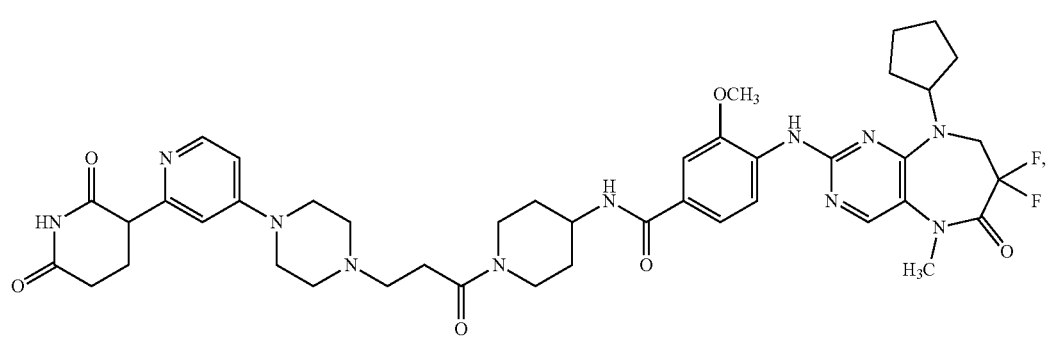
37

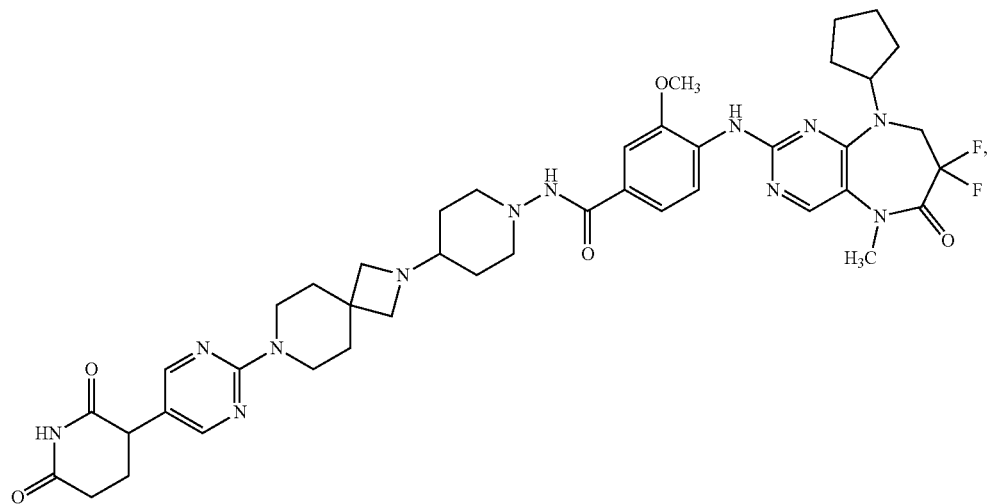
38
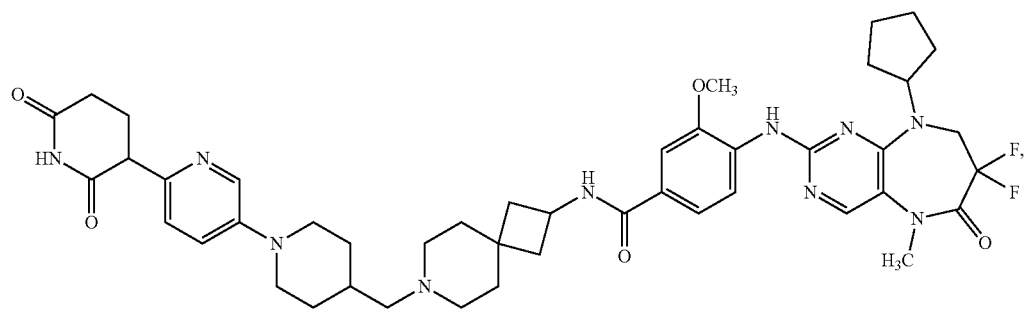
39
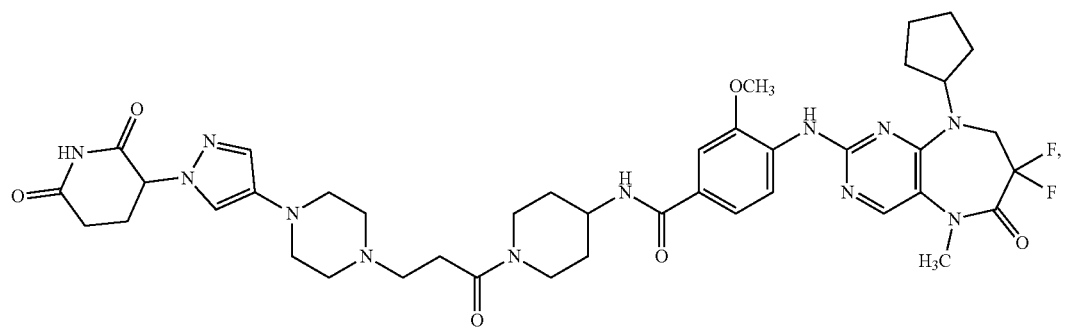
40
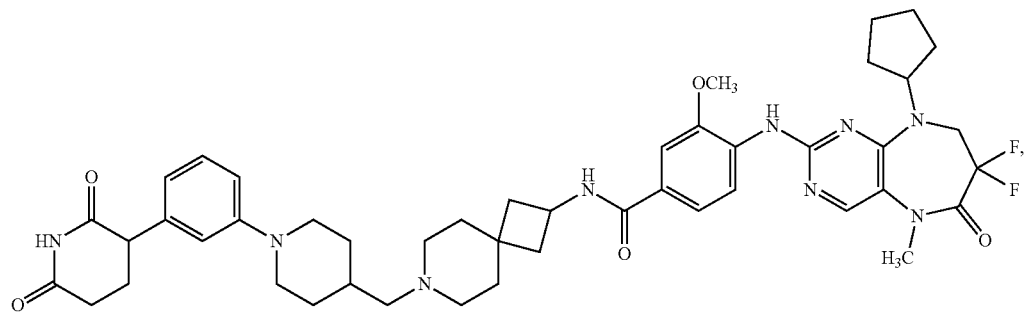
41

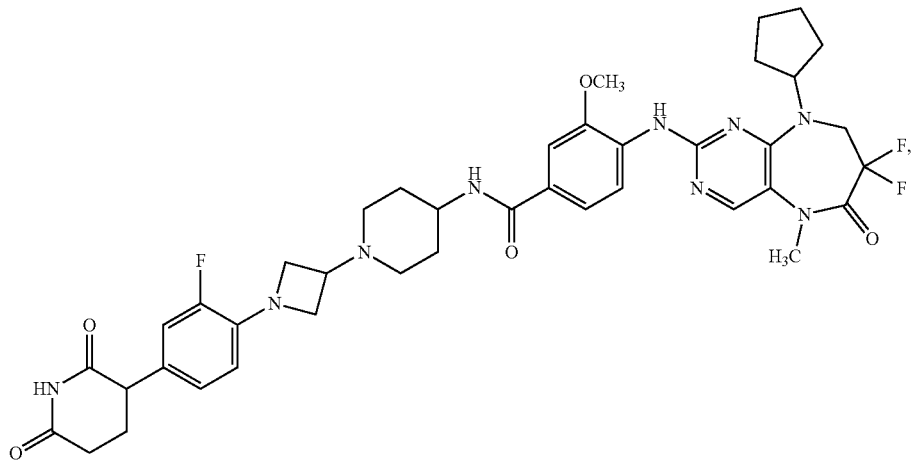
42
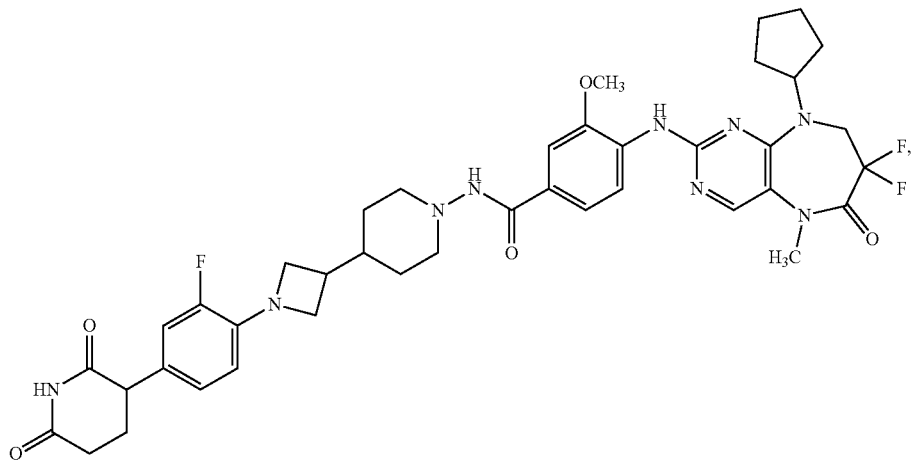
43
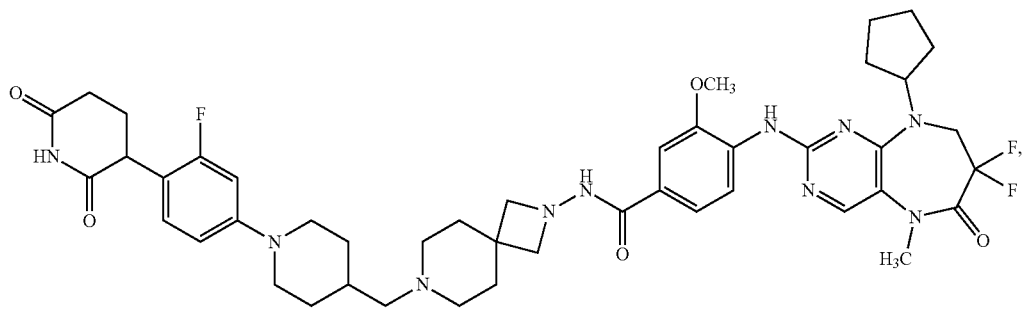
44

45

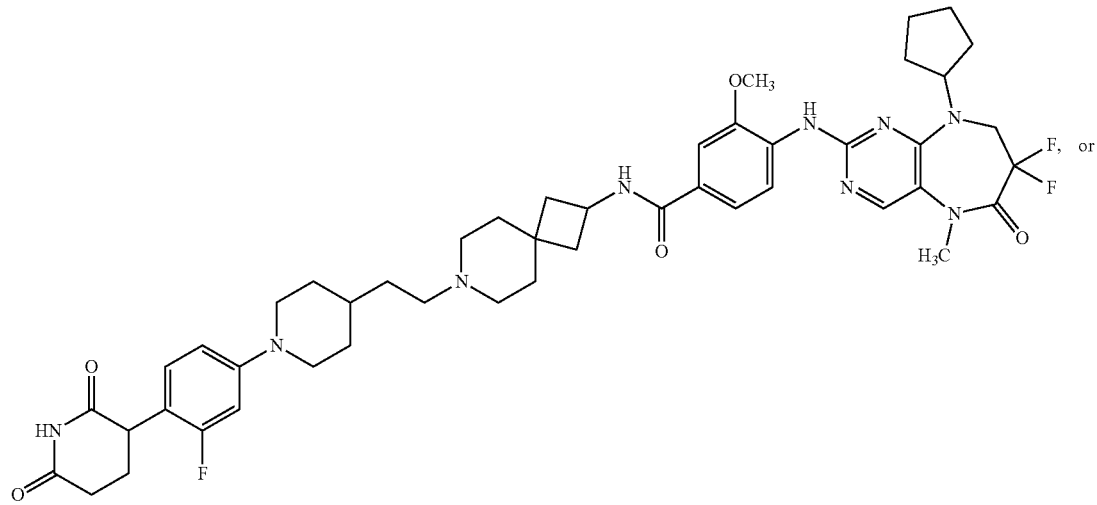

46

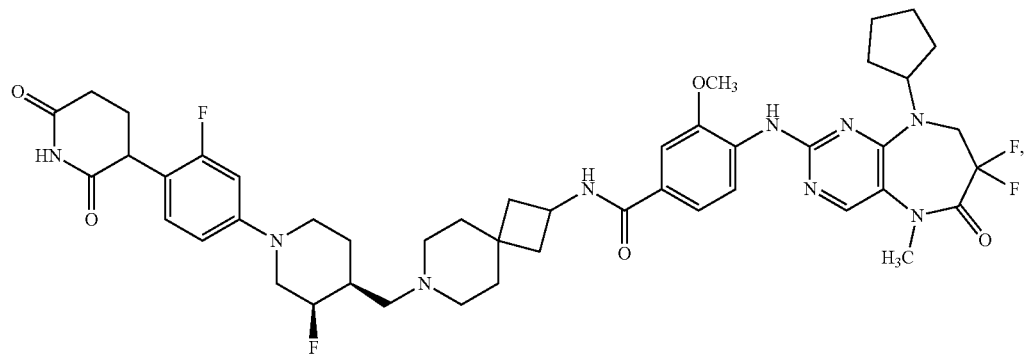

or a pharmaceutically acceptable salt thereof.

7. A pharmaceutical composition comprising a pharmaceutically acceptable carrier and a compound according to claim 1, or a pharmaceutically acceptable salt or stereoisomer thereof.

8. A method for inducing polo-like kinase 1 (PLK1) degradation in a subject, wherein the method comprises administering to the subject in need thereof a therapeutically effective amount of the pharmaceutical composition according to claim 7.

9. The method according to claim 8, wherein the subject has a PLK1-related disease selected from a benign tumor, a cancer, or a neurological disorder.

10. The method according to claim 9, wherein the benign tumor or the cancer is selected from acute leukemia, adrenal cancer, anal muscle cancer, Barrett's esophagus, bladder cancer, brain cancer, breast cancer, breast cyst, breast fibroadenoma, cervical cancer, chronic leukemia, colon adenoma, colon cancer, colon polyp, colorectal cancer, endocrine cancer, endometrial cancer, esophageal cancer, gastric cancer, gastrointestinal cancer, glioblastoma, head and neck cancer, hepatocellular carcinoma, intraocular melanoma, kidney cancer, liver cancer, liver tumor, lung adenocarcinoma, lymphocytic lymphoma, monoclonal gammopathy of undetermined significance (MGUS), monoclonal lymphocytosis, non-small cell lung cancer, osteosarcoma, ovarian cancer, pancreatic cancer, parathyroid cancer, peritoneal cancer, prostate cancer, rectal cancer, salivary gland cancer, skin cancer, skin melanoma, small cell lung cancer, small intestine cancer, soft tissue sarcoma, a squamous cell carcinoma, thyroid cancer, urethral cancer, uterine cancer, or vulvar cancer, or a combination thereof.

11. The method according to claim 10, wherein the squamous cell carcinoma is lung squamous cell carcinoma.

12. The method according to claim 9, wherein the neurological disorder is selected from Alzheimer's disease, an axonal degeneration-related disorder following brain injury, an axonal degeneration-related disorder following spinal cord injury, a central nervous system disease, epilepsy, Huntington's disease, Lou Gehrig's disease, multiple sclerosis, nerve damage, a neurodegenerative disease, Parkinson's disease, senile dementia, or stroke, or a combination thereof.

* * * * *